US008933229B2

(12) United States Patent
Horiuchi et al.

(10) Patent No.: US 8,933,229 B2
(45) Date of Patent: Jan. 13, 2015

(54) 8-AZABICYCLO[3.2.1]OCTANE-8-CARBOXAMIDE DERIVATIVE

(75) Inventors: Yoshihiro Horiuchi, Suita (JP); Kiyoto Sawamura, Suita (JP); Hiroaki Fujiwara, Suita (JP)

(73) Assignee: Sumitomo Dainippon Pharma Co., Ltd., Osaka (JP)

( * ) Notice: Subject to any disclaimer, the term of this patent is extended or adjusted under 35 U.S.C. 154(b) by 0 days.

(21) Appl. No.: 13/508,905

(22) PCT Filed: Nov. 11, 2010

(86) PCT No.: PCT/JP2010/070095
§ 371 (c)(1),
(2), (4) Date: May 9, 2012

(87) PCT Pub. No.: WO2011/059021
PCT Pub. Date: May 19, 2011

(65) Prior Publication Data
US 2012/0225876 A1 Sep. 6, 2012

(30) Foreign Application Priority Data

Nov. 11, 2009 (JP) ................................. 2009-258451
Jul. 8, 2010 (JP) ................................. 2010-156263

(51) Int. Cl.
C07D 451/02 (2006.01)
A61K 31/44 (2006.01)
C07D 451/06 (2006.01)

(52) U.S. Cl.
CPC .................................. C07D 451/06 (2013.01)
USPC .......................................... 546/124; 514/299

(58) Field of Classification Search
None
See application file for complete search history.

(56) References Cited

U.S. PATENT DOCUMENTS

2009/0227631 A1 9/2009 Carniato et al.
2011/0294809 A1* 12/2011 Braun et al. ............... 514/235.2

FOREIGN PATENT DOCUMENTS

| CN | 101331114 A | 12/2008 |
| CN | 101479265 A | 7/2009 |
| JP | 2009-040693 A | 2/2009 |
| JP | 2009-525262 A | 7/2009 |
| JP | 2009-535420 A | 10/2009 |
| WO | 98/22462 A1 | 5/1998 |
| WO | 2006/048750 A2 | 5/2006 |
| WO | 2007/068330 A1 | 6/2007 |
| WO | 2007/130898 A1 | 11/2007 |
| WO | 2008/024497 A2 | 2/2008 |
| WO | 2008/101914 A2 | 8/2008 |
| WO | 2008/134221 A1 | 11/2008 |
| WO | 2009/001817 A1 | 12/2008 |
| WO | 2009/020140 A1 | 2/2009 |
| WO | 2009/005531 A2 | 4/2009 |
| WO | 2009/111207 A1 | 9/2009 |
| WO | 2009/112691 A2 | 9/2009 |
| WO | 2009/114173 A1 | 9/2009 |
| WO | 2010/046445 A2 | 4/2010 |
| WO | 2010/049635 A1 | 5/2010 |

OTHER PUBLICATIONS

Hook, V., Biodrugs 2006, vol. 20, pp. 105-119.*
Daviglus, M. Ann Inter Med 2010 vol. 153 pp. 176-181.*
Translation of the International Preliminary Report on Patentability and Written Opinion mailed Jun. 21, 2012, in International Application No. PCT/JP2010/070095.
Saishin Igaku, vol. 62, 2007, pp. 83-90 with English Abstract.
R.H. Stimson and B.R. Walker, "Glucocorticoids and 11β-hydroxysteroid dehydrogenase type 1 in obesity and metabolic syndrome", Minerva Endocrinology, vol. 32, 2007, pp. 141-159.
Alan F. Schatzberg and Steven Lindley, "Glucocorticoid antagonists in neuropsychotic disorders", European Journal of Pharmacology, vol. 583, 2008, pp. 358-364.
J. Herbert et al., "Do Corticosteroids Damage the Brain?", Journal of Neuroendocrinology, vol. 18, 2006, pp. 393-411.

(Continued)

Primary Examiner — Heidi Reese
(74) Attorney, Agent, or Firm — Sughrue Mion, PLLC

(57) ABSTRACT

Disclosed is a compound represented by formula (1) or a pharmacologically acceptable salt thereof (In the formula, A represents a group that is represented by formula (A-1); $R^{1a}$ and $R^{1b}$ may be the same or different and each independently represents a $C_{1-6}$ alkyl group which may be substituted by one to three halogen atoms; m and n each independently represents an integer of 0-5; $X^1$ represents a hydroxyl group or an aminocarbonyl group; $Z^1$ represents a single bond or the like; and $R^2$ represents an optionally substituted $C_{1-6}$ alkyl group, an optionally substituted $C_{6-10}$ aryl group or the like).

42 Claims, No Drawings

(56) References Cited

OTHER PUBLICATIONS

Joyce L. W. Yau, et al., "Lack of tissue glucocorticoid reactivation in 11β-hydroxysteroid dehydrogenase type 1 knockout mice ameliorates age-related learning impairments", Proceedings of the National Academy of Sciences, vol. 98, No. 8, Apr. 10, 2001, pp. 4716-4721.

Kim N. Green, et al., "Glucocorticoids Increase Amyloid-β and Tau Pathology in a Mouse Model of Alzheimer's Disease", The Journal of Neuroscience, vol. 26, No. 35, Aug. 30, 2006, pp. 9047-9056.

Joyce L.W. Yau, et al., "Enhanced Hippocampal Long-Term Potentiation and Spatial Learning in Aged 11β-Hydroxysteroid Dehydrogenase Type 1 Knock-Out Mice", The Journal of Neuroscience, vol. 27, No. 39, Sep. 26, 2007, pp. 10487-10496.

Extended European Search Report issued Feb. 25, 2013 in European Patent Application No. 10829980.1 to Dainippon Sumitomo Pharma Co., Ltd.

First Office Action issued Dec. 30, 2013 in counterpart Chinese Patent Application No. 201080051243.8 with English translation.

Scott P. Webster, et al., "Discovery and biological evaluation of adamantyl amide 11(β)-HSD1 inhibitors", Bioorganic & Medicinal Chemistry Letters, vol. 17, 2007, pp. 2838-2843.

Patrick W.F. Hadoke, et al., "Therapeutic manipulation of glucocorticoid metabolism in cardiovascular disease", British Journal of Pharmacology, vol. 156, 2009, pp. 689-712.

Kim N. Green, et al., "Glucocorticoids Increase Amyloid-(β) and Tau Pathology in a Mouse Model of Alzheimer's Disease", The Journal of Neuroscience, vol. 26, No. 35, Aug. 30, 2006, pp. 9047-9056.

F. Giubilei, et al., "Altered Circadian Cortisol Secretion in Alzheimer's Disease: Clinical and Neuroradiological Aspects", Journal of Neuroscience Research, vol. 22, 2001, pp. 262-265.

Thekkepat C. Sandeep, et al., "11 (beta)-Hydroxysteroid dehydrogenase inhibition improves cognitive function in healthy elderly men and type 2 diabetics", PNAS, vol. 101, No. 17, Apr. 27, 2004, pp. 6734-6739.

Office Action issued Nov. 18, 2014 in counterpart Japanese Patent Application No. 2011-540534 with English translation.

\* cited by examiner

8-AZABICYCLO[3.2.1]OCTANE-8-CARBOXAMIDE DERIVATIVE

CROSS REFERENCE TO RELATED APPLICATIONS

This application is a National Stage of International Application No. PCT/JP2010/070095 filed Nov. 11, 2010, claiming priority based on Japanese Patent Application Nos. 2009-258451, filed Nov. 11, 2009 and 2010-156263, filed Jul. 8, 2010, the contents of all of which are incorporated herein by reference in their entirety.

TECHNICAL FIELD

The present invention relates to a 8-azabicyclo[3.2.1]octane-8-carboxamide derivative, or a pharmaceutically acceptable salt thereof, which is useful as a medicament. The present invention also relates to a pharmaceutical composition, comprising a 8-azabicyclo[3.2.1]octane-8-carboxamide derivative or a pharmaceutically acceptable salt thereof. The present invention also relates to a therapeutic or preventive agent for diseases associated with glucocorticoid comprising the compound, or an inhibitor of 11β hydroxysteroid dehydrogenase type 1 enzyme (referred to as 11βHSD1, hereinafter).

BACKGROUND ART

Glucocorticoid adjusts peripheral glucose metabolism and amino-acid metabolism. In human being, glucocorticoid is produced in adrenal glands, and in addition, it is metabolized in peripheral tissues such as adipose tissue or liver. Since 11βHSD1 is an enzyme which converts inactive cortisone into activated cortisol and is expressed mainly in adipose tissue or liver, 11βHSD1 is believed to have some relations to the activation of glucocorticoid in adipose tissue or liver. Since cortisol shows promoting activities for fat accumulation to adipocyte and for gluconeogenesis in liver, 11βHSD1 is believed to contribute to the maintenance of homeostasis in whole body by adjusting peripheral glucose and lipid metabolism. On the other hand, 11βHSD1 activity in adipose tissue significantly increases in insulin resistance patients in human being, and 11βHSD1 activity is remarkably higher in visceral fat than that in subcutaneous fat. Visceral fat accumulation and development of abnormal glucose and lipid metabolism are suppressed on high-fat diet feeding in 11βHSD1 gene defect mice, and adipose cell-specific 11βHSD1-overexpressed mice show remarkable visceral fat-type obesity or abnormal glucose and lipid metabolism. This indicates that overactivation of 11βHSD1 is intimately related to visceral fat accumulation and development of metabolic syndrome in human and mice (Nonpatent Documents 1 and 2). In other words, suppression of gluconeogenesis in liver and fat accumulation in adipocyte, and improvement of glucose and lipid metabolism in whole body are expected by inhibiting this enzyme activity.

As far as the improvement of glucose metabolism, since it has been reported that 11βHSD1 activity in pancreatic β cells could contribute to the suppression of insulin secretion or 11βHSD1 activity in human muscle cells could have some relations to the suppression of glucose uptake of muscle cells, 11βHSD1 inhibitor has potential to remedy hyperglycemia directly.

11βHSD1 is also expressed in central nervous systems including hippocampus. It has been known that patients with Cushing's disease wherein glucocorticoid overexpresses and those whom a kind of synthetic glucocorticoids dexamethasone is administered show depression symptom. It has been also known that glucocorticoid receptor antagonist is effective for depression and manic depression, and it has been indicated that glucocorticoid in central nervous systems is intimately related to the expression of symptom of depression as well as manic depression (Nonpatent Documents 3 and 4). Since 11βHSD1 plays a role in the production of active glucocorticoid in central nervous systems, it has been expected that 11βHSD1 inhibitor would show effectiveness in the treatment of depression and manic depression.

Furthermore, 11βHSD1 is indicated to have much relation to the adjustment of cognitive function, since depositions of amyloid β protein which is strongly indicated to relate to Alzheimer's dementia have been caused in mice to which glucocorticoid have been administered for a long term, and it is recognized that age-related cognitive function loss is inhibited and the increase of cognition maintenance is increased in 11βHSD1 gene defect mice (Nonpatent Documents 5 to 7). The knowledge as shown above indicates that 11βHSD1 inhibitor is useful as a therapeutic agent of dementia including Alzheimer's dementia. It has been shown that 11βHSD1 functions in immunocytes, and 11βHSD1 inhibitor is expected to show therapeutic effectiveness in diseases caused by abnormal immune function.

Various 11βHSD1 inhibitors have been reported, and for example, Patent Document 1 discloses a compound of formula:

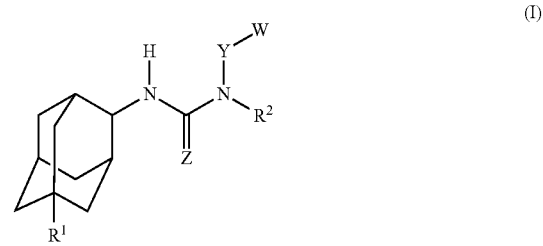

(I)

wherein $R^1$ is hydrogen atom, hydroxyl, etc., Z is oxygen atom or sulfur atom, $R^2$ is hydrogen atom, methyl, ethyl or isopropyl, or $R^2$, Y and N adjacent thereto may form saturated $C_5$-$C_8$ ring, the ring may be optionally substituted by $R^3$, $R^4$ and/or $R^5$, Y is a single bond, $C_1$-$C_4$ alkyl, etc., W is $C_4$-$C_8$cycloalkyl, etc., $R^3$, $R^4$ and $R^5$ are independently hydrogen atom, halogen atom, etc. However, the compounds disclosed in Patent Document 1 do not have an 8-azabicyclo[3.2.1]octane-8-carboxamide skeleton, so they are structurally different from the present invention.

Compounds disclosed in Patent Documents 2 and 3 have been known as a compound having an azabicyclo skeleton. Patent Document 2 discloses an example compound of formula:

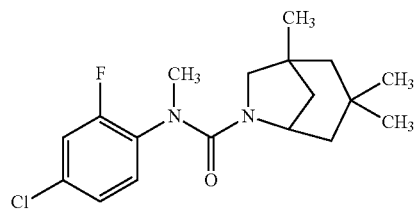 [SMILES: CN(C(=O)N1CC2(C)CC1CC(C)(C)C2)c1ccc(Cl)cc1F]

However, a compound of Example 17 is structurally different from the present invention in that it has 6-azabicyclo[3.2.1]octane-6-carboxamide and phenyl.

Patent Document 3 discloses a compound of formula:

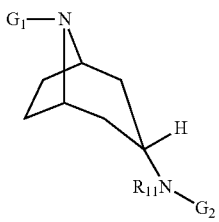

A wherein $G_1$ and $G_2$ are different and $R_2$ or —N($R_{11}$)C(=X)-$L_1$-$R_1$, $R_1$ is selected from the following group:

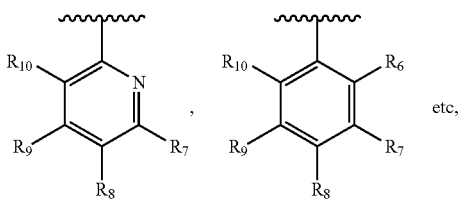

etc, $R_2$ is selected from phenyl, —C(O)-phenyl, benzyl and 5 to 6-membered heteroaryl, $R_6$, $R_7$, $R_8$, $R_9$ and $R_{10}$ are each independently alkyl which may be optionally substituted by 1 to 5 halogen atoms, etc., $R_{11}$ is hydrogen atom, etc., $R_{12}$ is hydrogen atom, etc., $R_{13}$ is halogen atom, etc., $L_1$ is —C($R_{12}$)($R_{13}$)—, etc., X is oxygen atom or sulfur atom. However, a compound represented by A is structurally different from the present invention in that it is characterized by a structural feature that $G_1$ is aryl or heteroaryl.

[Patent Document 1] WO 2007/068330 pamphlet
[Patent Document 2] WO 2007/130898 pamphlet
[Patent Document 3] WO 2009/114173 pamphlet
[Nonpatent Document 1] Saishin Igaku, vol. 62, pp. 83-90, 2007
[Nonpatent Document 2] Stimson et al., Minerva Endocrinology, 32, 141 (2007)
[Nonpatent Document 3] Schatzberg et al., European Journal of Pharmacology., 583, 358 (2008)
[Nonpatent Document 4] Herbert et al., Journal of Neuroendocrinology., 18, 393 (2006)
[Nonpatent Document 5] Yau et al., Proceedings of the National Academy of Sciences., 98, 4716 (2001)
[Nonpatent Document 6] Green et al., Journal of Neuroscience, 26(35), 9047 (2006)
[Nonpatent Document 7] Yau et al., The Journal of Neuroscience, 27 (39), 10487 (2007)

SUMMARY OF INVENTION

Problems to be Solved by the Invention

Recently, a pharmaceutically satisfiable compound having 11βHSD1 inhibitory action has been desired as an agent for preventing and/or treating diseases including type II diabetes, abnormal glucose tolerance, hyperglycemia, insulin resistance, hypo HDL-emia, hyper LDL-emia, dyslipidemia, hyperlipidemia, hypertriglyceridemia, hypercholesterolemia, hypertension, arteriosclerosis, angiostenosis, atherosclerosis, obesity, dementia, cognitive disorder, glaucoma, retinopathy, dementia, Alzheimer's disease, osteoporosis, immune disorder, metabolic syndrome, depression, cardiovascular disease, neurodegenerative disease.

In the past, 8-azabicyclo[3.2.1]octane-8-carboxamide derivatives represented by the following formula (1) have never been prepared as an 11βHSD1 inhibitor, and their 11βHSD1 inhibitory activities have never been known. According to the extensive studies of the derivatives for solving the problems, the inventors have found that 8-azabicyclo[3.2.1]octane-8-carboxamide derivatives have strong 11βHSD1 inhibitory activities. The inventors have also found that the derivatives have balanced properties essential for a medicament, including metabolic stability, solubility, pharmacokinetics as well as 11βHSD1 inhibitory activity, and achieved the present invention.

Means of Solving the Problems

Specifically, the present invention is as follows.

Item 1: A compound of formula (1):

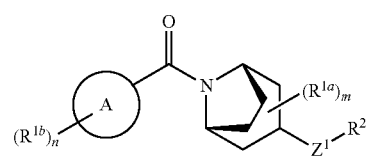

(1)

wherein A is a group of the following formula (A-1):

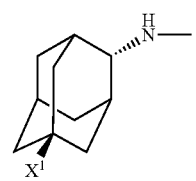

(A-1)

$R^{1a}$ and $R^{1b}$ are the same or different and each independently $C_{1-6}$ alkyl which may be optionally substituted by 1 to 3 halogen atoms;

m and n are each independently an integer of 0 to 5;

$X^1$ is hydroxyl, or aminocarbonyl;

$Z^1$ is a single bond, oxygen atom, sulfur atom, —SO—, —SO$_2$—, or —N($R^3$)—;

$R^2$ is cyano, optionally substituted $C_{1-6}$ alkyl, optionally substituted $C_{3-7}$ cycloalkyl, optionally substituted $C_{6-10}$ aryl, optionally substituted $C_{7-16}$ aralkyl, optionally substituted heterocycle, optionally substituted heterocyclic $C_{1-6}$ alkyl, optionally substituted 5 to 12-membered mono- or poly-cyclic heteroaryl, optionally substituted 5 to 12-membered mono- or poly-cyclic heteroaryl-$C_{1-6}$ alkyl, or optionally substituted 5 to 7-membered cyclic amino;

provided that if $R^2$ is cyano and optionally substituted 5 to 7-membered cyclic amino, then $Z^1$ is a single bond;

$R^3$ is hydrogen atom, optionally substituted $C_{1-6}$ alkyl, optionally substituted $C_{3-7}$ cycloalkyl, optionally substituted $C_{6-10}$ aryl, optionally substituted $C_{7-16}$ aralkyl, optionally substituted heterocycle, optionally substituted heterocyclic $C_{1-6}$ alkyl, optionally substituted 5 to 12-membered mono- or poly-cyclic heteroaryl, or optionally substituted 5 to 12-membered mono- or poly-cyclic heteroaryl-$C_{1-6}$ alkyl; or a pharmaceutically acceptable salt thereof.

Item 2: The compound of Item 1, wherein m and n are 0, or a pharmaceutically acceptable salt thereof.

Item 3: The compound of either one of Item 1 or 2, wherein $X^1$ is hydroxyl, or a pharmaceutically acceptable salt thereof.

Item 4: The compound of either one of Item 1 or 2, wherein $X^1$ is aminocarbonyl, or a pharmaceutically acceptable salt thereof.

Item 5: The compound of any one of Items 1 to 4, wherein $Z^1$ has the following configuration in formula (1):

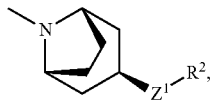

or a pharmaceutically acceptable salt thereof

Item 6: The compound of any one of Items 1 to 4, wherein $Z^1$ has the following configuration in formula (1):

or a pharmaceutically acceptable salt thereof

Item 7: The compound of any one of Items 1 to 6, wherein $Z^1$ is a single bond, oxygen atom, sulfur atom, or —$SO_2$—, or a pharmaceutically acceptable salt thereof.

Item 8: The compound of any one of Items 1 to 6, wherein $Z^1$ is sulfur atom, —SO—, or —$SO_2$—, or a pharmaceutically acceptable salt thereof.

Item 9: The compound of Item 8, wherein $Z^1$ is sulfur atom, or —$SO_2$—, or a pharmaceutically acceptable salt thereof.

Item 10: The compound of Item 7, wherein $Z^1$ is a single bond, or oxygen atom, or a pharmaceutically acceptable salt thereof.

Item 11: The compound of Item 10, wherein $Z^1$ is a single bond, or a pharmaceutically acceptable salt thereof.

Item 12: The compound of Item 10, wherein $Z^1$ is oxygen atom, or a pharmaceutically acceptable salt thereof.

Item 13: The compound of Item 9, wherein $Z^1$ is sulfur atom, or a pharmaceutically acceptable salt thereof.

Item 14: The compound of any one of Items 1 to 6, wherein $Z^1$ is —$N(R^3)$—, or a pharmaceutically acceptable salt thereof.

Item 15: The compound of any one of Items 1 to 14, wherein $R^2$ is optionally substituted $C_{1-6}$ alkyl, optionally substituted $C_{3-7}$ cycloalkyl, optionally substituted $C_{6-10}$ aryl, optionally substituted $C_{7-16}$ aralkyl, optionally substituted heterocycle, optionally substituted heterocyclic $C_{1-6}$ alkyl, optionally substituted 5 to 12-membered mono- or poly-cyclic heteroaryl, or optionally substituted 5 to 12-membered mono- or poly-cyclic heteroaryl-$C_{1-6}$ alkyl, or a pharmaceutically acceptable salt thereof.

Item 16: The compound of Item 15, wherein $R^2$ is optionally substituted $C_{6-10}$ aryl, optionally substituted $C_{7-16}$ aralkyl, optionally substituted 5 to 12-membered mono- or poly-cyclic heteroaryl, or optionally substituted 5 to 12-membered mono- or poly-cyclic heteroaryl-$C_{1-6}$ alkyl, or a pharmaceutically acceptable salt thereof.

Item 17: The compound of Item 16, wherein $R^2$ is optionally substituted $C_{6-10}$ aryl, or optionally substituted 5 to 12-membered mono- or poly-cyclic heteroaryl, or a pharmaceutically acceptable salt thereof.

Item 18: The compound of Item 16, wherein $R^2$ is optionally substituted $C_{7-16}$ aralkyl, or optionally substituted 5 to 12-membered mono- or poly-cyclic heteroaryl-$C_{1-6}$ alkyl, or a pharmaceutically acceptable salt thereof.

Item 19: The compound of Item 16, wherein $R^2$ is optionally substituted $C_{6-10}$ aryl, or optionally substituted $C_{7-16}$ aralkyl, or a pharmaceutically acceptable salt thereof.

Item 20: The compound of Item 16, wherein $R^2$ is optionally substituted 5 to 12-membered mono- or poly-cyclic heteroaryl, or optionally substituted 5 to 12-membered mono- or poly-cyclic heteroaryl-$C_{1-6}$ alkyl, or a pharmaceutically acceptable salt thereof.

Item 21: The compound of Item 19, wherein $R^2$ is optionally substituted $C_{6-10}$ aryl, or a pharmaceutically acceptable salt thereof.

Item 22: The compound of any one of Items 1 to 21, wherein the substituent group in the optionally substituted $C_{6-10}$ aryl, optionally substituted 5 to 12-membered mono- or poly-cyclic heteroaryl, optionally substituted $C_{7-16}$ aralkyl, and optionally substituted 5 to 12-membered mono- or poly-cyclic heteroaryl-$C_{1-6}$ alkyl in $R^2$ is selected from the group consisting of:

(1) halogen atom,
(2) cyano,
(3) hydroxy,
(4) $C_{1-4}$ alkoxy (in which the alkoxy may be optionally substituted by
  (a) 1 to 3 halogen atoms,
  (b) $C_{1-4}$ alkoxy (in which the alkoxy may be optionally substituted by 1 to 3 halogen atoms),
  (c) carboxy,
  (d) $C_{1-4}$alkoxycarbonyl,
  (e) $C_{7-16}$ aralkyloxycarbonyl,
  (f) mono- or di-$C_{1-6}$ alkylaminocarbonyl,
  (g) 5 to 7-membered cyclic aminocarbonyl, or
  (h) $C_{3-6}$ cycloalkyl),
(5) $C_{1-4}$ alkylsulfonyl,
(6) $C_{3-6}$ cycloalkyl (in which the group may be optionally substituted by 1 to 3 halogen atoms),
(7) $C_{3-6}$ cycloalkoxy (in which the group may be optionally substituted by 1 to 3 halogen atoms),
(8) mono- or di-$C_{1-6}$ alkylamino,
(9) mono- or di-$C_{1-6}$ alkylcarbonylamino,
(10) mono- or di-$C_{1-6}$ alkylsulfonylamino,
(11) $C_{1-4}$ alkyl (in which the alkyl may be optionally substituted by
  (a) 1 to 3 halogen atoms,
  (b) $C_{1-4}$ alkoxy (in which the alkoxy may be optionally substituted by 1 to 3 halogen atoms),
  (c) carboxy,
  (d) $C_{1-4}$ alkoxycarbonyl,
  (e) $C_{7-16}$ aralkyloxycarbonyl,
  (f) mono- or di-$C_{1-6}$ alkylaminocarbonyl,
  (g) 5 to 7-membered cyclic aminocarbonyl, or
  (h) $C_{3-6}$ cycloalkyl),
(12) $C_{1-6}$ alkylcarbonyl,
(13) carboxy,
(14) $C_{1-4}$ alkoxycarbonyl,
(15) aminocarbonyl, and
(16) $C_{1-6}$ alkylthio, or a pharmaceutically acceptable salt thereof Item 23: The compound of Item 22, wherein the substituent group in the optionally substituted $C_{6-10}$ aryl, optionally substituted 5 to 12-membered mono- or poly-cyclic heteroaryl, optionally substituted $C_{7-16}$ aralkyl, and optionally substituted 5 to 12-membered mono- or poly-cyclic heteroaryl-$C_{1-6}$ alkyl in $R^2$ is selected from the group consisting of:

(1) halogen atom,
(2) cyano,
(3) hydroxy,
(4) $C_{1-4}$ alkoxy (in which the alkoxy may be optionally substituted by
  (a) 1 to 3 halogen atoms,
  (b) $C_{1-4}$ alkoxy (in which the alkoxy may be optionally substituted by 1 to 3 halogen atoms),
  (c) carboxy,
  (d) $C_{1-4}$ alkoxycarbonyl, or
  (e) $C_{3-6}$ cycloalkyl),
(5) $C_{1-4}$ alkylsulfonyl,
(6) $C_{3-6}$ cycloalkyl (in which the group may be optionally substituted by 1 to 3 halogen atoms),
(7) $C_{3-6}$ cycloalkoxy (in which the group may be optionally substituted by 1 to 3 halogen atoms),
(8) mono- or di-$C_{1-6}$ alkylamino,
(9) mono- or di-$C_{1-6}$ alkylcarbonylamino,
(10) mono- or di-$C_{1-6}$ alkylsulfonylamino,
(11) $C_{1-4}$ alkyl (in which the alkyl may be optionally substituted by
  (a) 1 to 3 halogen atoms,
  (b) $C_{1-4}$ alkoxy (in which the alkoxy may be optionally substituted by 1 to 3 halogen atoms),
  (c) carboxy,
  (d) $C_{1-4}$ alkoxycarbonyl, or
  (e) $C_{3-6}$ cycloalkyl),
(12) $C_{1-6}$ alkylcarbonyl,
(13) carboxy,
(14) $C_{1-4}$ alkoxycarbonyl,
(15) aminocarbonyl, and
(16) $C_{1-6}$ alkylthio, or a pharmaceutically acceptable salt thereof.

Item 24: The compound of Item 23, wherein the substituent group in the optionally substituted $C_{6-10}$ aryl, optionally substituted 5 to 12-membered mono- or poly-cyclic heteroaryl, optionally substituted $C_{7-16}$ aralkyl, and optionally substituted 5 to 12-membered mono- or poly-cyclic heteroaryl-$C_{1-6}$ alkyl in $R^2$ is the same or different 1 to 5 substituent groups selected from the group consisting of:
(1) halogen atom,
(2) cyano,
(3) $C_{1-4}$ alkoxy (in which the alkoxy may be optionally substituted by
  (a) 1 to 3 halogen atoms,
  (b) $C_{3-6}$ cycloalkyl, or
  (c) $C_{1-4}$ alkoxy (in which the alkoxy may be optionally substituted by 1 to 3 halogen atoms)),
(4) $C_{1-4}$ alkylsulfonyl,
(5) $C_{3-6}$ cycloalkyl (in which the group may be optionally substituted by 1 to 2 halogen atoms),
(6) mono- or di-$C_{1-6}$ alkylcarbonylamino,
(7) $C_{1-4}$ alkyl (in which the alkyl may be optionally substituted by
  (a) 1 to 3 halogen atoms, or
  (b) $C_{1-4}$ alkoxy (in which the alkoxy may be optionally substituted by 1 to 3 halogen atoms)),
(8) carboxy,
(9) $C_{1-4}$ alkoxycarbonyl,
(10) aminocarbonyl, and
(11) $C_{1-6}$ alkylthio, or a pharmaceutically acceptable salt thereof Item 25: The compound of Item 23, wherein the substituent group in the optionally substituted $C_{6-10}$ aryl, optionally substituted 5 to 12-membered mono- or poly-cyclic heteroaryl, optionally substituted $C_{7-16}$ aralkyl, and optionally substituted 5 to 12-membered mono- or poly-cyclic heteroaryl-$C_{1-6}$ alkyl in $R^2$ is selected from the group consisting of:
(1) halogen atom,
(2) cyano,
(3) $C_{1-4}$ alkoxy (in which the alkoxy may be optionally substituted by
  (a) 1 to 3 halogen atoms,
  (b) $C_{1-4}$ alkoxy (in which the alkoxy may be optionally substituted by 1 to 3 halogen atoms), or
  (c) $C_{3-6}$ cycloalkyl),
(4) $C_{3-6}$ cycloalkyl,
(5) $C_{1-4}$ alkyl (in which the alkyl may be optionally substituted by
  (a) 1 to 3 halogen atoms,
  (b) $C_{1-4}$ alkoxy (in which the alkoxy may be optionally substituted by 1 to 3 halogen atoms), or
  (c) $C_{3-6}$ cycloalkyl), and
(6) $C_{1-6}$ alkylcarbonyl, or a pharmaceutically acceptable salt thereof.

Item 26: The compound of Item 25, wherein the substituent group in the optionally substituted $C_{6-10}$ aryl, optionally substituted 5 to 12-membered mono- or poly-cyclic heteroaryl, optionally substituted $C_{7-16}$ aralkyl, and optionally substituted 5 to 12-membered mono- or poly-cyclic heteroaryl-$C_{1-6}$ alkyl in $R^2$ is selected from the group consisting of:
(1) halogen atom,
(2) cyano,
(3) $C_{1-4}$ alkyl (in which the group may be optionally substituted by
  (a) 1 to 3 halogen atoms, or
  (b) $C_{1-4}$ alkoxy (in which the alkoxy may be optionally substituted by 1 to 3 halogen atoms)), and
(4) $C_{1-4}$ alkoxy (in which the group may be optionally substituted by
  (a) 1 to 3 halogen atoms,
  (b) $C_{3-6}$ cycloalkyl, or
  (c) $C_{1-4}$ alkoxy), or a pharmaceutically acceptable salt thereof Item 27: The compound of any one of Items 1 to 14, wherein $R^2$ is $C_{6-10}$ aryl (in which the aryl may be optionally substituted by the same or different 1 to 5 groups selected from the group consisting of:
(1) halogen atom,
(2) cyano,
(3) hydroxy,
(4) $C_{1-4}$ alkoxy (in which the alkoxy may be optionally substituted by
  (a) 1 to 3 halogen atoms,
  (b) $C_{1-4}$ alkoxy,
  (c) carboxy,
  (d) $C_{1-4}$ alkoxycarbonyl, or
  (e) $C_{3-6}$ cycloalkyl),
(5) $C_{1-4}$ alkylsulfonyl,
(6) $C_{3-6}$ cycloalkyl,
(7) $C_{3-6}$ cycloalkoxy,
(8) mono- or di-$C_{1-6}$ alkylamino,
(9) mono- or di-$C_{1-6}$ alkylcarbonylamino,
(10) mono- or di-$C_{1-6}$ alkylsulfonylamino,
(11) $C_{1-4}$ alkyl (in which the alkyl may be optionally substituted by
  (a) 1 to 3 halogen atoms,
  (b) $C_{1-4}$ alkoxy (in which the alkoxy may be optionally substituted by 1 to 3 halogen atoms),
  (c) carboxyl,
  (d) $C_{1-4}$ alkoxycarbonyl, or
  (e) $C_{3-6}$ cycloalkyl),

(12) $C_{1-6}$ alkylcarbonyl,
(13) carboxy,
(14) $C_{1-4}$ alkoxycarbonyl, and
(15) aminocarbonyl), or a pharmaceutically acceptable salt thereof.

Item 28: The compound of Item 27, wherein $R^2$ is $C_{6-10}$ aryl (in which the aryl may be optionally substituted by the group(s) selected from the group consisting of:
(1) halogen atom,
(2) cyano,
(3) $C_{1-4}$ alkoxy (in which the alkoxy may be optionally substituted by
  (a) 1 to 3 halogen atoms,
  (b) $C_{1-4}$ alkoxy (in which the alkoxy may be optionally substituted by 1 to 3 halogen atoms), or
  (c) $C_{3-6}$ cycloalkyl),
(4) $C_{3-6}$ cycloalkyl,
(5) $C_{1-4}$ alkyl (in which the alkyl may be optionally substituted by
  (a) 1 to 3 halogen atoms,
  (b) $C_{1-4}$ alkoxy (in which the alkoxy may be optionally substituted by 1 to 3 halogen atoms), or
  (c) $C_{3-6}$ cycloalkyl), and
(6) $C_{1-6}$ alkylcarbonyl), or a pharmaceutically acceptable salt thereof Item 29: The compound of Item 28, wherein $R^2$ is $C_{6-10}$ aryl (in which the aryl may be optionally substituted by the group(s) selected from the group consisting of:
(1) halogen atom,
(2) cyano,
(3) $C_{1-4}$ alkoxy (in which the group may be optionally substituted by
  (a) 1 to 3 halogen atoms,
  (b) $C_{1-4}$ alkoxy (in which the alkoxy may be optionally substituted by 1 to 3 halogen atoms), or
  (c) $C_{3-6}$ cycloalkyl), and
(4) $C_{1-4}$ alkyl (in which the alkyl may be optionally substituted by
  (a) 1 to 3 halogen atoms,
  (b) $C_{1-4}$ alkoxy (in which the alkoxy may be optionally substituted by 1 to 3 halogen atoms), or
  (c) $C_{3-6}$ cycloalkyl)), or a pharmaceutically acceptable salt thereof Item 30: The compound of any one of Items 1 to 14, wherein $R^2$ is $C_{7-16}$ aralkyl (in which the aryl may be optionally substituted by the same or different 1 to 5 groups selected from the group consisting of:
(1) halogen atom,
(2) cyano,
(3) $C_{1-4}$ alkoxy (in which the alkoxy may be optionally substituted by
  (a) 1 to 3 halogen atoms, or
  (b) $C_{1-4}$ alkoxy),
(4) $C_{1-4}$ alkylsulfonyl,
(5) $C_{1-4}$ alkyl (in which the alkyl may be optionally substituted by
  (a) 1 to 3 halogen atoms, or
  (b) $C_{1-4}$ alkoxy), and
(6) $C_{1-6}$ alkylthio), or a pharmaceutically acceptable salt thereof.

Item 31: The compound of Item 30, wherein $R^2$ is $C_{7-16}$ aralkyl (in which the aryl may be optionally substituted by the same or different 1 to 5 groups selected from the group consisting of:
(1) halogen atom,
(2) cyano,
(3) $C_{1-4}$ alkoxy (in which the alkoxy may be optionally substituted by 1 to 3 halogen atoms),
(4) $C_{1-4}$ alkylsulfonyl,
(5) $C_{1-4}$ alkyl (in which the alkyl may be optionally substituted by 1 to 3 halogen atoms), and
(6) $C_{1-6}$ alkylthio), or a pharmaceutically acceptable salt thereof.

Item 32: The compound of any one of Items 1 to 14, wherein $R^2$ is 5 to 12-membered mono- or poly-cyclic heteroaryl (in which the heteroaryl may be optionally substituted by the same or different 1 to 3 groups selected from the group consisting of:
(1) halogen atom,
(2) cyano,
(3) $C_{1-4}$ alkoxy (in which the alkoxy may be optionally substituted by
  (a) 1 to 3 halogen atoms,
  (b) $C_{1-4}$ alkoxy (in which the alkoxy may be optionally substituted by 1 to 3 halogen atoms), or
  (c) $C_{3-6}$ cycloalkyl),
(4) $C_{3-6}$ cycloalkyl,
(5) $C_{3-6}$ cycloalkylalkoxy,
(6) $C_{1-4}$ alkyl (in which the alkyl may be optionally substituted by
  (a) 1 to 3 halogen atoms,
  (b) $C_{1-4}$ alkoxy, or
  (c) $C_{3-6}$ cycloalkyl), and
(7) $C_{1-6}$ alkylcarbonyl), or a pharmaceutically acceptable salt thereof Item 33: The compound of Item 32, wherein $R^2$ is 5 to 12-membered mono- or poly-cyclic heteroaryl (in which the heteroaryl may be optionally substituted by the same or different 1 to 3 groups selected from the group consisting of:
(1) halogen atom,
(2) cyano,
(3) $C_{1-4}$ alkoxy (in which the group may be optionally substituted by
  (a) 1 to 3 halogen atoms,
  (b) $C_{1-4}$ alkoxy (in which the alkoxy may be optionally substituted by 1 to 3 halogen atoms), or
  (c) $C_{3-6}$ cycloalkyl), and
(4) $C_{1-4}$ alkyl (in which the alkyl may be optionally substituted by
  (a) 1 to 3 halogen atoms,
  (b) $C_{1-4}$ alkoxy, or
  (c) $C_{3-6}$ cycloalkyl)), or a pharmaceutically acceptable salt thereof Item 34: The compound of any one of Items 1 to 14, wherein $R^2$ is
(1) $C_{1-6}$ alkyl (in which the group may be optionally substituted by
  (a) $C_{6-10}$ aryloxy (in which the aryl may be optionally substituted by
    halogen atom,
    $C_{1-4}$ alkyl, or
    $C_{1-4}$ alkoxy),
  (b) $C_{6-10}$ arylthio (in which the aryl may be optionally substituted by
    halogen atom, or
    $C_{1-4}$ alkyl),
  (c) $C_{6-10}$ arylsulfonyl (in which the aryl may be optionally substituted by
    halogen atom,
    $C_{1-4}$ alkyl, or
    $C_{1-4}$ alkoxy),
  (d) $C_{3-6}$ cycloalkyl,
  (e) $C_{1-4}$ alkoxy, or
  (f) $C_{7-14}$ aralkyloxy), (2) $C_{3-7}$ cycloalkyl,
(3) $C_{6-10}$ aryl (in which the aryl may be optionally substituted by the same or different 1 to 5 groups selected from the group consisting of:
- (a) halogen atom,
- (b) cyano,
- (c) hydroxy,
- (d) $C_{1-4}$ alkoxy (in which the alkoxy may be optionally substituted by
  - 1 to 3 halogen atoms,
  - $C_{1-4}$ alkoxy (in which the alkoxy may be optionally substituted by 1 to 3 halogen atoms),
  - carboxy,
  - $C_{1-4}$ alkoxycarbonyl, or
  - $C_{3-6}$ cycloalkyl),
- (e) $C_{1-4}$ alkylsulfonyl,
- (f) $C_{3-6}$ cycloalkyl,
- (g) $C_{3-6}$ cycloalkoxy,
- (h) mono- or di-$C_{1-6}$ alkylamino,
- (i) mono- or di-$C_{1-6}$ alkylcarbonylamino,
- (j) mono- or di-$C_{1-6}$ alkylsulfonylamino,
- (k) $C_{1-4}$ alkyl (in which the alkyl may be optionally substituted by
  - 1 to 3 halogen atoms,
  - $C_{1-4}$ alkoxy (in which the alkoxy may be optionally substituted by 1 to 3 halogen atoms),
  - carboxyl,
  - $C_{1-4}$ alkoxycarbonyl, or
  - $C_{3-6}$ cycloalkyl),
- (l) $C_{1-6}$ alkylcarbonyl,
- (m) carboxy,
- (n) $C_{1-4}$ alkoxycarbonyl, and
- (o) aminocarbonyl), (4) $C_{7-16}$ aralkyl (in which the group may be optionally substituted by the same or different 1 to 5 groups selected from the group consisting of:
- (a) halogen atom,
- (b) cyano,
- (c) $C_{1-4}$ alkoxy (in which the alkoxy may be optionally substituted by
  - 1 to 3 halogen atoms,
  - $C_{3-6}$ cycloalkyl, or
  - $C_{1-4}$ alkoxy),
- (d) $C_{1-4}$ alkylsulfonyl,
- (e) $C_{1-4}$ alkyl (in which the alkyl may be optionally substituted by
  - 1 to 3 halogen atoms, or
  - $C_{1-4}$ alkoxy), and
- (f) $C_{1-6}$ alkylthio), (5) heterocycle (in which the cycle may be optionally substituted by $C_{6-10}$ aryl, or 5 to 12-membered mono- or poly-cyclic heteroaryl, and the $C_{6-10}$ aryl and 5 to 12-membered mono- or poly-cyclic heteroaryl may be optionally substituted by 1 to 3 groups selected from the group consisting of:
- (a) halogen atom,
- (b) cyano,
- (c) $C_{1-4}$ alkyl (in which the alkyl may be optionally substituted by
  - 1 to 3 halogen atoms,
  - $C_{1-4}$ alkoxy, or
  - $C_{3-6}$ cycloalkyl),
- (d) $C_{1-4}$ alkoxy (in which the alkoxy may be optionally substituted by
  - 1 to 3 halogen atoms,
  - $C_{1-4}$ alkoxy, or
  - $C_{3-6}$ cycloalkyl),
- (e) $C_{3-6}$ cycloalkyl,
- (f) mono- or di-$C_{1-6}$ alkylamino, and
- (g) $C_{1-6}$ alkylcarbonyl), (6) heterocyclic $C_{1-6}$ alkyl, (7) 5 to 12-membered mono- or poly-cyclic heteroaryl (in which the heteroaryl may be optionally substituted by the same or different 1 to 3 groups selected from the group consisting of:
- (a) halogen atom,
- (b) cyano,
- (c) $C_{1-4}$ alkoxy (in which the alkoxy may be optionally substituted by
  - 1 to 3 halogen atoms,
  - $C_{1-4}$ alkoxy, or
  - $C_{3-6}$ cycloalkyl),
- (d) $C_{3-6}$ cycloalkyl,
- (e) $C_{3-6}$ cycloalkylalkoxy,
- (f) mono- or di-$C_{1-6}$ alkylamino,
- (g) $C_{1-4}$ alkyl (in which the alkyl may be optionally substituted by
  - 1 to 3 halogen atoms,
  - $C_{1-4}$ alkoxy, or
  - $C_{3-6}$ cycloalkyl), and
- (h) $C_{1-6}$ alkylcarbonyl), (8) 5 to 12-membered mono- or poly-cyclic heteroaryl-$C_{1-6}$ alkyl (in which the group may be optionally substituted by $C_{1-4}$ alkyl, or $C_{1-4}$ alkoxy), or (9) 5 to 7-membered cyclic amino, or a pharmaceutically acceptable salt thereof Item 35: The compound of Item 34, wherein $R^2$ is
(1) $C_{1-6}$ alkyl (in which the group may be optionally substituted by $C_{6-10}$ aryloxy),
(2) $C_{6-10}$ aryl (in which the aryl may be optionally substituted by the same or different 1 to 5 groups selected from the group consisting of:
- (a) halogen atom,
- (b) cyano,
- (c) $C_{1-4}$ alkoxy (in which the alkoxy may be optionally substituted by
  - 1 to 3 halogen atoms, or
  - $C_{1-4}$ alkoxy),
- (d) $C_{1-4}$ alkylsulfonyl,
- (e) mono- or di-$C_{1-6}$ alkylcarbonylamino,
- (f) $C_{1-4}$ alkyl (in which the alkyl may be optionally substituted by
  - 1 to 3 halogen atoms, or
  - $C_{1-4}$ alkoxy (in which the alkoxy may be optionally substituted by 1 to 3 halogen atoms)),
- (g) $C_{1-4}$ alkylcarbonyl,
- (h) carboxy,
- (i) $C_{1-4}$ alkoxycarbonyl, and
- (j) aminocarbonyl), (3) $C_{7-16}$ aralkyl (in which the group may be optionally substituted by the same or different 1 to 5 groups selected from the group consisting of:
- (a) halogen atom,
- (b) cyano,
- (c) $C_{1-4}$ alkoxy (in which the alkoxy may be optionally substituted by 1 to 3 halogen atoms),
- (d) $C_{1-4}$ alkylsulfonyl,
- (e) $C_{1-4}$ alkyl (in which the alkyl may be optionally substituted by 1 to 3 halogen atoms), and
- (f) $C_{1-6}$ alkylthio), (4) heterocycle (in which the cycle may be optionally substituted by $C_{6-10}$ aryl, or 5 to 12-membered mono- or poly-cyclic heteroaryl, and the $C_{6-10}$ aryl and 5 to 12-membered mono- or poly-cyclic heteroaryl may be optionally substituted by the same or different 1 to 3 groups selected from the group consisting of:
  (a) halogen atom, and
  (b) $C_{1-4}$ alkyl),
(5) 5 to 12-membered mono- or poly-cyclic heteroaryl (in which the heteroaryl may be optionally substituted by the same or different 1 to 3 groups selected from the group consisting of:
  (a) halogen atom,
  (b) cyano,
  (c) $C_{1-4}$ alkoxy (in which the alkoxy may be optionally substituted by
    1 to 3 halogen atoms, or
    $C_{3-6}$ cycloalkyl),
  (d) $C_{1-4}$ alkyl (in which the alkyl may be optionally substituted by
    1 to 3 halogen atoms, or
    $C_{1-4}$ alkoxy),
  (e) $C_{1-4}$ alkylcarbonyl, and
  (f) $C_{3-6}$ cycloalkyl), or
(6) 5 to 12-membered mono- or poly-cyclic heteroaryl-$C_{1-6}$ alkyl (in which the group may be optionally substituted by
  (a) $C_{1-4}$ alkyl, or
  (b) $C_{1-4}$ alkoxy), or a pharmaceutically acceptable salt thereof.

Item 36: The compound of Item 34, wherein $R^2$ is
(1) $C_{6-10}$ aryl (in which the aryl may be optionally substituted by the same or different 1 to 5 groups selected from the group consisting of:
  (a) halogen atom,
  (b) cyano,
  (c) $C_{1-4}$ alkoxy (in which the alkoxy may be optionally substituted by
    1 to 3 halogen atoms, or
    $C_{3-6}$ cycloalkyl),
  (d) $C_{1-4}$ alkylsulfonyl,
  (e) mono- or di-$C_{1-6}$ alkylcarbonylamino,
  (f) $C_{1-4}$ alkyl (in which the alkyl may be optionally substituted by
    1 to 3 halogen atoms, or
    $C_{1-4}$ alkoxy (in which the alkoxy may be optionally substituted by 1 to 3 halogen atoms)),
  (g) $C_{1-4}$ alkylcarbonyl,
  (h) carboxy,
  (i) $C_{1-4}$ alkoxycarbonyl, and
  (j) aminocarbonyl), or
(2) 5 to 12-membered mono- or poly-cyclic heteroaryl (in which the heteroaryl may be optionally substituted by the same or different 1 to 3 groups selected from the group consisting of:
  (a) halogen atom,
  (b) cyano,
  (c) $C_{1-4}$ alkoxy (in which the alkoxy may be optionally substituted by
    1 to 3 halogen atoms, or
    $C_{3-6}$ cycloalkyl), and
  (d) $C_{1-4}$ alkyl (in which the alkyl may be optionally substituted by
    1 to 3 halogen atoms, or
    $C_{1-4}$ alkoxy)), or a pharmaceutically acceptable salt thereof Item 37: The compound of any one of Items 1 to 14, wherein $R^2$ is optionally substituted $C_{1-6}$ alkyl, or a pharmaceutically acceptable salt thereof.

Item 38: The compound of Item 37, wherein $R^2$ is $C_{1-6}$ alkyl (in which the group may be optionally substituted by
(1) $C_{6-10}$ aryloxy (in which the aryl may be optionally substituted by 1 to 5 groups selected from the group consisting of:
  (a) halogen atom,
  (b) cyano,
  (c) $C_{1-4}$ alkyl (in which the alkyl may be optionally substituted by
    1 to 3 halogen atoms, or
    $C_{1-4}$ alkoxy), and
  (d) $C_{1-4}$ alkoxy (in which the alkoxy may be optionally substituted by
    1 to 3 halogen atoms, or
    $C_{1-4}$ alkoxy)),
(2) 5 to 12-membered heteroaryloxy (in which the heteroaryl moiety may be optionally substituted by the same substituent groups as the above (1)),
(3) $C_{6-10}$ arylthio (in which the aryl may be optionally substituted by
  (a) halogen atom, or
  (b) $C_{1-4}$ alkyl),
(4) $C_{6-10}$ arylsulfonyl (in which the aryl may be optionally substituted by
  (a) halogen atom,
  (b) $C_{1-4}$ alkyl, or
  (c) $C_{1-4}$ alkoxy),
(5) $C_{3-6}$ cycloalkyl,
(6) $C_{1-4}$ alkoxy, or
(7) $C_{7-14}$ aralkyloxy), or a pharmaceutically acceptable salt thereof.

Item 39: The compound of Item 38, wherein $R^2$ is $C_{1-6}$ alkyl (in which the group is substituted by
(1) $C_{6-10}$ aryloxy, or
(2) 5 to 12-membered heteroaryloxy, and the aryl and heteroaryl are substituted by group(s) selected from the group consisting of:
  (a) halogen atom,
  (b) cyano,
  (c) $C_{1-4}$ alkyl (in which the alkyl may be optionally substituted by
    1 to 3 halogen atoms, or
    $C_{1-4}$ alkoxy), and
  (d) $C_{1-4}$ alkoxy (in which the alkoxy may be optionally substituted by
    1 to 3 halogen atoms, or
    $C_{1-4}$ alkoxy)), or a pharmaceutically acceptable salt thereof.

Item 40: The compound of any one of Items 1 to 14, wherein $R^2$ is optionally substituted heterocycle, or a pharmaceutically acceptable salt thereof.

Item 41: The compound of Item 40, wherein $R^2$ is heterocycle (in which the group may be optionally substituted by
(1) $C_{6-10}$ aryl, or
(2) 5 to 12-membered mono- or poly-cyclic heteroaryl, and the $C_{6-10}$ aryl and 5 to 12-membered mono- or poly-cyclic heteroaryl may be optionally substituted by 1 to 3 groups selected from the group consisting of:
  (a) halogen atom,
  (b) cyano,
  (c) $C_{1-4}$ alkyl (in which the alkyl may be optionally substituted by
    1 to 3 halogen atoms,
    $C_{1-4}$ alkoxy, or
    $C_{3-6}$ cycloalkyl),
  (d) $C_{1-4}$ alkoxy (in which the alkoxy may be optionally substituted by
    1 to 3 halogen atoms,
    $C_{1-4}$ alkoxy, or
    $C_{3-6}$ cycloalkyl), (e) $C_{3-6}$ cycloalkyl, (f) mono- or di-$C_{1-6}$ alkylamino, and (g) $C_{1-6}$ alkylcarbonyl), or a pharmaceutically acceptable salt thereof Item 42: The compound of either one of Item 40 or 41, wherein the heterocycle in $R^2$ is 4-piperidinyl, or a pharmaceutically acceptable salt thereof.

Item 43: The compound of any one of Items 1 to 36, wherein the aryl moiety of $C_{6-10}$ aryl and $C_{7-14}$ aralkyl in $R^2$ and the aryl moiety of the substituent group $C_{6-10}$ aryloxy of $C_{1-6}$ alkyl in $R^2$ are phenyl, or a pharmaceutically acceptable salt thereof.

Item 44: The compound of any one of Items 1 to 36, wherein the heteroaryl moiety of 5 to 12-membered mono- or poly-cyclic heteroaryl and 5 to 12-membered mono- or poly-cyclic heteroaryl-$C_{1-6}$ alkyl in $R^2$, the substituent group heteroaryl of heterocycle in $R^2$, and the heteroaryl moiety of the substituent group heteroaryloxy of $C_{1-6}$ alkyl in $R^2$ are heteroaryl selected from the group consisting of the following groups:

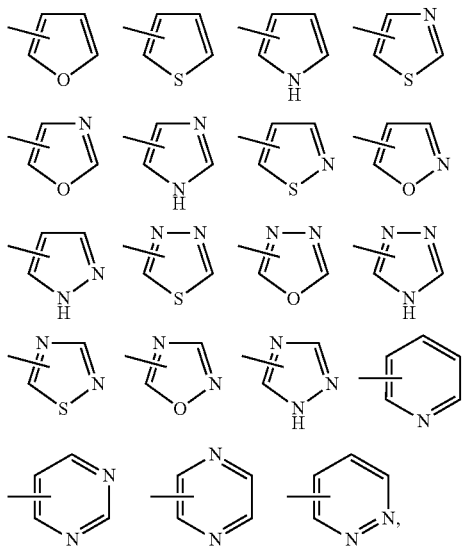

or a pharmaceutically acceptable salt thereof

Item 45: The compound of Item 44, wherein the heteroaryl moiety of 5 to 12-membered mono- or poly-cyclic heteroaryl and 5 to 12-membered mono- or poly-cyclic heteroaryl-$C_{1-6}$ alkyl in $R^2$, and the heteroaryl moiety of the substituent group heteroaryloxy of $C_{1-6}$ alkyl in $R^2$ are heteroaryl selected from the group consisting of the following groups:

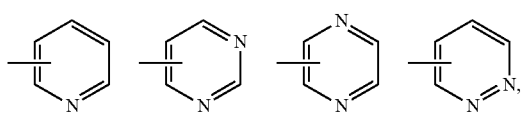

or a pharmaceutically acceptable salt thereof

Item 46: The compound of Item 45, wherein the heteroaryl moiety of 5 to 12-membered mono- or poly-cyclic heteroaryl and 5 to 12-membered mono- or poly-cyclic heteroaryl-$C_{1-6}$ alkyl in $R^2$, and the heteroaryl moiety of the substituent group heteroaryloxy of $C_{1-6}$ alkyl in $R^2$ are heteroaryl of the following formula:

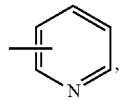

or a pharmaceutically acceptable salt thereof

Item 47: The compound of any one of Items 14 to 46, wherein $R^3$ is hydrogen atom, optionally substituted $C_{1-6}$ alkyl, optionally substituted $C_{3-7}$ cycloalkyl, optionally substituted heterocycle, optionally substituted $C_{7-14}$ aralkyl, or optionally substituted 5 to 12-membered mono- or poly-cyclic heteroaryl-$C_{1-6}$ alkyl, or a pharmaceutically acceptable salt thereof.

Item 48: The compound of Item 47, wherein $R^3$ is (1) hydrogen atom, (2) $C_{1-6}$ alkyl (in which the alkyl may be optionally substituted by (a) $C_{6-10}$ aryloxy, (b) saturated heterocycle, or (c) $C_{3-6}$ cycloalkyl), (3) $C_{3-7}$ cycloalkyl, (4) saturated heterocycle, (5) $C_{7-16}$ aralkyl, or (6) 5 to 6-membered monocyclic heteroaryl-$C_{1-6}$ alkyl, or a pharmaceutically acceptable salt thereof Item 49: A compound of formula (2):

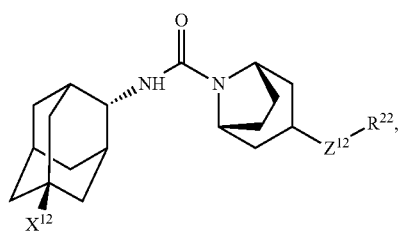

(2)

wherein $X^{12}$ is hydroxyl, or aminocarbonyl;

$Z^{12}$ is a single bond, or oxygen atom;

$R^{22}$ is $C_{7-16}$ aralkyl (in which the aryl moiety of the aralkyl may be optionally substituted by the same or different groups selected from the group consisting of:

(1) halogen atom, (2) cyano, (3) $C_{1-4}$ alkoxy (in which the alkoxy may be optionally substituted by 1 to 3 halogen atoms, $C_{3-6}$ cycloalkyl or $C_{1-4}$ alkoxy), (4) $C_{1-4}$ alkylsulfonyl, (5) $C_{1-4}$ alkyl (in which the alkyl may be optionally substituted by 1 to 3 halogen atoms, or $C_{1-4}$ alkoxy), and (6) $C_{1-4}$ alkylthio)], or a pharmaceutically acceptable salt thereof.

Item 50: A compound of formula (3):

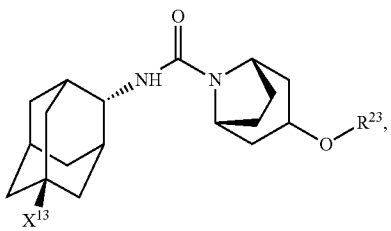

(3)

wherein $X^{13}$ is hydroxyl, or aminocarbonyl;
$R^{23}$ is phenyl or 5 to 12-membered mono- or poly-cyclic heteroaryl (in which the phenyl and heteroaryl may be optionally substituted by the same or different 1 to 3 groups selected from the group consisting of:
(1) halogen atom,
(2) cyano,
(3) $C_{1-4}$ alkoxy (in which the alkoxy may be optionally substituted by
  (a) 1 to 3 halogen atoms,
  (b) $C_{1-4}$ alkoxy (in which the alkoxy may be optionally substituted by 1 to 3 halogen atoms), or
  (c) $C_{3-6}$ cycloalkyl),
(4) $C_{3-6}$ cycloalkyl,
(5) $C_{1-4}$ alkyl (in which the alkyl may be optionally substituted by
  (a) 1 to 3 halogen atoms,
  (b) $C_{1-4}$ alkoxy (in which the alkoxy may be optionally substituted by 1 to 3 halogen atoms), or
  (c) $C_{3-6}$ cycloalkyl), and
(6) $C_{1-6}$ alkylcarbonyl), or a pharmaceutically acceptable salt thereof.

Item 51: A compound of formula (3a):

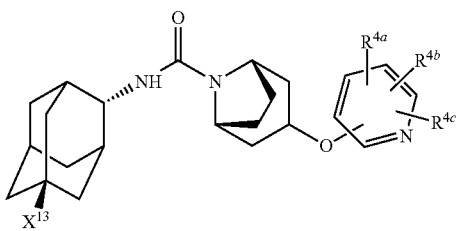

(3a)

wherein $X^{13}$ is hydroxyl, or aminocarbonyl;
$R^{4a}$, $R^{4b}$ and $R^{4c}$ are each independently
(1) hydrogen atom,
(2) halogen atom,
(3) cyano,
(4) $C_{1-4}$ alkoxy (in which the alkoxy may be optionally substituted by
  (a) 1 to 3 halogen atoms,
  (b) $C_{1-4}$ alkoxy, or
  (c) $C_{3-6}$ cycloalkyl),
(5) $C_{3-6}$ cycloalkyl,
(6) $C_{3-6}$ cycloalkyloxy,
(7) $C_{1-4}$ alkyl (in which the alkyl may be optionally substituted by
  (a) 1 to 3 halogen atoms,
  (b) $C_{1-4}$ alkoxy, or
  (c) $C_{3-6}$ cycloalkyl), or
(8) $C_{1-6}$ alkylcarbonyl, or a pharmaceutically acceptable salt thereof.

Item 52: A compound of formula (3b):

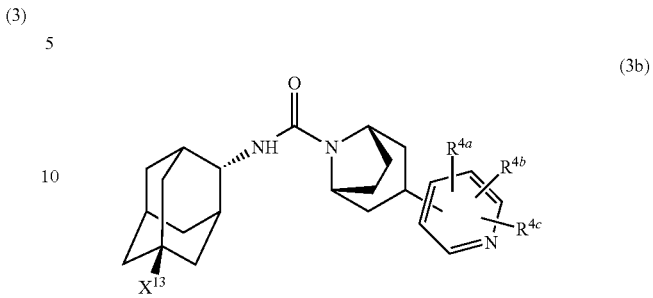

(3b)

wherein $X^{13}$ is hydroxyl, or aminocarbonyl;
$R^{4a}$, $R^{4b}$ and $R^{4c}$ are each independently
(1) hydrogen atom,
(2) halogen atom,
(3) cyano,
(4) $C_{1-4}$ alkoxy (in which the alkoxy may be optionally substituted by 1 to 3 halogen atoms, $C_{1-4}$ alkoxy, or $C_{3-6}$ cycloalkyl),
(5) $C_{3-6}$ cycloalkyl,
(6) $C_{3-6}$ cycloalkyloxy,
(7) $C_{1-4}$ alkyl (in which the alkyl may be optionally substituted by 1 to 3 halogen atoms, $C_{1-4}$ alkoxy, or $C_{3-6}$ cycloalkyl), or
(8) $C_{1-6}$ alkylcarbonyl, or a pharmaceutically acceptable salt thereof.

Item 53: A compound of formula (4):

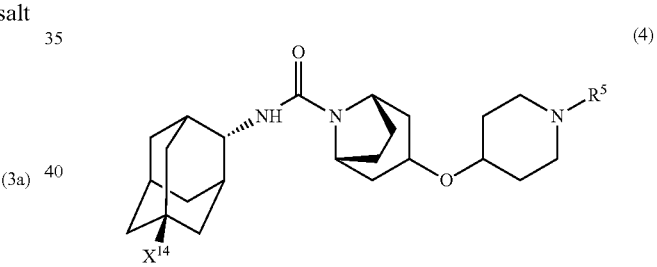

(4)

wherein $X^{14}$ is hydroxyl, or aminocarbonyl;
$R^5$ is
(1) $C_{6-10}$ aryl, or
(2) 5 to 12-membered mono- or poly-cyclic heteroaryl (in which the $C_{6-10}$ aryl and 5 to 12-membered mono- or poly-cyclic heteroaryl may be optionally substituted by 1 to 3 groups selected from the group consisting of:
  (a) halogen atom,
  (b) cyano,
  (c) $C_{1-4}$ alkyl (in which the alkyl may be optionally substituted by
    1 to 3 halogen atoms,
    $C_{1-4}$ alkoxy, or
    $C_{3-6}$ cycloalkyl),
  (d) $C_{1-4}$ alkoxy (in which the alkoxy may be optionally substituted by
    1 to 3 halogen atoms,
    $C_{3-6}$ cycloalkyl, or
    $C_{1-4}$ alkoxy),
  (e) $C_{3-6}$ cycloalkyl,
  (f) mono- or di-$C_{1-6}$ alkylamino, and
  (g) $C_{1-6}$ alkylcarbonyl), or a pharmaceutically acceptable salt thereof Item 54: A medicament, comprising as the active ingredient the compound of any one of Items 1 to 53 or a pharmaceutically acceptable salt thereof.

Item 55: A therapeutic agent for type II diabetes, abnormal glucose tolerance, hyperglycemia, insulin resistance, dyslipidemia, hypertension, arteriosclerosis, angiostenosis, obesity, Cushing's syndrome, subclinical Cushing's syndrome, glaucoma, osteoporosis, metabolic syndrome, cardiovascular disease, atherosclerosis, cognitive disorder, dementia, Alzheimer's disease, depression, anxiety or manic depression, comprising as the active ingredient the compound of any one of Items 1 to 53 or a pharmaceutically acceptable salt thereof.

Item 56: A method for prevention and/or treatment of type II diabetes, abnormal glucose tolerance, hyperglycemia, insulin resistance, dyslipidemia, hypertension, arteriosclerosis, angiostenosis, obesity, Cushing's syndrome, subclinical Cushing's syndrome, glaucoma, osteoporosis, metabolic syndrome, cardiovascular disease, atherosclerosis, cognitive disorder, dementia, Alzheimer's disease, depression, anxiety or manic depression, comprising administering the compound of any one of Items 1 to 53 or a pharmaceutically acceptable salt thereof as the active ingredient.

Item 57: Use of the compound of any one of Items 1 to 53 or a pharmaceutically acceptable salt thereof for prevention and/or treatment of type II diabetes, abnormal glucose tolerance, hyperglycemia, insulin resistance, dyslipidemia, hypertension, arteriosclerosis, angiostenosis, obesity, Cushing's syndrome, subclinical Cushing's syndrome, glaucoma, osteoporosis, metabolic syndrome, cardiovascular disease, atherosclerosis, cognitive disorder, dementia, Alzheimer's disease, depression, anxiety or manic depression.

Effect of the Invention

A compound of formula (1) or a pharmaceutically acceptable salt thereof is useful as an 11βHSD1 inhibitor.

DESCRIPTION OF EMBODIMENTS

The present invention is explained in more detail as below. The number of carbon atoms in the definition of "substituent group" herein may be described as "$C_{1-6}$", for example. Specifically, the description "$C_{1-6}$ alkyl" has the same meaning as an alkyl group having 1 to 6 carbon atoms. A substituent group herein which the term "optionally substituted" or "substituted" is not specified means a "unsubstituted" substituent group. For example, "$C_{1-6}$ alkyl" means a "unsubstituted" group.

The term "group" herein means a monovalent group. For example, the "alkyl group" means a monovalent saturated hydrocarbon group. In definitions of substituent groups herein, the term "group" may be abbreviated. The number of substituent groups in the group defined by using the term "optionally substituted" or "substituted" is not limited if they could be substituted, and is 1 or multiple. The definition of each group is applied to parts of other groups or substituent groups thereof, unless otherwise specified.

The "halogen atom" includes fluorine atom, chlorine atom, bromine atom or iodine atom. Preferable one is fluorine atom, or chlorine atom.

"$C_{1-6}$ alkyl" means straight or branched-chain saturated hydrocarbon having 1 to 6 carbon atoms. Preferable one is "$C_{1-4}$ alkyl". Concrete examples of "$C_{1-6}$ alkyl" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl.

"$C_{3-7}$ cycloalkyl" means cyclic saturated or unsaturated hydrocarbon having 3 to 7 carbon atoms. Preferable one is "$C_{3-6}$ cycloalkyl". Concrete examples of "$C_{3-7}$ cycloalkyl" include cyclopropyl, cyclobutyl, cyclopentyl, cyclohexyl, cyclopentenyl, cyclohexenyl.

The above "$C_{3-7}$ cycloalkyl" includes a condensed ring of "$C_{3-7}$ cycloalkyl" with phenyl or a 5 to 6-membered ring containing the same or different and one or more (e.g., 1 to 4) heteroatoms selected from nitrogen atom, sulfur atom or oxygen atom. Concrete examples of the group include groups of the following formulae.

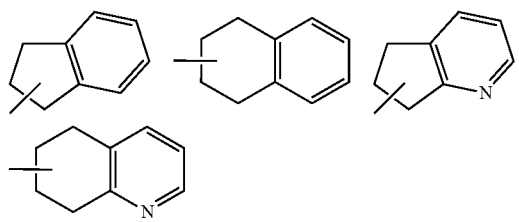

"$C_{6-10}$ aryl" means aromatic hydrocarbon having 6 to 10 carbon atoms. Preferable one is "$C_6$ aryl" (phenyl). Concrete examples of "$C_{6-10}$ aryl" include phenyl, 1-naphthyl or 2-naphthyl.

The above "$C_{6-10}$ aryl" includes a condensed ring of "$C_6$ aryl" with 5 to 6-membered ring or 5 to 6-membered cycloalkyl ring (e.g., cyclopentane, or cyclohexane) containing the same or different and one or more (e.g., 1 to 4) heteroatoms selected from nitrogen atom, sulfur atom or oxygen atom. Concrete examples of the group include groups of the following formulae.

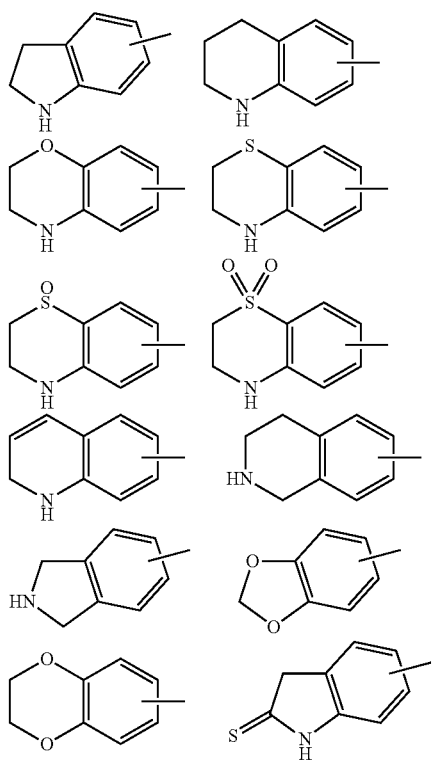

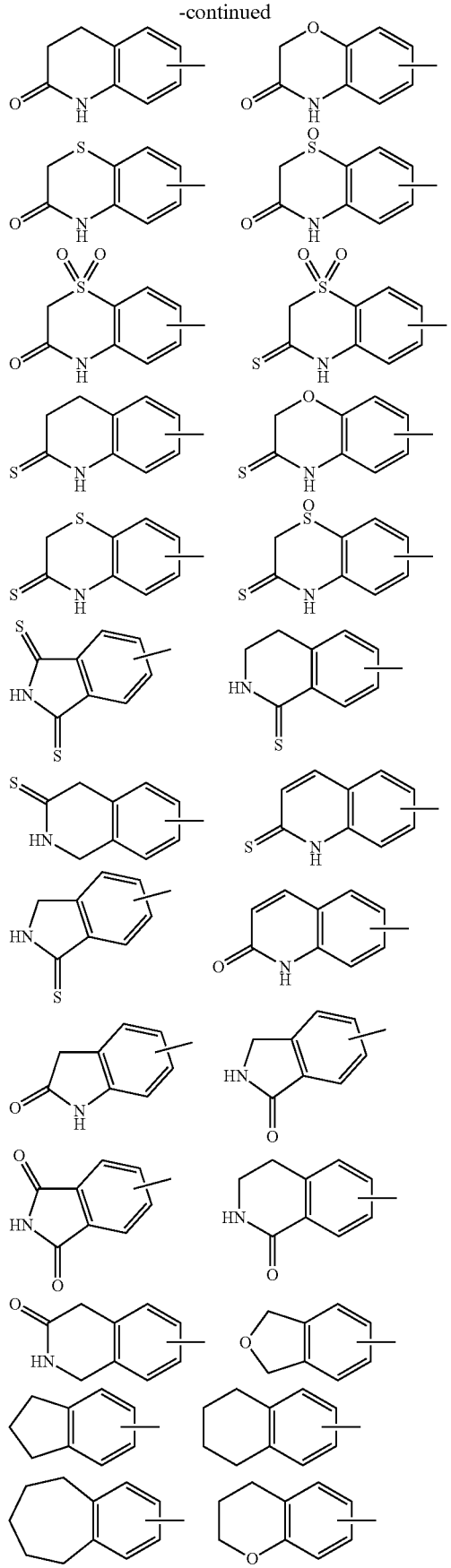

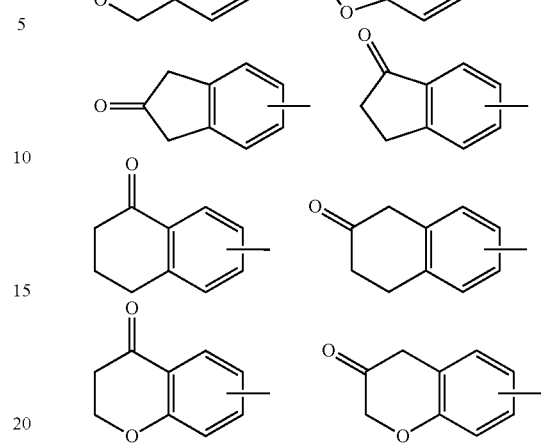

If $C_{6-10}$ aryl is a condensed ring, an aromatic ring moiety has a binding site of the "group". For example, if the group is "$C_{6-10}$ aryl" of the following formula:

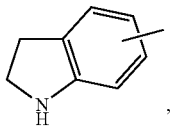

the "group" has a binding site on 4-, 5-, 6-, or 7-position.

"$C_{7-16}$ aralkyl" means "$C_{6-10}$ aryl-$C_{1-6}$ alkyl", and a group wherein the above "$C_{6-10}$ aryl" is substituted on the above "$C_{1-6}$ alkyl". Preferable one is "$C_{7-14}$ aralkyl" ($C_{6-10}$ aryl-$C_{1-4}$ alkyl), more preferably "$C_{7-10}$ aralkyl" ($C_6$ aryl-$C_{1-4}$ alkyl). Concrete examples of "$C_{7-16}$ aralkyl" include benzyl, 2-phenylethyl, 1-phenylpropyl or 1-naphthylmethyl.

$C_{1-6}$ alkyl moiety in the aralkyl may form a $C_{3-4}$ ring on one carbon atom in the alkyl moiety. Concrete examples of the group include the following groups:

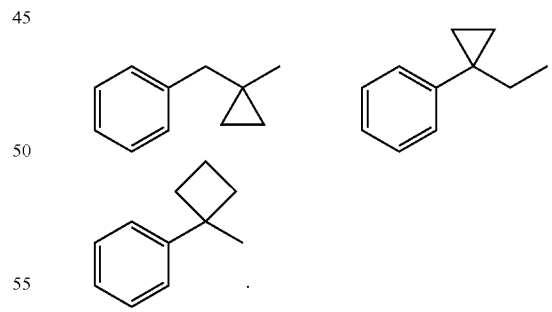

The "heteroaryl" includes 5 to 12-membered mono- or poly-cyclic aromatic group, and comprises the same or different and one or more (e.g., 1 to 4) heteroatoms selected from nitrogen atom, sulfur atom or oxygen atom. A preferable "polycyclic heteroaryl" is bi- or tri-cyclic group, more preferably bicyclic group. The polycyclic heteroaryl includes a condensed ring of the above monocyclic heteroaryl with an aromatic ring (including benzene, pyridine) or a non-aromatic ring (including cyclohexyl). Concrete examples of the "heteroaryl" include the following groups.

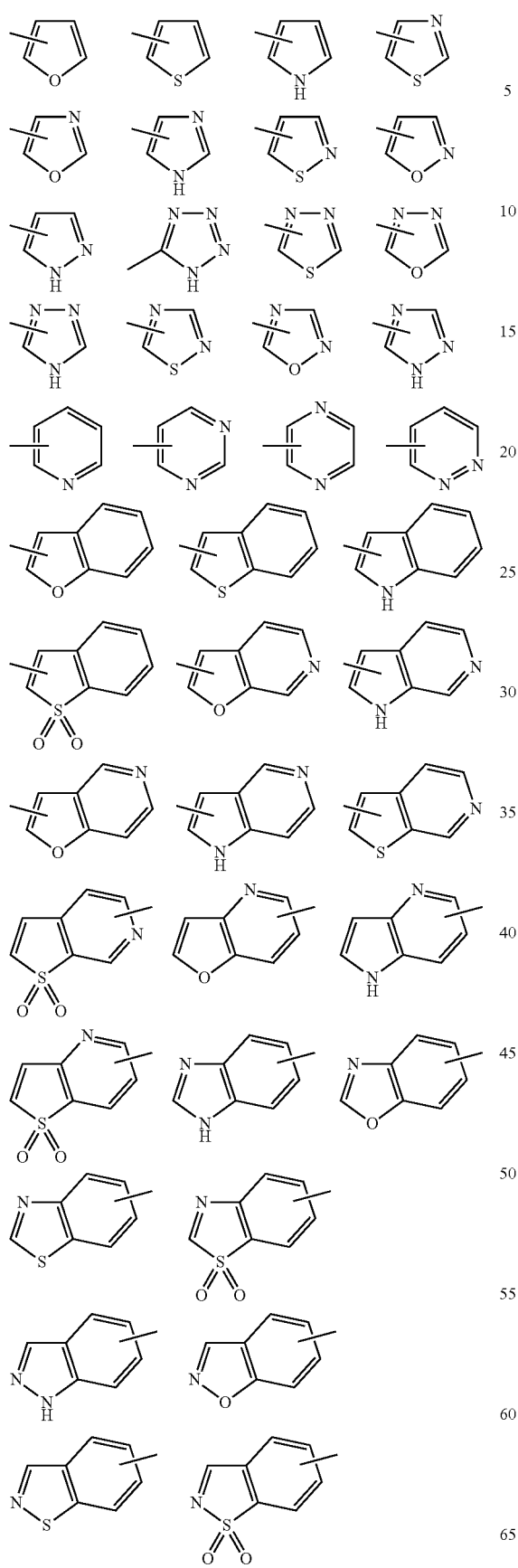
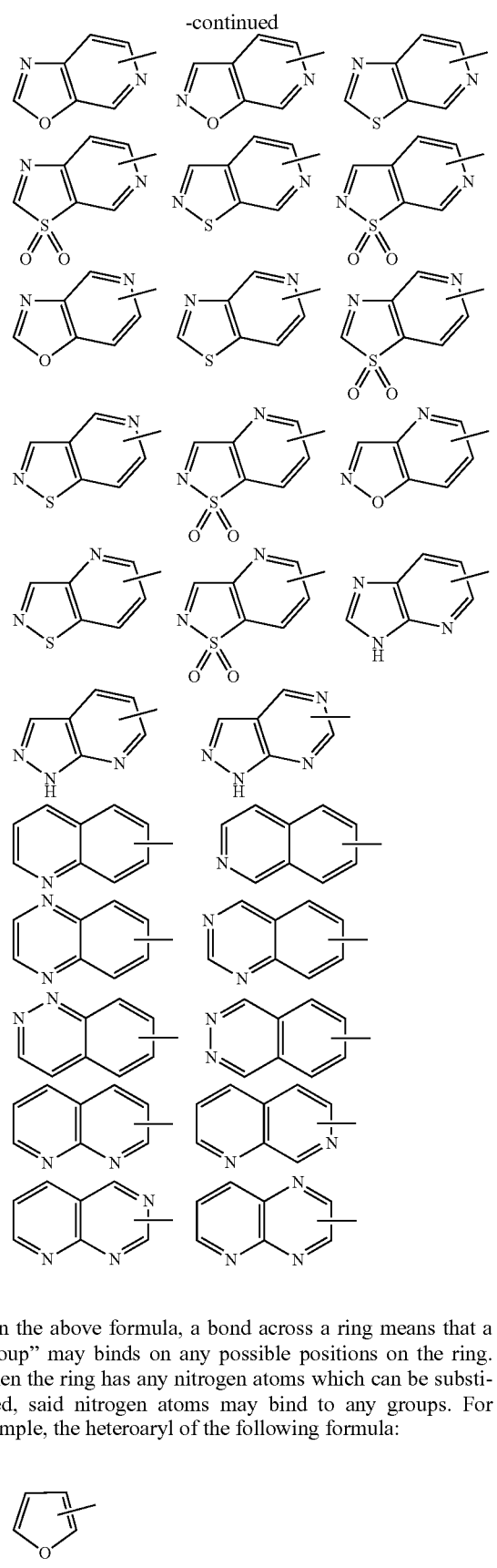
In the above formula, a bond across a ring means that a "group" may binds on any possible positions on the ring. When the ring has any nitrogen atoms which can be substituted, said nitrogen atoms may bind to any groups. For example, the heteroaryl of the following formula:
means 2-furyl, or 3-furyl.

If the "heteroaryl" is polycyclic group and is for example the following formula:

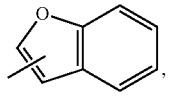

it may be 4-, 5-, 6- or 7-benzofuryl as well as 2-benzofuryl, or 3-benzofuryl. In a polycyclic heteroaryl wherein an aromatic ring is condensed with a non-aromatic ring (including piperidine), an aromatic ring moiety has a binding site of the "group". For example, in the "polycyclic heteroaryl" of the following formula:

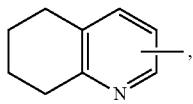

the "group" binds on 2-, 3-, or 4-position.

A preferable "heteroaryl" is 5 to 10-membered mono- or poly-cyclic aromatic group, more preferably 5 to 6-membered monocyclic aromatic group.

The "heteroaryl-$C_{1-6}$ alkyl" means a group wherein the above "heteroaryl" binds to the above "$C_{1-6}$ alkyl". Preferable one is "heteroaryl-$C_{1-4}$ alkyl". The heteroaryl moiety includes the same concrete examples as illustrated in the above heteroaryl. Specifically, it includes 2-pyridylmethyl.

The "heterocycle" includes 3 to 7-membered heterocycle having the same or different and 1 to 3 atoms selected from nitrogen atom, oxygen atom and sulfur atom. All the nitrogen atom, oxygen atom and sulfur atom are ring atoms. The heterocycle may be either saturated or partly-unsaturated. Specifically, it includes pyranyl, tetrahydrofuryl, pyrrolidinyl, imidazolidinyl, piperidinyl, morpholinyl, thiomorpholinyl, dioxothiomorpholinyl, hexamethyleneiminyl, oxazolidinyl, thiazolidinyl, imidazolidinyl, oxoimidazolidinyl, dioxoimidazolidinyl, oxooxazolidinyl, dioxooxazolidinyl, dioxothiazolidinyl, tetrahydrofuranyl, tetrahydropyranyl or tetrahydropyridinyl. In the group, the ring nitrogen atom may not be a binding site of a "group". Specifically, the group does not include a concept such as 1-pyrrolidino.

The above "heterocycle" may form a condensed ring with 6-membered aromatic hydrocarbon or 6-membered heteroaryl. For example, it includes bicyclic 11 or 12-membered "heterocycle" wherein the above 5 to 6-membered "heterocycle" is condensed with 6-membered aromatic hydrocarbon or 6-membered heteroaryl. The 6-membered aromatic hydrocarbon includes benzene. The 6-membered unsaturated heterocycle includes pyridine, pyrimidine or pyridazine. Specifically, it includes dihydroindolyl, dihydroisoindolyl, dihydropurinyl, dihydrothiazolopyrimidinyl, dihydrobenzodioxanyl, isoindolinyl, indazolyl, pyrrolidinyl, tetrahydroquinolinyl, decahydroquinolinyl, tetrahydroisoquinolinyl, decahydroisoquinolinyl, tetrahydronaphthyridinyl or tetrahydropyridoazepinyl. A preferable "heterocycle" is saturated heterocycle, more preferably 5 to 6-membered saturated heterocycle.

The "heterocyclic $C_{1-6}$ alkyl" means a group wherein the "heterocycle" binds to the "$C_{1-6}$alkyl". Preferable one is "heterocyclic $C_{1-4}$ alkyl". The heterocyclic moiety includes the same concrete examples as illustrated in the above heterocycle. Specifically, it includes pyranylmethyl.

The "$C_{1-6}$ alkyl" moiety of "$C_{1-6}$ alkoxy" has the same meaning as defined in the "$C_{1-6}$ alkyl". Preferable one is "$C_{1-4}$ alkoxy". Concrete examples of "$C_{1-6}$ alkoxy" include methoxy, ethoxy, propoxy, isopropoxy, butoxy, isobutoxy, sec-butoxy, tert-butoxy.

The "$C_{6-10}$ aryl" moiety of "$C_{6-10}$ arylthio" has the same meaning as defined in the "$C_{6-10}$ aryl". Concrete examples of "$C_{6-10}$ arylthio" include phenylthio, 1-naphthylthio or 2-naphthylthio.

The "$C_{1-6}$ alkyl" moiety of "$C_{1-6}$ alkylsulfonyl" has the same meaning as defined in the "$C_{1-6}$ alkyl". Preferable one is "$C_{1-4}$ alkylsulfonyl". Concrete examples of "$C_{1-6}$ alkylsulfonyl" include methylsulfonyl, ethylsulfonyl, propylsulfonyl, isopropylsulfonyl, butylsulfonyl, pentylsulfonyl or hexylsulfonyl.

The "$C_{3-6}$ cycloalkyl" moiety of "$C_{3-6}$ cycloalkylsulfonyl" has the same meaning as defined in the "$C_{3-6}$ cycloalkyl". Concrete examples include cyclopropylsulfonyl, cyclobutylsulfonyl, cyclopentylsulfonyl, cyclohexylsulfonyl.

The "$C_{6-10}$ aryl" moiety of "$C_{6-10}$ arylsulfonyl" has the same meaning as defined in the "$C_{6-10}$ aryl". Concrete examples include phenylsulfonyl, 1-naphthylsulfonyl.

The "$C_{3-6}$ cycloalkyl" moiety of "$C_{3-6}$ cycloalkoxy" has the same meaning as defined in the "$C_{3-6}$ cycloalkyl". Concrete examples include cyclopropyloxy, cyclobutyloxy, cyclopentyloxy, cyclohexyloxy.

The "$C_{6-10}$ aryl" moiety of "$C_{6-10}$ aryloxy" has the same meaning as defined in the "$C_{6-10}$ aryl". Preferable one is "$C_6$ aryloxy" (phenyloxy). Concrete examples of "$C_{6-10}$ aryloxy" include phenoxy, 1-naphthyloxy or 2-naphthyloxy.

The "$C_{7-14}$ aralkyl" moiety of "$C_{7-14}$ aralkyloxy" ($C_{6-10}$ aryl-$C_{1-4}$ alkyloxy) has the same meaning as defined in the "$C_{7-14}$ aralkyl". Preferable one includes "$C_{7-10}$ aralkyloxy" ("phenyl-$C_{1-4}$ alkyl"). Concrete examples of "$C_{7-14}$ aralkyloxy" include benzyloxy, phenethyloxy, naphthylmethyloxy.

The "$C_{1-4}$ alkoxycarbonyl" means a group wherein the "$C_{1-4}$ alkoxy" binds to carbonyl. Specifically, it includes methoxycarbonyl, ethoxycarbonyl, propoxycarbonyl, 2-propoxycarbonyl or tert-butoxycarbonyl.

The "$C_{3-6}$ cycloalkoxycarbonyl" means a group wherein the "$C_{3-6}$ cycloalkoxy" binds to carbonyl. Specifically, the $C_{3-6}$ cycloalkoxy moiety includes groups illustrated in the $C_{3-7}$ cycloalkoxy.

The "$C_{7-14}$ aralkyl" moiety of "$C_{7-14}$ aralkyloxycarbonyl" has the same meaning as defined in the "$C_{7-14}$ aralkyl". Preferable one includes "$C_{7-10}$ aralkyloxycarbonyl". Concrete examples of "$C_{7-14}$ aralkyloxycarbonyl" include benzyloxycarbonyl, phenethyloxycarbonyl, naphthylmethyloxycarbonyl.

The "$C_{1-6}$ alkylcarbonyl" means a group wherein the "$C_{1-6}$ alkyl" binds to carbonyl. Specifically, it includes acetyl, propionyl or butyryl.

The "$C_{3-6}$ cycloalkylcarbonyl" means a group wherein the "$C_{3-6}$ cycloalkyl" binds to carbonyl. Specifically, the $C_{3-6}$ cycloalkyl moiety includes groups illustrated in the $C_{3-7}$ cycloalkyl.

The "$C_{1-4}$ alkyl" moiety of "$C_{1-4}$ alkylcarbonyloxy" has the same meaning as defined in the "$C_{1-4}$ alkyl". Concrete examples include methylcarbonyloxy, ethylcarbonyloxy, isopropylcarbonyloxy.

The "$C_{3-6}$ cycloalkyl" moiety of "$C_{3-6}$ cycloalkylcarbonyloxy" has the same meaning as defined in the "$C_{3-6}$ cycloalkyl".

The "5 to 7-membered cyclic amino" means cyclic amino group comprising 5 to 7-membered ring. It means that nitrogen atom in the ring is directly a binding site of a "group". Preferable one is 5 to 7-membered one, more preferably 5 or 6-membered one. Concrete examples include pyrrolidino, piperidino, morpholino, thiomorpholino, thiomorpholino-oxide, thiomorpholino-dioxide, piperadino, 2-pyrrolidon-1-yl. The ring may be may be optionally substituted by halogen atom, $C_{1-4}$ alkyl, or $C_6$ aryl which may be optionally substituted by $C_{1-4}$ alkoxy. The group includes cyclic amino group comprising a partly-unsaturated ring.

The "5 to 7-membered cyclic amino" may form a condensed ring with 6-membered aromatic hydrocarbon or 5 to 6-membered heterocycle. Concrete examples include the following "groups".

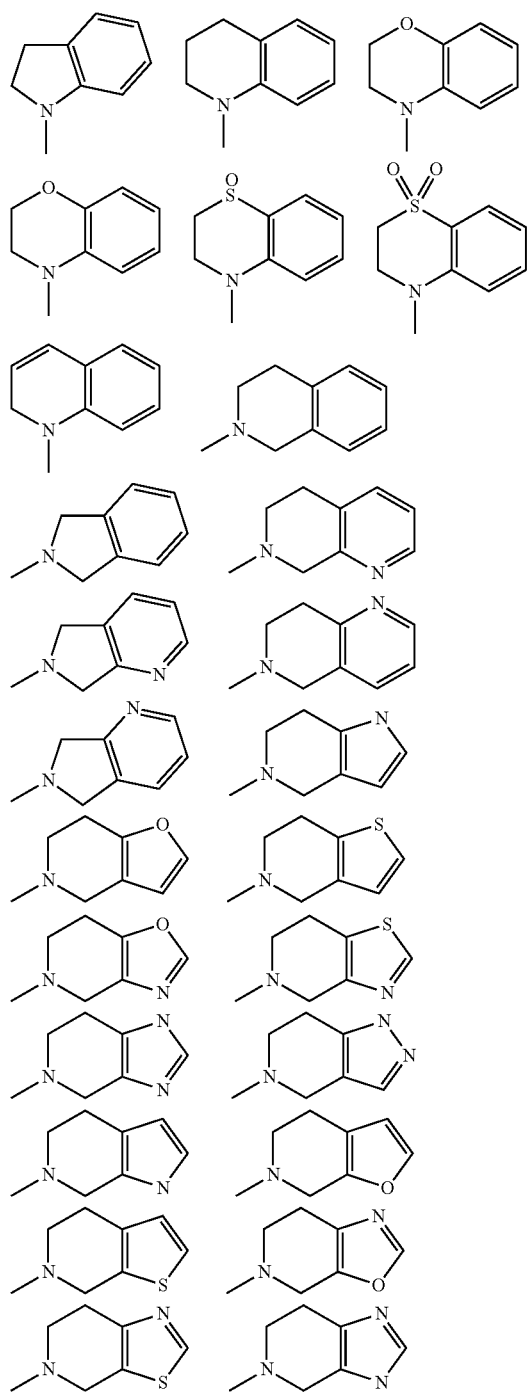

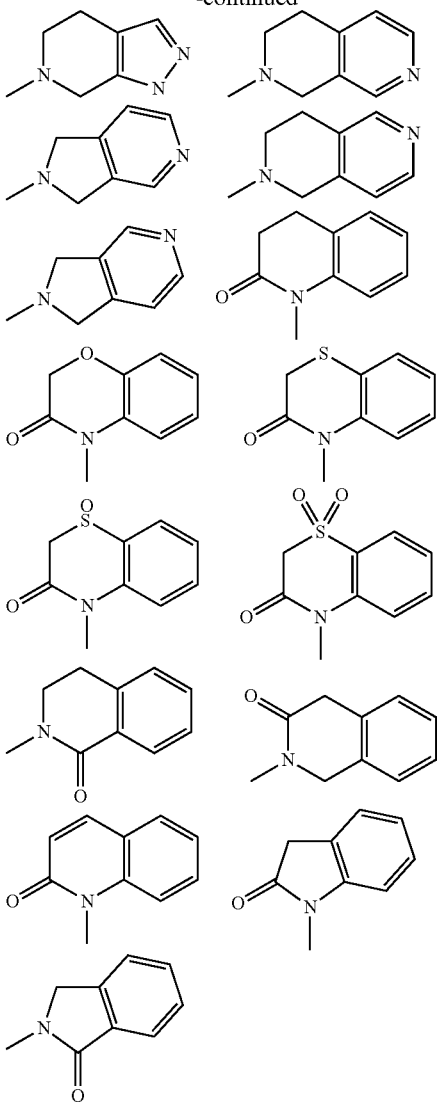

The substituent group in the "optionally substituted $C_{1-6}$ alkyl" includes
(a) halogen atom,
(b) hydroxyl,
(c) cyano,
(d) $C_{1-4}$ alkoxy (in which the alkoxy may be optionally substituted by
  (d1) 1 to 3 halogen atoms,
  (d2) hydroxy,
  (d3) $C_{1-4}$ alkoxy (in which the alkoxy may be optionally substituted by 1 to 3 halogen atoms),
  (d4) $C_{3-6}$ cycloalkoxy,
  (d5) $C_{3-6}$ cycloalkyl,
  (d6) mono- or di-$C_{1-6}$ alkylamino, or
  (d7) 5 to 7-membered cyclic amino),
(e) $C_{3-7}$ cycloalkoxy (in which the cycloalkoxy may be optionally substituted by
  (e1) 1 to 3 halogen atoms,
  (e2) hydroxy,
  (e3) $C_{1-4}$ alkoxy (in which the alkoxy may be optionally substituted by 1 to 3 halogen atoms),
  (e4) $C_{1-4}$ alkyl (in which the alkyl may be optionally substituted by 1 to 3 halogen atoms), (e5) $C_{3-6}$ cycloalkoxy,
(e6) $C_{3-6}$ cycloalkyl,
(e7) amino, or
(e8) mono- or di-$C_{1-6}$ alkylamino),
(f) $C_{1-4}$ alkylcarbonyloxy,
(g) $C_{3-6}$ cycloalkylcarbonyloxy,
(h) $C_{1-4}$ alkylcarbonyl (in which the alkyl may be optionally substituted by group(s) selected from the group consisting of the above (d1) to (d7)),
(i) $C_{3-6}$ cycloalkylcarbonyl (in which the cycloalkyl may be optionally substituted by group(s) selected from the group consisting of the above (e1) to (e8)),
(j) $C_{1-4}$ alkoxycarbonyl,
(k) $C_{3-6}$ cycloalkoxycarbonyl (in which the cycloalkoxy may be optionally substituted by group(s) selected from the group consisting of the above (e1) to (e8)),
(l) $C_{3-7}$ cycloalkyl,
(m) optionally substituted amino,
(n) carboxy,
(o) optionally substituted aminocarbonyl,
(p) $C_{1-4}$ alkylsulfonyl (in which the alkyl may be optionally substituted by group(s) selected from the group consisting of the above (d1) to (d7)),
(q) $C_{3-6}$ cycloalkylsulfonyl (in which the cycloalkyl may be optionally substituted by group(s) selected from the group consisting of the above (e1) to (e8)),
(r) $C_{6-10}$ aryloxy (in which the aryl may be optionally substituted by
  (r1) halogen atom,
  (r2) $C_{1-4}$ alkyl, or
  (r3) $C_{1-4}$ alkoxy),
(s) $C_{7-14}$ aralkyloxy,
(t) 5 to 12-membered mono- or poly-cyclic heteroaryloxy
(u) $C_{6-10}$ arylthio (in which the aryl may be optionally substituted by halogen atom, or $C_{1-4}$ alkyl), or
(v) $C_{6-10}$ arylsulfonyl (in which the aryl may be optionally substituted by
  (v1) halogen atom,
  (v2) $C_{1-4}$ alkyl, or
  (v3) $C_{1-4}$ alkoxy).

A preferable substituent group in the "optionally substituted $C_{1-6}$ alkyl" includes
(a2) 1 to 3 halogen atoms,
(b2) hydroxyl,
(c2) $C_{1-4}$ alkoxy (which may be optionally substituted by 1 to 3 halogen atoms),
(d2) $C_{1-4}$ alkylsulfonyl, or
(e2) carboxyl. More preferable substituent group includes halogen atom, or $C_{1-4}$ alkoxy.

The substituent group in the "optionally substituted $C_{3-7}$ cycloalkyl" includes the groups of the above (a) to (v), $C_{6-10}$ aryl, 5 to 12-membered mono- or poly-cyclic heteroaryl, $C_{1-4}$ alkyl (in which the alkyl may be optionally substituted by $C_{1-4}$ alkoxy, hydroxyl, or halogen atom), and oxo. When the group is a condensed group with phenyl or 5 to 6-membered ring comprising the same or different and one or more (e.g., 1 to 4) heteroatoms selected from nitrogen atom, sulfur atom and oxygen atom, a cyclic moiety such as phenyl may be optionally substituted by the following substituent group of the optionally substituted $C_{6-10}$ aryl, optionally substituted $C_{7-16}$ aralkyl, optionally substituted 5 to 12-membered mono- or poly-cyclic heteroaryl, or optionally substituted 5 to 12-membered mono- or poly-cyclic heteroaryl-$C_{1-6}$ alkyl.

The substituent group in the "optionally substituted $C_{6-10}$ aryl", "optionally substituted $C_{7-16}$ aralkyl", "optionally substituted 5 to 12-membered mono- or poly-cyclic heteroaryl" and "optionally substituted 5 to 12-membered mono- or poly-cyclic heteroaryl-$C_{1-6}$ alkyl" includes
(a3) halogen atom,
(b3) hydroxyl,
(c3) nitro,
(d3) cyano,
(e3) heterocycle,
(f3) $C_{3-7}$ cycloalkyl (in which the alkoxy may be optionally substituted by 1 to 3 halogen atoms),
(g3) $C_{3-7}$ cycloalkyloxy (in which the alkoxy may be optionally substituted by 1 to 3 halogen atoms),
(h3) $C_{1-4}$ alkyl (in which the alkyl may be optionally substituted by
  (h301) 1 to 3 halogen atoms,
  (h302) hydroxy,
  (h303) $C_{3-6}$ cycloalkyloxy,
  (h304) $C_{1-4}$ alkoxy (in which the alkoxy may be optionally substituted by
    1 to 3 halogen atoms,
    $C_{1-4}$ alkoxy, or
    hydroxy),
  (h305) $C_{3-6}$ cycloalkyl,
  (h306) $C_{1-4}$ alkylsulfonyl,
  (h307) $C_{3-6}$ cycloalkylsulfonyl,
  (h308) $C_{1-4}$ alkoxycarbonyl,
  (h309) $C_{7-14}$ aralkyloxycarbonyl,
  (h310) carboxyl,
  (h311) mono- or di-$C_{1-6}$ alkylaminocarbonyl, or
  (h312) 5 to 7-membered cyclic aminocarbonyl),
(i3) $C_{1-4}$ alkoxy (in which the alkoxy may be optionally substituted by
  (i31) 1 to 3 halogen atoms,
  (i32) hydroxy,
  (i33) $C_{1-4}$ alkoxy,
  (i34) carboxyl,
  (i35) $C_{1-4}$ alkoxycarbonyl,
  (i36) mono- or di-$C_{1-6}$ alkylaminocarbonyl,
  (i37) 5 to 7-membered cyclic aminocarbonyl, or
  (i38) $C_{3-6}$ cycloalkyl),
(j3) $C_{3-6}$ cycloalkylsulfonyl,
(k3) $C_{1-4}$ alkylcarbonyl (in which the alkyl may be optionally substituted by
  (k31) hydroxy,
  (k32) 1 to 3 halogen atoms,
  (k33) $C_{1-4}$ alkoxy (in which the alkoxy may be optionally substituted by 1 to 3 halogen atoms),
  (k34) $C_{3-6}$ cycloalkoxy, or
  (k35) $C_{3-6}$ cycloalkyl),
(l3) $C_{3-6}$ cycloalkylcarbonyl (in which the cycloalkyl may be optionally substituted by
  (l31) hydroxy,
  (l32) 1 to 3 halogen atoms,
  (l33) $C_{1-4}$ alkoxy (in which the alkoxy may be optionally substituted by 1 to 3 halogen atoms),
  (l34) $C_{3-6}$ cycloalkoxy,
  (l35) $C_{1-4}$ alkyl, or
  (l36) $C_{3-6}$ cycloalkyl),
(m3) $C_{1-4}$ alkoxycarbonyl,
(n3) $C_{3-6}$ cycloalkoxycarbonyl,
(o3) carboxy,
(p3) amino (in which the amino may be optionally substituted by the same or different and 1 to 2 groups selected from the group consisting of
  (p31) $C_{1-6}$ alkyl,
  (p32) $C_{3-6}$ cycloalkyl,
  (p33) $C_{1-4}$ alkylcarbonyl, (p34) $C_{3-6}$ cycloalkylcarbonyl, and
(p35) $C_{1-6}$alkylsulfonyl,
in which (p31) and (p33) may be further optionally substituted by group(s) selected from the group consisting of the above (k31) to (k35), and (p32) and (p34) may be further optionally substituted by group(s) selected from the group consisting of the above (l31) to (l36)),
(q3) 5 to 7-membered cyclic amino,
(r3) aminocarbonyl (in which the amino may be optionally substituted by the same or different and 1 to 2 groups selected from the group consisting of the above (p31) to (p35)),
(s3) 5 to 7-membered cyclic aminocarbonyl,
(t3) aminosulfonyl (in which the amino may be optionally substituted by the same or different and 1 to 2 groups selected from the group consisting of the above (p31) and (p32)),
(u3) 5 to 7-membered cyclic aminosulfonyl,
(v3) $C_{6-10}$ aryl (in which the aryl may be optionally substituted by
   (v31) halogen atom,
   (v32) $C_{1-4}$ alkyl, or
   (v33) $C_{1-4}$ alkoxy),
(w3) 5 to 10-membered mono- or poly-cyclic heteroaryl (in which the heteroaryl may be optionally substituted by halogen atoms),
(x3) $C_{1-4}$alkylsulfonyl, or
(y3) $C_{3-6}$ cycloalkylsulfonyl. The substituent group in the "optionally substituted $C_{6-10}$ aryl" and "optionally substituted 5 to 12-membered mono- or poly-cyclic heteroaryl" excludes the above (q3), (v3) and (w3).

A preferable substituent group in the "optionally substituted $C_{6-10}$ aryl", "optionally substituted $C_{7-16}$ aralkyl", "optionally substituted 5 to 12-membered mono- or poly-cyclic heteroaryl" and "optionally substituted 5 to 12-membered mono- or poly-cyclic heteroaryl-$C_{1-6}$ alkyl" is the same or different and 1 to 5 groups selected from the group consisting of
(a4) halogen atom,
(b4) cyano,
(c4) hydroxy,
(d4) $C_{1-4}$ alkoxy (in which the group may be optionally substituted by
   1 to 3 halogen atoms,
   carboxy,
   $C_{3-5}$ cycloalkyl,
   $C_{1-4}$ alkoxy, or
   $C_{1-4}$ alkoxycarbonyl),
(e4) 5 to 6-membered monocyclic heteroaryl (in which the group may be optionally substituted by halogen atom),
(f4) 5 to 7-membered cyclic amino,
(g4) $C_{1-4}$ alkylsulfonyl,
(h4) $C_{3-6}$ cycloalkyl,
(i4) mono- or di-$C_{1-6}$ alkylamino,
(j4) mono- or di-$C_{1-6}$ alkylcarbonylamino,
(k4) mono- or di-$C_{1-6}$ alkylsulfonylamino,
(l4) $C_{6-10}$ aryl (in which the aryl may be optionally substituted by halogen atom),
(m4) $C_{1-4}$ alkyl (in which the alkyl may be optionally substituted by
   1 to 3 halogen atoms,
   carboxy,
   $C_{1-4}$ alkoxycarbonyl, or
   $C_{1-4}$ alkoxy (in which the alkoxy may be optionally substituted by 1 to 3 halogen atoms)),
(n4) $C_{1-6}$ alkylcarbonyl,
(o4) carboxy, and
(p4) $C_{1-4}$ alkoxycarbonyl. The preferable substituent group in the "optionally substituted $C_{6-10}$ aryl" and "optionally substituted 5 to 12-membered mono- or poly-cyclic heteroaryl" excludes the above (e4), (f4) and (l4).

More preferable substituent group is the same or different and 1 to 5 groups selected from the group consisting of
(a5) halogen atom,
(b5) cyano,
(c5) $C_{1-4}$ alkoxy (in which the group may be optionally substituted by
   1 to 3 halogen atoms,
   $C_{1-4}$alkoxy (in which the alkoxy may be optionally substituted by 1 to 3 halogen atoms), or
   $C_{3-6}$ cycloalkyl),
(d5) $C_{3-6}$ cycloalkyl,
(e5) $C_{1-4}$ alkyl (in which the alkyl may be optionally substituted by
   1 to 3 halogen atoms,
   $C_{1-4}$alkoxy (in which the alkoxy may be optionally substituted by 1 to 3 halogen atoms), or
   $C_{3-6}$ cycloalkyl), and
(f5) $C_{1-6}$ alkylcarbonyl.

When the aryl moiety of "$C_{6-10}$ aryl" and "$C_{7-16}$ aralkyl" is condensed, the condensed ring moiety may be optionally substituted by the substituent group in the "optionally substituted heterocycle" or "optionally substituted $C_{3-7}$ cycloalkyl".

The heterocyclic substituent group in the "optionally substituted heterocycle" and "optionally substituted heterocyclic $C_{1-6}$ alkyl" includes the groups selected from the group consisting of the above (d) to (v), $C_{1-4}$ alkyl (in which the alkyl may be optionally substituted by 1 to 3 halogen atoms, or $C_{1-4}$ alkoxy), $C_{6-10}$ aryl, 5 to 12-membered mono- or poly-cyclic heteroaryl (in which the $C_{6-10}$ aryl and 5 to 12-membered mono- or poly-cyclic heteroaryl may be optionally substituted by the same or different and 1 to 3 groups selected from the group consisting of halogen atom; cyano; $C_{1-4}$ alkoxy which may be optionally substituted by 1 to 3 halogen atoms, $C_{3-6}$ cycloalkyl or $C_{1-4}$ alkoxy; $C_{3-6}$ cycloalkyl; mono- or di-$C_{1-6}$ alkylamino; $C_{1-4}$ alkyl which may be optionally substituted by 1 to 3 halogen atoms, $C_{1-4}$ alkoxy, or $C_{3-6}$ cycloalkyl; and $C_{1-4}$ alkylcarbonyl), or oxo.

The "optionally substituted amino" means amino, mono- or di-substituted amino, and optionally substituted 5 to 7-membered cyclic amino.

The substituent group of the "mono- or di-substituted amino" may be optionally substituted by the same or different and 1 to 2 groups selected from the group consisting of
(a6) $C_{1-4}$ alkyl,
(b6) $C_{3-6}$ cycloalkyl,
(c6) $C_{1-4}$ alkylcarbonyl,
(d6) $C_{3-6}$ cycloalkylcarbonyl,
(e6) aminocarbonyl,
(f6) 5 to 7-membered cyclic aminocarbonyl,
(g6) $C_{1-4}$ alkylsulfonyl, and
(h6) $C_{3-7}$ cycloalkylsulfonyl.

The substituent group in the "optionally substituted 5 to 7-membered cyclic amino" is the same as the substituent group in the "optionally substituted heterocycle". When the group may form a condensed ring with 6-membered aromatic hydrocarbon or 5 to 6-membered heterocycle, the 6-membered aromatic hydrocarbon or 5 to 6-membered heterocycle may be optionally substituted by the substituent group (e.g., (a4) to (p4), etc.) in the "optionally substituted $C_{6-10}$ aryl", "optionally substituted $C_{7-16}$ aralkyl", "optionally substituted 5 to 12-membered mono- or poly-cyclic heteroaryl", or "optionally substituted 5 to 12-membered mono- or poly-cyclic heteroaryl-$C_{1-6}$ alkyl".

The "optionally substituted amino" in the "optionally substituted aminocarbonyl" has the same meaning as defined in the "optionally substituted amino".

"$R^{1a}$" and "$R^{1b}$" across A and azabicyclo[3.2.1]octane in formula (1) mean that they may bind on any possible positions on each ring. When m and n are 0, $R^{1a}$ and $R^{1b}$ are absent. Specifically, said compound means the following compound:

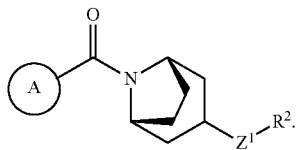

(1)

A preferable embodiment in the present invention is explained in more detail.

In a compound of formula (1), both "m" and "n" are preferably 0.

"$Z^1$" is preferably a single bond, or oxygen atom. "$Z^1$" preferably binds either in the following configuration:

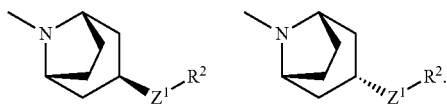

"$R^2$" is preferably
(1) $C_{1-6}$ alkyl (in which the group may be optionally substituted by
  (a) $C_{6-10}$ aryloxy (in which the aryl may be optionally substituted by
    halogen atom,
    $C_{1-4}$ alkyl, or
    $C_{1-4}$ alkoxy),
  (b) $C_{6-10}$ arylthio (in which the aryl may be optionally substituted by
    halogen atom, or
    $C_{1-4}$ alkyl),
  (c) $C_{6-10}$ arylsulfonyl (in which the aryl may be optionally substituted by
    halogen atom,
    $C_{1-4}$ alkyl, or
    $C_{1-4}$ alkoxy),
  (d) $C_{3-6}$ cycloalkyl,
  (e) $C_{1-4}$ alkoxy, or
  (f) $C_{7-14}$ aralkyloxy),
(2) $C_{3-7}$ cycloalkyl,
(3) $C_{6-10}$ aryl (in which the aryl may be optionally substituted by the same or different 1 to 5 groups selected from the group consisting of
  (a) halogen atom,
  (b) cyano,
  (c) hydroxy,
  (d) $C_{1-4}$ alkoxy (in which the alkoxy may be optionally substituted by
    1 to 3 halogen atoms,
    $C_{1-4}$ alkoxy (in which the alkoxy may be optionally substituted by 1 to 3 halogen atoms),
    carboxy,
    $C_{1-4}$ alkoxycarbonyl, or
    $C_{3-6}$ cycloalkyl),
  (e) $C_{1-4}$ alkylsulfonyl,
  (f) $C_{3-6}$ cycloalkyl,
  (g) $C_{3-6}$ cycloalkoxy,
  (h) mono- or di-$C_{1-6}$ alkylamino,
  (i) mono- or di-$C_{1-6}$ alkylcarbonylamino,
  (j) mono- or di-$C_{1-6}$ alkylsulfonylamino,
  (k) $C_{1-4}$ alkyl (in which the alkyl may be optionally substituted by
    1 to 3 halogen atoms,
    $C_{1-4}$ alkoxy (in which the alkoxy may be optionally substituted by 1 to 3 halogen atoms),
    carboxyl,
    $C_{1-4}$ alkoxycarbonyl, or
    $C_{3-6}$ cycloalkyl),
  (l) $C_{1-6}$ alkylcarbonyl,
  (m) carboxy,
  (n) $C_{1-4}$ alkoxycarbonyl, and
  (o) aminocarbonyl),
(4) $C_{7-16}$ aralkyl (in which the group may be optionally substituted by the same or different 1 to 5 groups selected from the group consisting of
  (a) halogen atom,
  (b) cyano,
  (c) $C_{1-4}$ alkoxy (in which the alkoxy may be optionally substituted by
    1 to 3 halogen atoms,
    $C_{3-6}$ cycloalkyl, or
    $C_{1-4}$ alkoxy),
  (d) $C_{1-4}$ alkylsulfonyl,
  (e) $C_{1-4}$ alkyl (in which the alkyl may be optionally substituted by
    1 to 3 halogen atoms, or
    $C_{1-4}$ alkoxy), and
  (f) $C_{1-6}$ alkylthio),
(5) heterocycle (in which the ring may be optionally substituted by $C_{6-10}$ aryl, or 5 to 12-membered mono- or poly-cyclic heteroaryl, and the $C_{6-10}$ aryl and 5 to 12-membered mono- or poly-cyclic heteroaryl may be optionally substituted by 1 to 3 groups selected from the group consisting of
  (a) halogen atom,
  (b) cyano,
  (c) $C_{1-4}$ alkyl (in which the alkyl may be optionally substituted by
    1 to 3 halogen atoms,
    $C_{1-4}$ alkoxy, or
    $C_{3-6}$ cycloalkyl),
  (d) $C_{1-4}$ alkoxy (in which the alkoxy may be optionally substituted by
    1 to 3 halogen atoms,
    $C_{1-4}$ alkoxy, or
    $C_{3-6}$ cycloalkyl),
  (e) $C_{3-6}$ cycloalkyl,
  (f) mono- or di-$C_{1-6}$ alkylamino, and
  (g) $C_{1-6}$ alkylcarbonyl),
(6) heterocyclic $C_{1-6}$ alkyl,
(7) 5 to 12-membered mono- or poly-cyclic heteroaryl (in which the heteroaryl may be optionally substituted by the same or different 1 to 3 groups selected from the group consisting of
  (a) halogen atom,
  (b) cyano,
  (c) $C_{1-4}$ alkoxy (in which the alkoxy may be optionally substituted by
    1 to 3 halogen atoms,
    $C_{1-4}$ alkoxy, or
    $C_{3-6}$ cycloalkyl),
  (d) $C_{3-6}$ cycloalkyl,
  (e) $C_{3-6}$ cycloalkylalkoxy, (f) mono- or di-$C_{1-6}$ alkylamino,
(g) $C_{1-4}$ alkyl (in which the alkyl may be optionally substituted by
1 to 3 halogen atoms,
$C_{1-4}$ alkoxy, or
$C_{3-6}$ cycloalkyl), and
(h) $C_{1-6}$ alkylcarbonyl),
(8) 5 to 12-membered mono- or poly-cyclic heteroaryl-$C_{1-6}$ alkyl (in which the group may be optionally substituted by $C_{1-4}$ alkyl, or $C_{1-4}$ alkoxy), or
(9) 5 to 7-membered cyclic amino.

"$R^2$" is more preferably
(1) $C_{1-6}$ alkyl (in which the group may be optionally substituted by $C_{6-10}$ aryloxy),
(2) $C_{6-10}$ aryl (in which the aryl may be optionally substituted by the same or different 1 to 5 groups selected from the group consisting of
(a) halogen atom,
(b) cyano,
(c) $C_{1-4}$ alkoxy (in which the alkoxy may be optionally substituted by
1 to 3 halogen atoms, or
$C_{1-4}$ alkoxy),
(d) $C_{1-4}$ alkylsulfonyl,
(e) mono- or di-$C_{1-6}$ alkylcarbonylamino,
(f) $C_{1-4}$ alkyl (in which the alkyl may be optionally substituted by
1 to 3 halogen atoms, or
$C_{1-4}$ alkoxy (in which the alkoxy may be optionally substituted by 1 to 3 halogen atoms)),
(g) $C_{1-4}$ alkylcarbonyl,
(h) carboxy,
(i) $C_{1-4}$ alkoxycarbonyl, and
(j) aminocarbonyl),
(3) $C_{7-16}$ aralkyl (in which the group may be optionally substituted by the same or different 1 to 5 groups selected from the group consisting of
(a) halogen atom,
(b) cyano,
(c) $C_{1-4}$ alkoxy (in which the alkoxy may be optionally substituted by 1 to 3 halogen atoms),
(d) $C_{1-4}$ alkylsulfonyl,
(e) $C_{1-4}$ alkyl (in which the alkyl may be optionally substituted by 1 to 3 halogen atoms), and
(f) $C_{1-6}$ alkylthio),
(4) heterocycle (in which the ring may be optionally substituted by
(a) $C_{6-10}$ aryl, or
(b) 5 to 12-membered mono- or poly-cyclic heteroaryl (in which the heteroaryl may be optionally substituted by group(s) selected from the group consisting of
halogen atom,
$C_{1-4}$ alkyl, and
$C_{1-4}$ alkoxy)),
(5) 5 to 12-membered mono- or poly-cyclic heteroaryl (in which the heteroaryl may be optionally substituted by the same or different 1 to 3 groups selected from the group consisting of
(a) halogen atom,
(b) cyano,
(c) $C_{1-4}$ alkoxy (in which the alkoxy may be optionally substituted by
1 to 3 halogen atoms, or
$C_{3-6}$ cycloalkyl), and
(d) $C_{1-4}$ alkyl (in which the alkyl may be optionally substituted by
1 to 3 halogen atoms, or
$C_{1-4}$ alkoxy), (e) $C_{1-4}$ alkylcarbonyl, and
(f) $C_{3-6}$ cycloalkyl), or
(6) 5 to 12-membered mono- or poly-cyclic heteroaryl-$C_{1-6}$ alkyl (in which the group may be optionally substituted by $C_{1-4}$ alkyl, or $C_{1-4}$ alkoxy).

The present invention encompasses compounds of the following formulae (2) to (4) as well as a compound of formula (1).

(1) A compound of formula (2):

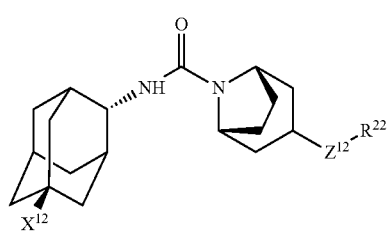

(2)

wherein $X^{12}$ is hydroxyl, or aminocarbonyl;
$Z^{12}$ is a single bond, or oxygen atom;
$R^{22}$ is $C_{7-16}$ aralkyl (in which the aryl moiety of the aralkyl may be optionally substituted by the same or different groups selected from the group consisting of
(1) halogen atom,
(2) cyano,
(3) $C_{1-4}$ alkoxy (in which the alkoxy may be optionally substituted by 1 to 3 halogen atoms, $C_{3-6}$ cycloalkyl or $C_{1-4}$ alkoxy),
(4) $C_{1-4}$ alkylsulfonyl,
(5) $C_{1-4}$ alkyl (in which the alkyl may be optionally substituted by 1 to 3 halogen atoms, or $C_{1-4}$ alkoxy), and
(6) $C_{1-4}$ alkylthio), or a pharmaceutically acceptable salt thereof.

$R^{22}$ in a compound of formula (2), or a pharmaceutically acceptable salt thereof is preferably phenyl or 5 to 12-membered mono- or poly-cyclic heteroaryl (in which the phenyl and heteroaryl may be optionally substituted by the same or different groups selected from the group consisting of
(1) halogen atom,
(2) cyano,
(3) $C_{1-4}$ alkoxy (in which the alkoxy may be optionally substituted by 1 to 3 halogen atoms, or $C_{1-4}$ alkoxy), and
(4) $C_{1-4}$ alkyl (in which the alkyl may be optionally substituted by 1 to 3 halogen atoms, or $C_{1-4}$ alkoxy)).

(2) A compound of formula (3):

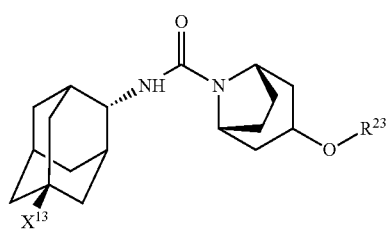

(3)

wherein $X^{13}$ is hydroxyl, or aminocarbonyl;
$R^{23}$ is phenyl or 5 to 12-membered mono- or poly-cyclic heteroaryl (in which the phenyl and heteroaryl may be option ally substituted by the same or different 1 to 3 groups selected from the group consisting of
(1) halogen atom,
(2) cyano,
(3) C$_{1-4}$ alkoxy (in which the alkoxy may be optionally substituted by
  (a) 1 to 3 halogen atoms,
  (b) C$_{1-4}$ alkoxy (in which the alkoxy may be optionally substituted by 1 to 3 halogen atoms), or
  (c) C$_{3-6}$ cycloalkyl),
(4) C$_{3-6}$ cycloalkyl,
(5) C$_{1-4}$ alkyl (in which the alkyl may be optionally substituted by
  (a) 1 to 3 halogen atoms,
  (b) C$_{1-4}$ alkoxy (in which the alkoxy may be optionally substituted by 1 to 3 halogen atoms), or
  (c) C$_{3-6}$ cycloalkyl), and
(6) C$_{1-6}$ alkylcarbonyl), or a pharmaceutically acceptable salt thereof.
(3) A compound of formula (3a):

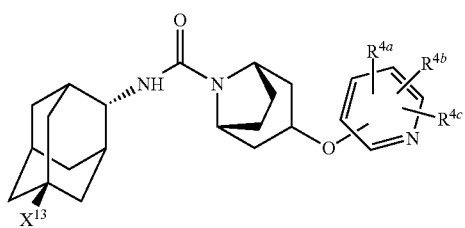

(3a)

wherein X$^{13}$ is hydroxyl, or aminocarbonyl;
R$^{4a}$, R$^{4b}$ and R$^{4c}$ are each independently
(1) hydrogen atom,
(2) halogen atom,
(3) cyano,
(4) C$_{1-4}$ alkoxy (in which the alkoxy may be optionally substituted by 1 to 3 halogen atoms, C$_{1-4}$alkoxy, or C$_{3-6}$ cycloalkyl),
(5) C$_{3-6}$ cycloalkyl,
(6) C$_{3-6}$ cycloalkyloxy,
(7) C$_{1-4}$ alkyl (in which the alkyl may be optionally substituted by 1 to 3 halogen atoms, C$_{1-4}$ alkoxy, or C$_{3-6}$ cycloalkyl), or
(8) C$_{1-6}$ alkylcarbonyl), or a pharmaceutically acceptable salt thereof.
(4) A compound of formula (3b):

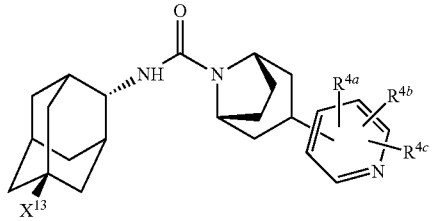

(3b)

wherein X$^{13}$ is hydroxyl, or aminocarbonyl;
R$^{4a}$, R$^{4b}$ and R$^{4c}$ are each independently
(1) hydrogen atom,
(2) halogen atom,
(3) cyano,
(4) C$_{1-4}$ alkoxy (in which the alkoxy may be optionally substituted by 1 to 3 halogen atoms, C$_{1-4}$alkoxy, or C$_{3-6}$ cycloalkyl),
(5) C$_{3-6}$ cycloalkyl,
(6) C$_{3-6}$ cycloalkyloxy,
(7) C$_{1-4}$ alkyl (in which the alkyl may be optionally substituted by 1 to 3 halogen atoms, C$_{1-4}$ alkoxy, or C$_{3-6}$ cycloalkyl), or
(8) C$_{1-6}$ alkylcarbonyl, or a pharmaceutically acceptable salt thereof.
(5) A compound of formula (4):

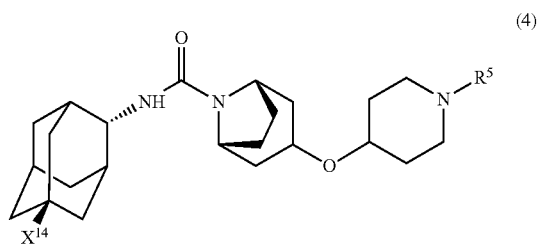

(4)

wherein X$^{14}$ is hydroxyl, or aminocarbonyl;
R$^{5}$ is
(1) C$_{6-10}$ aryl, or
(2) 5 to 12-membered mono- or poly-cyclic heteroaryl (in which the C$_{6-10}$ aryl and 5 to 12-membered mono- or poly-cyclic heteroaryl may be optionally substituted by 1 to 3 groups selected from the group consisting of
  (a) halogen atom,
  (b) cyano,
  (c) C$_{1-4}$ alkyl (in which the alkyl may be optionally substituted by
    1 to 3 halogen atoms,
    C$_{1-4}$ alkoxy, or
    C$_{3-6}$ cycloalkyl),
  (d) C$_{1-4}$ alkoxy (in which the alkoxy may be optionally substituted by
    1 to 3 halogen atoms,
    C$_{3-6}$ cycloalkyl, or
    C$_{1-4}$ alkoxy),
  (e) C$_{3-6}$ cycloalkyl,
  (f) mono- or di-C$_{1-6}$ alkylamino, and
  (g) C$_{1-6}$ alkylcarbonyl), or a pharmaceutically acceptable salt thereof.

Preferable embodiments of compounds of formulae (2) to (4) also encompass compounds with configurations of Items 5 and 6 in a compound of formula (1) or a pharmaceutically acceptable salt thereof. Said compounds include any compounds of the following formulae:

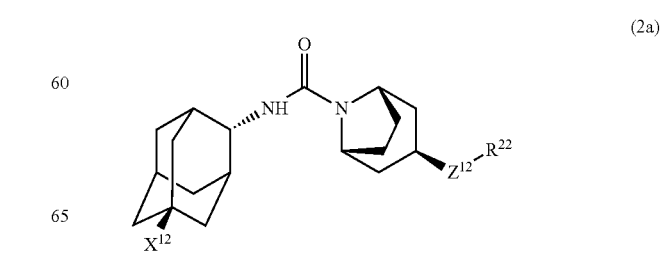

(2a)

-continued (2b)
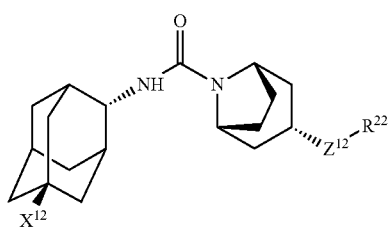

(3-1)
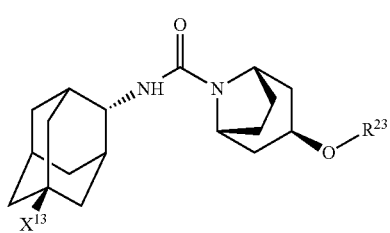

(3-2)
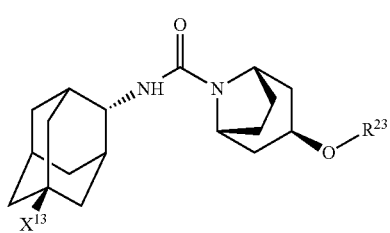

(3a-1)
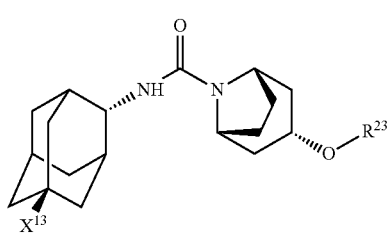

(3a-2)
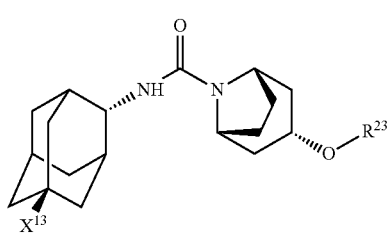

(3b-1)
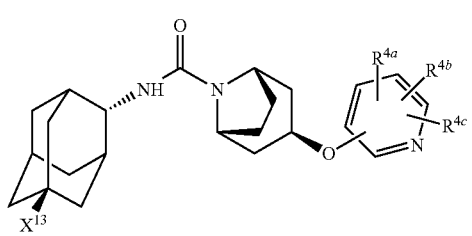

(3b-2)
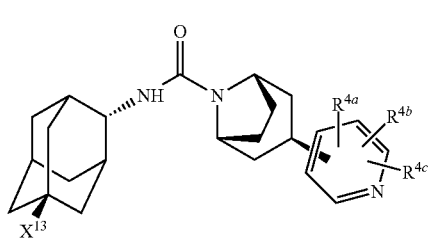

-continued (4a)
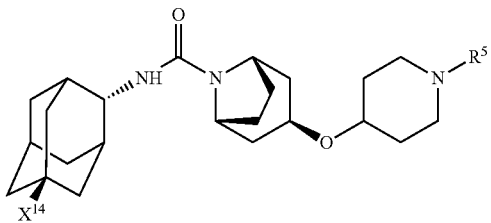

(4b)
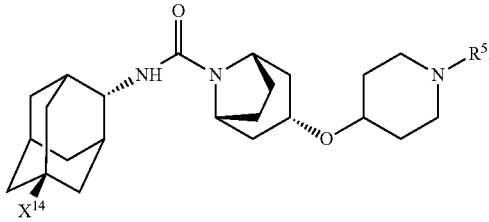

A method for preparing a compound of formula (1) is explained. A compound of formula (1), or a pharmaceutically acceptable salt thereof (referred to as the compound of the present invention, hereinafter) is illustrated as below, but the present invention is not intended to be limited thereto.

The compound of formula (1) of the present invention may be prepared from known compounds according to the following Preparations 1 to 2, similar methods to the following preparations, or a combination of any synthetic methods known to a skilled person.

Preparation 1

Preparation of Compound (1)

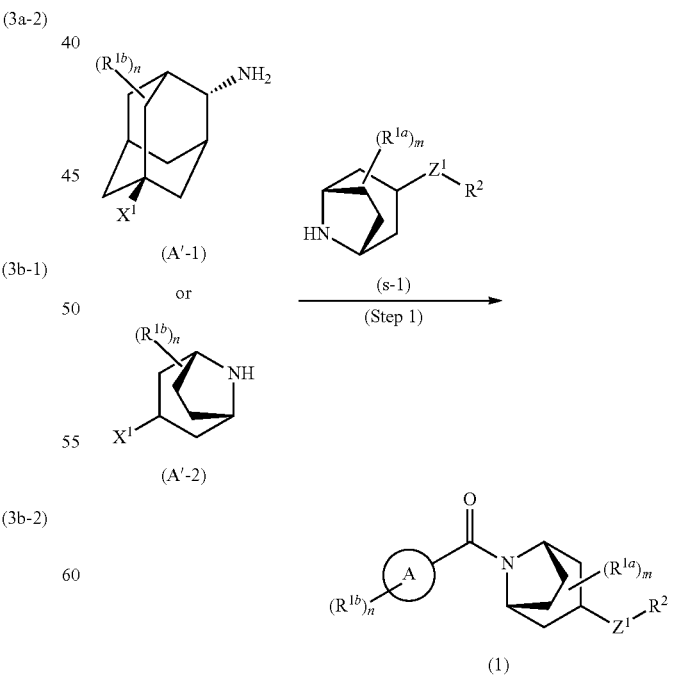

(In the scheme, A, $R^{1a}$, $R^{1b}$, m, n, $X^1$, $Z^1$ and $R^2$ have the same meanings as defined in the above Item 1.)

Compound (1) may be prepared according to the following methods by using a compound of formula (A'-1) or (A'-2) and a compound of formula (s-1). A compound of formula (A'-1) or (A'-2) and a compound of formula (s-1) may be used in the reaction in the form of salt.

Preparation 1-1

A compound of formula (A'-1) or (A'-2) is reacted with 1,1'-carbonyldiimidazole, triphosgene, or phosgene, etc., for example, usually at −10° C. to 30° C. for 0.5 to 6 hours in an inactive solvent. Sequentially, the mixture may be usually reacted with a compound of formula (s-1) at −10° C. to reflux temperature for 0.5 to 8 hours to give Compound (1). The reacting order of a compound of formula (s-1) and a compound of formula (A'-1) or (A'-2) may be switched each other.

Preparation 1-2

A compound of formula (A'-1) or (A'-2) in an inactive solvent may be reacted with para-nitrophenyl chloroformate, trichloromethylchloroformate (diphosgene) or phenylchloroformate usually at −10° C. to reflux temperature in the presence of a base, and then thereto may be added a compound formula (s-1) and the mixture may be treated usually at −10° C. to reflux temperature to give Compound (1). The reacting order of formula (s-1) and a compound of formula (A'-1) or (A'-2) may be switched each other. The base includes nitrogen-containing organic bases such as triethylamine, diisopropylethylamine, tributylamine, 1,5-diazabicyclo[4.3.0]non-5-ene (DBN), 1,4-diazabicyclo[2.2.2]octane (DABCO), 1,8-diazabicyclo[5.4.0]undec-7-ene (DBU), pyridine, dimethylaminopyridine, picoline or N-methylmorpholine (NMM), inorganic bases such as potassium carbonate, sodium carbonate, sodium hydrogen carbonate.

The inactive solvent includes ether type solvents such as tetrahydrofuran, diethylether, dioxane, 1,2-dimethoxyethane, cyclopentylmethylether, hydrocarbons such as toluene, benzene, halogenated hydrocarbon type solvents such as dichloromethane, chloroform, 1,2-dichloroethane, aprotic polar solvents such as dimethyl sulfoxide, N,N-dimethylformamide, N,N-dimethylacetamide, N-methyl-2-pyrrolidinone, 1,3-dimethyl-2-imidazolidinone, a mixed solvent thereof, or a mixed solvent of these solvents and water.

Preparation 2

Preparation of a Compound of Formula (S-4)

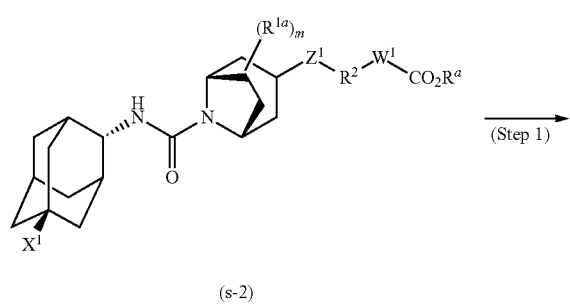

(s-2)

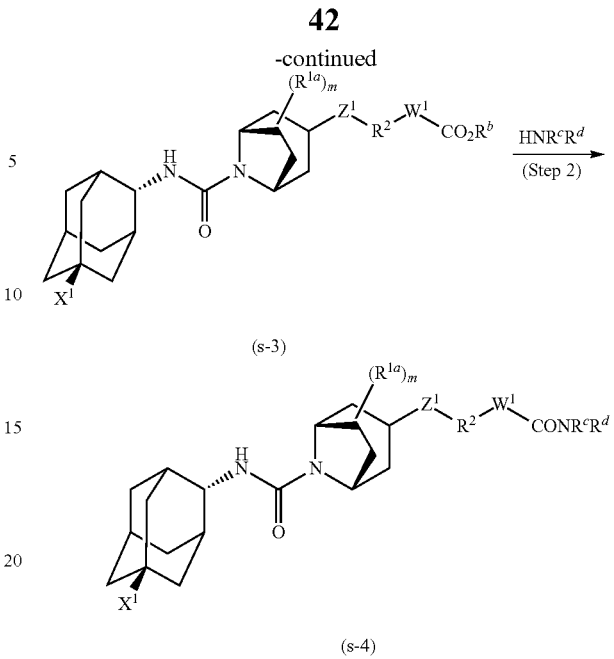

(s-3)

(s-4)

(In the above formula, $R^{1a}$, m, $X^1$ and $Z^1$ are the same as the above Item 1, $R^2$ is optionally substituted $C_{6-10}$ aryl, optionally substituted $C_{7-16}$ aralkyl, optionally substituted 5 to 12-membered mono- or poly-cyclic heteroaryl-$C_{1-6}$alkyl, or optionally substituted 5 to 12-membered mono- or poly-cyclic heteroaryl (in which —$W^1$—$CO_2R^a$, —$W^1$—$CO_2R^b$ and —$W^1$—$CONR^cR^d$ are the substituent group in the above $R^2$, $W^1$ is a single bond, $C_{1-4}$ alkylene, or $C_{1-4}$ alkoxy, $R^a$ is $C_{1-4}$ alkyl, or $C_{7-14}$ aralkyl, $R^b$ is hydrogen atom, sodium, potassium, lithium, calcium, etc., $R^c$ and $R^d$ are the same or different and $C_{1-6}$ alkyl, or —$NR^cR^d$ is 5 to 7-membered cyclic amino).)

Step 1:

The Step is directed to the conversion into a carboxylic acid compound derivative of formula (s-3) via deprotection of ester group of a compound of formula (s-2) prepared in the similar manner to Preparation 1.

The Step includes the method of Greene, Protective Groups in Organic Synthesis, John Wiley & Sons Inc. (1981).

Specifically, the step is carried out in the following procedure, for example.

(A) When $R^a$ is $C_{1-4}$ alkyl, the carboxlic acid compound derivative (s-3) may be prepared by alkali hydrolysis, or acid hydrolysis. For example, in case of alkali hydrolysis, Compound (s-3) may be prepared by the reaction using water in the presence of alkali metal hydroxide or alkaline-earth metal hydroxide such as sodium hydroxide, potassium hydroxide, lithium hydroxide, magnesium hydroxide, for example in the presence or absence of alcohol type solvent such as methanol, ethanol, 2-propanol, butanol, ether type solvent such as diethylether, diisopropylether, tetrahydrofuran, 1,4-dioxane, aromatic hydrocarbon type solvent such as benzene, toluene, xylene, usually in the range of room temperature to reflux temperature for 0.5 to 48 hours.

(B) When $R^a$ is $C_{7-14}$ aralkyl, Compound (s-3) may be prepared by the reaction in the presence of a metal catalyst such as palladium/carbon, palladium hydroxide, nickel under hydrogen atmosphere, and the optional addition of ammonium formate etc. The solvent includes alcohol type solvents such as methanol, ethanol, 2-propanol, butanol, ether type solvents such as diethylether, diisopropylether, tetrahydrofuran, 1,4-dioxane, aromatic hydrocarbon type solvents such as benzene, toluene, xylene, esters such as ethyl acetate, methyl acetate, organic acids such as acetic acid, or a mixed solvent thereof Step 2:

In the Step, a carboxy group of Compound (s-3) is activated, and then reacted with amine $HNR^cR^d$ or a salt thereof to give Compound (s-4).

The activation of carboxy group includes a method of converting carboxy group into acid anhydride, mixed acid anhydride, acid halide, active ester or acid azide or a method using a condensing agent.

In the method via acid halide, Compound (s-3) may be reacted with a halogenating agent such as oxalyl chloride, thionyl chloride, phosphorus oxychloride, phosphorus pentachloride, for example, to give an acid halide, and then reacted with amine $HNR^cR^d$ or a salt thereof in the presence of a base to give Compound (s-4). Any bases may be used as the base without limitations, but for example, the base includes organic bases such as triethylamine, diisopropylethylamine, tributylamine, 1,5-diazabicyclo[4.3.0]non-5-ene (DBN), 1,4-diazabicyclo[2.2.2]octane (DABCO), 1,8-diazabicyclo[5.4.0]undec-7-ene (DBU), pyridine, dimethylaminopyridine, picoline or N-methylmorpholine (NMM), or inorganic bases such as sodium hydrogen carbonate, potassium hydrogen carbonate, sodium carbonate, potassium carbonate, sodium hydroxide, potassium hydroxide. Any solvents may be used as the solvent unless they react under the reaction condition of the Step. For example, the solvent includes halogenated hydrocarbon type solvents such as dichloromethane, chloroform, 1,2-dichloroethane, carbon tetrachloride, ether type solvents such as diethylether, diisopropylether, tetrahydrofuran, 1,4-dioxane, aromatic hydrocarbon type solvents such as benzene, toluene, xylene, esters such as ethyl acetate, methyl acetate, water, or a mixture thereof. The reaction temperature is in the range of $-80°$ C. to reflux temperature, and usually in the range of $-20°$ C. to ice-cold temperature. The reaction time is between 10 minutes and 48 hours.

In the method via mixed acid anhydride, Compound (s-3) may be reacted with acid halide in the presence of a base to give a mixed acid anhydride, and then reacted with amine $HNR^cR^d$ or a salt thereof to give Compound (s-4). The acid halide includes methoxycarbonyl chloride, ethoxycarbonyl chloride, isopropyloxycarbonyl chloride, isobutyloxycarbonyl chloride, para-nitrophenoxycarbonyl chloride or t-butylcarbonyl chloride, for example. Any bases may be used as the base without limitations, but for example, the base includes organic bases such as triethylamine, diisopropylethylamine, tributylamine, 1,5-diazabicyclo[4.3.0]non-5-ene (DBN), 1,4-diazabicyclo[2.2.2]octane (DABCO), 1,8-diazabicyclo[5.4.0]undec-7-ene (DBU), pyridine, dimethylaminopyridine, picoline or N-methylmorpholine (NMM), or inorganic bases such as sodium hydrogen carbonate, potassium hydrogen carbonate, sodium carbonate or potassium carbonate. Any solvents may be used as the solvent unless they react under the reaction condition of the Step. For example, the solvent includes halogenated hydrocarbon type solvents such as dichloromethane, chloroform, 1,2-dichloroethane, carbon tetrachloride, ether type solvents such as diethylether, diisopropylether, tetrahydrofuran, 1,4-dioxane, aromatic hydrocarbon type solvents such as benzene, toluene or xylene, esters such as ethyl acetate, methyl acetate, water, or a mixture thereof. The reaction temperature is in the range of $-80°$ C. to reflux temperature, and usually at $-20°$ C. to ice-cold temperature. The reaction time is between 30 minutes and 48 hours.

Compound (s-3) may be also reacted with amine $HNR^cR^d$ or a salt thereof using a condensing agent in the presence or absence of a base to give Compound (s-4). The condensing agent includes agents described in Jikken-Kagaku Koza (The Chemical Society of Japan, Maruzen), vol. 22. For example, it includes phosphoric acid esters such as diethyl cyanophosphate, diphenylphosphoryl azide; carbodiimides such as 1-ethyl-3-(3-dimethylaminopropyl)-carbodiimide hydrochloride, dicyclohexylcarbodiimide; combinations of disulfides such as 2,2'-dipyridyl disulfide and phosphines such as triphenylphosphine; phosphorus halides such as N,N'-bis(2-oxo-3-oxazolidinyl)phosphinic chloride; combinations of azodicarboxylic acid diesters such as diethyl azodicarboxylate and phosphines such as triphenylphosphine; 2-halo-1-lower alkylpyridinium halides such as 2-chloro-1-methylpyridinium iodide; 1,1'-carbonyldiimidazole; diphenylphosphoryl azide (DPPA); diethyl phosphoryl cyanide (DEPC); dicyclohexylcarbodiimide (DCC); carbonyldiimidazole (CDI); 1-ethyl-3-(3-dimethylaminopropyl)carbodiimide hydrochloride (EDC HCl); O-(1H-benzotriazol-1-yl)-1,1,3,3-tetramethyl-uronium tetrahydroborate (TBTU); O-(1H-benzotriazol-1-yl)-N,N,N',N'-tetramethyl-uronium hexafluorophosphate (HBTU); (benzotriazol-1-yloxy)tris(dimethylamino)phosphonium hexafluorophosphate. Any solvents may be used as the solvent unless they react under the reaction condition of the Step. Specifically, the same solvents as used in the method via acid halide, or aprotic polar solvents such as N,N-dimethylformamide, N,N-dimethylacetamide, N-methyl-2-pyrrolidinone, 1,3-dimethyl-2-imidazolidinone, dimethyl sulfoxide, water, or a mixed solvent thereof may be used. Any bases may be used as the base without limitations, but for example, the base includes organic bases such as triethylamine, diisopropylethylamine, tributylamine, 1,5-diazabicyclo[4.3.0]non-5-ene (DBN), 1,4-diazabicyclo[2.2.2]octane (DABCO), 1,8-diazabicyclo[5.4.0]undec-7-ene (DBU), pyridine, dimethylaminopyridine, picoline or N-methylmorpholine (NMM). The reaction is usually carried out in the range of $-10°$ C. to reflux temperature. The reaction time mainly varies according to conditions such as reaction temperatures, starting materials used, and solvents, but is usually between 0.5 hours and 48 hours.

In the above-mentioned preparations, any functional groups other than reaction sites may be converted under the above-mentioned reaction condition, or in case that it is inappropriate to carry out the above method, such groups other than reaction sites may be protected to react, and sequentially, deprotected to give the desired compound. A conventional protective group described in the above Protective Groups in Organic Synthesis, etc. may be used as the protective group, and specifically, the protective group of amine includes ethoxycarbonyl, t-butoxycarbonyl, acetyl, or benzyl, etc., and the protective group of hydroxyl includes tri-lower alkylsilyl, acetyl, or benzyl, etc.

The introduction and removal of the protective group may be carried out in accordance with the conventional method (e.g., Protective Groups in Organic Synthesis).

The intermediates or final products in the above preparations may be optionally converted in their functional groups to introduce other compounds encompassed in the present invention. The conversions of functional groups may be carried out by conventional methods (e.g., see R. C. Larock, Comprehensive Organic Transformations (1989), etc.).

The intermediates and desired compound in the above each preparation may be isolated and purified by the conventional purification methods in the organic synthetic chemistry, for example neutralization, filtration, extraction, washing, drying, concentration, recrystallization, each type of chromatography. The intermediates may be also used in the next reaction without any specific purification.

The optical isomers may be separated by carrying out known separation steps, including the method using an optically active column, fractionated crystallization, in an appropriate step in the above preparations. An optical isomer may be used as a starting material.

When the compound of the present invention may also exist in the form of an optical isomer, stereoisomer, tautomer such as keto-enol, and/or geometric isomer, the present invention encompasses all possible isomers including these isomers and a mixture thereof.

The starting materials and intermediates in the above preparations may be known compounds or synthesized by the known methods with known compounds.

In the compound of the present invention, configurations of two substituent groups on the adamantane are defined as the following Z- or E-relative configuration (see; C. D. Jones, M. Kaselj, et al., J. Org. Chem. 63:2758-2760, 1998).

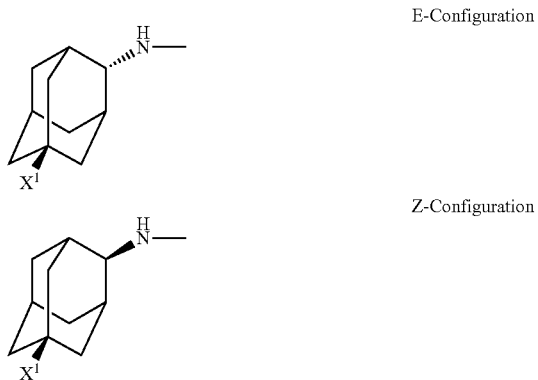

The present invention encompasses a compound of formula (1) or a prodrug thereof, or a pharmaceutically acceptable salt thereof. The present invention also encompasses its solvate such as hydrate or ethanolate. The present invention also encompasses every crystalline form.

The wording "a prodrug of a compound of formula (1)" used herein means a compound which is converted into a compound of formula (1) in the living body by reaction by enzymes or gastric acid under physiological conditions, namely, a compound which is converted into a compound of formula (1) by oxidization, reduction, hydrolysis, etc. enzymatically, or by hydrolysis by gastric acid.

The "pharmaceutically acceptable salt" includes alkali metal salt such as potassium salt or sodium salt, alkaline-earth metal salt such as calcium salt or magnesium salt, water-soluble amine addition salt such as ammonium, N-methyl glucamine (megulmine), or lower alkanol ammonium salt of organic amines, and hydrochloride, hydrobromide, hydroiodide, nitrate, sulfate, hydrogen sulfate, phosphate, acetate, lactate, citrate, tartrate, hydrogen tartrate, succinate, maleate, fumarate, gluconate, saccharate, benzoate, methanesulfonate, ethanesulfonate, benzenesulfonate, para-toluenesulfonate, or a salt with pamoate [1,1'-methylene-bis-(2-hydroxy-3-naphthoate)].

When a salt of the compound of the present invention is desired, a salt form of the compound of the present invention may be directly purified, and a free form thereof may be dissolved or suspended in an appropriate organic solvent with the addition of acids or bases in conventional manners to form its salt.

The compound of the present invention and a pharmaceutically acceptable salt thereof may exist in the form of adduct with water or each type of solvent, and the adduct is also encompassed in the present invention. Further, the present invention encompasses every tautomers, every stereoisomers existed, and every crystalline form of the compound of the present invention.

The compound of the present invention is useful as a therapeutic agent for preventing and/or treating diseases such as type II diabetes, dyslipidemia, hyperglycemia, insulin resistance, hypo HDL-emia, hyper LDL-emia, abnormality of lipid metabolism, hyperlipidemia, hypertriglyceridemia, hypercholesterolemia, hypertension, arteriosclerosis, cerebral arteriosclerosis, angiostenosis, atherosclerosis, obesity, osteoporosis, immunological disorder, metabolic syndrome, cardiovascular disease, Cushing's syndrome, subclinical Cushing's syndrome, NASH (non-alcoholic), NAFLD (non-alcoholic fatty liver), glaucoma, retinopathy, dementia, cognitive disorder, depression, anxiety, manic depression, neurodegenerative disease, Alzheimer's dementia, cerebrovascular dementia, dementia with Lewy bodies, Pick disease, Creutzfeldt-Jakob disease, Kraepelin disease, Parkinson disease, Huntington's disease, Hallervorden-Spats disease, spinocerebellar degeneration, progressive myoclonus epilepsy, progressive supranuclear palsy, myxedema, parathyroid disorder, Wilson's disease, liver disease, hypoglycemia, remote symptom of cancer, uremia, chronic cerebral circulatory insufficiency, cerebral hemorrhage, cerebral infarction, cerebral embolism, subarachnoid hemorrhage, chronic subdural hemorrhage, pseudobulbar paralysis, aortic arch syndrome, Binswanger disease, arteriovenous malformation-thromboangiitis arterits, hypoxia, anoxia, normal pressure hydrocephalus, Wernicke-Korsakoff syndrome, pellagra, Marchiafava-Bignami disease, vitamin B12 deficiency, brain tumor, open and closed head trauma, Banti's syndrome, fever attack, infection disease, bacterial meningitis, fungal meningitis, encephalitis, progressive multifocal leukoencephalopathy, Behcet syndrome, Kuru, lues, multiple sclerosis, muscular dystrophy, Whipple disease, camp syndrome, disseminated lupus erythematosus, cardiac arrest, human immunodeficiency virus encephalopathy, hypothyroidism, hypopituitarism, dementia accompanied by chronic alcoholic intoxication; disorders by metal, organic compounds, carbon monoxide, toxic substances or drugs; cognitive disorders wherein behavioral and psychological symptoms are accompanied or peripheral symptoms, depressive disorder, bipolar disorder, major depressive disorder, dysthymic disorder, seasonal affective disorder, anxiety disorder, phobia, panic disorder, obsessive-compulsive disorder, posttraumatic stress disorder, acute stress disorder, agoraphobia, social phobia, avoidant personality disorder, psychosomatic disorder, depression or anxiety conditions associated with other diseases (including schizophrenia, dementia), neurogenic anorexia, disturbed eating behavior, sleep disorders, schizophrenia, drug dependency, cluster headache, migraine, chronic paroxysmal hemicrania, headache related to angiopathy, dementia of Parkinson disease, dysphoria, anxiety, neuroleptic drug-induced Parkinson syndrome and Parkinson disease including tardive dyskinesia.

When the compound of the present invention is used in the therapy, it may be administered orally or parenterally (e.g., intravenously, subcutaneously or intramuscularly, locally, rectally, percutaneously, or transnasally) in the form of a pharmaceutical composition. The composition for oral administration includes, for example, tablets, capsules, pills, granules, powders, solutions, suspensions, etc. The composition for parenteral administration includes, for example, aqueous solutions for injection, or oils, ointments, creams, lotions, aerosols, suppositories, adhesive preparations, etc. These preparations may be prepared by a conventional known method, and may contain a nontoxic and inactive carrier or excipient that is usually used in the pharmaceutical field.

The dosage may vary depending on diseases, ages, administration routes, etc., and for example, it is preferable that in the oral administration, the compound may be administered depending on the conditions in a single unit or several units in the range of 0.01 mg (preferably, 1 mg) as a lower limit to 5000 mg (preferably, 500 mg) as a upper limit per a day for adults. In the intravenous administration, it is effective for the compound to be administered depending on the conditions in a single unit or several units in the range of 0.01 mg (preferably, 0.1 mg) as a lower limit to 1000 mg (preferably, 30 mg) as an upper limit per a day for adults.

Aiming at the enhancement of the pharmacological activity, the compound of the present invention may be used in combination with a medicament such as an antidiabetic agent, a therapeutic agent for diabetic complications, an antilipidemic agent, a hypotensive agent, an antiobesity agent, a diuretic agent (hereinafter referred to as combined medicine). The administration timing of the compound of the present invention and a combined medicine is not necessarily limited, and they may be administered to a subject simultaneously or administered with time-interval. In addition, the compound of the present invention and a combined medicine may be used in the form of a combination drug. The dosage of a combined medicine may be optionally selected based on the dosage in the clinical use. In addition, the mixing ratio of the present compound and a combined medicine may be optionally determined depending on the subject to be administered, the administration route, the disease to be treated, the conditions of a patient, and a kind of combination. For example, when the subject to be administered is human, then a combined medicine may be used in an amount of 0.01 to 100 parts for weight of one part of the compound of the present invention.

The antidiabetic agent includes insulin formulations (e.g., animal insulin formulations extracted from the bovine pancreas or swine pancreas; genetically-engineered human insulin formulations using *Escherichia coli* or yeast, etc.), improving agents of insulin resistance (e.g., pioglitazone or a hydrochloride salt thereof, troglitazon, rosiglitazone or a maleate salt thereof, GI-262570, JTT-501, MCC-555, YM-440, KRP-297, CS-011, etc.), α-glucosidase inhibitors (e.g., voglibose, acarbose, miglitol, emiglitate, etc.), biguanides (e.g., metformine, etc.), insulin secretagogues (e.g., sulfonylureas such as tolbutamide, glibenclamide, gliclazide, chlorpropamide, tolazamide, acetohexamide, glyclopyramide, glimepiride, etc.; repaglinide, senaglinide, nateglinide, mitiglinide, etc.), dipeptidyl peptase-IV (DPP-IV) inhibitors (e.g., sitagliptin or a phosphate thereof, vildagliptin, alogliptin or a benzoate thereof, denagliptin or a tosylate thereof, etc.), GLP-1, GLP-1 analogues (exenatide, liraglutide, SUN-E7001, AVE010, BIM-51077, CJC1131, etc.), protein tyrosine phosphatase inhibitors (e.g., vanadic acid, etc.), β3 agonists (e.g., GW-427353B, N-5984, etc.).

The therapeutic agent for diabetic complications includes aldose reductase inhibitors (e.g., tolrestat, epalrestat, zenarestat, zopolrestat, minarestat, fidarestat, ranirestat, SK-860, CT-112, etc.), neurotrophic factors (e.g., NGF, NT-3, BDNF, etc.), PKC inhibitors (e.g., LY-333531, etc.), AGE inhibitors (e.g., ALT946, pimagedine, pyratoxatin, N-phenacylthiazolium bromide (ALT766), etc.), active oxygen scavengers (e.g., thioctic acid, etc.), cerebral vasodilators (e.g., tiapride, mexiletine, etc.). The antilipidemic agent includes HMG-CoA reductase inhibitors (e.g., pravastatin, simvastatin, lovastatin, atorvastatin, fluvastatin, itavastatin or a sodium salt thereof, etc.), squalene synthetase inhibitors, ACAT inhibitors, etc. The hypotensive agent includes angiotensin-converting enzyme inhibitors (e.g., captopril, enalapril, alacepril, delapril, lisinopril, imidapril, benazepril, cilazapril, temocapril, trandolapril, etc.), angiotensin II antagonists (e.g., olmesartan medoxomil, candesartan cilexetil, losartan, eprosartan, valsartan, telmisartan, irbesartan, tasosartan, etc.), calcium antagonists (e.g., nicardipine hydrochloride, manidipine hydrochloride, nisoldipine, nitrendipine, nilvadipine, amlodipine, etc.).

The antiobesity agent includes, for example, central antiobesity drugs (e.g., phentermine, sibutramine, amfepramone, dexamphetamine, Mazindol, SR-141716A, etc.), pancreatic lipase inhibitors (e.g., Orlistat, etc.), peptidic anorexiants (e.g., leptin, CNTF (ciliary neurotrophic factor), etc.), cholecystokinin agonists (e.g., lintitript, FPL-15849, etc.). The diuretic agent includes, for example, xanthine derivatives (e.g., theobromine sodium salicylate, theobromine calcium salicylate. etc.), thiazide preparations (e.g., ethiazide, cyclopenthiazide, trichloromethiazide, hydrochlorothiazide, hydroflumethiazide, bentylhydrochlorothiazide, penflutizide, polythiazide, methychlothiazide, etc.), antialdosterone preparations (e.g., spironolactone, triamterene, etc.), carbonic anhydrase inhibitors (e.g., acetazolamide, etc.), chlorbenzenesulfonamide preparations (e.g., chlorthalidone, mefruside, indapamide, etc.), azosemide, isosorbide, ethacrynic acid, piretanide, bumetanide, furosemide, etc.

The combined medicine is preferably GLP-1, GLP-1 analog, α-glucosidase inhibitor, biguanide preparation, insulin secretagogue, insulin resistance-improving agent, DPP-IV inhibitor, etc. The above combined medicines may be optionally used in combination with two or more of them in optional ratios.

When the present compound is used in combination with a combined medicine, the dosage of these drugs can be lessened within the safe range in view of the side effects of the drugs. For example, the use of biguanides may reduce the dosage compared to the usual dosage. Accordingly, any possible side effects caused by these drugs may be safely inhibited. In addition, the dosage of a therapeutic agent for diabetic complications, antihyperlipidemic agent, antihypertensive drug, etc. may be also reduced, and hence, any possible side effects caused by these drugs may be effectively inhibited.

Aiming at the enhancement of the pharmacological activity, the compound of the present invention or a pharmaceutically acceptable salt thereof may be also used in combination with a medicament (hereinafter referred to as combined medicine) such as antidepressant agent, anti-anxiety agent, a therapeutic agent for schizophrenia, a hypnotic pill, a dopamine receptor agonist, a therapeutic agent for Parkinson disease, an antiepileptic drug, an anticonvulsant agent, an analgesic agent, a hormonal preparation, a therapeutic agent for migraine, an adrenergic β receptor antagonist, a therapeutic agent for mood disorder, an acetylcholinesterase inhibitor, NMDA receptor antagonist, COX-2 inhibitor, PPARγ agonist, LTB4 antagonist, muscarine M1 receptor agonist, AMPA receptor antagonist, nicotine receptor agonist, 5-HT4 receptor agonist, 5-HT6 receptor antagonist, PDE4 inhibitor, Aβ aggregation inhibitor, BACE inhibitor, γ secretase inhibitor or modulator, GSK-3β inhibitor, NGF receptor agonist, Aβ antibody, human immunoglobulin, Aβ vaccine, a neuroprotective agent, Dimebon.

The administration timing of the compound of the present invention and a combined medicine is not necessarily limited, and they may be administered to a subject simultaneously or administered with time-interval. In addition, the compound of the present invention and a combined medicine may be used in the form of a combination drug. The dosage of a combined medicine may be optionally selected based on the dosage in the clinical use. In addition, the mixing ratio of the compound of the present invention and a combined medicine may be optionally determined depending on the subject to be administered, the administration route, the disease to be treated, the conditions of a patient, and a kind of combination. For example, when the subject to be administered is human, then a combined medicine may be used in an amount of 0.01 to 100 parts for weight of one part of the compound of the present invention. For the purpose of inhibiting its side effects, it may be also used in combination with drugs (combined medicines) such as an antiemetic drug, a hypnotic pill, an anticonvulsant agent.

EXAMPLES

The present invention is illustrated in more detail by Reference Examples, Examples and Experiments as below, but the present invention is not intended to be limited thereto. In addition, compound names used in the following Reference Examples and Examples are not necessarily based on IUPAC nomenclature.

The following abbreviations may be used in the Examples and Reference Examples.
THF: tetrahydrofuran
NaBH(OAc)$_3$: sodium triacetoxyborohydride
(Boc)$_2$O: di-tert-butyldicarbonate
DMF: N,N-dimethylformamide
DIAD: diisopropyl azodicarboxylate
Me: methyl
Et: ethyl
Bu: butyl
Ph: phenyl
Bn: benzyl
Ms: methylsulfonyl
Ac: acetyl
Boc: tert-butoxycarbonyl
Cbz or Z: benzyloxycarbonyl
Tf: trifluoromethanesulfonyl
N: normal (e.g., 2N HCl means 2 normal hydrochloric acid)
M: mol concentration (mol/L) (e.g., 2M methylamine means 2 mol/L methylamine solution)
atm: atmosphere pressure
Pr: propyl
i-: iso
n-: normal
t- or tert-: tertiary
MeOH: methanol
MeCN: acetonitrile
NMP: N-methylpyrrolidinone
TFA: trifluoroacetic acid
DBU: 1,8-diazabicyclo[5.4.0]undec-7-ene
MPa: magapascal
tR: retention time
Obs [M+1]: observed protonated molecules
NaOH: sodium hydroxide
DMA: N,N-dimethylacetamide
dba: dibenzylideneacetone
LC/MS analytic conditions for identifying compounds are as follows.
Measurement method SA1:
Detection instrument: API 150EX LC/MS mass spectrometer (Applied Biosystems)
HPLC: Agilent 1100 for API series
Column: YMC CombiSA3reen ODS-A (S-5 μm, 12 nm, 4.6×50 mm)
Solvent: Solution A: 0.05% TFA/H$_2$O, Solution B: 0.035% TFA/MeCN
Gradient condition: 0.0-1.0 min A 75%, 1.0-4.7 min Linear gradient from A 75% to 1%, 4.7-5.7 min A 1%, 5.7-6.1 min Linear gradient from A 1% to 75%, 6.1-7.1 min Linear gradient from A 75% to 100%, 7.1-7.2 min A 100%
Flow rate: 3.5 mL/min
UV: 220 nm
Measurement method SA2:
Detection instrument: API 150EX LC/MS mass spectrometer (Applied Biosystems)
HPLC: Agilent 1100 for API series
Column: YMC CombiSA3reen ODS-A (S-5 μm, 12 nm, 4.6×50 mm)
Solvent: Solution A: 0.05% TFA/H$_2$O, Solution B: 0.035% TFA/MeCN
Gradient condition: 0.0-1.0 min A 60%, 1.0-4.7 min Linear gradient from A 60% to 1%, 4.7-5.7 min A 1%, 5.7-6.1 min Linear gradient from A 1% to 60%, 6.1-7.1 min Linear gradient from A 60% to 100%, 7.1-7.2 min A 100%
Flow rate: 3.5 mL/min
UV: 220 nm
Measurement method SA3:
Detection instrument: ACQUITY SQ deteceter (Waters)
HPLC: ACQUITY SQ deteceter (Waters)
Column: Waters ACQUITY HPLC BEH C18 (1.7 um, 2.1 mm×50 mm)
Solvent: Solution A: 0.05% HCO$_2$H/H$_2$O, Solution B: 0.05% HCO$_2$H/MeOH
Gradient condition: 0.0-1.3 min Linear gradient from A 75% to 1%
Flow rate: 0.75 mL/min
UV: 220 nm
Measurement method SA4:
Detection instrument: LCMS-2010EV <Shimadzu Corporation>
Column: Weltch Xtimate C18 (2.1 um, 30 mm×3 um)
Solvent: Solution A: 0.05% TFA/H$_2$O, Solution B: 0.05% TFA/MeCN
Gradient condition: 0.0-2.25 min Linear gradient from A 90% to 20%
Flow rate: 0.8 mL/min
UV: 220 nm Reference Example 1

(E)-4-amino-1-adamantanecarboxamide

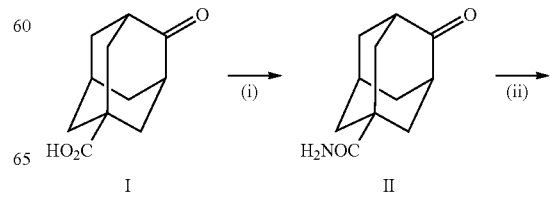

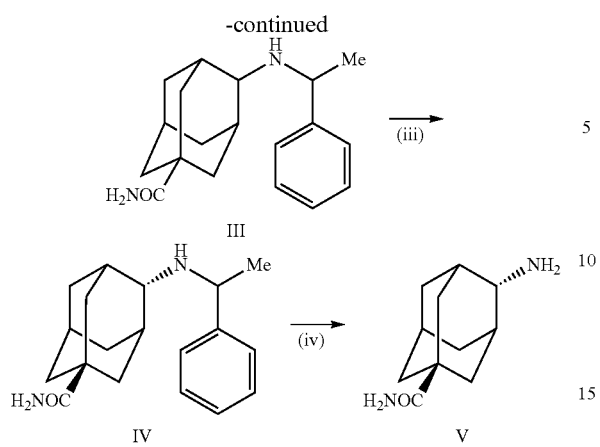

Step (i):

To a mixture of 1,1'-carbonyldiimidazole (70 g) and THF (170 mL) was added dropwise a mixed solution of Compound I (70 g) in THF (250 mL) at room temperature. After the addition was completed, the mixture was stirred at 50° C. for 3 hours. The reaction solution was let stand to cool and added dropwise to ice-cold ammonia water (200 mL). The mixture was stirred at room temperature for 30 minutes, and then the reaction mixture was concentrated under reduced pressure. To the ice-cold residue was added concentrated hydrochloric acid (80 mL), and the mixture was adjusted to pH 1 to 2. Under ice cooling, the mixture was stirred for 15-20 minutes, and the resulted solid was filtered, washed with 1N hydrochloric acid (50 mL), and dried under reduced pressure. To the filtrate was added sodium chloride, and the mixture was adjusted to a saturated solution and extracted with chloroform (250 mL, five times). The organic layer was dried over magnesium sulfate, filtered, concentrated, and dried to give a solid. The solid was combined with the filtered solid to give Compound II (133.4 g).

Step (ii):

To a mixture of ice-cold Compound II (60 g) and dichloromethane (1500 ml) was added (S)-phenylethylamine (39.4 g). The mixture was stirred for 10 minutes, and then thereto was added NaBH(OAc)$_3$ (101 g), and the reaction mixture was allowed to warm up to room temperature and was stirred overnight. To the ice-cold reaction mixture were added water (150 mL) and 2N NaOH (300 mL), and the mixture was adjusted to around pH 9-10. The mixed solution was filtered through Celite, and the cake was washed with chloroform (200 mL). The filtrate was separated and extracted with chloroform. The organic layer was dried over sodium sulfate, filtered and concentrated to give Compound III (133 g, E/Z=about 2.6/1).

Step (iii):

Compound III (1311 g) obtained in Step (ii) was purified by silica gel column chromatography (eluent: chloroform/methanol=100/1 to 10/1) to give Compound IV (618 g).

Step (iv):

Compound IV (618 g), 10% palladium-carbon (122 g, 50% wet) and methanol (15 L) were stirred at room temperature for 74 hours under hydrogen air (4-5 kg/cm$^2$). The reaction mixture was filtered through Celite, and the cake was washed with methanol (10 L, twice). The filtrate was concentrated to give the title compound V (371.8 g) as a solid.

$^1$H-NMR (DMSO-d$_6$) δ1.27 (m, 2H), 1.65-1.85 (m, 9H), 1.99 (m, 2H), 2.70 (br, 2H), 2.82 (brs, 1H), 6.66 (brs, 1H), 6.93 (brs, 1H)

Reference Example 2 tert-Butyl (3-endo)-3-(benzyloxy)-8-azabicyclo[3.2.1]octane-8-carboxylate

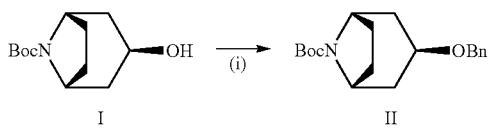

Step (i):

Compound I (4.23 g) was dissolved in DMF (100 mL), and thereto were added benzyl bromide (3.32 mL) and sodium hydride (1.62 g), and the mixture was stirred at room temperature overnight. To the reaction mixture was added water, and the mixture was extracted with diisopropylether. The organic layer was dried over sodium sulfate, and then concentrated under reduced pressure. The residue was purified by silica gel column chromatography (eluent: hexane/ethyl acetate=3/1) to give the title compound II (4.98 g).

$^1$H-NMR (CDCl$_3$) δ1.47 (s, 9H), 1.93-2.05 (m, 6H), 2.13-2.19 (m, 2H), 3.72 (m, 1H), 4.12-4.26 (m, 2H), 4.49-4.50 (m, 2H), 7.26-7.30 (m, 1H), 7.32-7.41 (m, 4H)

Reference Example 3 tert-Butyl (3-endo)-3-phenoxy-8-azabicyclo[3.2.1]octane-8-carboxylate

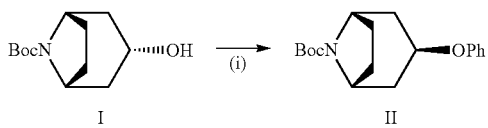

Step (i):

Compound I (490.6 mg) was dissolved in THF (4 mL), and then thereto were added DIAD (0.66 mL), triphenylphosphine (869 mg) and phenol (312 mg), and the mixture was stirred at room temperature overnight. The reaction mixture was concentrated under reduced pressure, and the residue was diluted with ethyl acetate and washed with 1N aqueous sodium hydroxide solution and brine. The organic layer was dried over sodium sulfate, and then concentrated under reduced pressure. The residue was purified by silica gel column chromatography (eluent: hexane/ethyl acetate=9/1) to give the title compound II (451 mg).

$^1$H-NMR (CDCl$_3$) δ1.48 (s, 9H), 1.96-2.16 (m, 7H), 2.33-2.35 (m, 1H), 4.23 (m, 2H), 4.62-4.63 (m, 1H), 6.82-6.84 (m, 2H), 6.91-6.95 (m, 1H), 7.25-7.30 (m, 2H)

Reference Example 4 tert-Butyl (3-endo)-3-(phenylsulfonyl)-8-azabicyclo[3.2.1]octane-8-carboxylate

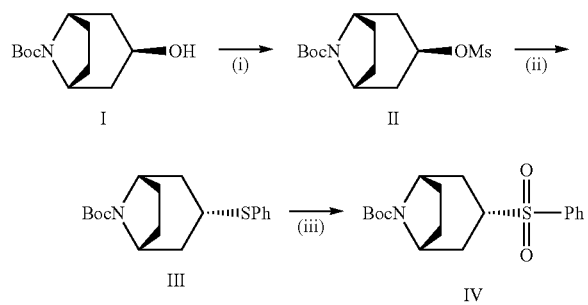

Step (i):

Compound I (13.4 g) was dissolved in dichloromethane (600 mL), and then thereto were added methanesulfonyl chloride (5.63 mL) and triethylamine (20.3 mL), and the mixture was stirred at room temperature overnight. The reaction mixture was diluted with saturated aqueous ammonium chloride solution, and extracted with chloroform. The organic layer was dried over sodium sulfate, and then concentrated under reduced pressure. The residue was purified by silica gel column chromatography (eluent: hexane/ethyl acetate=4/1) to give Compound II (15.4 g).

Step (ii):

Compound II (1.2 g) was dissolved in DMF (20 mL), and then thereto were added benzenethiol (0.43 mL) and sodium hydride (183 mg), and the mixture was stirred at 60° C. for 4 hours. The reaction mixture was diluted with brine and extracted with diisopropylether. The organic layer was dried over sodium sulfate, and then concentrated under reduced pressure. The residue was purified by silica gel column chromatography (eluent: hexane/ethyl acetate=6/1) to give Compound III (1.09 g).

$^1$H-NMR (CDCl$_3$) δ1.42 (s, 9H), 1.57-1.64 (m, 3H), 1.83-1.95 (m, 5H), 3.40-3.48 (m, 1H), 4.14-4.25 (m, 2H), 7.24-7.31 (m, 3H), 7.41-7.43 (m, 2H)

Step (iii):

Compound III (36.7 mg) was dissolved in dichloromethane (2 mL), and then thereto was added meta-chloroperbenzoic acid (39 mg), and the mixture was stirred at room temperature overnight. The reaction mixture was diluted with sodium bicarbonate water, and extracted with chloroform. The organic layer was dried over sodium sulfate, and then concentrated under reduced pressure. The residue was purified by silica gel column chromatography (eluent: hexane/ethyl acetate=1/1) to give the title compound IV (30 mg).

$^1$H-NMR (CDCl$_3$) δ1.38 (m, 9H), 1.53-1.61 (m, 2H), 1.73-2.05 (m, 6H), 3.37-3.46 (m, 1H), 4.23-4.30 (m, 2H), 7.55-7.59 (m, 2H), 7.64-7.69 (m, 1H), 7.84-7.86 (m, 2H)

Reference Example 5 tert-Butyl (3-exo)-3-[benzyl(methyl)amino]-8-azabicyclo[3.2.1]octane-8-carboxylate

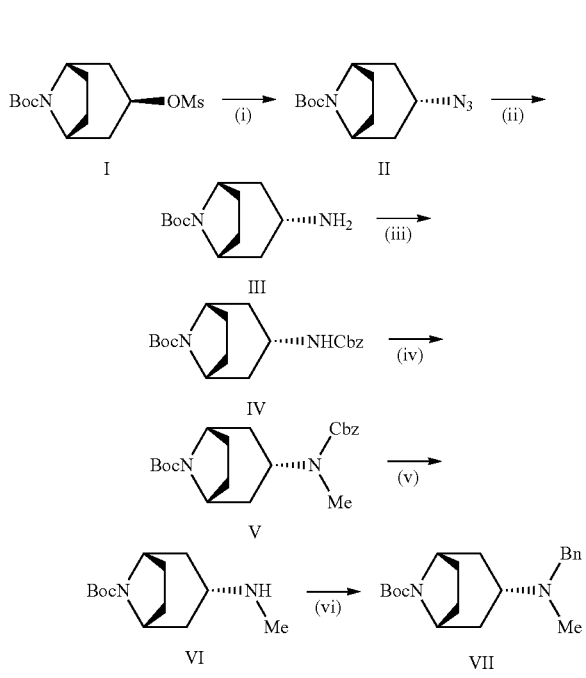

Step (i):

Compound I (48.28 g) was dissolved in DMF (500 mL), and then thereto was added sodium azide (15.4 g), and the mixture was stirred at 55° C. overnight. The reaction mixture was diluted with brine, and extracted with ethyl acetate. The organic layer was dried over sodium sulfate, and then concentrated under reduced pressure to give Compound II (30 g) as a crude product.

Step (ii):

Compound II (30 g) was dissolved in methanol (300 mL), and then thereto was added 10%-palladium carbon (3 g, 50% wet), and the mixture was stirred overnight under hydrogen atmosphere (1 atm). The reaction mixture was filtered through Celite, and then concentrated under reduced pressure to give Compound III (30 g) as a crude product.

$^1$H-NMR (CDCl$_3$) δ1.46 (s, 9H), 1.48-1.64 (m, 5H), 1.85-1.96 (m, 4H), 4.22-4.29 (m, 2H)

Step (iii):

Compound III (10 g) was dissolved in chloroform/water (volume ratio 1:1, 100 mL), and then thereto were added sodium hydrogen carbonate (5.6 g) and benzyl chloroformate (7.17 mL), and the mixture was stirred at room temperature overnight. The reaction mixture was diluted with water, and extracted with chloroform. The organic layer was dried over sodium sulfate, and then concentrated under reduced pressure. The residue was purified by silica gel column chromatography (eluent: hexane/ethyl acetate=2/1) to give Compound IV (6.71 g).

Step (iv):

Compound IV (6.71 g) was dissolved in DMF (60 mL), and then thereto were added methyl iodide (1.4 mL) and sodium hydride (973 mg), and the mixture was stirred at room temperature overnight. The reaction mixture was diluted with water, and extracted with diisopropylether. The organic layer was dried over sodium sulfate, and then concentrated under reduced pressure. The residue was purified by silica gel column chromatography (eluent: hexane/ethyl acetate=2/1) to give Compound V (6.00 g).

Step (v):

Compound V (1.09 g) was dissolved in methanol (10 mL), and thereto was added 10%-palladium/carbon (300 mg, 50% wet), and the mixture was stirred overnigh under hydrogen atmosphere (1 atm). The reaction mixture was filtered on Celite, and the filtrate was concentrated under reduced pressure to give Compound VI (900 mg) as a crude product.

Step (vi):

Compound VI (504 mg) was dissovled in methanol (10 mL), and thereto were added benzaldehyde (0.32 mL) and acetic acid (10 μL), and the mixture was stirred for one hour. To the ice-cold mixture was added NaBH(OAc)$_3$ (664 mg), and then the mixture was stirred overnight at room temperature. The reaction mixture was concentrated under reduced pressure, and the residue was diluted with brine, and extracted with ethyl acetate. The organic layer was dried over sodium sulfate, and concentrated under reduced pressure. The residue was purified by silica gel column chromatography (eluent: hexane/ethyl acetate=1/1) to give the title compound VII (403 mg).

$^1$H-NMR (CDCl$_3$) δ 1.49 (s, 9H), 1.53-1.61 (m, 2H), 1.72-1.73 (m, 4H), 1.92-1.95 (m, 3H), 2.18 (s, 3H), 3.53 (s, 2H), 4.22-4.32 (m, 2H), 7.29-7.35 (m, 5H)

Reference Example 6

(3-Endo)-3-phenyl-8-azabicyclo[3.2.1]octane hydrochloride

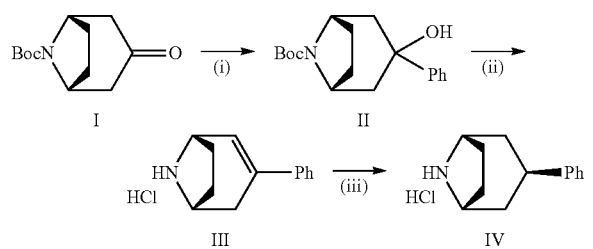

Step (i):

Compound I (2.8 g) was dissolved in THF (200 mL), and thereto was added phenyllithium (23 mL, 1.15 M solution in cyclohexane-diethyl ether) at −78° C., and then the mixture was allowed to warm up to room temperature and was stirred overnight. The reaction mixture was diluted with water and 1N hydrochloric acid, and extracted with ethyl acetate. The organic layer was dried over sodium sulfate, and concentrated under reduced pressure. The residue was purified by silica gel column chromatography (eluent: hexane/ethyl acetate=2/1) to give Compound II (2.52 g).

Step (ii):

Compound II (2.52 g) was dissolved in 4N hydrochloric acid/dioxane, and the mixture was stirred overnight. The reaction mixture was concentrated under reduced pressure to give Compound III (2.6 g) as a crude product.

Step (iii):

Compound III (2.6 g) was dissolved in methanol (100 mL), and thereto was added 10%-palladium/carbon (500 mg, 50% wet), and stirred overnight under hydrogen atmosphere (4 atm). The reaction mixture was filtered through Celite, and washed with chloroform. The filtrate was concentrated under reduced pressure to give the title compound IV (2.51 g).

$^1$H-NMR (CDCl$_3$) δ1.77-1.98 (m, 4H), 2.22 (m, 2H), 2.43-2.52 (m, 1H), 3.31-3.48 (m, 1H), 4.14 (m, 1H), 4.40 (m, 1H), 7.21 (m, 1H), 7.31-7.38 (m, 4H), 10.41-10.6 (m, 1H)

Reference Example 7 tert-Butyl (3-endo)-3-(2-pyridinyl)-8-azabicyclo [3.2.1]octane-8-carboxylate

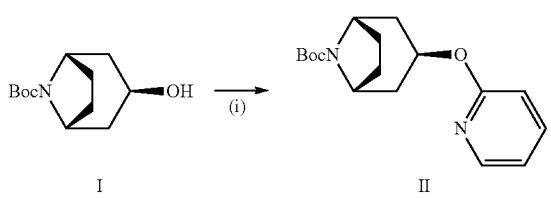

Step (i):

Compound I (606.6 mg) was dissolved in DMF (10 mL), and thereto were added 2-chloropyridine (0.4 mL) and sodium hydride (178 mg), and then the mixture was stirred at 50° C. overnight. The reaction mixture was diluted with brine, and extracted with ethyl acetate. The organic layer was dried over sodium sulfate, and concentrated under reduced pressure. The residue was purified by silica gel column chromatography (eluent: hexane/ethyl acetate=2/1) to give the title compound II (456.8 mg).

$^1$H-NMR (CDCl$_3$) δ1.47 (s, 9H), 1.90-1.97 (m, 4H), 2.02-2.20 (m, 4H), 4.09-4.25 (m, 2H), 5.34-5.37 (m, 1H), 6.68 (d, J=8 Hz, 1H), 6.81-6.84 (m, 1H), 7.53-7.58 (m, 1H), 8.12-8.13 (m, 1H)

Reference Example 8 tert-Butyl (3-exo)-3-(4-pyridinyl)-8-azabicyclo [3.2.1]octane-8-carboxylate

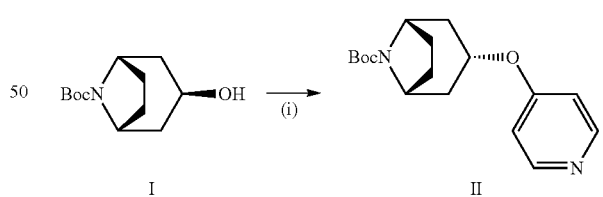

Step (i):

Compound I (453 mg) was dissolved in THF (4 mL), and thereto were added DIAD (0.61 mL), triphenylphosphine (802 mg), and 4-hydroxypyridine (291 mg), and the mixture was stirred at room temperature overnight. The reaction mixture was concentrated under reduced pressure, diluted with ethyl acetate, and washed with 1N aqueous sodium hydroxide solution and brine. The organic layer was dried over sodium sulfate and concentrated under reduced pressure. The residue was purified by silica gel column chromatography (eluent: hexane/ethyl acetate=9/1) to give the title compound II (43.4 mg).

$^1$H-NMR (CDCl$_3$) δ1.22 (d, J=8 Hz, 2H), 1.45 (s, 9H), 1.68-1.70 (m, 2H), 2.05 (m, 4H), 4.25-4.33 (m, 2H), 4.71-4.79 (m, 1H), 6.74-6.75 (m, 2H), 8.36-8.38 (m, 2H)

Reference Example 9 tert-Butyl (3-endo)-3-(4-cyanophenyl)-8-azabicyclo[3.2.1]octane-8-carboxylate

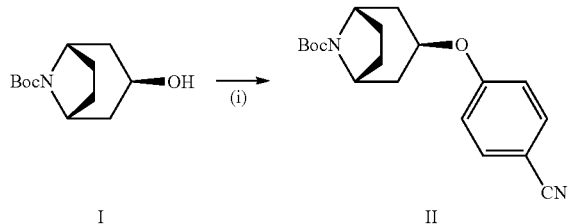

Step (i):

Compound I (2.03 g) was dissolved with DMF (20 mL), and thereto were added potassium tert-butoxide (1.2 g) and 4-cyanofluorobenzene (1.3 g), and the mixture was stirred at room temperature for one hour. The reaction mixture was diluted with water, and thereto was added 1N hydrochloric acid, and the mixture was extracted with ethyl acetate. The organic layer was dried over sodium sulfate, and concentrated under reduced pressure. The residue was purified by silica gel column chromatography (eluent: hexane/ethyl acetate=4/1) to give the title compound II (2.96 g).

$^1$H-NMR (CDCl$_3$) δ1.47 (s, 9H), 1.91 (s, 1H), 1.95-1.99 (m, 3H), 2.04-2.07 (m, 3H), 2.20 (m, 1H), 4.18-4.25 (m, 2H), 4.67-4.69 (m, 1H), 6.86 (d, J=8 Hz, 2H), 7.58 (d, J=8 Hz, 2H)

Reference Example 10

3-(3-Pyridinyl)-8-azabicyclo[3.2.1]octane hydrochloride

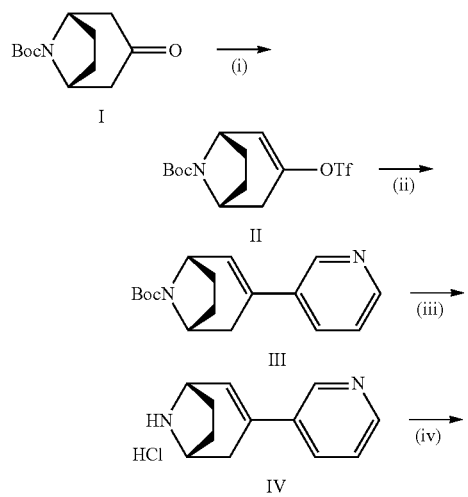

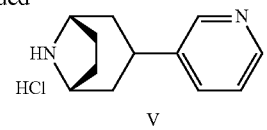

Step (i):

Compound I (2.02 g) was dissolved with THF (40 mL), and thereto was added lithium bis(trimethylsilyl)amide (11 mL, 1.02M solution in hexane) at −78° C., and the mixture was stirred for one hour. To the mixture was added N-phenyl (bistrifluoromethanesulfonimide) (3.84 g), and then the mixture was allowed to warm up to room temperature and was stirred overnight. To the reaction mixture was added a saturated aqueous ammonium chloride solution, and the mixture was extracted with ethyl acetate. The organic layer was dried over sodium sulfate, and concentrated under reduced pressure to give Compound II (7.0 g) as a crude product.

Step (ii):

Compound II (1.22 g) obtained in Step (i) was dissolved in ethylene glycol/water (20 mL, volume ratio 1:1), and thereto were added tetrakistriphenylphosphinepalladium (200 mg), 3-pyridylboronic acid (251 mg), and sodium carbonate (723 mg), and the resulting mixture was refluxed with heating for 3 hours. The reaction mixture was concentrated under reduced pressure, and to the residue was added brine, and the mixture was extracted with ethyl acetate. The organic layer was dried over sodium sulfate, and concentrated under reduced pressure. The residue was purified by silica gel column chromatography (eluent: hexane/ethyl acetate=1/1) to give Compound III (332.7 mg).

Step (iii):

To Compound III (252 mg) was added 4N hydrochloric acid/dioxane (20 mL), and the mixture was stirred overnight. The reaction mixture was concentrated under reduced pressure to give Compound IV (246 mg) as a crude product.

Step (iv):

Compound IV (246 mg) was dissolved in methanol (4 mL), and thereto was added 10%-palladium/carbon (20 mg, 50% wet), and the mixture was stirred overnight under hydrogen atmosphere (1 atm). The reaction mixture was filtered through Celite, and washed with chloroform. The filtrate was concentrated under reduced pressure to give the title compound V (230 mg).

$^1$H-NMR (CDCl$_3$) δ2.03-2.10 (m, 1H), 2.22-2.30 (m, 1H), 2.35-2.46 (m, 2H), 2.17-2.18 (m, 1H), 3.30-3.31 (m, 4H), 4.40-4.43 (m, 1H), 4.49-4.52 (m, 1H), 6.85 (m, 1H), 8.12 (m, 1H), 8.76-8.83 (m, 2H), 9.02 (s, 1H)

Reference Example 11 tert-Butyl-(3-endo)-3-methoxy-8-azabicyclo[3.2.1]octane-8-carboxylate

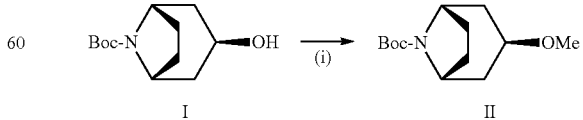

Step (i):

To a solution of the ice-cold Compound I (4.0 g) in dimethylformamide (88 mL) was added sodium hydride (1.25 g), and subsequently, thereto was added dropwise methane iodide (2.2 mL). After the addition was completed, the mixture was stirred at room temperature for 6 hours. The reaction mixture was poured into a saturated aqueous ammonium chloride solution, and extracted with ethyl acetate. The organic layer was dehydrated with sodium sulfate, and concentrated under reduced pressure. The residue was purified by silica gel column chromatography (eluent: hexane/ethyl acetate=100/0 to 75/25) to give the title compound II (3.8 g).

$^1$H-NMR (CDCl$_3$) δ1.41 (s, 9H), 1.78-2.00 (m, 8H), 3.23 (s, 3H), 3.43 (s, 1H), 4.06-4.12 (m, 2H)

Reference Example 12

(3-Endo)-3-benzyl-8-azabicyclo[3.2.1]octane

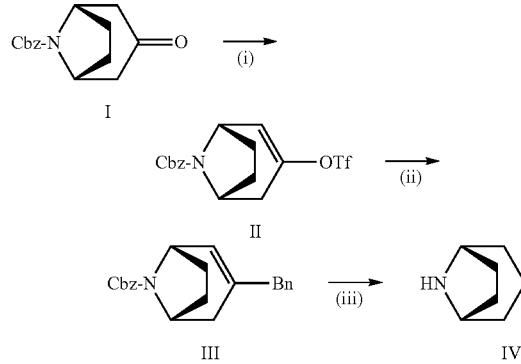

Step (i):

To a solution of Compound I (500 mg) in THF (19 mL) at −70° C. was added dropwise lithium hexamethyldisilazide (1M toluene solution, 2.1 mL). The mixture was stirred for 30 minutes, and thereto was added N-phenyltrifluorosulfonimide (830 mg), and then the mixture was allowed to warm up to room temperature and was stirred overnight. The reaction mixture was diluted with ethyl acetate, and washed with brine, dehydrated with sodium sulfate, and concentrated under reduced pressure to give Compound II (1.46 g) as a crude product.

Step (ii):

To a solution of Compound II (1.46 g) obtained in Step (i) in THF (13 mL) were added benzylzinc bromide (0.5M THF solution, 7.7 mL) and tetrakistriphenylphosphinepalladium (400 mg), and the mixture was stirred at room temperature overnight. To the reaction mixture was added water, and filtered through Celite, and washed with ethyl acetate. The filtrate was washed with brine, dehydrated with sodium sulfate, and concentrated under reduced pressure. The residue was purified by silica gel column chromatography (eluent: hexane/ethyl acetate=100/0 to 75/25) to give Compound III (406 mg).

Step (iii):

A solution of Compound III (406 mg) and 10%-palladium/carbon (260 mg, 50% wet) in THF (12 mL) was stirred overnight under hydrogen atmosphere (1 atm). The reaction mixture was filtered through Celite, and concentrated under reduced pressure. To residue was added water, and the mixture was extracted with chloroform. The organic layer was dehydrated with sodium sulfate, and concentrated under reduced pressure to give the title compound IV (41 mg).

$^1$H NMR (CDCl$_3$) δ1.31-1.34 (m, 2H), 1.78-2.04 (m, 7H), 2.51 (m, 1H), 2.68 (d, J=8.8 Hz, 2H), 3.47 (m, 2H), 7.11-7.17 (m, 3H), 7.23-7.27 (m, 2H)

Reference Example 13 tert-Butyl (3-endo)-3-hydroxy-8-azabicyclo[3.2.1] octane-8-carboxylate (Compound III) tert-Butyl (3-exo)-3-hydroxy-8-azabicyclo[3.2.1]octane-8-carboxylate (Compound IV)

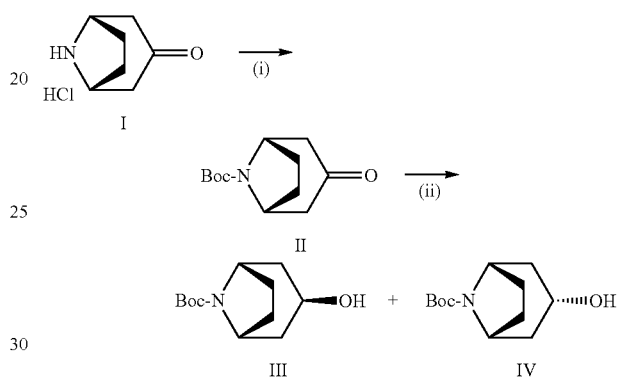

Step (i):

To a mixture of the ice-cold nortropinone hydrochloride (80.3 g), sodium hydroxide (40 g) and water (400 mL) was added dropwise a solution of (Boc)$_2$O (109 g) in tetrahydrofuran (240 ml). After the addition was completed, the resulting mixture was allowed to warm up to room temperature and was stirred for one hour, and the obtained solid was collected by filtration. The filtrate was extracted with ethyl acetate, and the organic layer was washed with brine, dried over sodium sulfate, and filtered. The filtrate was concentrated under reduced pressure, and to the obtained residue was added hexane, and the obtained solid was collected by filtration. Thus obtained solids were combined, and dried to give Compound II (60.3 g).

Step (ii):

An ice-cold mixture of Compound II (3.0 g), calcium chloride (1.78 g) and methanol (66 mL) was stirred for 30 minutes, and thereto was added portionwise sodium borohydride. The mixture was stirred for one hour, and water was added to the reaction mixture, and concentrated under reduced pressure. The residue was extracted with ethyl acetate, and the organic layer was washed with brine. The organic layer was dried over sodium sulfate, and concentrated under reduced pressure. The residue was purified by silica gel column chromatography (eluent: hexane/ethyl acetate=80/20 to 40/60) to give the title compound III (840 mg) and the title compound IV (2.0 g).

Compound III $^1$H NMR (CDCl$_3$) δ1.43 (s, 9H), 1.53 (m, 1H), 1.66-1.69 (m, 2H), 1.89-2.15 (m, 6H), 4.01-4.18 (m, 3H)

Compound IV

¹H NMR (CDCl₃) δ1.45 (s, 9H), 1.52-1.61 (m, 5H), 1.91-2.1.96 (m, 4H), 4.04-4.12 (m, 1H), 4.21 (m, 2H)

Reference Example 14 tert-Butyl (3-exo)-3-[methyl(phenyl)amino]-8-azabicyclo[3.2.1]octane-8-carboxylate

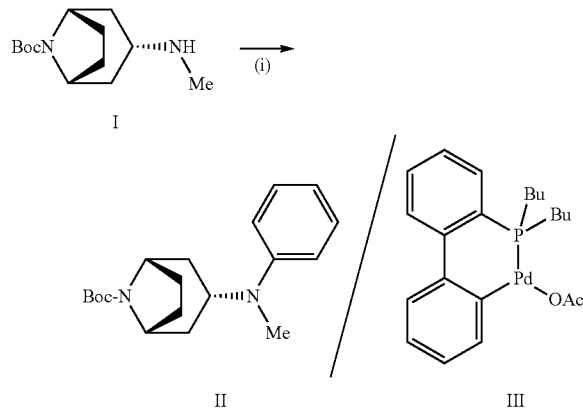

Step (i):

Compound I (155 mg; Compound VI in Reference Example 5) was dissolved in toluene (10 mL), and thereto were added bromobenzene (0.14 mL), sodium t-butoxide (93 mg), and Compound III (30 mg), and the resulting mixture was stirred at 90° C. overnight. After the reaction was completed, the mixture was filtered through Celite, and the filtrate was concentrated under reduced pressure. The residue was diluted with brine, and extracted with ethyl acetate. The organic layer was dried over sodium sulfate, and concentrated under reduced pressure. The residue was purified by silica gel column chromatography (eluent: hexane/ethyl acetate=5/1) to give the title compound II (170 mg).

¹H-NMR (CDCl₃) δ1.48 (s, 9H), 1.60-1.64 (m, 2H), 1.72-1.74 (m, 2H), 2.03 (m, 4H), 2.69 (s, 3H), 4.16-4.32 (m, 3H), 6.68-6.71 (m, 1H), 6.75-6.78 (m, 2H), 7.19-7.23 (m, 2H)

Reference Example 15 tert-Butyl (1R,5S)-3-(1-phenoxyethyl)-8-azabicyclo[3.2.1]octane-8-carboxylate

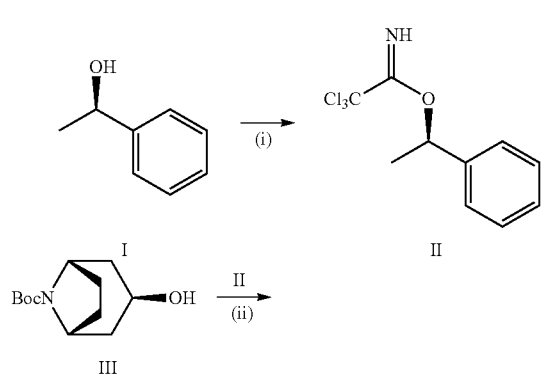

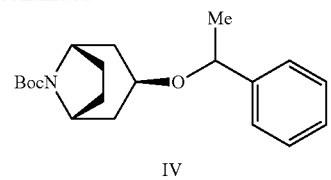

Step (i):

To a mixture of Compound I (2 mL) and cyclohexane/dichloromethane (volume ratio 4:1, 50 mL) were added trichloroacetonitrile (2.5 mL) and DBU (25 µL), and the resulting mixture was stirred at room temperature overnight. To the reaction mixture was added water, and the mixture was extracted with ethyl acetate. The organic layer was dried over sodium sulfate, and concentrated under reduced pressure. The residue was purified by silica gel column chromatography (eluent: hexane/ethyl acetate=10/1) to give Compound II (1.03 g).

Step (ii):

To a mixture of Compound III (660 mg) and heptane (20 mL), which was cooled with a freezing mixture (a mixture of ice and sodium chloride) were added Compound II (1.16 g) and HBF₄ (25 mg), and then the mixture was allowed to warm up to room temperature and was stirred overnight. To the reaction mixture was added brine, and extracted with ethyl acetate. The organic layer was dried over sodium sulfate, and concentrated under reduced pressure. The residue was purified by silica gel column chromatography (eluent: hexane/ethyl acetate=6/1) to give the title compound IV (382 mg).

¹H-NMR (CDCl₃) δ1.37 (d, J=8 Hz, 3H), 1.42 (s, 9H), 1.60 (m, 1H), 1.70 (m, 1H), 1.88-1.92 (m, 4H), 2.14-2.18 (m, 2H), 3.50 (m, 1H), 4.06-4.18 (m, 2H), 4.47 (q, J=8 Hz, 1H), 7.21-7.40 (m, 5H)

Reference Example 16 tert-Butyl (3-endo)-3-[(4-ethyl-2-pyridinyl)oxy]-8-azabicyclo[3.2.1]octane-8-carboxylate

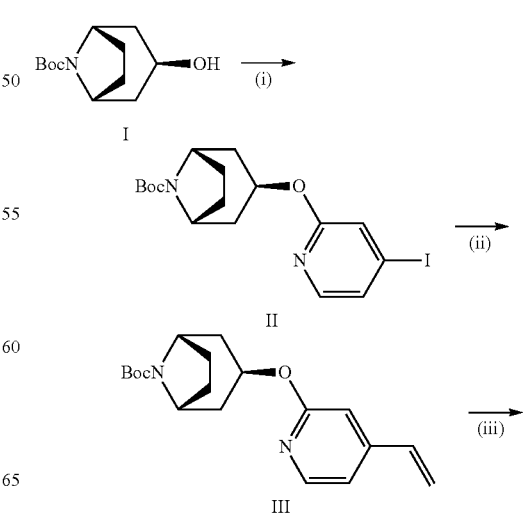

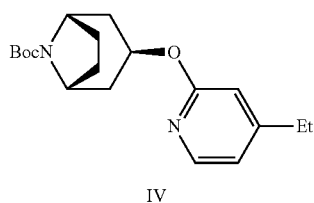

Step (i):

To a mixture of Compound I (2.38 g) and THF (24 mL) were added sodium hydride (685 mg) and 2-chloro4-iodopyridine (3.01 g), and the resulting mixture was heated at reflux and stirred overnight. To the reaction mixture was added water, and the mixture was diluted with brine, and extracted with ethyl acetate. The organic layer was diluted with sodium sulfate, and concentrated under reduced pressure. The residue was purified by silica gel column chromatography (eluent: hexane/ethyl acetate=9/1) to give Compound II (3.0 g).

Step (ii):

To a mixture of Compound II (745 mg) and ethylene glycol/water (volume ratio 2:1, 15 mL) were added sodium carbonate (381 mg), tetrakistriphenylphosphinepalladium (40 mg) and vinyl boronic acid pinacol ester (0.3 mL), and the mixture was stirred at 80° C. overnight. The reaction mixture was filtered through Celite, and the cake was washed with toluene. The filtrate was concentrated under reduced pressure, and the residue was purified by silica gel column chromatography (eluent: hexane/ethyl acetate=10/1) to give Compound III (700 mg).

Step (iii):

To Compound III (700 mg) were added methanol (10 mL) and 10% palladium/carbon-50% wet (50 mg), and the mixture was stirred overnight under hydrogen atmosphere (ordinary pressure). The reaction mixture was filtered through Celite, and the cake was washed with toluene. The filtrate was concentrated under reduced pressure to give the title compound IV (680 mg).

$^1$H-NMR (CDCl$_3$) δ1.22 (t, J=8 Hz, 3H), 1.46 (s, 9H), 1.89-1.97 (m, 2H), 2.10-2.18 (m, 2H), 2.58 (q, J=8 Hz, 2H), 4.12-4.24 (m, 2H), 5.33 (m, 1H), 6.51 (m, 1H), 6.69 (m, 1H), 8.00 (d, J=4 Hz, 1H)

Reference Example 17 tert-Butyl (3-endo)-3-[(4-isopropyl-2-pyridinyl)oxy]-8-azabicyclo[3.2.1]octane-8-carboxylate

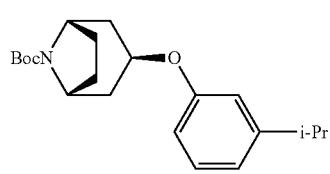 [SMILES: CC(C)c1cccc(O[C@H]2C[C@H]3CC[C@@H](C2)N3C(=O)OC(C)(C)C)c1]

In a similar manner to Reference Example 16, the title compound was synthesized from Compound II and isopropenyl boronic acid pinacol ester.

tR=5.27 min, Measurement method SA2, Obs[M+1] 346

Reference Example 18 tert-Butyl (1R,5S)-3-(phenoxymethyl)-8-azabicyclo[3.2.1]octane-8-carboxylate

Step (i):

To a mixture of the ice-cold Compound I (726.8 mg) and THF (14 mL) were added a solution of bistrimethylsilyllithium amide in hexane (1.02 mol/L, 4.5 mL) and (methoxymethyl)triphenylphosphonium chloride (1.44 g), and then the mixture was allowed to warm up to room temperature and was stirred overnight. To the reaction mixture was added water, and diluted with brine, and extracted with ethyl acetate. The organic layer was diluted with sodium sulfate, and concentrated under reduced pressure. The residue was purified by silica gel column chromatography (eluent: hexane/ethyl acetate=6/1) to give Compound II (230 mg).

Step (ii):

Compound II (230 mg) was added into a 4N hydrochloric acid/dioxane (3 mL), and the mixture was stirred at room temperature for one hour. The reaction solution was concentrated, and thereto were added THF/water (1:1, 4 mL), potassium carbonate (125 mg) and di-t-butyl dicarbonate (198 mg), and the resulting mixture was stirred overnight. The reaction mixture was diluted with brine, and extracted with ethyl acetate. The organic layer was dried over sodium sulfate, and concentrated under reduced pressure. The residue was purified by silica gel column chromatography (eluent: hexane/ethyl acetate=2/1) to give Compound III (168.6 mg).

Step (iii):

To Compound III (168.6 mg) were added methanol (10 mL) and sodium borohydride (15 mg), and the mixture was stirred overnight. To the reaction mixture was added water, and the mixture was concentrated. The resultant was diluted with brine and extracted with ethyl acetate. The organic layer was dried over sodium sulfate, and concentrated under reduced pressure. The residue was purified by silica gel column chromatography (eluent: hexane/ethyl acetate=3/2) to give Compound IV (135.4 mg).

Step (iv):

To Compound IV (135.4 mg) were added THF (10 mL), phenol (79 mg), triphenylphosphine (221 mg) and diisopropyl azodicarboxylate (0.17 mL), and the resulting mixture was stirred overnight. The reaction mixture was concentrated under reduced pressure, diluted with ethyl acetate, and washed with 1N aqueous sodium hydroxide solution and brine. The organic layer was dried over sodium sulfate, and concentrated under reduced pressure. The residue was purified by silica gel column chromatography (eluent: hexane/ethyl acetate=6/1) to give the title compound V (141.6 mg).

$^1$H-NMR (CDCl$_3$) δ1.48 (s, 9H), 1.64-1.71 (m, 6H), 1.98-1.99 (m, 2H), 2.36 (m, 1H), 3.74 (m, 2H), 4.26 (m, 2H), 6.84-6.95 (m, 4H), 7.21-7.35 (m, 1H)

Reference Example 19 tert-Butyl-(3-endo)-3-[(6-methoxy-2-pyridinyl)oxy]-8-azabicyclo[3.2.1]octane-8-carboxylate

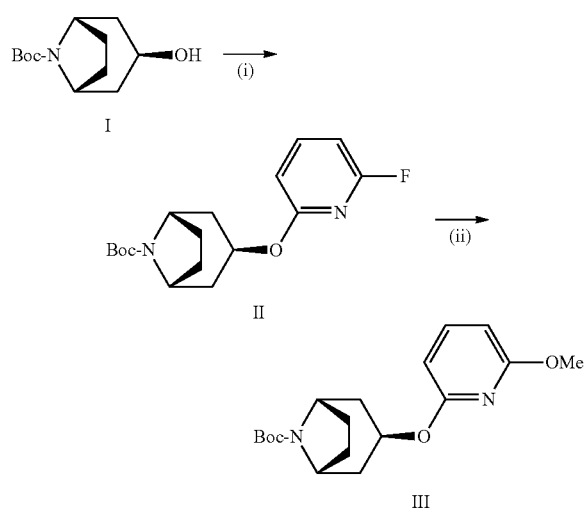

Step (i):

To a solution of Compound I (500 mg) in THF:DMF (volume ratio 1:1, 14 mL) were added sodium hydride (144 mg) and 2,6-difluoropyridine (399 µL), and the mixture was stirred at 80° C. overnight. The reaction mixture was diluted with water, and extracted with ethyl acetate. The organic layer was washed with brine, and dehydrated with sodium sulfate, and then concentrated under reduced pressure. The residue was purified by silica gel column chromatography (eluent: hexane/ethyl acetate=100/0 to 80/20) to give Compound II (695 mg).

Step (ii):

To a solution of Compound II (150 mg) in MeOH:DMF (volume ratio 1:1, 2 mL) was added sodium hydride (80 mg), and the mixture was stirred at 80° C. overnight. The reaction mixture was diluted with water, and extracted with ethyl acetate. The organic layer was washed with brine, and dehydrated with sodium sulfate, and then concentrated under reduced pressure. The residue was purified by silica gel column chromatography (eluent: hexane/ethyl acetate=100/0 to 80/20) to give the title compound III (136 mg).

$^1$H-NMR (CDCl$_3$) δ1.46 (s, 9H), 1.92-1.95 (m, 4H), 2.11-2.13 (m, 4H), 3.83 (s, 3H), 4.13-4.22 (m, 2H), 5.31 (t, J=4.8 Hz, 1H), 6.24 (dd, J=4.8 Hz, 8.0 Hz, 2H), 7.45 (t, J=8.0 Hz, 1H)

Reference Example 20 tert-Butyl (1R,5S)-3-(2-pyridinyl)-8-azabicyclo[3.2.1]octane-8-carboxylate

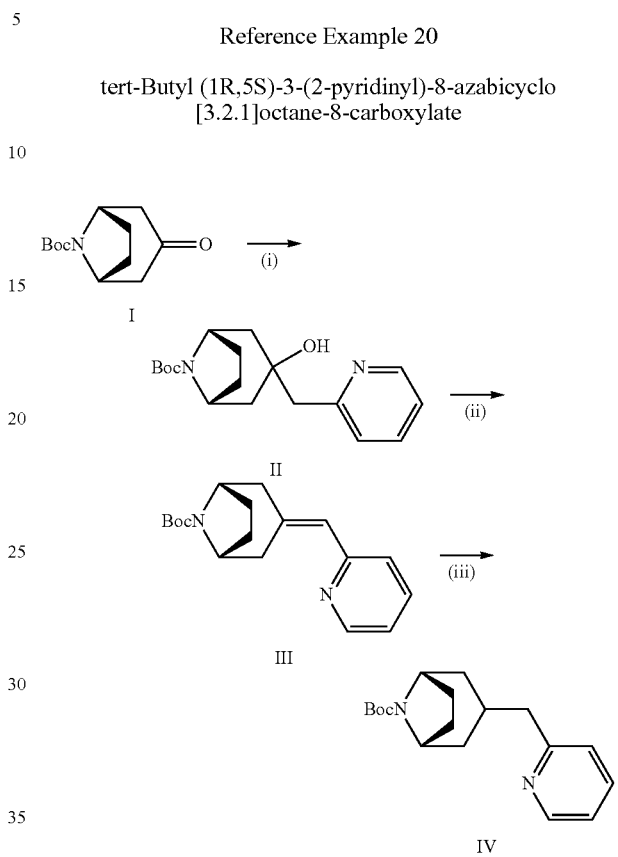

Step (i):

To a solution of 2-picoline (0.7 mL) in THF (10 mL) at −78° C. was added n-butyl lithium (5.1 mL, 1.6M hexane solution), and the resulting mixture was stirred for one hour. To the mixture was added Compound I (1.07 g), and then the mixture was allowed to warm up to room temperature and was stirred overnight. The reaction mixture was diluted with brine, and extracted with ethyl acetate, dehydrated with sodium sulfate, and concentrated under reduced pressure. The residue was purified by silica gel column chromatography (eluent: hexane/ethyl acetate=1/2) to give Compound II (687 mg).

Step (ii):

To a solution of Compound II (500 mg) in 1,2-dichloroethane (10 mL) were added methanesulfonyl chloride (0.3 mL) and triethylamine (0.8 mL), and the mixture was heated at reflux and stirred overnight. The reaction mixture was diluted with brine, extracted with chloroform, dehydrated with sodium sulfate, and concentrated under reduced pressure. The residue was purified by silica gel column chromatography (eluent: hexane/ethyl acetate=2/1) to give Compound III (200 mg).

Step (iii):

To Compound III (200 mg) were added methanol (10 mL) and 10% palladium/carbon-50% wet (50 mg), and the resulting mixture was stirred overnight under hydrogen atmosphere (ordinaryl pressure). The reaction mixture was filtered through Celite, and the cake was washed with toluene. The filtrate was concentrated under reduced pressure to give the title compound IV (130 mg).

¹H-NMR (CDCl₃) δ1.43 (s, 9H), 1.58-1.67 (m, 4H), 1.78-2.03 (m, 4H), 2.62 (m, 1H), 4.10-4.20 (m, 4H), 7.05-7.11 (m, 2H), 7.53-7.60 (m, 1H), 8.50-8.52 (m, 1H)

Reference Example 21 tert-Butyl (3-endo)-3-(phenylthio)-8-azabicyclo[3.2.1]octane-8-carboxylate

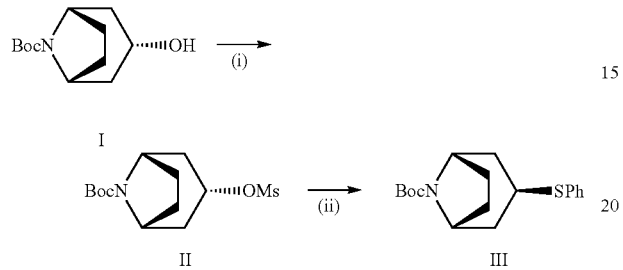

Step (i):

To an ice-cold solution of Compound I (6.02 g) in dichloromethane (30 mL) were added triethylamine (10 mL), methanesulfonyl chloride (2.7 mL), and then the mixture was allowed to warm up to room temperature and was stirred overnight. The reaction mixture was diluted with brine, extracted with ethyl acetate, dehydrated with sodium sulfate, and concentrated under reduced pressure. The residue was purified by silica gel column chromatography (eluent: hexane/ethyl acetate=1/1) to give Compound II (7.5 g).

Step (ii):

Compound II (508 mg) was dissolved in DMF (5 mL), and thereto were added sodium hydride (159 mg) and thiophenol (0.24 mL), and the resulting mixture was stirred at 80° C. overnight. The reaction mixture was diluted with brine, extracted with ethyl acetate, dehydrated with sodium sulfate, and concentrated under reduced pressure. The residue was purified by silica gel column chromatography (eluent: hexane/ethyl acetate=6/1) to give the title compound III (500 mg).

¹H-NMR (CDCl₃) δ1.44 (s, 9H), 1.79-1.82 (m, 2H), 1.99-2.04 (m, 2H), 2.20-2.35 (m, 4H), 3.63 (s, 1H), 4.16-4.23 (m, 2H), 7.19-7.36 (m, 5H)

Reference Example 22 tert-Butyl (3-endo)-3-[methyl(phenyl)amino]-8-azabicyclo[3.2.1]octane-8-carboxylate

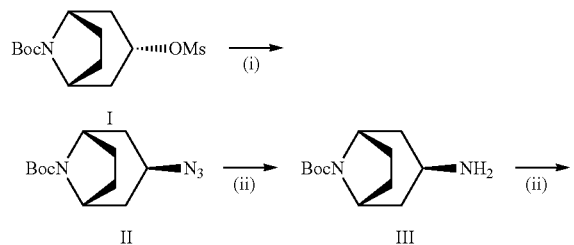

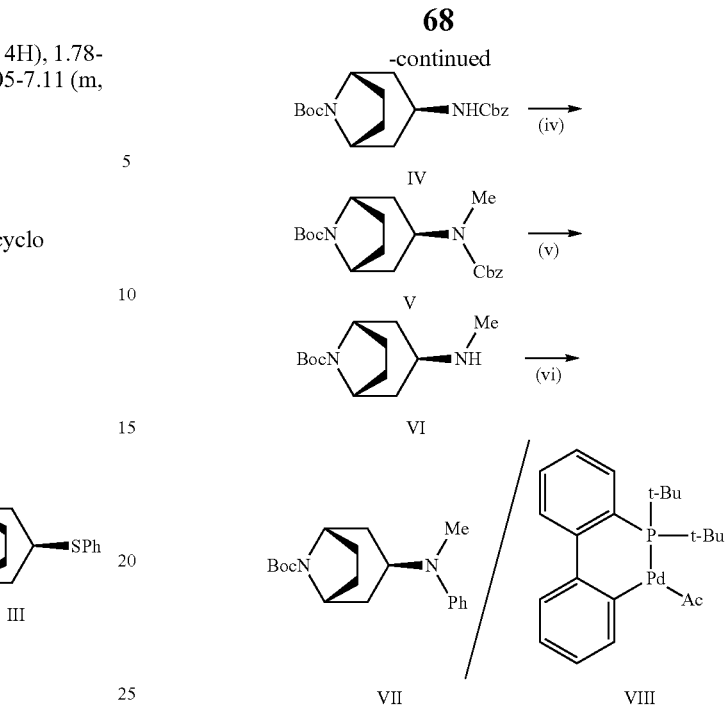

Step (i):

To a solution of Compound I (5.65 g: Compound II in Reference Example 21) in DMF (50 mL) was added sodium azide (1.8 g), and the resulting mixture was stirred at 60° C. for 4 days. To the reaction mixture was added brine, and the mixture was extracted with ethyl acetate. The organic layer was dried over sodium sulfate and concentrated under reduced pressure to give Compound II (4.32 g) as a crude product.

Step (ii):

To a crude Compound II (4.32 g) were added methanol (50 mL) and 10% palladium/carbon-50% wet (500 mg), and the mixture was stirred overnight under hydrogen atmosphere (0.4 MPa). The reaction mixture was filtered through Celite, and the cake was washed with methanol. The filtrate was concentrated under reduced pressure to give the title compound III (4.19 g).

Step (iii):

To a solution of Compound III (2.72 g) in chloroform/water (10 mL/10 mL) were added potassium carbonate (2.49 g) and CbZ-Cl (2 mL), and the mixture was stirred overnight. To the reaction mixture was added brine, and the mixture was extracted with chloroform, dried over sodium sulfate, and concentrated under reduced pressure. The residue was purified by silica gel column chromatography (eluent: hexane/ethyl acetate=1/1) to give Compound IV (4.19 g).

Step (iv):

To a solution of Compound IV (4.19 g) in DMF (40 mL) were added sodium hydride (607 mg) and iodomethane (0.87 mL), and the mixture was stirred overnight. To the reaction mixture was added brine, and the mixture was extracted with ethyl acetate, dried over sodium sulfate, and concentrated under reduced pressure. The residue was purified by silica gel column chromatography (eluent: hexane/ethyl acetate=2/1) to give Compound V (4.40 g).

Step (v):

To Compound V (4.40 g) were added methanol (50 mL) and 10% palladium/carbon-50% wet (500 mg), and the mixture was stirred under hydrogen atmosphere (0.4 MPa) overnight. The reaction mixture was filtered through Celite, and the cake was washed with methanol. The filtrate was concentrated under reduced pressure to give Compound VI (4.40 g).
Step (vi):
To a solution of Compound VI (229 mg) in toluene (4 mL) were added Compound VIII (176 mg), bromobenzene (0.2 mL) and sodium tert-butoxide (137 mg), and the resulting mixture was stirred at 100° C. overnight. To the reaction mixture was added brine, and the mixture was extracted with ethyl acetate, dried over sodium sulfate, and concentrated under reduced pressure. The residue was purified by silica gel column chromatography (eluent: hexane/ethyl acetate=4/1) to give the title compound VII (100 mg).
$^1$H-NMR (CDCl$_3$) δ1.24-1.34 (m, 4H), 1.51 (s, 9H), 1.62-1.79 (m, 4H), 4.17-4.34 (m, 3H), 6.70-6.94 (m, 4H), 7.10-7.24 (m, 4H)

Reference Example 23 tert-Butyl (3-endo)-3-[3-(methoxymethyl)phenoxy]-8-azabicyclo[3.2.1]octane-8-carboxylate

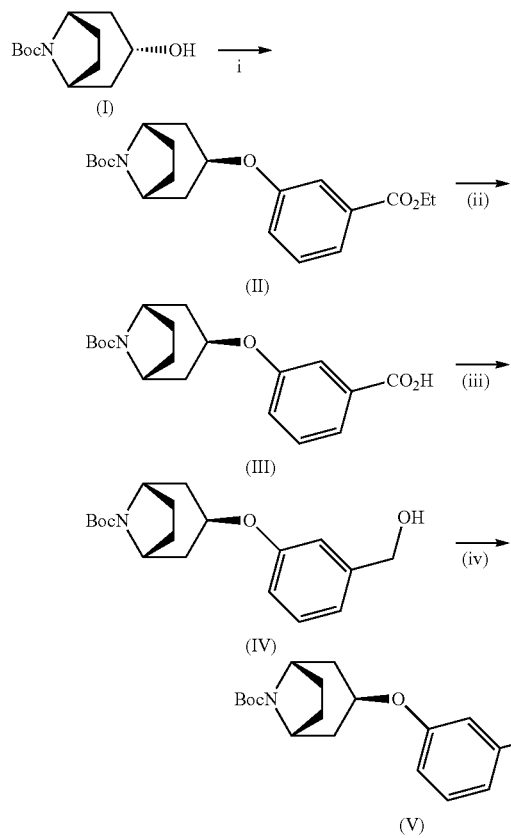

Step (i):
To a solution of Compound I (8.13 g) in toluene (180 mL) were added DIAD (8.7 mL), triphenylphosphine (11.5 mg) and 3-ethoxycarbonylphenol (7.3 g), and the mixture was stirred at room temperature overnight. The reaction mixture was diluted with ethyl acetate, and washed successively with 1N aqueous sodium hydroxide solution, 1N hydrochloric acid, and brine. The organic layer was dried over sodium sulfate, and concentrated under reduced pressure. To the residue was added hexane/diisopropyl ether (volume ratio 4/1, 180 mL), and the precipitated white solid was collected by filtration. The filtrate was concentrated under reduced pressure, and the resultant was purified by silica gel column chromatography (eluent: hexane/ethyl acetate=9/1) to give Compound II (13 g).
Step (ii):
Compound II (13 g) was dissolved in ethanol/water/THF (50 mL/50 mL/10 mL), and thereto was added sodium hydroxide (2.9 g), and the mixture was stirred at room temperature overnight. The reaction mixture was concentrated under reduced pressure. To the ice-cold residue was added 1N hydrochloric acid, and the mixture was diluted with brine and extracted with ethyl acetate. The organic layer was dried over sodium sulfate, and concentrated under reduced pressure to give Compound III (10 g).
Step (iii):
To a solution of Compound III (3.01 g) in THF (30 mL) were added boran-dimethyl sulfide (6.8 mL, 1.9 mol/L solution in THF), and the mixture was stirred at room temperature overnight. To the reaction mixture was added methanol, and the mixture was stirred for 10 minutes, and then, the reaction mixture was concentrated under reduced pressure. To the residue was added brine, and the mixture was extracted with ethyl acetate. The organic layer was dried over sodium sulfat, and concentrated under reduced pressure. The residue was purified by silica gel column chromatography (eluent: hexane/ethyl acetate=4/1) to give Compound IV (2.9 g).
Step (iv):
To a solution of Compound IV (367 mg) in THF (5 mL) were added sodium hydride (96 mg) and iodomethane (140 μL), and the mixture was stirred at room temperature overnight. To the ice-cold reaction mixture was added water, and the mixture was diluted with brine, and extracted with ethyl acetate. The organic layer was dried over sodium sulfat, and concentrated under reduced pressure. The residue was purified by silica gel column chromatography (eluent: hexane/ethyl acetate=4/1) to give the title compound V (290 mg).
$^1$H-NMR (CDCl$_3$) δ1.47 (s, 9H), 1.94-1.97 (m, 4H), 2.13-2.18 (m, 4H), 3.38 (s, 3H), 4.16 (m, 2H), 4.41 (s, 2H), 4.63 (m, 1H), 6.73 (m, 1H), 6.82 (m, 2H), 6.87 (m, 1H), 7.24 (m, 1H)

Reference Example 24 tert-Butyl (3-endo)-3-[(1-phenyl-4-piperidinyl)oxy]-8-azabicyclo[3.2.1]octane-8-carboxylate

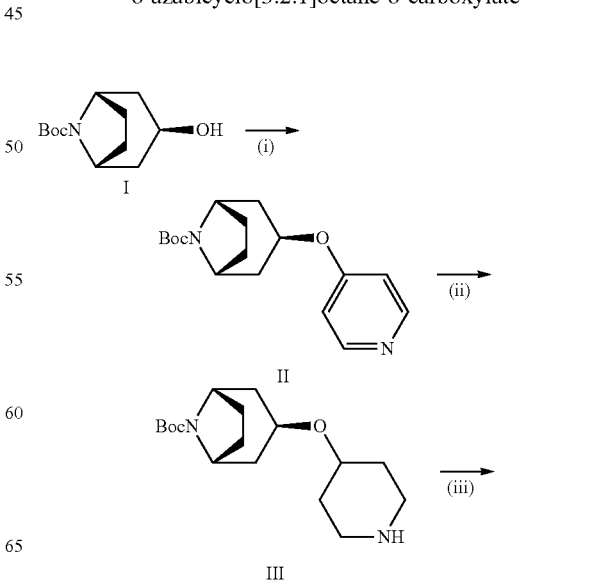

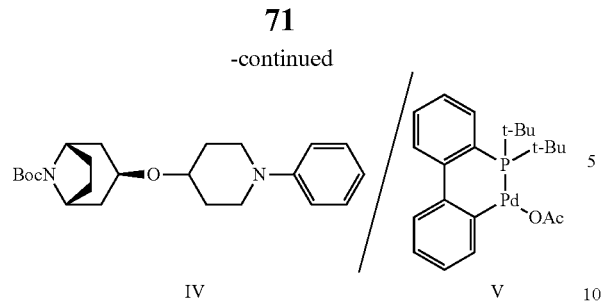

Step (i):

To a solution of Compound I (3.7 g) in DMF (40 mL) were added sodium hydride (2.2 g) and 4-chloropyridine.hydrochloride (3.7 g), and the mixture was stirred at 80° C. overnight. To the mixture was added brine, and the mixture was extracted with ethyl acetate. The organic layer was dried over sodium sulfate, and concentrated under reduced pressure. The residue was purified by silica gel column chromatography (eluent: chloroform/methanol=9/1) to give Compound II (5.40 g).

Step (ii):

To a solution of Compound II (2 g) in acetic acid (20 mL) was added platinum oxide (200 mg), and the mixture was stirred under hydrogen atmosphere (0.4 MPa) for 3 days. The reaction mixture was filtered through Celite, and to the filtrate was added toluene, and the mixture was concentrated under reduced pressure. To the residue was added a saturated sodium bicarbonate water, and the mixture was extracted with chloroform. The organic layer was dried over sodium sulfate, and concentrated under reduced pressure to give a mixture (2.00 g) of Compound III and Compound II.

Step (iii):

To a solution of the mixture (565.8 mg) of Compound III and II obtained in Step (ii) in toluene (5 mL) were added Compound V (84 mg), sodium tert-butoxide (335 mg), and bromobenzene (0.4 mL), and the mixture was stirred at 80° C. overnight. To the mixture was added brine, and the mixture was extracted with ethyl acetate. The organic layer was dried over sodium sulfate, and concentrated under reduced pressure. The residue was purified by silica gel column chromatography (eluent: hexane/ethyl acetate=6/1) to give the title compound IV (81.7 mg).

$^1$H-NMR (CDCl$_3$) δ1.47 (s, 9H), 1.64-2.16 (m, 14H), 2.09-3.07 (m, 2H), 3.39-3.53 (m, 3H), 3.74 (m, 1H), 4.17 (m, 2H), 6.81-6.97 (m, 4H), 7.20 (m, 1H)

Reference Example 25 tert-Butyl (3-endo)-3-{[1-(2-pyridinyl)-4-piperidinyl]oxy}-8-azabicyclo[3.2.1]octane-8-carboxylate

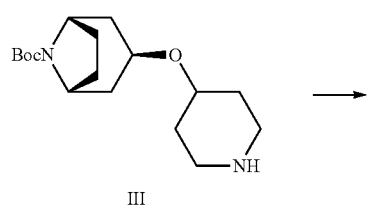

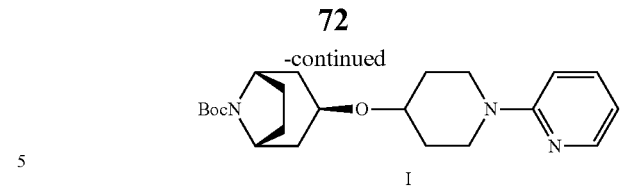

To a solution of the mixture (600 mg) of Compound III and II obtained in Reference Example 24 in NMP (10 mL) were added potassium carbonate (666 mg) and 2-chloropyridine (0.36 mL), and the mixture was stirred at 160° C. overnight. The reaction mixture was concentrated under reduced pressure, and to the residue was added brine, and the mixture was extracted with ethyl acetate. The organic layer was dried over sodium sulfate, and concentrated under reduced pressure. The residue was purified by silica gel column chromatography (eluent: hexane/ethyl acetate=3/1) to give the title compound II (53.3 mg).

$^1$H NMR (CDCl$_3$) δ1.44 (s, 1H), 1.55-1.63 (m, 2H), 1.72-1.94 (m, 8H), 2.09-2.14 (m, 2H), 3.30-3.36 (m, 2H), 3.52-3.57 (m, 1H), 3.73 (m, 1H), 3.77-3.82 (m, 1H), 4.08-4.17 (m, 2H), 6.55 (dd, J=4 Hz, 8 Hz, 1H), 6.64 (d, J=8 Hz, 1H), 7.42 (m, 1H), 8.14 (m, 1H)

Reference Example 26 tert-Butyl (3-endo)-3-[2-(methoxymethyl)phenoxy]-8-azabicyclo[3.2.1]octane-8-carboxylate

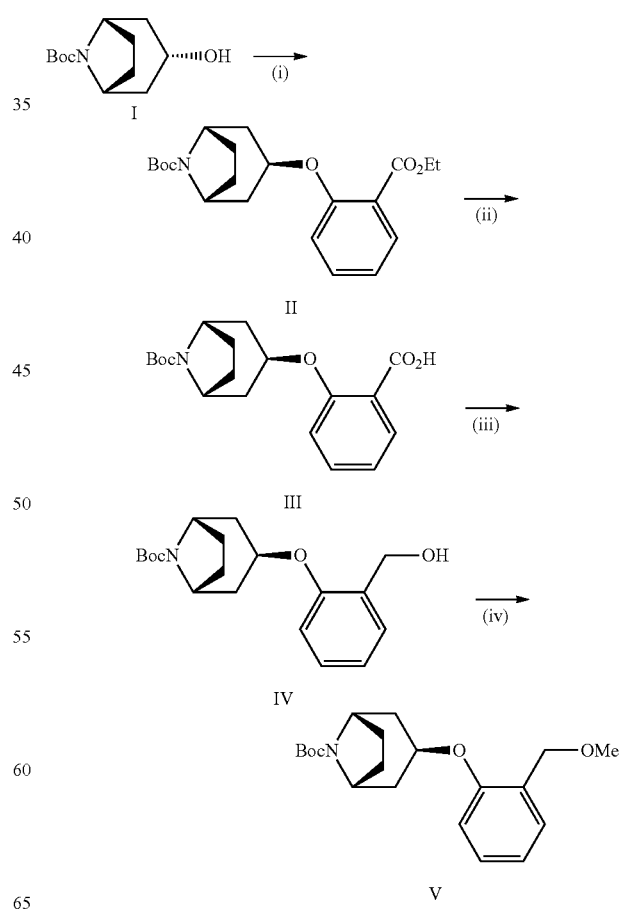

Step (i):

To a mixture of ethyl salicylate (2.8 mL), Compound I (3.46 g), triphenylphosphine (4.9 g) and toluene (78 mL) was added diisopropyl azodicarboxylate (3.7 mL), and the mixture was stirred at room temperature overnight. The reaction solution was washed successively with 1M aqueous sodium hydroxide solution, 1M hydrochloric acid and a saturated brine. The organic layer was dried over sodium sulfate, and concentrated under reduced pressure. The residue was purified by silica gel column chromatography (eluent: hexane/ethyl acetate=6/1) to give Compound II (5.17 g).

Step (ii):

To a mixture of Compound II (5.1 g), methanol (20 mL), tetrahydrofuran (20 mL) and water (20 mL) was added sodium hydroxide (1.1 g), and the mixture was stirred overnight. The reaction solution was concentrated under reduced pressure, and the mixture was acidified with 1M hydrochloric acid, and then extracted with ethyl acetate. The organic layer was dried over sodium sulfate, and concentrated under reduced pressure to give Compound III (5.1 g) as a crude product.

Step (iii):

To an ice-cold solution of crude Compound III (5.1 g) in tetrahydrofuran (50 mL) was added boran-dimethyl sulfide complex (12 mL), and the mixture was stirred at room temperature overnight. To the ice-cold reaction solution was added methanol, and the mixture was concentrated under reduced pressure. The residue was diluted with brine, extracted with ethyl acetate, and the organic layer was dehydrated with sodium sulfate, and then concentrated under reduced pressure. The residue was purified by silica gel column chromatography (eluent: hexane/ethyl acetate=2/1) to give Compound IV (4.18 g).

Step (iv):

To an ice-cold solution of Compound IV (495.8 mg) in tetrahydrofuran (10 mL) were added sodium hydride (130 mg) and iodomethane (0.2 mL), and the mixture was stirred overnight. The reaction mixture was diluted with brine, extracted with ethyl acetate, and the organic layer was dehydrated with sodium sulfate, and further concentrated under reduced pressure. The residue was purified by silica gel column chromatography (eluent: hexane/ethyl acetate=4/1) to give the title compound V (380.8 mg).

$^1$H-NMR (CDCl$_3$) δ 1.48 (s, 9H), 1.99-2.03 (m, 4H), 2.14-2.16 (m, 4H), 3.44 (s, 3H), 4.18-4.26 (m, 2H), 4.50 (s, 2H), 4.64 (t, 1H, J=4.8 Hz), 6.71 (d, 1H, J=8.3 Hz), 6.93 (t, 1H, J=7.4 Hz), 7.23 (td, 1H, J=7.9, 1.5 Hz), 7.37-7.39 (m, 1H)

Reference Example 27 tert-Butyl (3-endo)-3-{[4-(methoxymethyl)pyridin-2-yl]oxy}-8-azabicyclo[3.2.1]octane-8-carboxylate

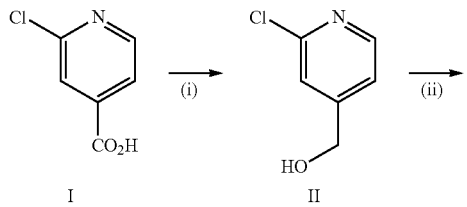

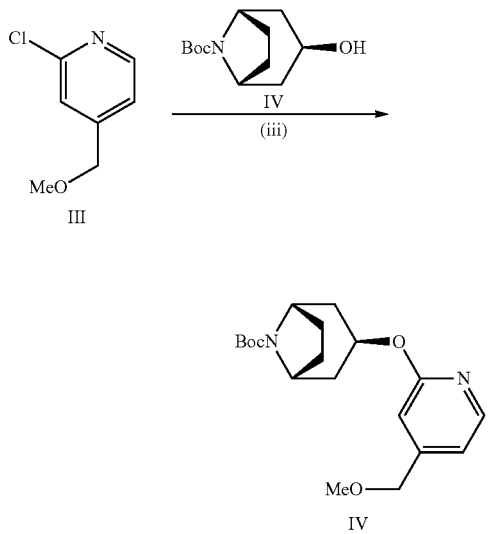

Step (i):

To an ice-cold solution of 2-chloroisonicotinic acid (1.1 g) in tetrahydrofuran (10 mL) was added borane-dimethyl sulfide complex (1.0 mL), and the mixture was stirred at room temperature overnight. The reaction solution was cooled with ice, and thereto was added methanol, and the mixture was concentrated under reduced pressure. The residue was diluted with brine, extracted with ethyl acetate, dehydrated with sodium sulfate, and concentrated under reduced pressure. The residue was purified by silica gel column chromatography (eluent: hexane/ethyl acetate=2/1) to give Compound II (4.18 g).

Step (ii):

To an ice-cold solution of Compound II (850 mg) in tetrahydrofuran (10 mL) were added sodium hydride (517 mg) and methyl iodide (0.74 mL), and the mixture was stirred overnight. The reaction mixture was diluted with brine, extracted with ethyl acetate, dehydrated with sodium sulfate, and concentrated under reduced pressure. The residue was purified by silica gel column chromatography (eluent: hexane/ethyl acetate=4/1) to give Compound III (674 mg).

Step (iii)

To a solution of Compound III (674 mg) and Compound IV (950 mg) in DMF was added sodium hydride (280 mg), and the mixture was stirred at 80° C. overnight. The reaction solution was diluted with aqueous ammonium chloride solution, and extracted with ethyl acetate. The organic layer was dried over sodium sulfate, and concentrated under reduced pressure, and the obtained residue was purified by silica gel column chromatography (eluent: hexane/ethyl acetate=4/1) to give the title compound IV (649.8 mg).

$^1$H-NMR (CDCl$_3$) δ 1.46 (s, 9H), 1.89-1.97 (m, 4H), 2.12-2.18 (m, 4H), 3.42 (s, 3H), 4.10-4.25 (m, 2H), 4.41 (s, 2H), 5.35 (t, 1H, J=5.0 Hz), 6.66-6.67 (m, 1H), 6.78 (dt, 1H, J=5.1, 0.7 Hz), 8.07 (dd, 1H, J=5.4, 0.5 Hz)

Reference Example 28 tert-Butyl (3-endo)-3-[3-(2-methoxyethyl)phenoxy]-8-azabicyclo[3.2.1]octane-8-carboxylate

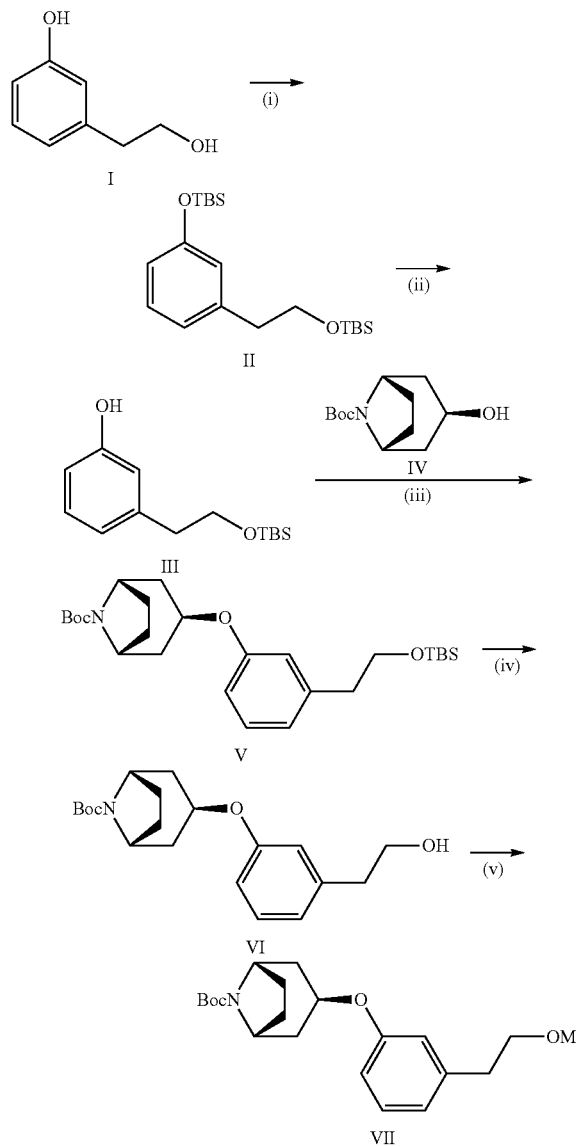

Step (i):

To a solution of 3-hydroxyphenethyl alcohol (2 g) in DMF (20 mL) were added imidazole (4.3 g) and tert-butyldimethylsilyl chloride (4.8 g), and the mixture was stirred overnight. The reaction solution was diluted with brine, and extracted with ethyl acetate. The organic layer was dried over sodium sulfate, and concentrated under reduced pressure to give a mixture (6.64 g) of Compound II and III.

Step (ii):

The mixture obtained in Step (i) was dissolved in ethanol/tetrahydrofuran/water (30 mL, volume ratio 1:1:1), and the mixture was stirred overnight. The reaction solution was neutralized with 1M hydrochloric acid, and extracted with ethyl acetate. The organic layer was dried over sodium sulfate, and concentrated under reduced pressure. The residue was purified by silica gel column chromatography (eluent: hexane/ethyl acetate=6/1) to give Compound III (4.48 g).

Step (iii):

To a mixture of Compound III (4.48 mL), Compound IV (2.58 g), triphenylphosphine (3.8 g) and toluene (70 mL) was added diisopropyl azodicarboxylate (2.9 mL), and the mixture was stirred at room temperature overnight. The reaction solution was washed successively with 1M aqueous sodium hydroxide solution, 1M hydrochloric acid and brine. The organic layer was dried over sodium sulfate, and concentrated under reduced pressure. The residue was purified by silica gel column chromatography (eluent: hexane/ethyl acetate=9/1) to give Compound V (2.16 g).

Step (iv):

To a solution of Compound V (2.16 g) in THF (20 mL) was added tetrabutylammonium fluoride (7 mL), and the mixture was stirred overnight. The reaction solution was diluted with aqueous ammonium chloride solution, and extracted with ethyl acetate. The organic layer was dried over sodium sulfate, and concentrated under reduced pressure. The residue was purified by silica gel column chromatography (eluent: hexane/ethyl acetate=3/1) to give Compound VI (1.55 g).

Step (v):

To a solution of Compound VI (230 mg) in DMF (5 mL) were added sodium hydride (43 mg) and iodomethane (62 μL), and the mixture was stirred at room temperature overnight. The reaction solution was diluted with aqueous ammonium chloride solution, and extracted with ethyl acetate. The organic layer was dried over sodium sulfate, and concentrated under reduced pressure. The residue was purified by silica gel column chromatography (eluent: hexane/ethyl acetate=9/1) to give the title compound VII (274 mg).

$^1$H-NMR (CDCl$_3$) δ 1.49 (s, 9H), 2.03-2.13 (m, 8H), 2.86 (t, 2H, J=7.1 Hz), 3.37 (s, 3H), 3.60 (t, 2H, J=7.2 Hz), 4.16-4.21 (m, 2H), 4.61-4.63 (m, 1H), 6.67-6.70 (m, 2H), 6.79-6.82 (m, 1H), 7.20 (t, 1H, J=7.9 Hz)

Reference Example 29 tert-Butyl (3-endo)-3-[3-(2-methoxyethoxy)phenoxy]-8-azabicyclo[3.2.1]octane-8-carboxylate

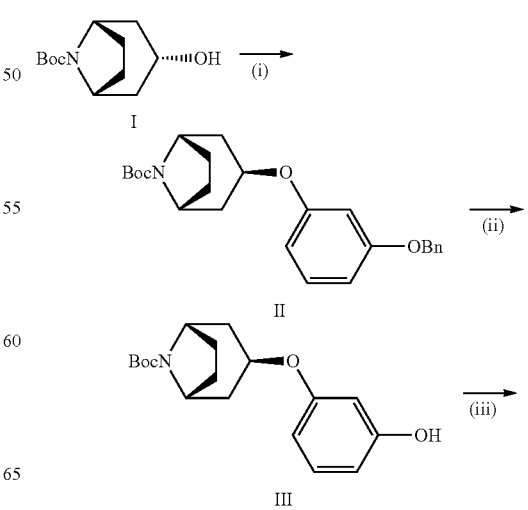

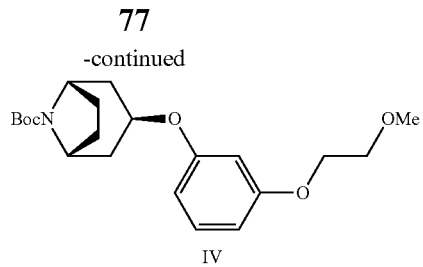

IV

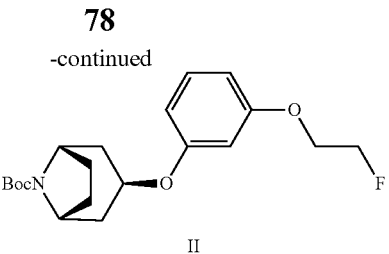

II

Step (i):

To a mixture of 3-benzyloxyphenol (2.96 g), Compound I (2.63 g), triphenylphosphine (3.88 g) and toluene (60 mL) was added diisopropyl azodicarboxylate (3.0 mL), and the mixture was stirred at room temperature overnight. The reaction solution was washed with 1M aqueous sodium hydroxide solution, 1M hydrochloric acid, and brine. The organic layer was dried over sodium sulfate, and concentrated under reduced pressure. The residue was purified by silica gel column chromatography (eluent: hexane/ethyl acetate=6/1) to give Compound II (4.2 g).

Step (ii):

Compound II (4.2 g), methanol (40 mL) and 10% palladium-carbon (1 g, 50% wet) were stirred under hydrogen atmosphere (ordinary pressure) overnight. The reaction solution was filtered through Celite, and the cake was washed with toluene, and the filtrate was concentrated under reduced pressure. The residue was purified by silica gel column chromatography (eluent: hexane/ethyl acetate=2/1) to give Compound III (3.1 g).

Step (iii):

To a solution of Compound III (200 mg) in DMF (4 mL) were added sodium hydride (27 mg) and 2-bromoethylmethyl ether (0.12 mL), and the resulting mixture was stirred at room temperature overnight. The reaction solution was diluted with brine, and extracted with ethyl acetate. The organic layer was dried over sodium sulfate, and concentrated under reduced pressure. The residue was purified by silica gel column chromatography (eluent: hexane/ethyl acetate=2/1) to give the title compound IV (205.4 mg).

$^1$H-NMR (CDCl$_3$) δ 1.48 (s, 9H), 1.98-2.14 (m, 8H), 3.45 (s, 3H), 3.74-3.75 (m, 2H), 4.09-4.12 (m, 2H), 4.16-4.20 (m, 2H), 4.58-4.59 (m, 1H), 6.42-6.44 (m, 2H), 6.49-6.52 (m, 1H), 7.16 (t, 1H, J=8.5 Hz)

Reference Example 30 tert-Butyl (3-endo)-3-[3-(2-fluoroethoxy)phenoxy]-8-azabicyclo[3.2.1]octane-8-carboxylate

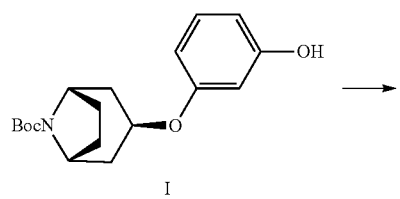

I

To a solution of Compound I (422 mg) in DMF (8 mL) were added potassium carbonate (274 mg) and 1-fluoro-2-iodoethane (275 mg), and the resulting mixture was stirred at room temperature overnight. The reaction solution was diluted with brine, and extracted with ethyl acetate. The organic layer was dried over sodium sulfate, and concentrated under reduced pressure. The residue was purified by silica gel column chromatography (eluent: hexane/ethyl acetate=1/1) to give the title compound II (550 mg).

$^1$H-NMR (CDCl$_3$) δ 1.48 (s, 9H), 1.99-2.15 (m, 8H), 4.15-4.23 (m, 5H), 4.61 (t, 1H, J=4.2 Hz), 4.76 (ddd, 1H, J=47.4, 5.0, 3.4 Hz), 6.45-6.51 (m, 3H), 7.19 (t, 1H, J=8.2 Hz)

Reference Example 31 tert-Butyl (3-endo)-3-[2-fluoro-5-(methoxymethyl)phenoxy]-8-azabicyclo[3.2.1]octane-8-carboxylate

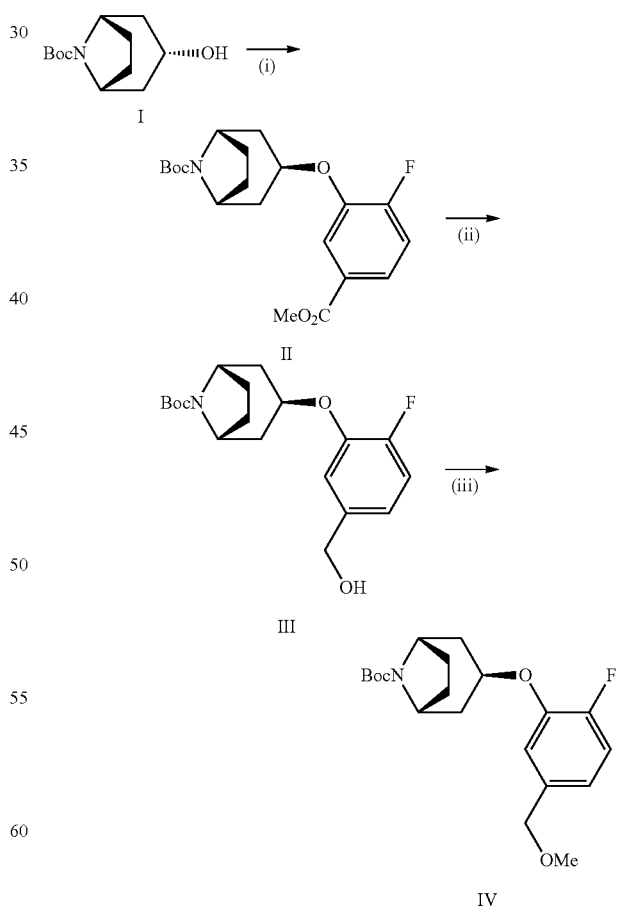

Step (i):

To a mixture of 4-fluoro-3-hydroxybenzoic acid methyl ester (890 mg), Compound I (990 mg), triphenylphosphine (1.37 g) and toluene (22 mL) was added diisopropyl azodicarboxylate (1.0 mL), and the resulting mixture was stirred at room temperature overnight. The reaction solution was washed successively with 1M aqueous sodium hydroxide solution, 1M hydrochloric acid, and brine. The organic layer was dried over sodium sulfate, and concentrated under reduced pressure. The residue was purified by silica gel column chromatography (eluent: hexane/ethyl acetate=6/1) to give Compound II (249 mg).

Step (ii):

To a solution of Compound II (240 mg) in THF (4 mL) was added lithium borohydride (28 mg), and the mixture was stirred overnight. The reaction solution was diluted with brine, and extracted with ethyl acetate. The organic layer was dried over sodium sulfate, and concentrated under reduced pressure. The residue was purified by silica gel column chromatography (eluent: hexane/ethyl acetate=1/1) to give Compound III (203 mg).

Step (iii):

To an ice-cold solution of Compound III (95.3 mg) in tetrahydrofuran (3 mL) were added sodium hydride (24 mg) and iodomethane (34 μL), and the mixture was stirred overnight. The reaction mixture was diluted with brine, extracted with ethyl acetate, dehydrated with sodium sulfate, and concentrated under reduced pressure. The residue was purified by silica gel column chromatography (eluent: hexane/ethyl acetate=4/1) to give the title compound V (83.5 mg).

$^1$H-NMR (CDCl$_3$) δ 1.48 (s, 9H), 1.97-2.25 (m, 8H), 3.37 (s, 3H), 4.18-4.24 (m, 2H), 4.37 (s, 2H), 4.65-4.66 (m, 1H), 6.80-6.89 (m, 2H), 7.04 (dd, 1H, J=11.0, 8.3 Hz)

Reference Example 32 tert-Butyl (3-endo)-3-[3-(methoxymethyl)-5-methylphenoxy]-8-azabicyclo[3.2.1]octane-8-carboxylate

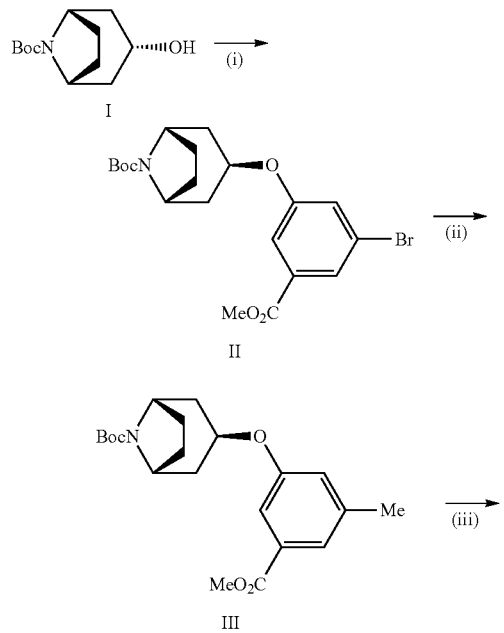

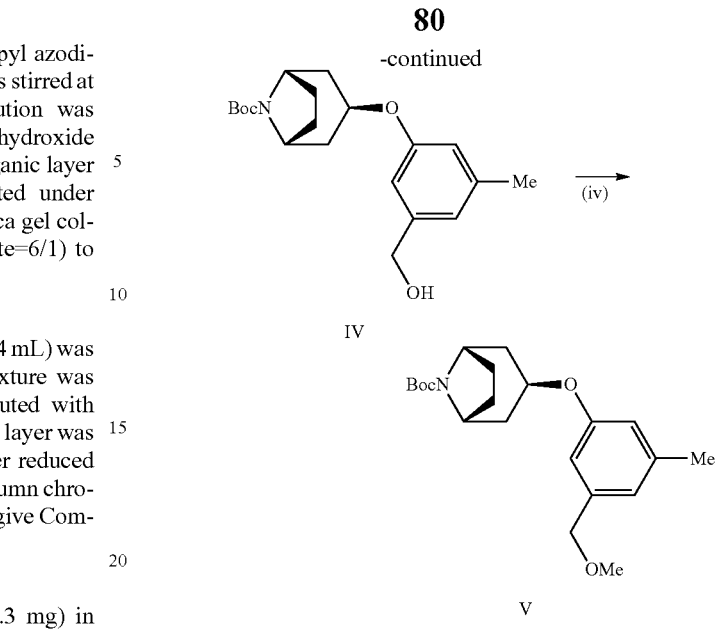

Step (i):

To a mixture of 3-bromo-5-hydroxybenzoic acidmethyl ester (3.15 g), Compound I (3.15 g), triphenylphosphine (3.9 g) and toluene (68 mL) was added diisopropyl azodicarboxylate (2.96 mL), and the resulting mixture was stirred at room temperature overnight. The reaction solution was washed successively with 1M aqueous sodium hydroxide solution, 1M hydrochloric acid and brine. The organic layer was dried over sodium sulfate, and concentrated under reduced pressure. The residue was purified by silica gel column chromatography (eluent: hexane/ethyl acetate=6/1) to give Compound II (3.82 g).

Step (ii):

To a solution of Compound II (934 mg) in tetrahydrofuran (10 mL) were added tris(dibenzylideneacetone)dipalladium (194 mg), tri-t-butylphosphine (0.2 mL) and dimethylzinc (2.3 mL, 2 M toluene solution), and the resulting mixture was stirred at 60° C. overnight. The reaction solution was filtered through Celite, and the filtrate was concentrated under reduced pressure, and the residue was purified by silica gel column chromatography (eluent: hexane/ethyl acetate=6/1) to give Compound III (660 mg).

Step (iii)

To a solution of Compound III (660 mg) in THF (10 mL) was added lithium borohydride (57 mg), and the resulting mixture was stirred overnight. The reaction solution was diluted with brine, and extracted with ethyl acetate. The organic layer was dried over sodium sulfate, and concentrated under reduced pressure. The residue was purified by silica gel column chromatography (eluent: hexane/ethyl acetate=2/1) to give Compound IV (493 mg).

Step (iv):

To an ice-cold solution of Compound IV (103 mg) in tetrahydrofuran (4 mL) were added sodium hydride (20 mg) and iodomethane (28 μL), and the resulting mixture was stirred overnight. The reaction mixture was diluted with brine, extracted with ethyl acetate, dehydrated with sodium sulfate, and concentrated under reduced pressure. The residue was purified by silica gel column chromatography (eluent: hexane/ethyl acetate=4/1) to give the title compound V (84.4 mg).

$^1$H-NMR (CDCl$_3$) δ 1.47 (s, 9H), 1.93-2.18 (m, 8H), 2.30 (s, 3H), 3.38 (s, 3H), 4.15-4.20 (m, 2H), 4.37 (s, 2H), 4.62 (t, 1H, J=4.5 Hz), 6.57 (s, 1H), 6.61 (s, 1H), 6.71 (s, 1H)

Reference Example 33 tert-Butyl (3-endo)-3-[3-(methoxymethyl)-5-methylphenoxy]-8-azabicyclo[3.2.1]octane-8-carboxylate $^1$H-NMR (CDCl$_3$) δ 1.48 (s, 9H), 1.93-2.18 (m, 8H), 2.28 (s, 3H), 3.45 (s, 3H), 3.72-3.75 (m, 2H), 4.07-4.10 (m, 2H), 4.15-4.20 (m, 2H), 4.56-4.59 (m, 1H), 6.25-6.27 (m, 2H), 6.34 (s, 1H)

Reference Example 34 tert-Butyl (3-endo)-3-[3-fluoro-5-(methoxymethyl)phenoxy]-8-azabicyclo[3.2.1]octane6-8-carboxylate

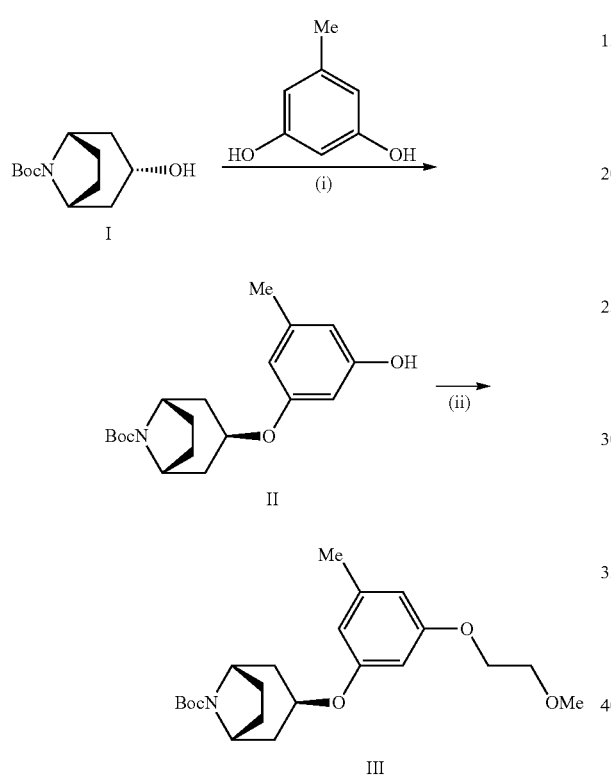

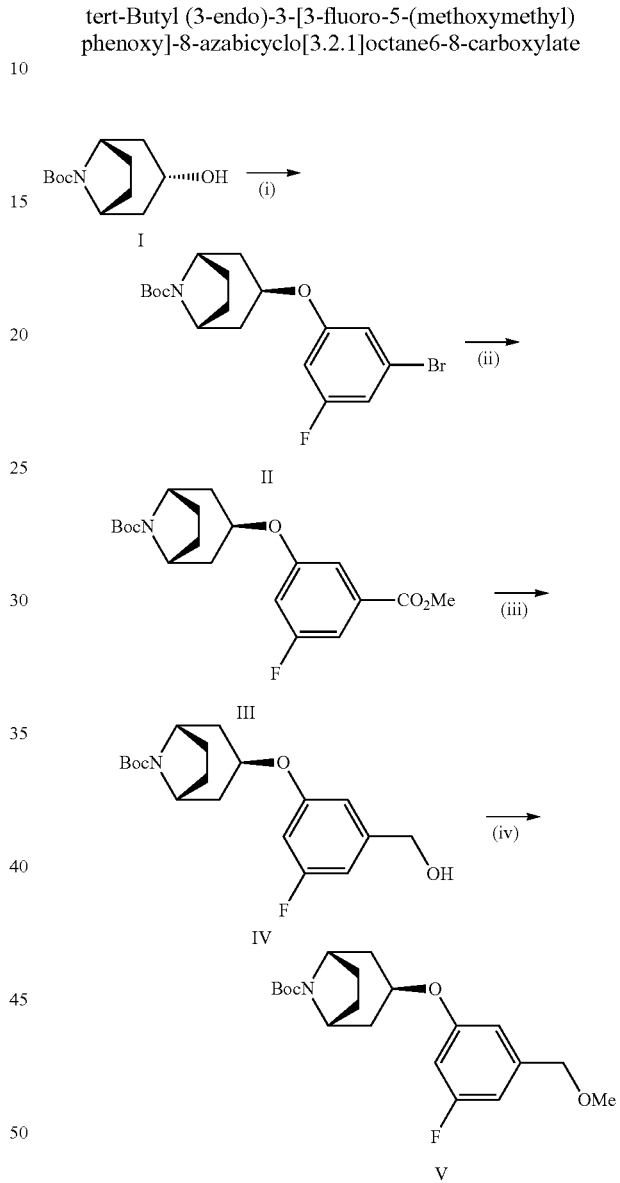

Step (i):

To a mixture of 5-methyl resorcinol (792 mg), Compound I (1.21 g), triphenylphosphine (1.67 g) and toluene (27 mL) was added diisopropyl azodicarboxylate (1.67 mL), and the resulting mixture was stirred at room temperature overnight. The reaction solution was washed successilvey with 1M aqueous sodium hydroxide solution, 1M hydrochloric acid, and brine. The organic layer was dried over sodium sulfate, and concentrated under reduced pressure. The residue was purified by silica gel column chromatography (eluent: hexane/ethyl acetate=3/1) to give Compound II (1.18 g).

Step (ii):

To a solution of Compound II (235 mg) in DMF (4 mL) were added sodium hydride (62 mg) and 2-bromoethylmethyl ether (0.13 mL), and the mixture was stirred at room temperature overnight. The reaction solution was diluted with brine, and extracted with ethyl acetate. The organic layer was dried over sodium sulfate, and concentrated under reduced pressure. The residue was purified by silica gel column chromatography (eluent: hexane/ethyl acetate=2/1) to give the title compound III (166.6 mg).

Step (i):

To a mixture of 3-fluoro-5-bromophenol (4.13 g), Compound I (3.78 g), triphenylphosphine (5.66 g) and toluene (60 mL) was added diisopropyl azodicarboxylate (4.3 mL), and the resulting mixture was stirred at room temperature overnight. The reaction solution was washed successively with 1M aqueous sodium hydroxide solution, 1M hydrochloric acid, and brine. The organic layer was dried over sodium sulfate, and concentrated under reduced pressure. The residue was purified by silica gel column chromatography (eluent: hexane/ethyl acetate=6/1) to give Compound II (6.84 g).

Step (ii)

To a solution of Compound II (1.13 g) in DMA/water (14 mL/7 mL) were added palladium acetate (63 mg), 1,3-bis (diphenylphosphino)propane (116 mg) and N-ethyldiisopropylamine (1 mL), and the resulting mixture was stirred at 80° C. under carbon monoxide atmosphere (1 atm) overnight. The reaction solution was filtered through Celite, and the filtrate was concentrated under reduced pressure. The residue was diluted with brine and extracted with ethyl acetate. The organic layer dried over sodium sulfate, and concentrated under reduced pressure. The residue was purified by silica gel column chromatography (eluent: hexane/ethyl acetate=6/1) to give Compound III (390 mg).

Step (iii):

To a solution of Compound III (390 mg) in THF (5 mL) was added lithium borohydride (67 mg), and the mixture was stirred overnight. The reaction solution was diluted with brine, and the mixture was extracted with ethyl acetate. The organic layer was dried over sodium sulfate, and concentrated under reduced pressure. The residue was purified by silica gel column chromatography (eluent: hexane/ethyl acetate=1/1) to give Compound IV (347 mg).

Step (iv):

To an ice-cold solution of Compound IV (347 mg) in tetrahydrofuran (5 mL) were added sodium hydride (130 mg) and iodomethane (0.12 mL), and the mixture was stirred overnight. The reaction mixture was diluted with brine, and extracted with ethyl acetate. The mixture was dehydrated with sodium sulfate, and concentrated under reduced pressure. The residue was purified by silica gel column chromatography (eluent: hexane/ethyl acetate=2/1) to give the title compound V (192 mg).

$^1$H-NMR (CDCl$_3$) δ 1.46 (s, 9H), 2.07-2.19 (m, 8H), 2.68 (s, 3H), 4.11-4.27 (m, 2H), 5.54 (t, 1H, J=5.4 Hz), 6.95 (dd, 1H, J=7.5, 4.8 Hz), 8.01 (dd, 1H, J=7.5, 2.0 Hz), 8.27 (dd, 1H, J=4.8, 2.0 Hz)

Reference Example 35 tert-Butyl (3-endo)-3-[4-fluoro-3-(methoxymethyl) phenoxy]-8-azabicyclo[3.2.1]octane-8-carboxylate

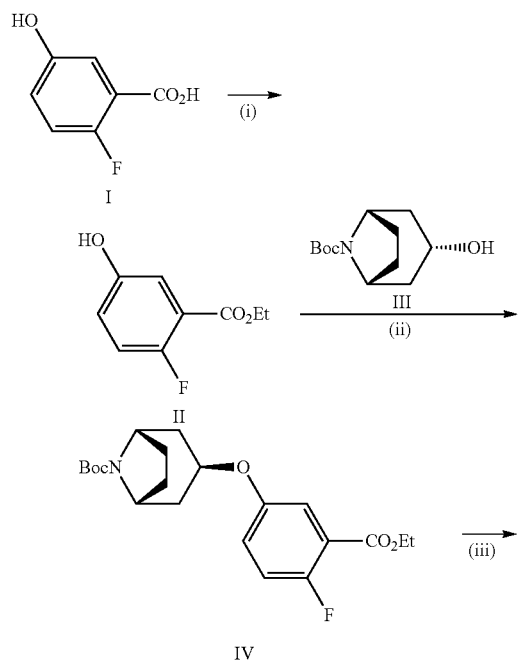

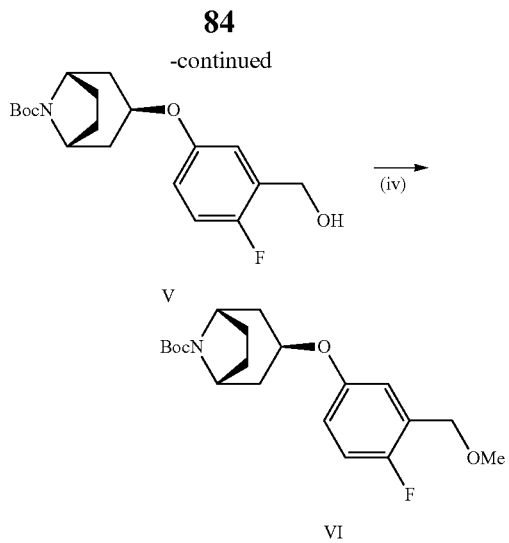

Step (i):

A mixture of 2-fluoro-5-hydroxybenzoic acid (4.00 g), ethanol (25.6 mL) and conc. sulfuric acid (3.8 mL) was stirred at 80° C. overnight. The reaction solution was concentrated under reduced pressure, and the resultant was neutralized with aqueous sodium bicarbonate solution, and extracted with ethyl acetate. The organic layer was dried over magnesium sulfate, and concentrated under reduced pressure to give Compound II (4.38 g).

Step (ii):

To a solution of Compound II (2.00 g) obtained in Step (i), Compound III (2.01 g) and triphenylphosphine (2.85 g) in toluene (45 mL) was added diisopropyl azodicarboxylate (2.15 mL), and the mixture was stirred at room temperature overnight. The reaction solution was washed successively with 1M aqueous sodium hydroxide solution, 1M hydrochloric acid, and brine. The organic layer was dried over sodium sulfate, and concentrated under reduced pressure. The residue was purified by silica gel column chromatography (eluent: hexane/ethyl acetate=6/1) to give Compound IV (3.48 g).

Step (iii):

To an ice-cold solution of Compound IV (500 mg) in tetrahydrofuran (6.4 mL) was added lithium aluminium hydride (12 mg), and the mixture was stirred for 30 minutes. To the mixture was added a saturated aqueous sodium sulfate solution (1 mL), and the mixture was stirred at room temperature for one hour. The reaction solution was filtered through Celite-silica gel pad, and the filtrate was concentrated under reduced pressure to give Compound V (408 mg).

Step (iv):

To an ice-cold solution of Compound V (495.8 mg) in tetrahydrofuran (1.4 mL) were added sodium hydride (24.8 mg) and iodomethane (36.3 μL), and the mixture was stirred overnight. The reaction mixture was diluted with brine, extracted with ethyl acetate, dehydrated with sodium sulfate, and concentrated under reduced pressure to give the title compound VI (128 mg).

$^1$H-NMR (CDCl$_3$) δ 0.81-0.93 (m, 1H), 1.18-1.32 (m, 1H), 1.47 (s, 9H), 1.90-2.20 (m, 6H), 3.42 (s, 3H), 4.11-4.28 (m,

2H), 4.48 (br s, 2H), 4.54-4.60 (m, 1H), 6.70 (ddd, 1H, J=9.0, 3.9, 3.3 Hz), 6.87 (dd, 1H, J=5.9, 2.9 Hz), 6.95 (t, 1H, J=9.1 Hz)

Reference Example 36 tert-Butyl (3-endo)-3-{[4-(methoxymethyl)-6-methylpyridin-2-yl]oxy}-8-azabicyclo[3.2.1]-octane-8-carboxylate

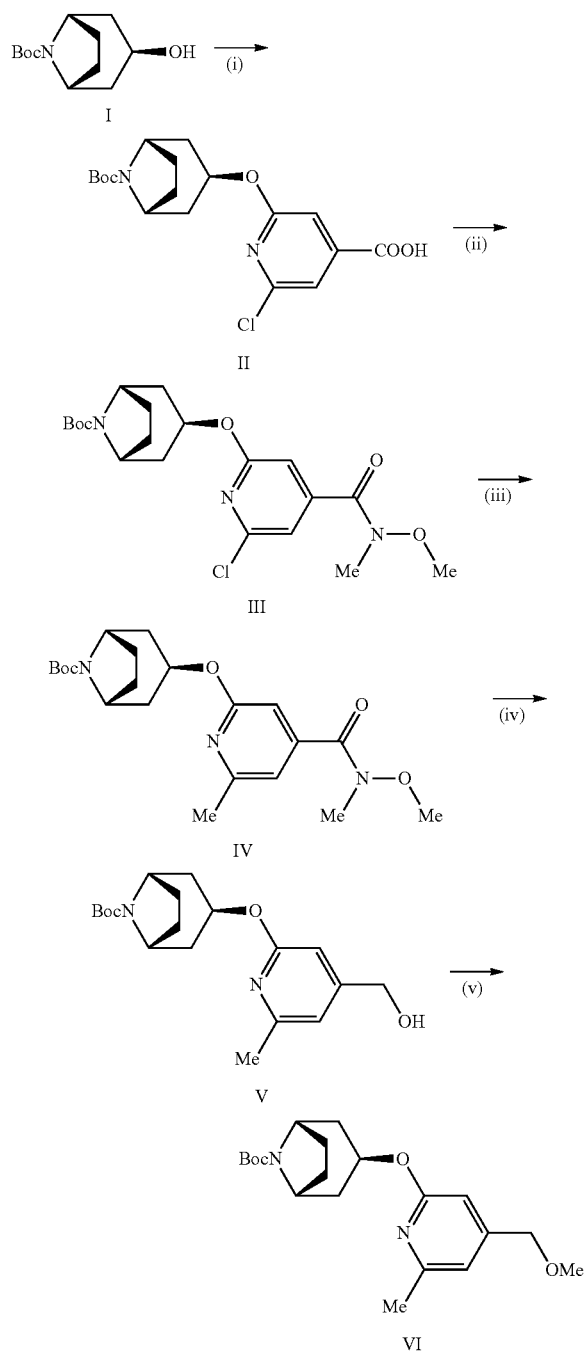

Step (i):

To a solution of 2,6-dichloronicotinic acid (1.20 g) and Compound I (1.00 g) in DMSO (23 mL) was added sodium hydride (1.18 g), and the mixture was stirred at 70° C. for 3 hours. The reaction mixture was acidified with 3N hydrochloric acid, and the mixture was extracted with ethyl acetate. The organic layer was washed with brine, dried over sodium sulfate and concentrated under reduced pressure to give Compound II as a crude product.

Step (ii):

To a solution of crude Compound II obtained in Step (i) in dichloromethane (20 mL) were WSC.HCl (2.01 g), HOBt.H$_2$O (1.61 g), N,O-dimethylhydroxyamine hydrochloride (1.03 g) and triethylamine (3.0 mL), and the mixture was stirred overnight. The reaction mixture was diluted with aqueous ammonium chloride solution, extracted with dichloromethane, and the organic layer was dehydrated with sodium sulfate, and concentrated under reduced pressure. The residue was purified by silica gel column chromatography (eluent: hexane/ethyl acetate=1/1) to give Compound III (3.02 g).

Step (iii):

To a solution of Compound III (200 mg) in tetrahydrofuran (3.5 mL) were added tris(dibenzylideneacetone)dipalladium (64.5 mg), tri-tert-butylphosphine (67.6 μL) and diethylzinc (775 μL, 2.0 M toluene solution), and the resulting mixture was stirred at 60° C. for 9 hours. The reaction solution was filtered through Celite, and the filtrate was concentrated under reduced pressure. The residue was purified by silica gel column chromatography (eluent: hexane/ethyl acetate=6/1) to give Compound IV (285 mg).

Step (iv):

To an ice-cold solution of Compound IV (285 mg) in tetrahydrofuran (3.5 mL) was added lithium aluminum hydride (66.8 mg), and the mixture was stirred for 30 minutes. To the mixture was added a saturated aqueous sodium sulfate solution (0.5 mL), and the mixture was stirred at room temperature for one hour. The reaction solution was filtered through Celite-silica gel pad, and the filtrate was concentrated under reduced pressure. To this residue were added methanol (3.5 mL) and sodium borohydride (53.3 mg), and the mixture was stirred for one hour. To the reaction solution was added an aqueous sodium bicarbonate solution, and the mixture was extracted with chloroform, dried over sodium sulfate, and concentrated under reduced pressure. The residue was purified by silica gel column chromatography (eluent: hexane/ethyl acetate=1/1) to give Compound V (188.4 mg).

Step (v):

To an ice-cold solution of Compound V (90.0 mg) in tetrahydrofuran (1.3 mL) were added sodium hydride (23.1 mg) and iodomethane (32.2 μL), and the mixture was stirred for one hour. The reaction mixture was diluted with brine, and extracted with ethyl acetate, dehydrated with sodium sulfate, and concentrated under reduced pressure to give the title compound VI (93.6 mg).

¹H-NMR (CDCl₃) δ 0.78-0.93 (m, 1H), 1.18-1.31 (m, 1H), 1.47 (s, 9H), 1.84-2.26 (m, 6H), 2.39 (s, 3H), 3.42 (s, 3H), 4.12-4.28 (m, 2H), 4.37 (s, 2H), 5.34-5.41 (m, 1H), 6.45 (s, 1H), 6.65 (s, 1H)

Reference Example 37 tert-Butyl (3-endo)-3-[2-fluoro-3-(methoxymethyl)phenoxy]-8-azabicyclo[3.2.1]octane-8-carboxylate

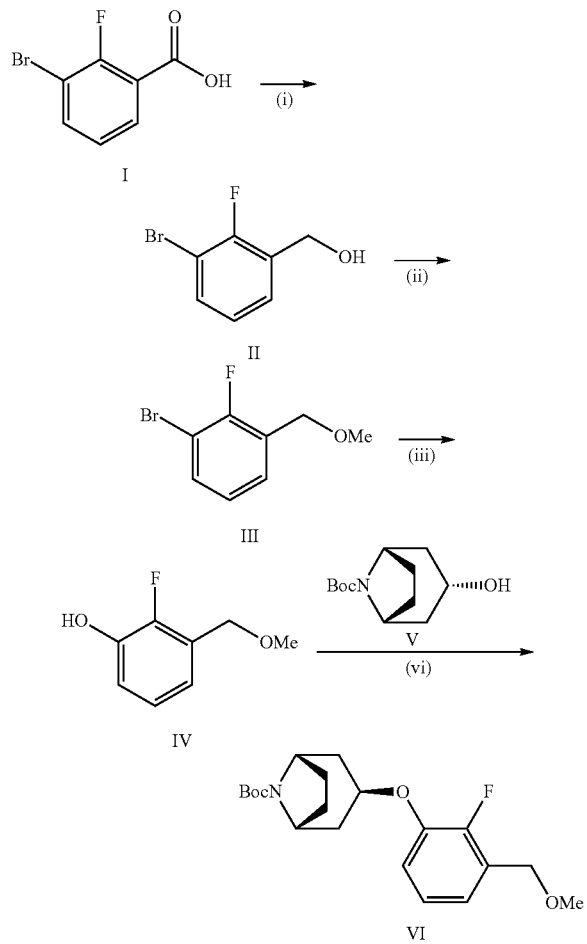

Step (i):

To an ice-cold solution of Compound I (2.5 g) in THF (23 mL) was added borane.THF complex (17 mL, 1.0 M THF solution), and the resulting mixture was stirred at room temperature overnight. To the ice-cold reaction mixture was added water, and the mixture was concentrated under reduced pressure. The residue was diluted with water, and extracted with ethyl acetate. The organic layer was washed with brine, dried over sodium sulfate, and concentrated under reduced pressure. The residue was purified by silica gel column chromatography (eluent: hexane/ethyl acetate=4/1) to give Compound II (2.4 g).

Step (ii):

To an ice-cold solution of Compound II (500 mg) in THF (5.0 mL) were added sodium hydride (160 mg, 55% contents) and methyl iodide (608 μL), and the resulting mixture was stirred at room temperature overnight. To the reaction mixture was added water, and the mixture was concentrated under reduced pressure. The residue was diluted with water, and extracted with ethyl acetate. The organic layer was washed with brine, dried over sodium sulfate, and concentrated under reduced pressure. The residue was purified by silica gel column chromatography (eluent: hexane/ethyl acetate=4/1) to give Compound III (426 mg).

Step (iii):

To a solution of Compound III (426 mg), 2-di-tert-butylphosphino-2',4',6'-triisopropylbiphenyl (165 mg) and potassium hydroxide (327 mg) in a mixture of 1,4-dioxane/water (1 mL/1 mL) was added Pd₂(dba)₃ (89 mg), and the mixture was stirred at 80° C. overnight. To the reaction mixture was added 1M hydrochloric acid, and the mixture was extracted with ethyl acetate. The organic layer was washed with brine, dried over sodium sulfate, and concentrated under reduced pressure. The residue was purified by silica gel column chromatography (eluent: hexane/ethyl acetate=4/1) to give Compound IV (103 mg).

Step (iv):

To a solution of Compound IV (103 mg), Compound V (150 mg), triphenylphosphine (260 mg) in toluene (2.2 mL) was added diisopropyl azodicarboxylate (196 μL), and the resulting mixture was stirred at room temperature overnight. To the reaction mixture was added 1M aqueous sodium hydroxide solution, and the mixture was extracted with ethyl acetate. The organic layer was washed with brine, dried over sodium sulfate, and concentrated under reduced pressure. The residue was purified by silica gel column chromatography (eluent: hexane/ethyl acetate=4/1) to give the title compound VI (144 mg).

¹H-NMR (CDCl₃) δ 1.47 (s, 9H), 1.96-2.23 (m, 8H), 3.42 (s, 3H), 4.22 (br s, 2H), 4.52 (d, 2H, J=1.5 Hz), 4.62 (t, 1H, J=4.6 Hz), 6.81 (td, 1H, J=7.9, 1.7 Hz), 6.94-7.06 (m, 2H).

Reference Example 38 tert-Butyl (3-endo)-3-{[4-(cyclopropylmethyl)pyridin-2-yl]oxy}-8-azabicyclo[3.2.1]octane-8-carboxylate

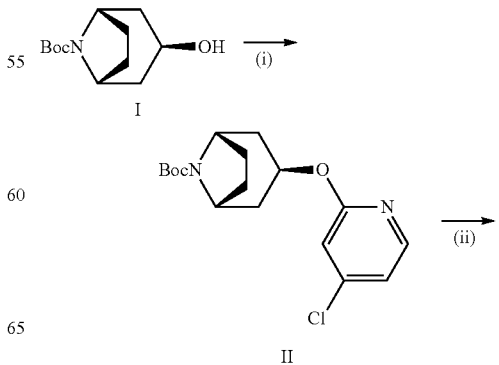

-continued

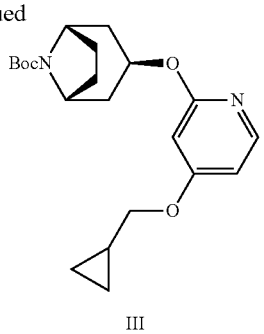

III

Step (i):

To a solution of Compound I (5.4 g) and 2,4-dichloropyridine (3.6 g) in tetrahydrofuran (80 mL) was added sodium hydride (2.1 g), and the mixture was heated at reflux and stirred overnight. The reaction solution was diluted with aqueous ammonium chloride solution, and extracted with ethyl acetate. The organic layer was dried over sodium sulfate, concentrated under reduced pressure, and the obtained residue was purified by silica gel column chromatography (eluent: hexane/ethyl acetate=6/1) to give Compound II (7.0 g).

Step (ii):

To a solution of Compound II (322 mg) in N-methylpiperidone (5 mL) were added cyclopropylmethanol (0.16 mL) and sodium hydride (86 mg), and the resulting mixture was heated at reflux and stirred overnight. The reaction solution was diluted with aqueous ammonium chloride solution, and extracted with ethyl acetate. The organic layers were combined, and the mixture was dried over sodium sulfate, and concentrated under reduced pressure. The obtained residue was purified by silica gel column chromatography (eluent: hexane/ethyl acetate=6/1) to give the title compound III (290 mg).

$^1$H-NMR (CDCl$_3$) δ 0.35-0.38 (m, 2H), 0.66-0.69 (m, 2H), 1.25-1.28 (m, 1H), 1.48 (s, 9H), 1.89-2.18 (m, 8H), 3.82 (d, 2H, J=7.2 Hz), 4.09-4.24 (m, 2H), 5.33 (t, 1H, J=4.7 Hz), 6.12 (d, 1H, J=2.2 Hz), 6.46 (dd, 1H, J=5.9, 2.2 Hz), 7.93 (d, 1H, J=6.1 Hz)

Reference Example 39 tert-Butyl (3-exo)-3-[(4-chloro-2-pyridinyl)oxy]-8-azabicyclo[3.2.1]octane-8-carboxylate

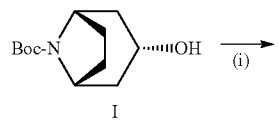

Step (i):

To a solution of Compound I (500 mg) and 2,4-dichloropyridine (238 μL) in THF (7.3 mL) was added sodium hydride (192 mg, 55% contents), and the resulting mixture was heated at reflux and stirred overnight. To the reaction mixture was added water, and the mixture was extracted with ethyl acetate. The organic layer was washed with brine, dried over sodium sulfate, and concentrated under reduced pressure. The residue was purified by silica gel column chromatography (eluent: hexane/ethyl acetate=4/1) to give the title compound II (600 mg).

$^1$H-NMR (CDCl$_3$) δ 1.49 (s, 9H), 1.70-1.83 (m, 4H), 1.99-2.15 (m, 4H), 4.24-4.33 (m, 2H), 5.43-5.55 (m, 1H), 6.69 (dd, 1H, J=1.7, 0.5 Hz), 6.83-6.85 (m, 1H), 8.00 (dd, 1H, J=5.5, 0.4 Hz) Reference Example 40 tert-Butyl (3-endo)-3-{3-[(2,2,2-trifluoroethoxy)methyl]phenoxy}-8-azabicyclo[3.2.1]octane-8-carboxylate

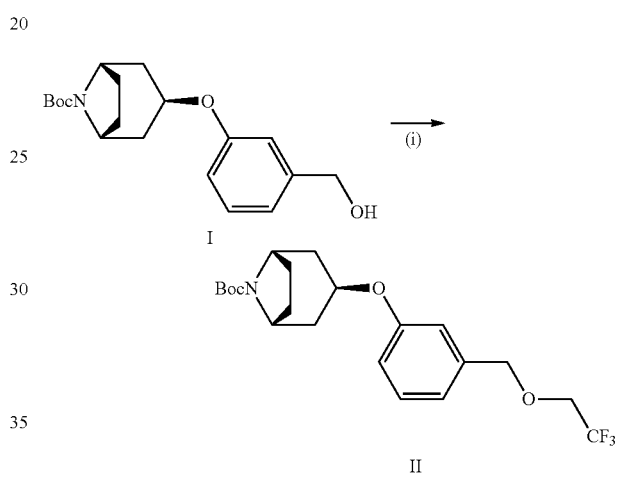

Step (i):

To a solution of Compound I (300 mg), 2,2,2-trifluoroethanol (438 μL) and triphenylphosphine (354 mg) in toluene (3.0 mL) was added diisopropyl azodicarboxylate (268 μL), and the resulting mixture was heated at reflux and stirred overnight. To the reaction mixture was added 1M aqueous sodium hydroxide solution, and the mixture was extracted with ethyl acetate. The organic layer was washed with brine, dried over sodium sulfate, and concentrated under reduced pressure. The residue was purified by silica gel column chromatography (eluent: hexane/ethyl acetate=4/1) to give the title compound II (299 mg).

$^1$H-NMR (CDCl$_3$) δ 1.48 (s, 9H), 1.94-1.98 (m, 4H), 2.12-2.18 (m, 4H), 3.82 (q, 2H, J=8.7 Hz), 4.16-4.25 (m, 2H), 4.63-4.65 (m, 3H), 6.77-6.83 (m, 2H), 6.90 (d, 1H, J=7.6 Hz), 7.26-7.29 (m, 1H)

Reference Example 41 tert-Butyl (3-endo)-3-[(4-cyclopropylpyridin-2-yl)oxy]-8-azabicyclo[3.2.1]octane-8-carboxylate

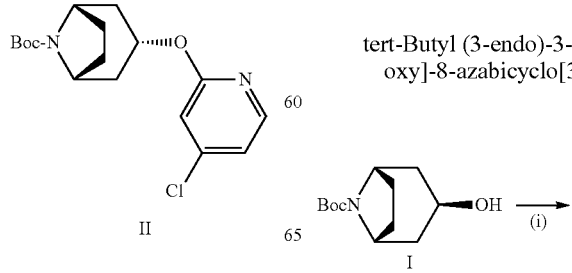

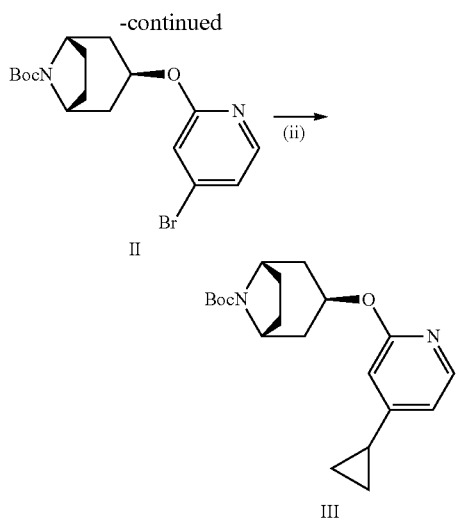

II

III

Step (i):

To a solution of Compound I (4.06 g) and 2-chloro-4-bromopyridine (2.4 mL) in tetrahydrofuran (60 mL) was added sodium hydride (1.1 g), and the mixture was heated at reflux and stirred overnight. The reaction mixture was diluted with aqueous ammonium chloride solution, and extracted with ethyl acetate. The organic layer was dried over sodium sulfate, and concentrated under reduced pressure. The obtained residue was purified by silica gel column chromatography (eluent: hexane/ethyl acetate=5/1) to give Compound II (5.22 g).

Step (ii):

To a solution of Compound II (230 mg) in tetrahydrofuran (10 mL) were added tris(dibenzylideneacetone)dipalladium (55 mg), tri-tert-butylphosphine (58 μL) and cyclopropylzinc bromide (2.6 mL, 0.5 M tetrahydrofuran solution), and the mixture was stirred at 60° C. overnight. The reaction mixture was filtered through Celite, concentrated under reduced pressure, and the residue was purified by silica gel column chromatography (eluent: hexane/ethyl acetate=6/1) to give the title compound III (233 mg).

$^1$H-NMR (CDCl$_3$) δ 0.76-0.78 (m, 2H), 1.02-1.05 (m, 2H), 1.47 (s, 9H), 1.79-1.82 (m, 1H), 1.90-1.95 (m, 4H), 2.10-2.15 (m, 4H), 4.14-4.21 (m, 2H), 5.32 (t, 1H, J=4.9 Hz), 6.37 (d, 1H, J=1.2 Hz), 6.50 (dd, 1H, J=5.4, 1.7 Hz), 7.95 (d, 1H, J=5.4 Hz)

Reference Example 42 tert-Butyl (3-endo)-3-[(6-ethylpyridin-2-yl)oxy]-8-azabicyclo[3.2.1]octane-8-carboxylate

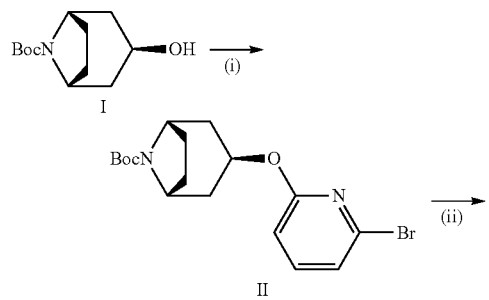

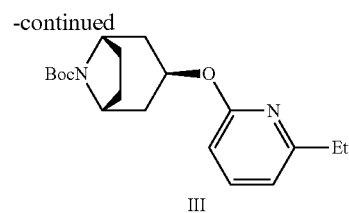

III

Step (i):

To a solution of Compound I (4.47 g) and 2,6-dibromopyridine (6.19 g) in DMF (60 mL) was added sodium hydride (1.3 g), and the mixture was stirred at 80° C. overnight. After the reaction was complete, the mixture was diluted with aqueous ammonium chloride solution, and extracted with ethyl acetate. The organic layers were combined, and dried over sodium sulfate, and concentrated under reduced pressure. The obtained residue was purified by silica gel column chromatography (eluent: hexane/ethyl acetate=6/1) to give Compound II (6.42 g).

Step (ii):

To a solution of Compound II (200 mg) in tetrahydrofuran (10 mL) were added tris(dibenzylideneacetone)dipalladium (48 mg), tri-tert-butylphosphine (51 μL) and diethylzinc (2.6 mL, 0.5 M tetrahydrofuran solution), and the mixture was stirred at 60° C. overnight. The reaction solution was filtered through Celite, and the filtrate was concentrated under reduced pressure. The residue was purified by silica gel column chromatography (eluent: hexane/ethyl acetate=6/1) to give the title compound III (196 mg).

$^1$H-NMR (CDCl$_3$) δ 1.24 (t, 3H, J=7.6 Hz), 1.46 (s, 9H), 1.92-2.18 (m, 8H), 2.66 (q, 2H, J=7.6 Hz), 4.16-4.21 (m, 2H), 5.40 (t, 1H, J=5.0 Hz), 6.47 (t, 1H, J=4.1 Hz), 6.67 (t, 1H, J=3.9 Hz), 7.45 (dd, 1H, J=8.2, 7.2 Hz)

Reference Example 43 tert-Butyl (3-endo)-3-[(3-ethylpyridin-2-yl)oxy]-8-azabicyclo[3.2.1]octane-8-carboxylate

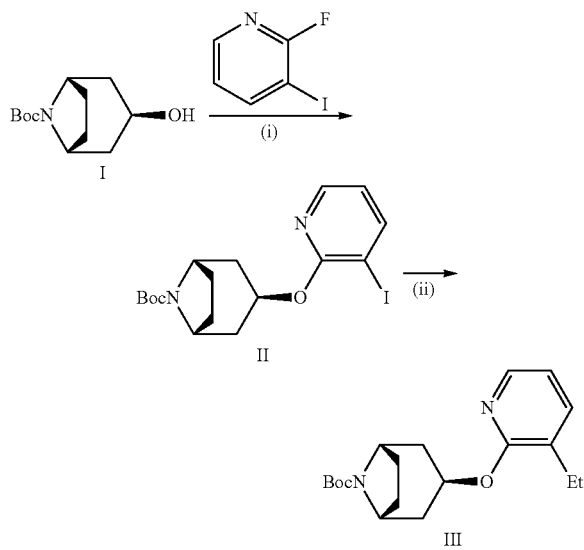

Step (i):

To a solution of Compound I (713 mg) and 2-fluoro3-iodopyridine (1.0 g) in tetrahydrofuran (15 mL) was added sodium hydride (258 mg), and the mixture was heated at reflux and stirred overnight. The reaction solution was diluted with aqueous ammonium chloride solution, and extracted with ethyl acetate. The organic layer was dried over sodium sulfate, concentrated under reduced pressure, and the obtained residue was purified by silica gel column chromatography (eluent: hexane/ethyl acetate=6/1) to give Compound II (1.39 g).

Step (ii):

To a solution of Compound II (300 mg) in tetrahydrofuran (10 mL) were added tris(dibenzylideneacetone)dipalladium (64 mg), tri-tert-butylphosphine (130 μL) and diethylzinc (1.5 mL, 1.05 M hexane solution), and the mixture was stirred at 60° C. overnight. The reaction solution was filtered through Celite, and the filtrate was concentrated under reduced pressure. The residue was purified by silica gel column chromatography (eluent: hexane/ethyl acetate=6/1) to give the title compound III (266 mg).

$^1$H-NMR (CDCl$_3$) δ 1.52 (s, 9H), 1.68-1.72 (m, 4H), 2.05-2.09 (m, 2H), 2.50 (s, 2H), 4.21-4.43 (m, 5H), 7.47-7.52 (m, 3H), 7.83 (d, 1H, J=7.5 Hz)

Reference Example 44 tert-Butyl (3-endo)-3-{[3-(difluoromethyl)pyridinyl-2-yl]oxy}-8-azabicyclo[3.2.1]octane-8-carboxylate

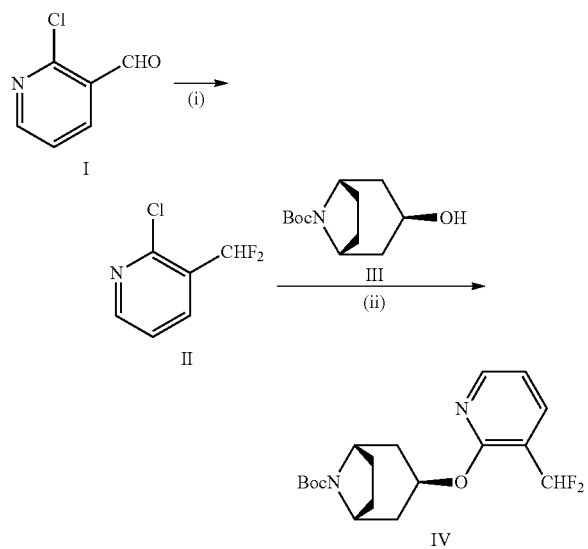

ride solution, and extracted with ethyl acetate. The organic layer was dried over sodium sulfate, and concentrated under reduced pressure. The obtained residue was purified by silica gel column chromatography (eluent: hexane/ethyl acetate=6/1) to give Compound IV (420 mg).

$^1$H-NMR (CDCl$_3$) δ 1.48 (s, 9H), 1.99-2.15 (m, 8H), 4.15-4.23 (m, 2H), 5.50 (t, 1H, J=5.0 Hz), 6.77 (t, 1H, J=47.0 Hz), 6.97 (dd, 1H, J=8.4, 3.5 Hz), 7.84-7.85 (m, 1H), 8.21-8.23 (m, 1H)

Reference Example 45 tert-Butyl (3-endo)-3-{[4-(1-fluoroethyl)pyridin-2-yl]oxy}-8-azabicyclo[3.2.1]octane-8-carboxylate

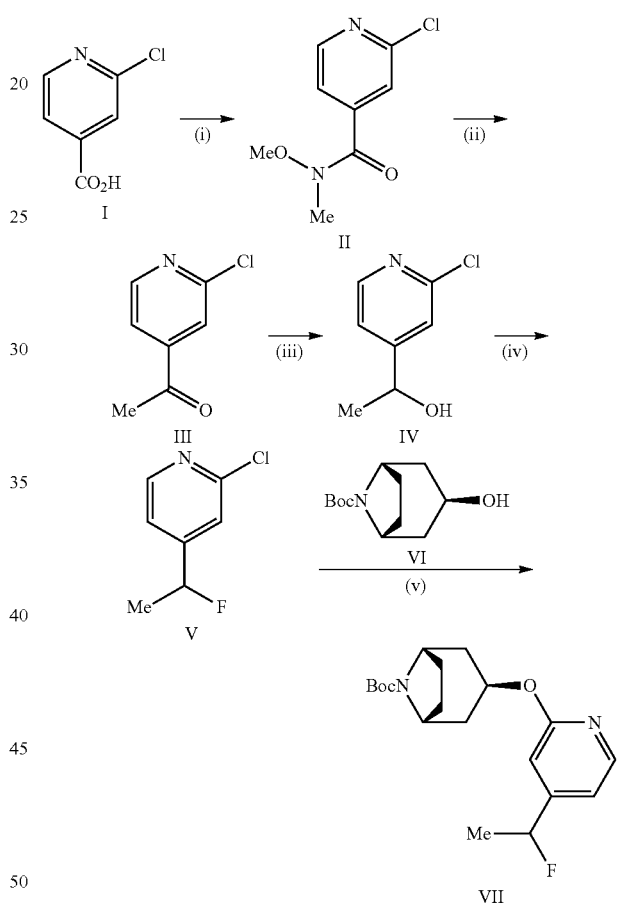

Step (i):

To a solution of 2-chloro-3-formylpyridine (1.0 g) in dichloromethane (20 mL) were added XtalFluor-M (2.57 g, manufactured by OmegaChem. Inc.) and triethylamine trihydrofluoride (1.2 mL), and the mixture was stirred overnight. To an ice-cold reaction solution was added an aqueous sodium bicarbonate solution, and the mixture was extracted with dichloromethane, dehydrated with sodium sulfate, and concentrated under reduced pressure. The residue was purified by silica gel column chromatography (eluent: hexane/ethyl acetate=6/1) to give Compound II (890 mg).

Step (ii):

To a solution of Compound II (890 mg) and Compound III (1.11 g) in DMF (15 mL) was added sodium hydride (356 mg), and the mixture was stirred at 80° C. overnight. The reaction solution was diluted with aqueous ammonium chlo- Step (i):

To a solution of 2-chloroisonicotinic acid (3.08 g) in dichloromethane (60 mL) were added WSC/HCl (5.62 g), HOBt (4.5 g), N,O-dimethylhydroxyamine hydrochloride (2.9 g) and triethylamine (8.3 mL), and the mixture was stirred overnight. The reaction mixture was diluted with aqueous ammonium chloride solution, extracted with dichloromethane, dehydrated with sodium sulfate, and concentrated under reduced pressure. The residue was purified by silica gel column chromatography (eluent: hexane/ethyl acetate=2/1) to give Compound II (3.51 g).

Step (ii):

To a solution of Compound II (2.69 g) in THF (30 mL) was added methylmagnesium bromide (5.4 mL, 3.0M diethyl ether solution), and the mixture was stirred overnight. The reaction mixture was diluted with aqueous ammonium chloride solution, extracted with ethyl acetate, dehydrated with sodium sulfate, and concentrated under reduced pressure. The residue was purified by silica gel column chromatography (eluent: hexane/ethyl acetate=3/1) to give Compound III (1.72 g).

Step (iii):

To a solution of sodium borohydride (418 mg) in methanol (20 mL) was added Compound III (1.72 g), and the mixture was stirred overnight. The reaction solution was concentrated under reduced pressure, and the residue was diluted with aqueous ammonium chloride solution, extracted with ethyl acetate, dehydrated with sodium sulfate, and concentrated under reduced pressure. The residue was purified by silica gel column chromatography (eluent: hexane/ethyl acetate=3/1) to give Compound IV (1.79 g).

Step (iv):

To a solution of Compound IV (519 mg) in dichloromethane solution (10 mL) were added XtalFluor-E (1.13 g, manufactured by OmegaChem. Inc.) and DBU 1,8-diazabicyclo[4.3.0]undecene (0.75 mL), and the mixture was stirred overnight. To an ice-cold reaction solution was added aqueous sodium bicarbonate solution, and the mixture was extracted with dichloromethane, dehydrated with sodium sulfate, and concentrated under reduced pressure. The residue was purified by silica gel column chromatography (eluent: hexane/ethyl acetate=3/1) to give Compound V (415 mg).

Step (v):

To a solution of Compound V (486.4 mg) and Compound VI (623 mg) in DMF (20 mL) was added sodium hydride (198 mg), and the mixture was stirred at 80° C. overnight. The reaction mixture was diluted with aqueous ammonium chloride solution, extracted with ethyl acetate, dehydrated with sodium sulfate, and concentrated under reduced pressure. The residue was purified by silica gel column chromatography (eluent: hexane/ethyl acetate=5/1) to give the title compound VII (116 mg).

¹H-NMR (CDCl₃) δ 1.47 (s, 9H), 1.61 (dd, 3H, J=24.2, 6.4 Hz), 1.80-2.32 (m, 8H), 4.15-4.22 (m, 2H), 5.37 (t, 1H, J=4.9 Hz), 5.55 (dq, 1H, J=47.8, 6.5 Hz), 6.65 (d, 1H, J=0.7 Hz), 6.77-6.78 (m, 1H), 8.11 (d, 1H, J=5.3 Hz)

Reference Example 46 tert-Butyl (3-endo)-3-{[4-(difluoromethyl)pyridin-2-yl]oxy}-8-azabicyclo[3.2.1]octane-8-carboxylate

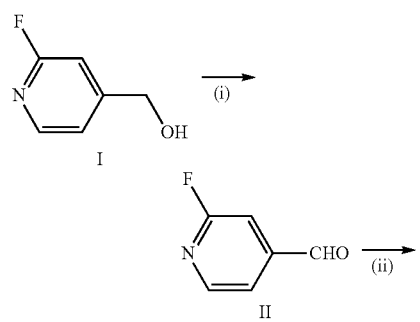

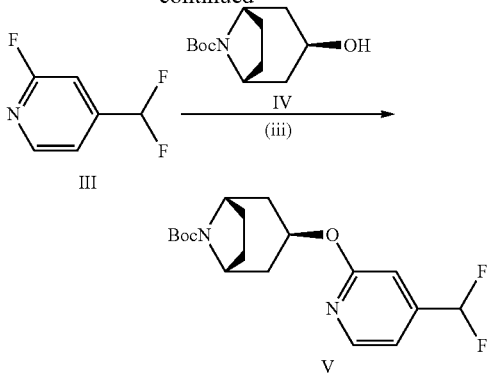

Step (i):

A mixture of 2-fluoro-4-pyridinemethanol (1.00 g), manganese dioxide (10.00 g) and methylene chloride (24 mL) was stirred at room temperature for 3 days. The reaction solution was filtered through Celite, and the filtrate was concentrated under reduced pressure to give Compound II (899 mg) as a crude product.

Step (ii):

To an ice-cold solution of Compound II (300 mg) obtained in Step (i) in dichloromethane (10 mL) was added deoxo-flour (1.08 mL, manufactured by Acros Chemicals Ltd.), and the mixture was stirred for one hour. To the reaction solution was added a saturated aqueous sodium carbonate solution, and the mixture was extracted with chloroform. The organic layer was washed with aqueous sodium bicarbonate solution and brine. The resultant was dehydrated with sodium sulfate, and concentrated under reduced pressure. The residue was purified by silica gel column chromatography (eluent: hexane/ethyl acetate=5/1) to give Compound V (151 mg).

Step (iii):

To a solution of Compound III (151 mg) and Compound IV (228 mg) in DMSO (2 mL) was added sodium hydride (67 mg), and the mixture was stirred at 60° C. for 3 hours. The reaction mixture was diluted with aqueous ammonium chloride solution, extracted with ethyl acetate, dehydrated with sodium sulfate, and concentrated under reduced pressure. The residue was purified by silica gel column chromatography (eluent: hexane/ethyl acetate=5/1) to give the title compound VI (173 mg).

¹H-NMR (CDCl₃) δ 1.48 (s, 9H), 1.67-2.29 (m, 6H), 4.11-4.43 (m, 3H), 4.72-4.85 (m, 1H), 5.37-5.44 (m, 1H), 6.57 (t, 1H, J=55.8 Hz), 6.81 (s, 1H), 6.96 (d, 1H, J=5.0 Hz), 8.23 (dd, 1H, J=5.3, 0.4 Hz)

Reference Example 47 tert-Butyl (3-endo)-3-{3-[(difluoromethoxy)methyl]phenoxy}-8-azabicyclo[3.2.1]octane-8-carboxylate

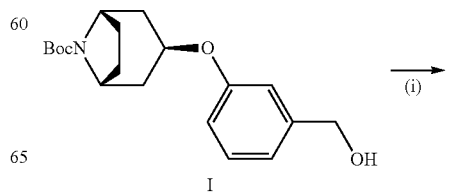

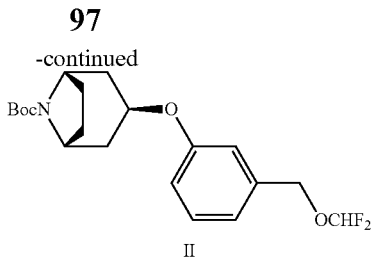

Step (i):

To a solution of Compound I (500 mg) and copper iodide (57 mg) in acetonitrile (3.0 mL) was added 2,2-difluoro-2-(fluorosulfonyl)acetic acid (155 μL), and the mixture was stirred at 50° C. for 2 hours. To an ice-cold reaction mixture was added water, and the mixture was extracted with ethyl acetate. The organic layer was washed with a saturated aqueous ammonium chloride solution and brine, dehydrated with sodium sulfate, and concentrated under reduced pressure. The residue was purified by silica gel column chromatography (eluent: hexane/ethyl acetate=4/1) to give the title compound II (151 mg).

$^1$H-NMR (CDCl$_3$) δ 1.48 (s, 9H), 1.94-2.15 (m, 8H), 4.16-4.25 (m, 2H), 4.64 (t, 1H, J=4.8 Hz), 4.85 (s, 2H), 6.31 (t, 1H, J=74.4 Hz), 6.79 (dd, 1H, J=8.2, 2.3 Hz), 6.83 (t, 1H, J=2.1 Hz), 6.92 (d, 1H, J=7.6 Hz), 7.26-7.30 (m, 1H)

Reference Example 48 tert-Butyl (3-endo)-3-{[6-(difluoromethoxy)-2-pyridinyl]oxy}-8-azabicyclo[3.2.1]octane-8-carboxylate

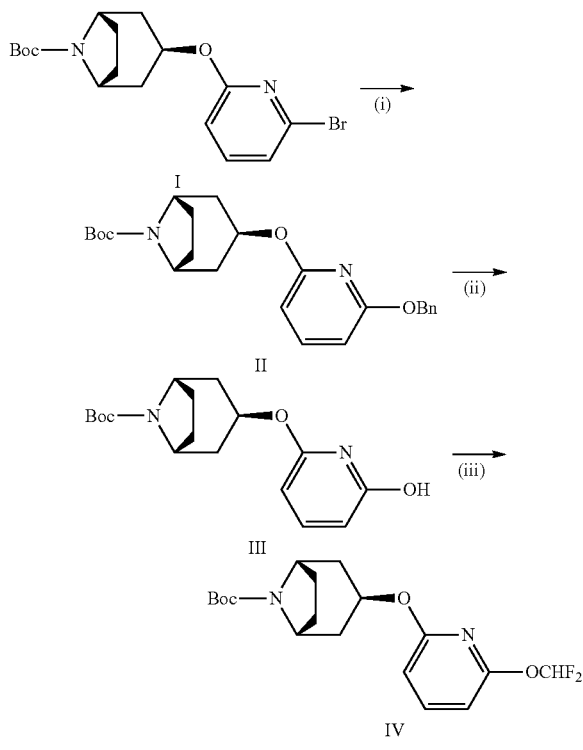

Step (i):

To a solution of Compound I (500 mg) and benzyl alcohol (161 μL) in DMF (2.6 mL) was added sodium hydride (85 mg, 55% contents), and the mixture was stirred at 100° C. overnight. To the reaction mixture was added water, and the mixture was extracted with ethyl acetate. The organic layer was washed with brine, dried over sodium sulfate, and concentrated under reduced pressure. The residue was purified by silica gel column chromatography (eluent: hexane/ethyl acetate=4/1) to give Compound II (389 mg).

Step (ii):

A solution of Compound II (389 mg) and 10% palladium-carbon (50 mg, 50% wet) in methanol (3.5 mL) was stirred under hydrogen atmosphere (ordinary pressure) overnight. The reaction mixture was filtered through Celite, and the filtrate was concentrated under reduced pressure. The residue was purified by silica gel column chromatography (eluent: chloroform/methanol=9/1) to give Compound III (204 mg).

Step (iii):

To a mixture of Compound III (204 mg), cesium carbonate (622 mg) and DMF (2.1 mL) was added methyl chlorodifluoroacetate (201 μL), and the mixture was stirred at 60° C. for 3 hours. To the reaction mixture was added water, and the mixture was extracted with ethyl acetate. The organic layer was washed with brine, dried over sodium sulfate, and concentrated under reduced pressure. The residue was purified by silica gel column chromatography (eluent: hexane/ethyl acetate=4/1) to give the title compound IV (50 mg).

$^1$H-NMR (CDCl$_3$) δ 1.48 (s, 9H), 1.90-2.21 (m, 8H), 4.16-4.25 (m, 2H), 5.21 (t, 1H, J=4.9 Hz), 6.43-6.49 (m, 2H), 7.30 (t, 1H, J=73.6 Hz), 7.60 (t, 1H, J=7.9 Hz).

Reference Example 49 tert-Butyl (3-endo)-3-[3-(difluoromethoxy)-4-fluorophenoxy]-8-azabicyclo[3.2.1]octane-8-carboxylate

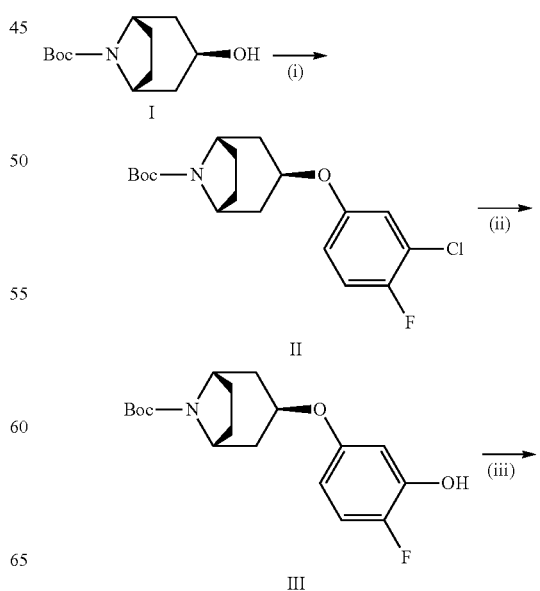

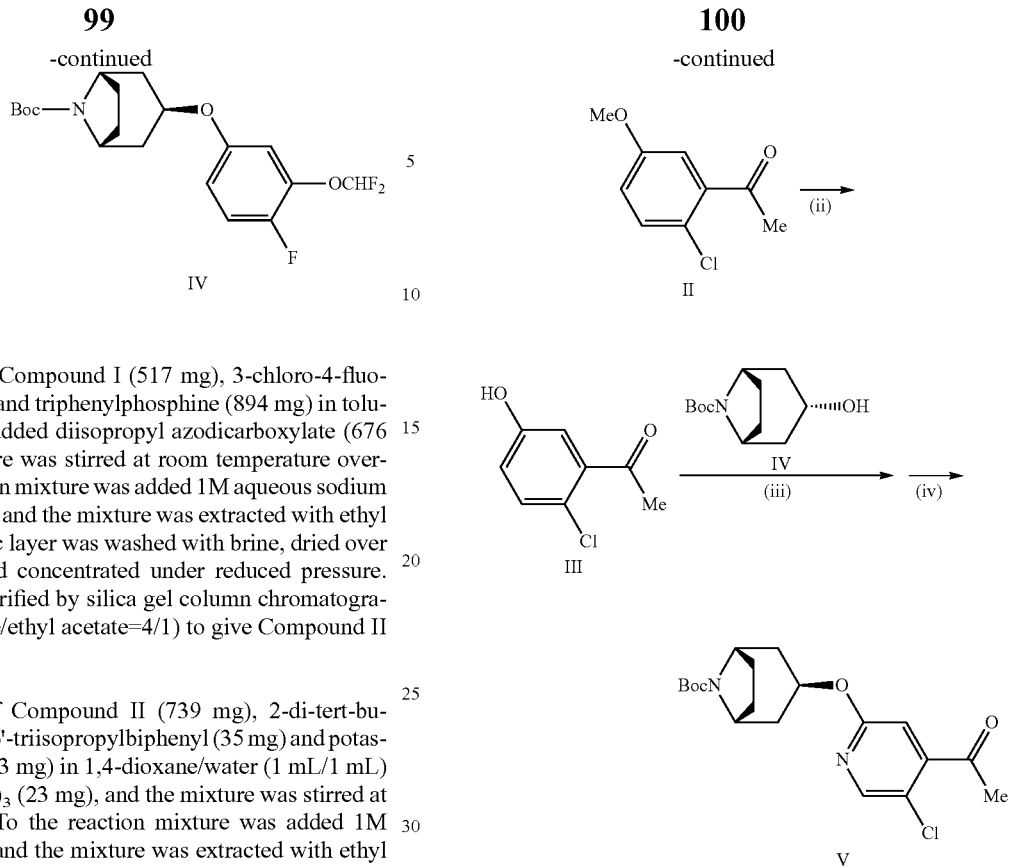

Step (i):

To a solution of Compound I (517 mg), 3-chloro-4-fluorophenol (500 mg) and triphenylphosphine (894 mg) in toluene (7.6 mL) was added diisopropyl azodicarboxylate (676 μL), and the mixture was stirred at room temperature overnight. To the reaction mixture was added 1M aqueous sodium hydroxide solution, and the mixture was extracted with ethyl acetate. The organic layer was washed with brine, dried over sodium sulfate, and concentrated under reduced pressure. The residue was purified by silica gel column chromatography (eluent: hexane/ethyl acetate=4/1) to give Compound II (739 mg).

Step (ii):

To a mixture of Compound II (739 mg), 2-di-tert-butylphosphino-2',4',6'-triisopropylbiphenyl (35 mg) and potassium hydroxide (233 mg) in 1,4-dioxane/water (1 mL/1 mL) was added $Pd_2(dba)_3$ (23 mg), and the mixture was stirred at 80° C. overnight. To the reaction mixture was added 1M hydrochloric acid, and the mixture was extracted with ethyl acetate. The organic layer was washed with brine, dried over sodium sulfate, and concentrated under reduced pressure. The residue was purified by silica gel column chromatography (eluent: hexane/ethyl acetate=4/1) to give Compound III (80 mg).

Step (iii):

To a mixture of Compound III (80 mg), cesium carbonate (77 mg) and DMF (0.5 mL) was added methyl chlorodifluoroacetate (37 μL), and the mixture was stirred at 80° C. for 5 hours. To the reaction mixture was added water, and the mixture was extracted with ethyl acetate. The organic layer was washed with brine, dried over sodium sulfate, and concentrated under reduced pressure. The residue was purified by silica gel column chromatography (eluent: hexane/ethyl acetate=4/1) to give the title compound IV (45 mg).

$^1$H-NMR ($CDCl_3$) δ 1.47 (s, 9H), 1.91-2.10 (m, 8H), 4.17-4.25 (m, 2H), 4.54 (t, 1H, J=4.8 Hz), 6.54 (t, 1H, J=73.6 Hz), 6.63 (dt, 1H, J=9.1, 2.9 Hz), 6.70 (dd, 1H, J=6.8, 2.9 Hz), 7.05-7.10 (m, 1H)

Reference Example 50 tert-Butyl (3-endo)-3-(3-acetyl-4-chlorophenoxy)-8-azabicyclo[3.2.1]octane-8-carboxylate

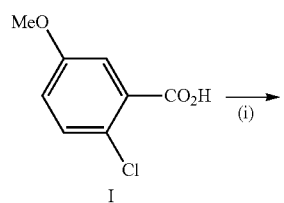

Step (i):

To a solution of 2-chloro-5-methoxybenzoic acid (1.50 g) in THF (8 mL) at −78° C. was added methyllithium (17.7 mL, 1M ether solution), and then the mixture was stirred at room temperature overnight. The reaction mixture was diluted with 1M hydrochloric acid, and the mixture was extracted with ethyl acetate. The organic layer was dehydrated with sodium sulfate, and concentrated under reduced pressure. The residue was purified by silica gel column chromatography (eluent: hexane/ethyl acetate=7/1) to give Compound II (335 mg).

Step (ii):

To a solution of Compound II (335 mg) in chlorobenzene (7.3 mL) was added aluminium chloride (605 mg), and the mixture was stirred at 120° C. for 30 minutes. The reaction solution was added dropwise into 1M hydrochloric acid, and the mixture was extracted with ethyl acetate, and washed with brine. The organic layer was dried over magnesium sulfate, and concentrated under reduced pressure, and the residue was purified by silica gel column chromatography (eluent: hexane/ethyl acetate=7/1) to give Compound III (279 mg).

Step (iii):

To a mixture of Compound III (227 mg), Compound IV (247 mg), triphenylphosphine (349 mg) and toluene (7 mL) was added diisopropyl azodicarboxylate (264 μL), and the mixture was stirred at room temperature overnight. The reaction solution was washed successively with 1M aqueous sodium hydroxide solution, 1M hydrochloric acid, and brine. The organic layer was dried over sodium sulfate, and concentrated under reduced pressure. The residue was purified by silica gel column chromatography (eluent: hexane/ethyl acetate=6/1) to give the title compound IV (359 mg).

¹H-NMR (CDCl₃) δ 1.47 (s, 9H), 1.87-2.26 (m, 8H), 2.65 (s, 3H), 4.10-4.31 (m, 2H), 4.58-4.64 (m, 1H), 6.85 (dd, 1H, J=8.8, 3.1 Hz), 6.98 (d, 1H, J=3.1 Hz), 7.31 (d, 1H, J=8.8 Hz)

Reference Example 51 tert-Butyl (3-endo)-3-(3-acetyl-2-methylphenoxy)-8-azabicyclo[3.2.1]octane-8-carboxylate

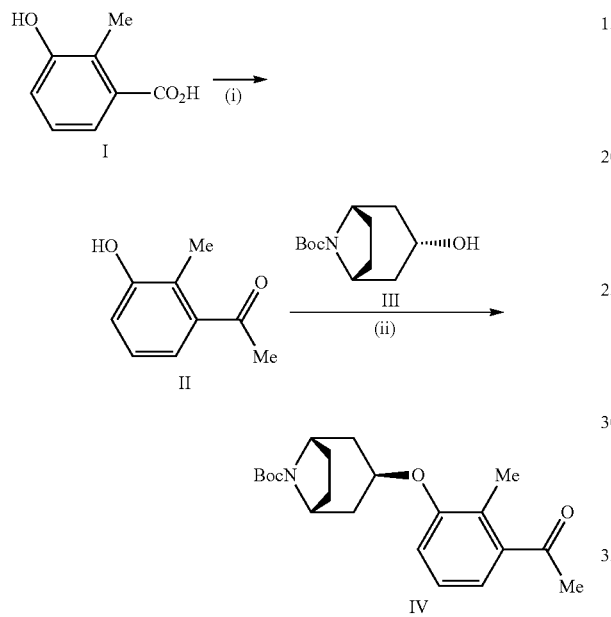

Step (i):

To a solution of 3-hydroxy-2-methylbenzoic acid (1.00 g) in THF (6.6 mL) at −78° C. was added methyllithium (21.7 mL, 1M ether solution), and then the mixture was stirred at room temperature overnight. The reaction mixture was diluted with 1M hydrochloric acid, extracted with ethyl acetate, dehydrated with sodium sulfate, and concentrated under reduced pressure. The residue was purified by silica gel column chromatography (eluent: hexane/ethyl acetate=7/1) to give Compound II (584 mg).

Step (ii):

To a mixture of Compound III (200 mg), Compound IV (247 mg), triphenylphosphine (349 mg) and toluene (7 mL) was added diisopropyl azodicarboxylate (264 μL), and the mixture was stirred at room temperature overnight. The reaction solution was washed successively with 1M aqueous sodium hydroxide solution, 1M hydrochloric acid, and brine. The organic layers were combined, and dried over sodium sulfate, and concentrated under reduced pressure. The residue was purified by silica gel column chromatography (eluent: hexane/ethyl acetate=6/1) to give the title compound IV (377 mg).

¹H-NMR (CDCl₃) δ 1.48 (s, 9H), 1.85-2.16 (m, 8H), 2.33 (s, 3H), 2.56 (s, 3H), 4.16-4.32 (m, 2H), 4.59-4.66 (m, 1H), 6.76-6.85 (m, 1H), 7.08-7.22 (m, 2H)

Reference Example 52 tert-Butyl (3-endo)-3-(3-acetyl-2-chlorophenoxy)-8-azabicyclo[3.2.1]octane-8-carboxylate

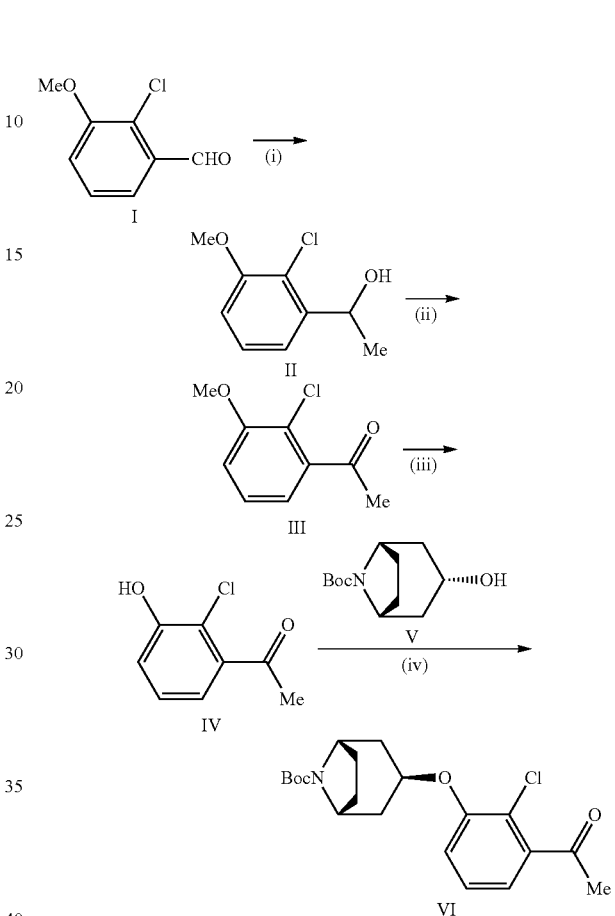

Step (i):

To an ice-cold 2-chloro-3-methoxybenzaldehyde (477 mg) in THF (10 mL) was added methylmagnesium bromide (1.12 mL, 3M ether solution), and the mixture was stirred 31.5 hours. The reaction mixture was diluted with 1M hydrochloric acid, extracted with ethyl acetate, and the organic layer was dehydrated with sodium sulfate, and concentrated under reduced pressure to give Compound II (653 mg) as a crude product.

Step (ii):

A mixture of Compound II (653 mg) obtained in Step (i), manganese dioxide (4.77 g) and methylene chloride (10 mL) was stirred at room temperature overnight. To the mixture was added manganese dioxide (2.0 g), and the mixture was stirred at 40° C. for 3 hours. The reaction mixture was filtered through Celite, and the filtrate was concentrated under reduced pressure to give Compound III (504 mg) as a crude product.

Step (iii):

To a solution of Compound II (504 mg) obtained in Step (ii) and chlorobenzene (11 mL) was added aluminum chloride (932 mg), and the mixture was stirred at 120° C. for 30 minutes. The reaction solution was added dropwise into 1M hydrochloric acid in a water bath, and the mixture was extracted with ethyl acetate and washed with brine. The organic layer was dried over magnesium sulfate, concentrated under reduced pressure, and the residue was purified by silica gel column chromatography (eluent: hexane/ethyl acetate=7/1) to give Compound III (429 mg).

Step (iv):

To a mixture of Compound III (227 mg), Compound IV (247 mg), triphenylphosphine (349 mg) and toluene (7 mL) was added diisopropyl azodicarboxylate (264 μL), and the mixture was stirred at room temperature overnight. The reaction solution was washed with 1M aqueous sodium hydroxide solution, 1M hydrochloric acid and brine. The organic layer was dried over sodium sulfate, and concentrated under reduced pressure. The residue was purified by silica gel column chromatography (eluent: hexane/ethyl acetate=6/1) to give the title compound IV (350 mg).

$^1$H-NMR (CDCl$_3$) δ 1.48 (s, 9H), 1.92-2.03 (m, 4H), 2.09-2.32 (m, 4H), 2.63 (s, 3H), 4.13-4.32 (m, 2H), 4.65-4.73 (m, 1H), 6.86 (dq, 1H, J=8.3, 0.6 Hz), 7.01 (dd, 1H, J=7.7, 1.5 Hz), 7.24 (t, 1H, J=8.0 Hz)

Reference Example 53 tert-Butyl (3-endo)-3-(3-acetyl-2-fluorophenoxy)-8-azabicyclo[3.2.1]octane-8-carboxylate

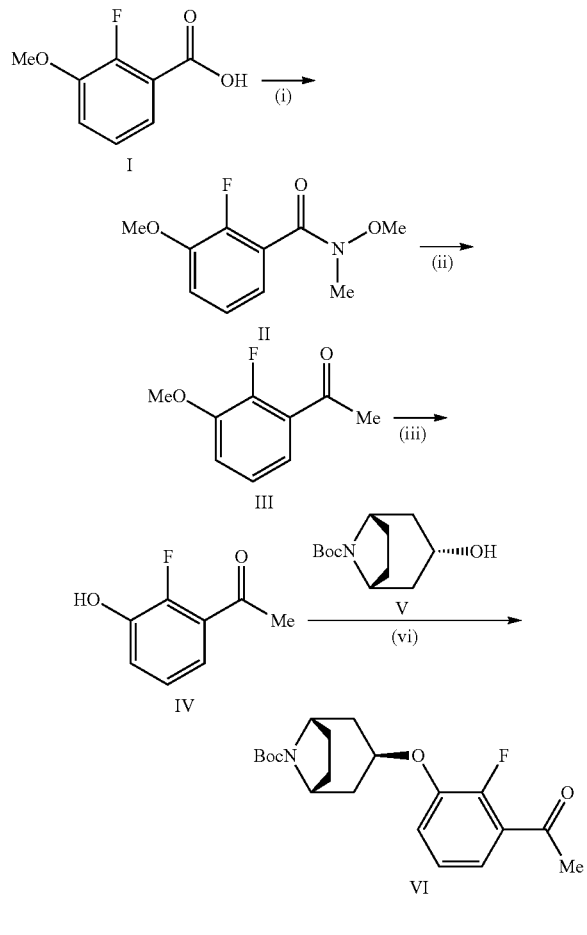

Step (i):

To an ice-cold mixture of Compound I (1.63 g), N,O-dimethylhydroxyamine hydrochloride (1.87 g), WSC.HCl (2.03 g), HOBt.H$_2$O (1.62 g) and dichloromethane (32 mL) was added triethylamine (5.4 mL), and the mixture was stirred at room temperature for 3 days. The reaction mixture was diluted with chloroform, and washed with 1M hydrochloric acid, and 1N aqueous sodium hydroxide solution. The organic layer was washed with brine, dried over sodium sulfate, and concentrated under reduced pressure. The residue was purified by silica gel column chromatography (eluent: hexane/ethyl acetate=1/1) to give Compound II (2.03 g).

Step (ii):

To an ice-cold Compound II (500 mg) in THF (4.7 mL) was added methylmagnesium bromide (1.2 mL, 3.0 M diethyl ether solution), and the mixture was stirred for 2 hours while it was allowed to warm up to room temperature. To the reaction mixture was added a saturated aqueous ammonium chloride solution, and the mixture was extracted with ethyl acetate. The organic layer was washed with brine, dried over sodium sulfate, and concentrated under reduced pressure. The residue was purified by silica gel column chromatography (eluent: hexane/ethyl acetate=4/1) to give Compound III (365 mg).

Step (iii):

To a solution of Compound III (365 mg) in chlorobenzene (7.2 mL) was added aluminium chloride (724 mg), and the mixture was stirred at 130° C. for 1.5 hour. To the reaction mixture was added water, and the mixture was extracted with ethyl acetate. The organic layer was washed with brine, dried over sodium sulfate, and concentrated under reduced pressure to give Compound IV (300 mg) as a crude product.

Step (iv):

To a solution of Compound IV (300 mg), Compound V (493 mg), triphenylphosphine (855 mg) in toluene (7.2 mL) was added diisopropyl azodicarboxylate (645 μL), and the mixture was stirred at room temperature overnight. To the reaction mixture was added 1M aqueous sodium hydroxide solution, and the mixture was extracted with ethyl acetate. The organic layer was washed with brine, dried over sodium sulfate, and concentrated under reduced pressure. The residue was purified by silica gel column chromatography (eluent: hexane/ethyl acetate=4/1) to give the title compound VI (431 mg).

$^1$H-NMR (CDCl$_3$) δ 1.48 (s, 9H), 1.97-2.22 (m, 8H), 2.65 (d, 3H, J=4.8 Hz), 4.22 (br s, 2H), 4.65 (t, 1H, J=4.5 Hz), 6.99-7.14 (m, 2H), 7.36-7.41 (m, 1H)

Reference Example 54 tert-Butyl (3-endo)-3-(3-acetyl-4-fluorophenoxy)-8-azabicyclo[3.2.1]octane-8-carboxylate

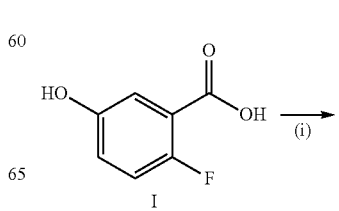

-continued

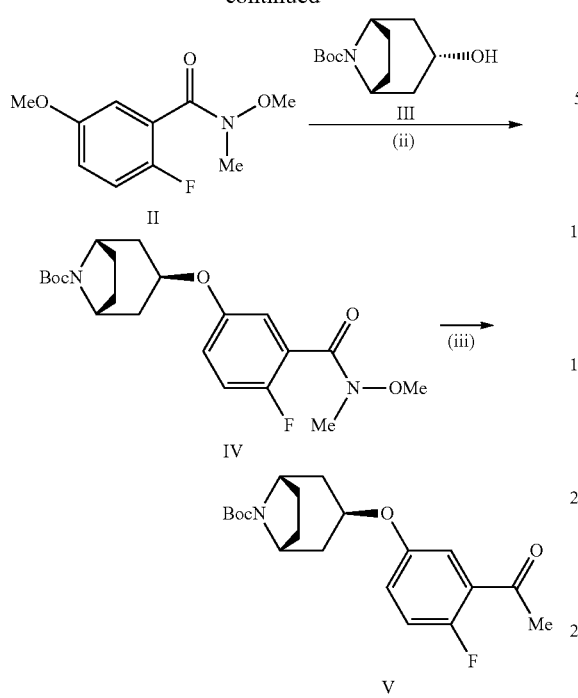

Step (i):

To an ice-cold mixture of Compound I (900 mg), N,O-dimethylhydroxyamine hydrochloride (1.12 g), WSC.HCl (1.22 g), HOBt.H$_2$O (970 mg) and dichloromethane (19 mL) was added triethylamine (3.24 mL), and the mixture was stirred at room temperature for 3 days. The reaction mixture was diluted with chloroform, and washed with 1M hydrochloric acid. The organic layer was washed with brine, dried over sodium sulfate, and concentrated under reduced pressure. The residue was purified by silica gel column chromatography (eluent: hexane/ethyl acetate=1/1) to give Compound II (453 mg).

Step (ii):

To a solution of Compound II (453 mg), Compound III (517 mg) and triphenylphosphine (897 mg) in toluene (7.6 mL) was added diisopropyl azodicarboxylate (678 µL), and the mixture was stirred at room temperature overnight. To the reaction mixture was added 1M aqueous sodium hydroxide solution, and the mixture was extracted with ethyl acetate. The organic layer was washed with brine, dried over sodium sulfate, and concentrated under reduced pressure. The residue was purified by silica gel column chromatography (eluent: hexane/ethyl acetate=1/1) to give Compound IV (956 mg).

Step (iii):

To an ice-cold Compound IV (665 mg) in THF (5.4 mL) was added ethylmagnesium bromide (1.6 mL, 3.0 M diethyl ether solution), and the mixture was stirred for 3 hours. To the reaction mixture was added a saturated aqueous ammonium chloride solution, and the mixture was extracted with ethyl acetate. The organic layer was washed with brine, dried over sodium sulfate, and concentrated under reduced pressure. The residue was purified by silica gel column chromatography (eluent: hexane/ethyl acetate=4/1) to give the title compound V (270 mg).

$^1$H-NMR (CDCl$_3$) δ 1.47 (s, 9H), 1.90-2.14 (m, 8H), 2.64 (d, 3H, J=5.1 Hz), 4.17-4.23 (m, 2H), 4.62 (t, 1H, J=4.7 Hz), 6.96-7.10 (m, 2H), 7.25-7.28 (m, 1H)

Reference Example 55 tert-Butyl (3-endo)-3-(3-propanoyl)-8-azabicyclo[3.2.1]octane-8-carboxylate

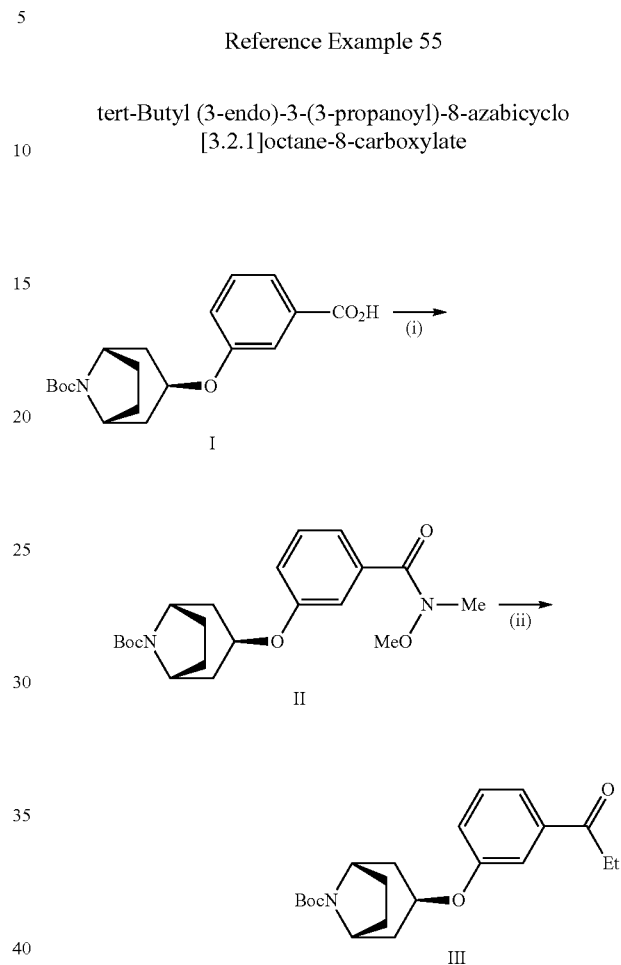

Step (i):

To a solution of Compound I (1.69 g) in dichloromethane (30 mL) were added WSC.HCl (1.4 g), HOBt.H$_2$O (1.11 g), N,O-dimethylhydroxyamine hydrochloride (711 mg) and triethylamine (2.04 mL), and the mixture was stirred overnight. The reaction mixture was diluted with aqueous ammonium chloride solution, extracted with dichloromethane, dehydrated with sodium sulfate, and concentrated under reduced pressure. The residue was purified by silica gel column chromatography (eluent: hexane/ethyl acetate=2/1) to give Compound II (1.88 g).

Step (ii):

To a solution of Compound II (262 mg) in THF (20 mL) was added ethylmagnesium chloride (2 mL, 2.0 M diethyl ether solution), and the mixture was stirred overnight. The reaction mixture was diluted with aqueous ammonium chloride solution, extracted with ethyl acetate, dehydrated with sodium sulfate, and concentrated under reduced pressure. The residue was purified by silica gel column chromatography (eluent: hexane/ethyl acetate=6/1) to give the title compound IV (113 mg).

$^1$H-NMR (CDCl$_3$) δ 1.22 (t, 3H, J=7.3 Hz), 1.48 (s, 9H), 1.94-2.18 (m, 8H), 2.99 (q, 2H, J=7.2 Hz), 4.15-4.20 (m, 2H), 4.70 (t, 1H, J=4.7 Hz), 7.01-7.04 (m, 1H), 7.36-7.40 (m, 2H), 7.51-7.54 (m, 1H)

Reference Example 56 tert-Butyl (3-endo)-3-[(3-acetylpyridin-2-yl)oxy]-8-azabicyclo[3.2.1]octane-8-carboxylate

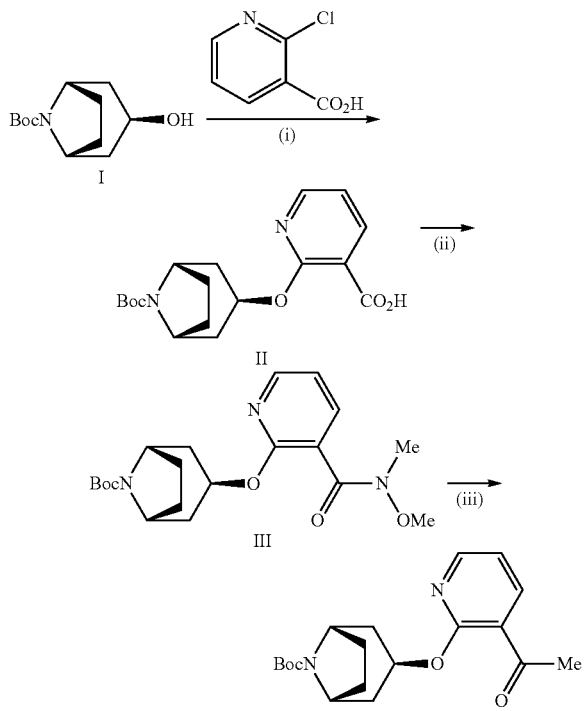

Step (i):
To a solution of 2-chloronicotinic acid (1.39 g) and Compound I (1.67 g) in DMSO (30 mL) was added sodium hydride (962 mg), and the mixture was stirred at 80° C. overnight. The reaction solution was acidified with 1M hydrochloric acid, and the mixture was extracted with chloroform. The organic layer was dried over sodium sulfate, and concentrated under reduced pressure to give Compound II as a crude product.

Step (ii):
To a solution of Compound II obtained in Step (i) in dichloromethane (30 mL) were added WSC.HCl (2.1 g), HOBt.H$_2$O (1.5 g), N,O-dimethylhydroxyamine hydrochloride (1.1 g) and triethylamine (3.0 mL), and the mixture was stirred overnight. The reaction mixture was diluted with aqueous ammonium chloride solution, extracted with dichloromethane, dehydrated with sodium sulfate, and concentrated under reduced pressure. The residue was purified by silica gel column chromatography (eluent: hexane/ethyl acetate=1/1) to give Compound III (1.99 g).

Step (iii):
To a solution of Compound III (1.0 g) in THF (10 mL) was added methylmagnesium bromide (1.7 mL, 3.0 M diethyl ether solution), and the mixture was stirred overnight. The reaction mixture was diluted with aqueous ammonium chloride solution, and the mixture was extracted with ethyl acetate, dehydrated with sodium sulfate, and concentrated under reduced pressure. The residue was purified by silica gel column chromatography (eluent: hexane/ethyl acetate=4/1) to give the title compound IV (560 mg).

$^1$H-NMR (CDCl$_3$) δ 1.46 (s, 9H), 2.07-2.19 (m, 8H), 2.68 (s, 3H), 4.11-4.27 (m, 2H), 5.54 (t, 1H, J=5.4 Hz), 6.95 (dd, 1H, J=7.5, 4.8 Hz), 8.01 (dd, 1H, J=7.5, 2.0 Hz), 8.27 (dd, 1H, J=4.8, 2.0 Hz)

Reference Example 57 tert-Butyl (3-endo)-3-(3-fluoro-5-methoxyphenoxy)-8-azabicyclo[3.2.1]octane-8-carboxylate

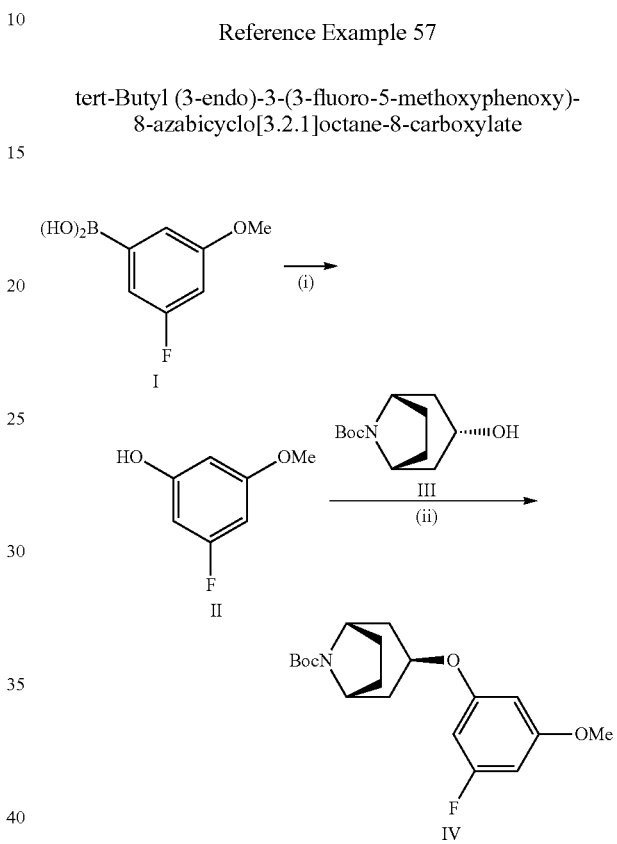

Step (i):
To an ice-cold solution of Compound I (432 mg) in a mixture of THF/1M aqueous sodium hydroxide solution (22 mL/4.7 mL) was added a 30% aqueous hydrogen peroxide solution (1.3 mL), and the mixture was stirred at room temperature overnight. The reaction mixture was concentrated under reduced pressure, diluted with water, and extracted with ethyl acetate. The organic layer was washed with brine, dried over sodium sulfate, and concentrated under reduced pressure. The residue was purified by silica gel column chromatography (eluent: hexane/ethyl acetate=3/1) to give Compound II (349 mg).

Step (ii):
To a solution of Compound II (327 mg), Compound III (523 mg) and triphenylphosphine (905 mg) in toluene (7.7 mL) was added diisopropyl azodicarboxylate (684 μL), and the mixture was stirred at room temperature overnight. To the reaction mixture was added 1M aqueous sodium hydroxide solution, and the mixture was extracted with ethyl acetate. The organic layer was washed with brine, dried over sodium sulfate, and concentrated under reduced pressure. The residue was purified by silica gel column chromatography (eluent: hexane/ethyl acetate=4/1) to give the title compound IV (500 mg).

$^1$H-NMR (CDCl$_3$) δ 1.47 (s, 9H), 1.93-2.13 (m, 8H), 3.77 (s, 3H), 4.15-4.23 (m, 2H), 4.55 (t, 1H, J=4.4 Hz), 6.13-6.17 (m, 2H), 6.19-6.28 (m, 1H).

Reference Example 58 tert-Butyl (3-endo)-3-[(2,2-difluoro-1,3-benzodioxol-5-yl)oxy]-8-azabicyclo[3.2.1]octane-8-carboxylate

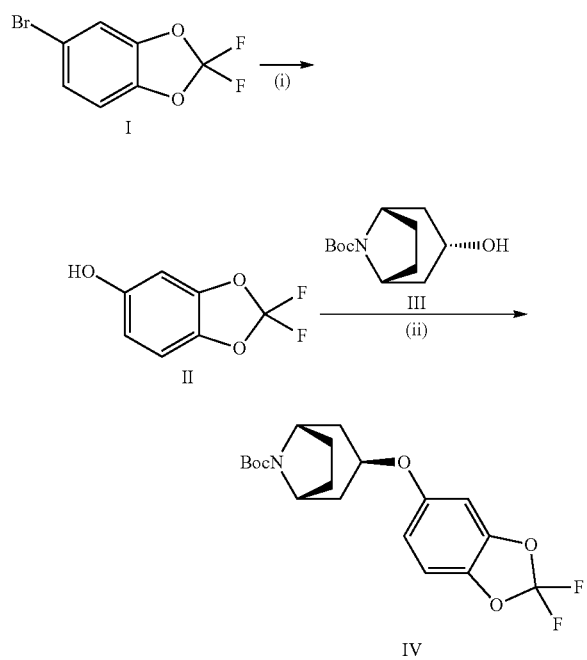

Step (i):

To a solution of Compound I (1.0 g), 2-di-tert-butylphosphino-3,4,5,6-tetramethyl-2',4',6'-triisopropylbiphenyl (190 mg) and potassium hydroxide (474 mg) in a mixture of 1,4-dioxane/water (2.1 mL/2.1 mL) was added Pd$_2$(dba)$_3$ (77 mg), and the resulting mixture was stirred at 100° C. overnight. To the reaction mixture was added 1M hydrochloric acid, and the mixture was extracted with ethyl acetate. The organic layer was washed with brine, dried over sodium sulfate, and concentrated under reduced pressure. The residue was purified by silica gel column chromatography (eluent: hexane/ethyl acetate=4/1) to give Compound II (605 mg).

Step (ii):

To a solution of Compound II (605 mg), Compound III (658 mg), triphenylphosphine (1.14 g) in toluene (10 mL) was added diisopropyl azodicarboxylate (862 µL), and the resulting mixture was stirred at room temperature overnight. To the reaction mixture was added 1M aqueous sodium hydroxide solution, and the mixture was extracted with ethyl acetate. The organic layer was washed with brine, dried over sodium sulfate, and concentrated under reduced pressure. The residue was purified by silica gel column chromatography (eluent: hexane/ethyl acetate=4/1) to give the title compound IV (918 mg).

$^1$H-NMR (CDCl$_3$) δ 1.47 (s, 9H), 1.91-2.11 (m, 8H), 4.20 (br s, 2H), 4.53 (t, 1H, J=4.8 Hz), 6.47-6.50 (m, 1H), 6.60-6.61 (m, 1H), 6.92-6.95 (m, 1H)

Reference Example 59 tert-Butyl (3-endo)-3-[(6-fluoro-3-oxo-2,3-dihydro-1H-inden-5-yl)oxy]-8-azabicyclo-[3.2.1]octane-8-carboxylate

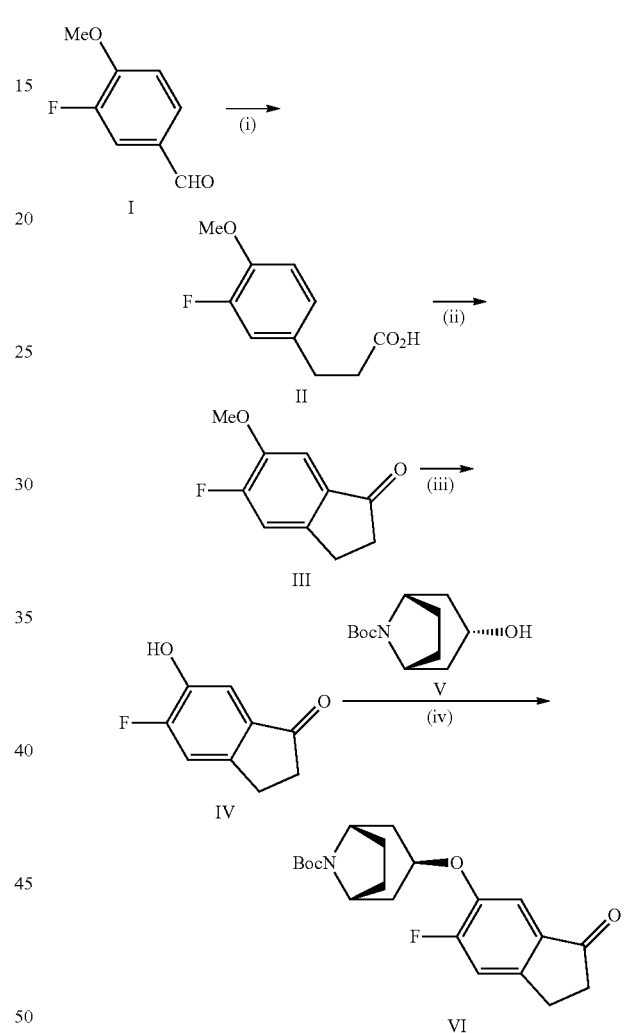

Step (i):

A mixture of 3-fluoro-4-methoxybenzaldehyde (2.00 g) and Meldrum's acid (1.87 g), formic acid.triethylamine complex (6.5 mL, 5:2 complex) was stirred at 100° C. for 5 hours. The mixture was cooled to room temperature, and thereto was added water (2 mL), then, further thereto was added conc. hydrochloric acid to adjust the pH value thereof to pH 1, and the mixture was stirred overnight. The precipitated solid was collected by filtration, washed with water, and dried to give Compound II (982 mg).

Step (ii):

A mixture of Compound II (900 mg), toluene (9 mL) and thionyl chloride (393 µL) was stirred at 90° C. for one hour, and concentrated under reduced pressure. The obtained residue was added to an ice-cold solution of aluminium chloride (605 mg) in methylene chloride (45 mL), and the mixture was stirred for one hour. The reaction solution was added dropwise into ice-cold water, and the mixture was stirred for one hour, and extracted with ether. The organic layer was washed with aqueous sodium bicarbonate solution, dried over magnesium sulfate, and concentrated under reduced pressure. The residue was purified by silica gel column chromatography (eluent: hexane/ethyl acetate=4/1) to give Compound III (666 mg).

Step (iii):

To an ice-cold solution of Compound III (666 mg) in methylene chloride (15 mL) was added dropwise boron tribromide (4.44 mL), and the mixture was stirred at room temperature for 7 hours. The reaction solution was cooled with ice, and thereto was added water, and the mixture was extracted with ethyl acetate. The organic layer was washed with brine, concentrated under reduced pressure, and the residue was purified by silica gel column chromatography (eluent: hexane/ethyl acetate=3/1) to give Compound III (52 mg).

Step (iv):

To a mixture of Compound IV (50 mg), Compound V (56 mg), triphenylphosphine (79 mg) and toluene (1.3 mL) was added diisopropyl azodicarboxylate (60 µL), and the resulting mixture was stirred at room temperature overnight. The reaction solution was washed successively with 1M aqueous sodium hydroxide solution, 1M hydrochloric acid and brine. The organic layer was dried over sodium sulfate, and concentrated under reduced pressure. The residue was purified by silica gel column chromatography (eluent: hexane/ethyl acetate=6/1) to give the title compound IV (48 mg).

$^1$H-NMR (CDCl$_3$) δ 1.24-1.33 (m, 2H), 1.48 (s, 9H), 1.92-2.26 (m, 6H), 2.65-2.73 (m, 2H), 3.02-3.10 (m, 2H), 4.11-4.32 (m, 2H), 4.65-4.71 (m, 1H), 7.16 (s, 1H), 7.19 (d, 1H, J=3.3 Hz)

Reference Example 60 tert-Butyl (3-endo)-3-[(2,2-difluoro-1,3-benzodioxol-5-yl)methoxy]-8-azabicyclo[3.2.1]octane-8-carboxylate

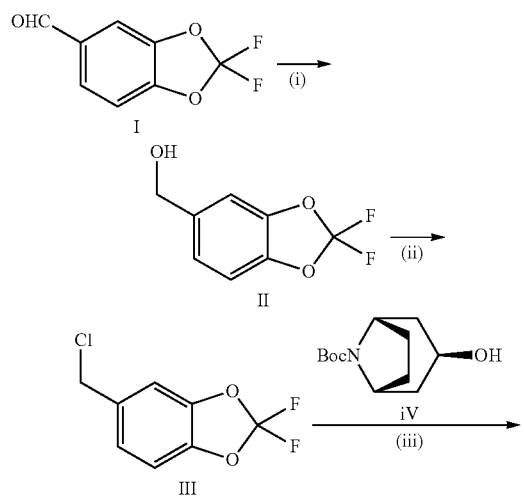

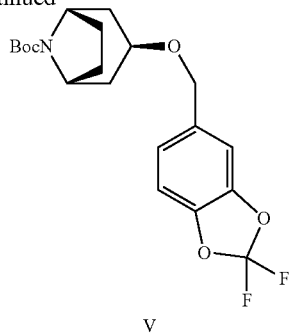

Step (i):

To a solution of sodium borohydride (609 mg) in methanol (20 mL) was added 2,2-difluoro-1,3-benzodioxol-5-carboaldehyde (3.0 g), and the resulting mixture was stirred overnight. The reaction solution was concentrated under reduced pressure, and the residue was diluted with aqueous ammonium chloride solution, and extracted with ethyl acetate. The organic layer was dehydrated with sodium sulfate, and concentrated under reduced pressure. The residue was purified by silica gel column chromatography (eluent: hexane/ethyl acetate=3/1) to give Compound II (3.09 g).

Step (ii):

To an ice-cold solution of Compound II (3.09 g) in dichloromethane (60 mL) was added thionyl chloride (1.54 mL), and then the mixture was stirred at room temperature for 3 hours. The reaction solution was concentrated under reduced pressure, and the residue was purified by silica gel column chromatography (eluent: hexane/ethyl acetate=5/1) to give Compound III (2.89 g).

Step (iii)

To a solution of Compound III (470 mg) and Compound IV (423 mg) in DMF (10 mL) was added sodium hydride (180 mg), and the mixture was stirred overnight. The reaction mixture was diluted with aqueous ammonium chloride solution, extracted with ethyl acetate, dehydrated with sodium sulfate, and concentrated under reduced pressure. The residue was purified by silica gel column chromatography (eluent: hexane/ethyl acetate=6/1) to give the title compound V (448 mg).

$^1$H-NMR (CDCl$_3$) δ 1.46 (s, 9H), 1.95-2.04 (m, 8H), 3.69-3.72 (m, 1H), 4.13-4.19 (m, 2H), 4.45 (s, 2H), 7.00 (s, 2H), 7.07 (s, 1H)

Reference Examples 61 and 62 tert-Butyl (3-endo)-3-(1-oxo-1,3-dihydro-2H-isoindol-2-yl)-8-azabicyclo[3.2.1]octane-8-carboxylate (Compound II)

tert-Butyl (3-endo)-3-(1,3-dihydro-2H-isoindol-2-yl)-8-azabicyclo[3.2.1]octane-8-carboxylate (Compound III)

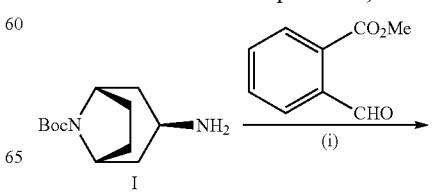

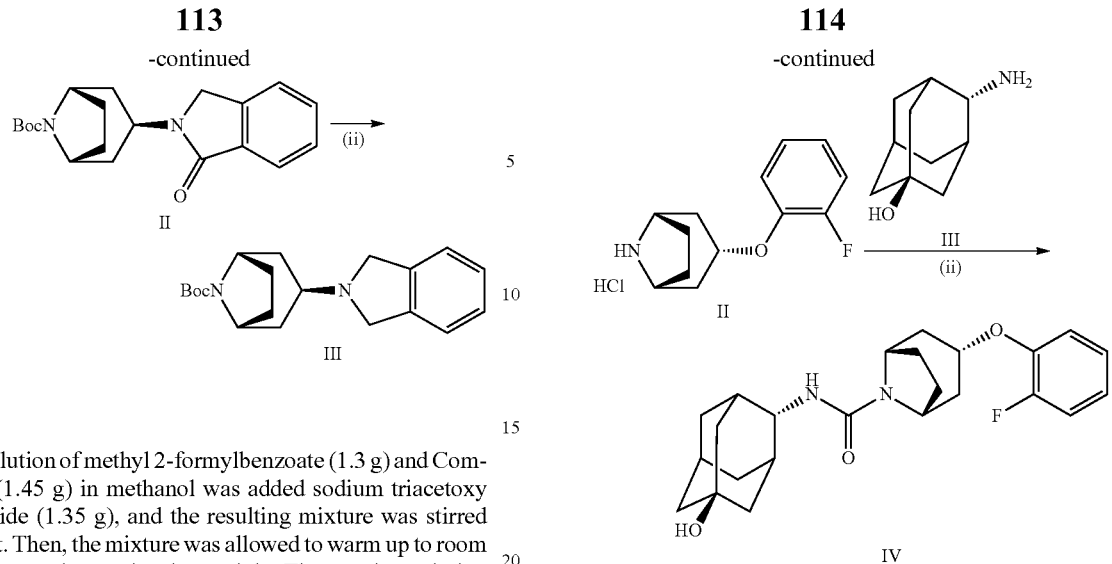

Step (i):

To a solution of methyl 2-formylbenzoate (1.3 g) and Compound I (1.45 g) in methanol was added sodium triacetoxy borohydride (1.35 g), and the resulting mixture was stirred overnight. Then, the mixture was allowed to warm up to room temperature and was stirred overnight. The reaction solution was concentrated under reduced pressure, and the residue was diluted with aqueous ammonium chloride solution, and extracted with ethyl acetate. The organic layer was dehydrated with sodium sulfate, and concentrated under reduced pressure. The residue was purified by silica gel column chromatography (eluent: hexane/ethyl acetate=1/1) to give Compound II (930 mg).

$^1$H-NMR (CDCl$_3$) δ 1.52 (s, 9H), 1.68-1.72 (m, 4H), 2.05-2.09 (m, 2H), 2.50 (s, 2H), 4.21-4.43 (m, 5H), 7.47-7.52 (m, 3H), 7.83 (d, 1H, J=7.5 Hz)

Step (ii):

To an ice-cold solution of Compound II (810 mg) in tetrahydrofuran (10 mL) was added borane-dimethylsulfide complex (0.3 mL), and the mixture was stirred at room temperature overnight. To an ice-cold reaction solution was added methanol, and the mixture was stirred, and then concentrated under reduced pressure. The residue was diluted with brine, extracted with ethyl acetate, dehydrated with sodium sulfate, and concentrated under reduced pressure. The residue was purified by silica gel column chromatography (eluent: hexane/ethyl acetate=4/1) to give the title compound III (632 mg).

$^1$H-NMR (CDCl$_3$) δ 1.52 (s, 9H), 1.68-1.72 (m, 4H), 2.05-2.09 (m, 2H), 2.50 (s, 2H), 4.21-4.43 (m, 5H), 7.47-7.52 (m, 3H), 7.83 (d, 1H, J=7.5 Hz)

Example 1

(3-Exo)-3-(2-fluorophenoxy)-N-[(E)-5-hydroxyadamantan-2-yl]-8-azabicyclo[3.2.1]octane-8-carboxyamide

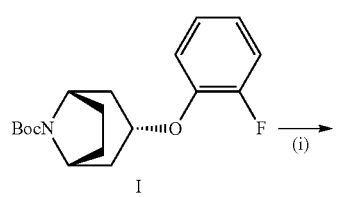

Step (i):

Compound I (356 mg) was added into 4N hydrochloric acid/dioxane (10 mL), and the mixture was stirred overnight. The reaction mixture was concentrated under reduced pressure to give Compound II (260 mg) as a crude product.

Step (ii):

To a mixture of Compound III (81 mg) and THF (4 mL) were added triethylamine (200 μL) and p-nitrophenyl chloroformate (64 mg), and the resulting mixture was stirred at room temperature for one hour. Then, Compound II (58 mg) was added thereto, the mixture was stirred at room temperature overnight. The reaction mixture was extracted with 1N aqueous sodium hydroxide solution and chloroform, and the mixture was washed with 1N hydrochloric acid solution. The organic layer was dried over sodium sulfate, and concentrated under reduced pressure. The residue was washed with ethyl acetate/diisopropylether (1:1) to give the title compound IV (92.2 mg).

$^1$H-NMR (CDCl$_3$) δ1.51-1.57 (m, 3H), 1.67-1.78 (m, 9H), 1.86-1.92 (m, 3H), 2.03-2.15 (m, 7H), 3.96-3.98 (m, 1H), 4.24 (m, 2H), 4.58-4.66 (m, 2H), 6.91-7.09 (m, 4H)

Example 2

(3-Exo)-N-[(E)-5-hydroxyadamantan-2-yl]-3-phenoxy-8-azabicyclo[3.2.1]octane-8-carboxyamide

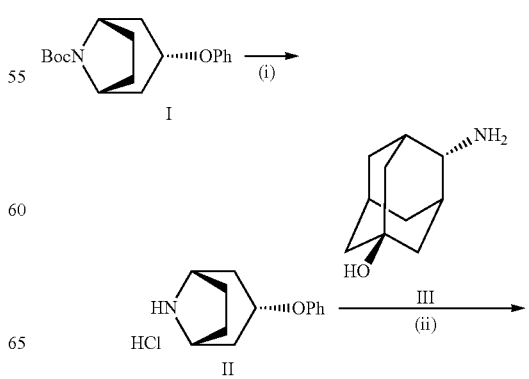

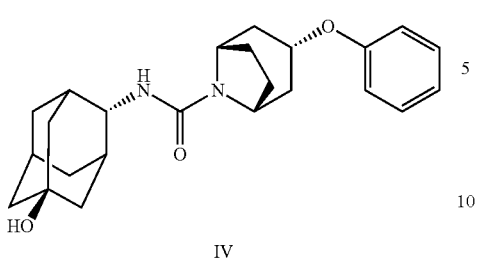

Step (i):

Compound I (2.7 g) was added to 4N hydrochloric acid/dioxane (10 mL), and the mixture was stirred overnight. The reaction mixture was concentrated under reduced pressure to give Compound II (2.27 g).

Step (ii):

To a mixture of Compound II (153.7 mg) obtained in Step (i) and THF (4 mL) was added a mixture of pyridine (150 μL), diphosgene (0.1 mL) and THF (4 mL), and the resulting mixture was stirred at room temperature for 2 hours. The reaction mixture was diluted with brine, and extracted with ethyl acetate. The organic layer was dried over sodium sulfate, and concentrated under reduced pressure. The residue was dissolved in dioxane/sodium bicarbonate water (4 mL, volume ratio=1:1), and thereto were added diisopropylethylamine (0.1 mL), and Compound III (58 mg, Reference Literature: WO2009020137), and the resulting mixture was stirred at room temperature overnight. The reaction solution was extracted with 1N hydrochloric acid and chloroform. The organic layer was dried over sodium sulfate, and concentrated under reduced pressure. The residue was purified by silica gel column chromatography (chloroform/methanol, 10:1) to give the title compound IV (26.8 mg).

$^1$H NMR (CDCl$_3$) δ1.50-1.53 (m, 2H), 1.67-1.92 (m, 13H), 2.05-2.14 (m, 7H), 3.97 (m, 1H), 4.24 (m, 2H), 4.64-4.72 (m, 2H), 6.88-6.96 (m, 3H), 7.24-7.28 (m, 2H)

Example 3

(3-Endo)-N-[(E)-5-carbamoyladamantan-2-yl]-3-phenoxy-8-azabicyclo[3.2.1]octane-8-carboxamide

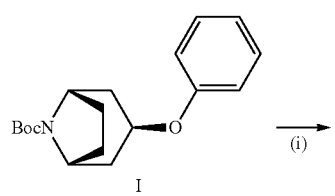

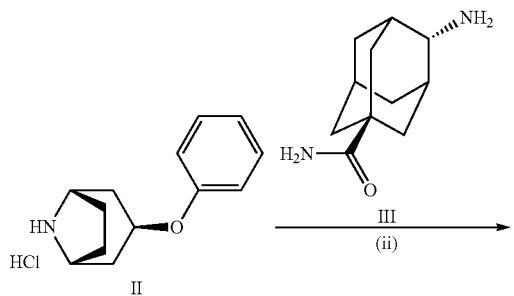

Step (i):

Compound I (451 mg) was added to 4N hydrochloric acid/dioxane (3 mL), and the mixture was stirred overnight. The reaction mixture was concentrated under reduced pressure to give Compound II (450 mg) as a crude product.

Step (ii):

To a solution of Compound III (40 mg) in THF (2 mL) were added triethylamine (55 μL) and p-nitrophenyl chloroformate (45 mg), and the resulting mixture was stirred at room temperature. One hour later, thereto was added Compound II (45 mg), and the mixture was stirred at room temperature overnight. The reaction mixture was extracted with 1N aqueous sodium hydroxide solution and chloroform, and the organic layer was washed with 1N hydrochloric acid. The organic layer was dried over sodium sulfate, and concentrated under reduced pressure. The residue was purified by silica gel column chromatography (chloroform/methanol, 10:1) to give the title compound IV (40 mg).

$^1$H NMR (CDCl$_3$) δ1.57-1.76 (m, 4H), 1.87-2.06 (m, 13H), 2.16-2.21 (m, 4H), 3.65-3.71 (m, 1H), 3.94 (m, 1H), 4.12 (m, 1H), 4.61 (m, 1H), 4.77 (s, 1H), 5.66 (s, 1H), 5.74 (s, 1H), 6.80 (d, J=8.0 Hz, 2H), 6.91 (t, J=7.2 Hz, 1H), 7.24-7.27 (m, 2H)

The compounds of Example 4 to Example 74 were synthesized by a similar method to those disclosed in Example 1 to Example 3.

TABLE 1

| Ex.No. | —X¹ | —Z¹—R² | NMR(solvent) δ |
|---|---|---|---|
| 4 | CONH₂ | phenoxy | ¹H NMR (CDCl₃) δ 1.41-1.91 (m, 11H), 1.97-2.15 (m, 10H), 3.99 (m, 1H), 4.26 (m, 2H), 4.65-4.75 (m, 2H), 5.40 (s, 1H), 5.65 (s, 1H), 6.89-6.97 (m, 3H), 7.27-7.29 (m, 2H) |
| 5 | OH | benzyloxy | ¹H NMR (CDCl₃) δ 1.49-1.56 (m, 3H), 1.66-1.76 (m, 7H), 1.88-1.97 (m, 6H), 2.03-2.12 (m, 4H), 2.18-2.23 (m, 2H), 3.72 (m, 1H), 3.95 (m, 1H), 4.11 (m, 2H), 4.49 (s, 2H), 4.59 (d, J = 8 Hz, 1H), 7.27-7.37 (m, 5H) |
| 6 | OH | 3-fluorophenoxy | ¹H NMR (CDCl₃) δ 1.51-1.54 (m, 3H), 1.66-1.92 (m, 12H), 2.09-2.14 (m, 7H), 3.96 (m, 1H), 4.25 (m, 2H), 4.64-4.61 (m, 2H), 6.58-6.67 (m, 3H), 7.17-7.23 (m, 1H) |
| 7 | OH | 4-fluorophenoxy | ¹H NMR (CDCl₃) δ 1.51-1.54 (m, 3H), 1.66-1.92 (m, 12H), 2.06-2.15 (m, 7H), 3.97 (m, 1H), 4.24 (m, 2H), 4.54-4.66 (m, 2H), 6.82-6.85 (m, 2H), 6.93-6.97 (m, 2H) |
| 8 | OH | phenoxy | ¹H-NMR (CDCl₃) δ 1.51-1.53 (m, 3H), 1.66-1.77 (m, 8H), 1.89-1.92 (m, 2H), 1.97-2.04 (m, 3H), 2.14-2.26 (m, 6H), 3.97 (m, 1H), 4.14-4.18 (m, 2H), 4.61-4.63 (m, 2H), 6.82-6.84 (m, 2H), 6.92-6.95 (m, 1H), 7.26-7.31 (m, 2H) |
| 9 | OH | 2,3-difluorophenoxy | ¹H NMR (CDCl₃) δ 1.39-1.40 (m, 1H), 1.52-1.55 (m, 2H), 1.62-1.77 (m, 8H), 1.87-1.93 (m, 4H), 2.05-2.16 (m, 7H), 3.97 (m, 1H), 4.25 (m, 2H), 4.62-4.66 (m, 2H), 6.75-6.83 (m, 2H), 6.93-6.98 (m, 1H) |
| 10 | OH | 3,4-difluorophenoxy | ¹H NMR (CDCl₃) δ1.50-1.54 (m, 3H), 1.65-1.83 (m, 10H), 1.89-1.92 (m, 2H), 2.06-2.15 (m, 7H), 3.97 (m, 1H), 4.24 (m, 2H), 4.52-4.61 (m, 1H), 4.64-4.66 (m, 1H), 6.58-6.60 (m, 1H), 6.68-6.73 (m, 1H), 7.04 (q, J = 8 Hz, 1H) |
| 11 | OH | 2,4-difluorophenoxy | ¹H NMR (CDCl₃) δ1.50-1.59 (m, 3H), 1.67-1.71 (m, 4H), 1.77 (m, 4H), 1.84-1.93 (m, 4H), 2.02-2.10 (m, 4H), 2.16 (m, 3H), 3.97 (m, 1H), 4.24 (m, 2H), 4.46-4.54 (m, 1H), 4.64-4.65 (m, 1H), 6.74-6.79 (m, 1H), 6.82-6.87 (m, 1H), 6.93-6.99 (m, 1H) |
| 12 | OH | 2,5-difluorophenoxy | ¹H NMR (CDCl₃) δ1.52-1.59 (m, 3H), 1.67-1.77 (m, 8H), 1.86-1.92 (m, 4H), 2.06-2.16 (m, 7H), 3.97 (m, 1H), 4.26 (m, 2H), 4.59-4.65 (m, 2H), 6.59-6.65 (m, 1H), 6.69-6.74 (m, 1H), 6.98-7.04 (m, 1H) |

TABLE 2

| Ex.No. | —X¹ | —Z¹—R² | NMR(solvent) δ |
|---|---|---|---|
| 13 | OH | 3,5-difluorophenoxy | ¹H NMR (CDCl₃) δ1.52-1.60 (m, 6H), 1.66-1.92 (m, 10H), 2.05-2.15 (m, 6H), 3.96 (m, 1H), 4.25 (m, 2H), 4.61-4.65 (m, 2H), 6.39-6.42 (m, 3H) |

TABLE 2-continued

| | | | |
|---|---|---|---|
| 14 | OH | 2,6-difluorophenoxy (wedge) | ¹H NMR (CDCl₃) δ1.52-1.77 (m, 11H), 1.90-2.16 (m, 11H), 3.99 (m, 1H), 4.23 (m, 2H), 4.47-4.51 (m, 1H), 4.65 (d, J = 4 Hz, 1H), 6.87-7.01 (m, 3H) |
| 15 | CONH₂ | 2,3-difluorophenoxy | ¹H NMR (CDCl₃) δ1.62-1.86 (m, 8H), 1.87-2.12 (m, 13H), 4.00 (m, 1H), 4.26 (m, 2H), 4.63-4.68 (m, 1H), 4.72-4.74 (m, 1H), 5.28 (s, 1H), 5.62 (s, 1H), 6.75-6.84 (m, 2H), 6.92 (m, 1H) |
| 16 | CONH₂ | 2,4-difluorophenoxy | ¹H NMR (CDCl₃) δ1.62-1.71 (m, 7H), 1.77-1.80 (m, 1H), 1.85-1.91 (m, 3H), 1.98-2.11 (m, 10H), 3.98-4.00 (m, 1H), 4,25 (m, 2H), 4.46-4.55 (m, 1H), 4.72 (d, J = 4.0 Hz, 1H), 5.26 (s, 1H), 5.61 (s, 1H), 6.74-6.69 (m, 1H), 6.82-6.87 (m, 1H), 6.93-6.99 (m, 1H) |
| 17 | CONH₂ | 3,5-difluorophenoxy | ¹H NMR (CDCl₃) δ1.56-1.65 (m, 3H), 1.76-1.91 (m, 8H), 2.01-2.03 (m, 5H), 2.11 (m, 5H), 3.99 (m, 1H), 4.26 (m, 2H), 4.60-4.68 (m, 1H), 4.72 (d, J = 4 Hz, 1H), 5.22 (s, 1H), 5.58 (s, 1H), 6.39-6.41 (m, 3H) |
| 18 | CONH₂ | 2,5-difluorophenoxy | ¹H NMR (CDCl₃) δ1.60-1.63(m, 2H), 1.72-2.10(m, 19H), 3.96(m, 1H), 4.25(m, 2H), 4.56-4.65(m, 1H), 4.99(s, 1H), 5.47(s, 1H), 5.81(s, 1H), 6.58-6.64(m, 1H), 6.67-6.72(m, 1H), 6.96-7.02(m, 1H) |
| 19 | CONH₂ | 2,6-difluorophenoxy | ¹H NMR (CDCl₃) δ1.60-1.80(m, 5H), 1.90-2.10(m, 16H), 3.97(m, 1H), 4.22(m, 2H), 4.46-4.50(m, 1H), 4.89(s, 1H), 5.33(s, 1H), 5.69(s, 1H), 6.85-6.98(m, 3H) |
| 20 | CONH₂ | 3,4-difluorophenoxy | ¹H NMR (CDCl₃) δ1.72-1.89(m, 8H), 1.99-2.10(m, 13H), 3.96(m, 1H), 4.24(m, 2H), 4.52-4.57(m, 1H), 4.93(s, 1H), 5.27(s, 1H), 5.63(s, 1H), 6.56-6.59(m, 1H), 6.67-6.72(m, 1H), 6.99-7.06(m, 1H) |
| 21 | CONH₂ | 2-fluorophenoxy | ¹H NMR (CDCl₃) δ1.59-1.62(m, 2H), 1.70-1.80(m, 3H), 1.89-2.10(m, 16H), 3.96(m, 1H), 4.23(m, 2H), 4.56-4.63(m, 1H), 4.97(s, 1H), 5.43(s, 1H), 5.80(s, 1H), 6.90-7.07(m, 4H) |
| 22 | CONH₂ | 3-fluorophenoxy | ¹H NMR (CDCl₃) δ1.59-1.63(m, 2H), 1.76-2.10(m, 19H), 3.96(m, 1H), 4.24(m, 2H), 4.60-4.69(m, 1H), 5.01(s, 1H), 5.43(s, 1H), 5.77(s, 1H), 6.56-6.66(m, 3H), 7.15-7.21(m, 1H) |

TABLE 3

| | | | |
|---|---|---|---|
| 23 | CONH₂ | 4-fluorophenoxy | ¹H NMR (CDCl₃) δ1.58-2.09(m, 21H), 3.96(m, 1H), 4.22(m, 2H), 4.50-4.60(m, 1H), 4.79(s, 1H), 5.26(s, 1H), 5.61(s, 1H), 6.80-6.84(m, 2H), 6.91-6.93(m, 2H) |
| 24 | CONH₂ | phenylthio | ¹H NMR (CDCl₃) δ1.58-1.61 (m, 2H), 1.67-1.89 (m, 10H), 1.98-2.02 (m, 9H), 3.43-3.52 (m, 1H), 3.93-3.94 (m, 1H), 4.11-4.21 (m, 2H), 4.65 (d, J = 4 Hz, 1H), 5.47 (s, 1H), 5.60 (s, 1H), 7.24-7.32 (m, 3H), 7.40-7.42 (m, 2H) |

TABLE 3-continued

| | | | |
|---|---|---|---|
| 25 | OH | *S-phenyl* | $^1$H NMR (CDCl$_3$) δ1.49-1.52 (m, 3H), 1.62-1.76 (m, 9H), 1.81-1.91 (m, 5H), 2.00-2.02 (m, 2H), 2.08-2.13 (m, 3H), 3.43-3.52 (m, 1H), 3.93 (M, 1H), 4.13-4.20 (m, 2H), 4,55 (d, J = 8 Hz, 1H), 7.24-7.34 (m, 3H), 7.40-7.43 (m, 2H) |
| 26 | OH | *SO$_2$-phenyl* | $^1$H NMR (CDCl$_3$) δ1.48-1.65 (m, 7H), 1.72-1.88 (m, 7H), 1.94-2.03 (m, 7H), 2.14 (m, 1H), 3.40-3.46 (m, 1H), 3.86 (m, 1H), 4.24 (m, 2H), 4.53 (d, J = 8 Hz, 1H), 7.57 (t, J = 8 Hz, 2H), 7.67 (t, J = 8 Hz, 1H), 7.84-7.86 (m, 2H) |
| 27 | CONH$_2$ | *SO$_2$-phenyl* | $^1$H NMR (CDCl$_3$) δ1.57-1.72 (m, 9H), 1.68-1.72 (m, 2H), 1.80-1.83 (m, 2H), 1.90 (m, 2H), 1.98-2.05 (m, 6H), 3.40-3.48 (m, 1H), 3.88 (m, 1H), 4.25 (s, 2H), 4.61 (d, J = 8 Hz, 1H), 5.23 (s, 1H), 5.59 (s, 1H), 7.55-7.59 (m, 2H), 7.65-7.69 (m, 1H), 7.84-7.86 (m, 2H) |
| 28 | OH | *N(CH$_3$)-benzyl* | $^1$H NMR (CDCl$_3$) δ1.38 (m, 1H), 1.50-1.92 (m, 16H), 1.97-1.98 (m, 2H), 2.14-2.17 (m, 6H), 3.05 (s, 1H), 3.53 (s, 2H), 3.96 (m, 1H), 4.22 (s, 2H), 4.63 (d, J = 8 Hz, 1, 7.26-7.30 (m, 5H) |
| 29 | CONH$_2$ | *N(CH$_3$)-benzyl* | $^1$H NMR (CDCl$_3$) δ1.62-1.64 (m, 7H), 1.77-1.86 (m, 4H), 1.91 (m, 2H), 1.99-2.05 (m, 6H), 2.10 (m, 2H), 2.17 (s, 3H), 3.05 (m, 1H), 3.53 (s, 2H), 3.98 (m, 1H), 4.23 (m, 2H), 4.70 (d, J = 8 Hz, 1H), 5.23 (s, 1H), 5.59 (s, 1H), 7.24-7.33 (m, 5H) |
| 30 | CONH$_2$ | OCH$_3$ | $^1$H NMR (CDCl$_3$) δ1.56-2.08(m, 21H), 3.26(s, 3H), 3.47(t, J = 6.4 Hz, 1H), 3.95(m, 1H), 4.06(m, 2H), 4.79(s, 1H), 5.24(s, 1H), 5.58(s, 1H) |
| 31 | OH | OCH$_3$ | $^1$H NMR (CDCl$_3$) δ1.47-1.74(m, 9H), 1.83-2.11(m, 13H), 3.26(s, 3H), 3.47(t, J = 4.8 Hz, 1H), 3.93(m, 1H), 4.06(m, 1H), 4.73(s, 1H) |
| 32 | OH | *N(CH$_3$)$_2$* | $^1$H NMR (CDCl$_3$) δ1.49-1.52 (m, 2H), 1.67-1.75 (m, 12H), 1.88-1.91 (m, 2H), 1.98-2.00 (m, 2H), 2,12 (m, 3H), 2.24 (s, 6H), 3.94 (m, 1H), 4.20 (s, 2H), 4.60 (d, J = 4 Hz, 1H) |
| 33 | CONH$_2$ | *N(CH$_3$)$_2$* | $^1$H NMR (CDCl$_3$) δ1.59-1.79 (m, 12H), 1.90 (m, 2H), 1.95-2.08 (m, 8H), 2.24 (s, 6H), 3.95-3.96 (m, 1H), 4.21 (s, 2H), 4.69 (d, J = 8 Hz, 1H), 5.44 (s, 1H), 5.67 (s, 1H) |

TABLE 4

| | | | |
|---|---|---|---|
| 34 | CONH$_2$ | *O-(4-F-phenyl)* | $^1$H NMR (CDCl$_3$) δ1.59-1.78(m, 4H), 1.89-2.08(m, 13H) 2.18-2.22(m, 4H), 3.96(m, 1H), 4.13(m, 2H), 4.54(t, J = 4.8 Hz, 1H), 4.85(s, 1H), 5.25(s, 1H), 5.60(s, 1H), 6.73-6.76(m, 2H), 6.93-6.98(m, 2H) |
| 35 | CONH$_2$ | *O-(2,4-diF-phenyl)* | $^1$H NMR (CDCl$_3$) δ1.60-2.28(m, 21H), 3.95(m, 1H), 4.14(m, 2H), 4.53(t, J = 4.8 Hz, 1H), 4.87(s, 1H), 5.21(s, 1H), 5.58(s, 1H), 6.74-6.88(m, 3H) |
| 36 | CONH$_2$ | *O-(3,4-diF-phenyl)* | 1H NMR (CDCl$_3$) δ1.59-1.77(m, 4H), 1.89-2.22(m, 17H), 3.95(m, 1H), 4.13(m, 2H), 4.50(t, J = 4.8 Hz, 1H), 4.70(s, 1H), 5.22(s, 1H), 5.57(s, 1H), 6.48-6.52(m, 1H), 6.60-6.65(m, 1H), 7.01-7.08(m, 1H) |
| 37 | OH | *phenyl* | $^1$H NMR (CDCl$_3$) δ 1.53-1.60 (m, 5H), 1.66-1.79 (m, 8H), 1.89-1.95 (m, 2H), 2.06-2.18 (m, 5H), 2.49-2.67 (m, 3H), 3.99 (m, 1H), 4.24 (m, 2H), 4.69 (d, J = 6.9 Hz, 1H), 7.17-7.31 (m, 5H). |

TABLE 4-continued

| 38 | OH | 4-F-C6H4-O-CH(CH3)- | ¹H NMR (CDCl₃) δ1.41-1.44 (m, 1H), 1.51-1.54 (m, 2H), 1.67-1.77 (m, 6H), 1.89-2.02 (m, 6H), 2.14-2.23 (m, 7H), 3.96 (m, 1H), 4.14 (s, 2H), 4.54-4.57 (m, 1H), 4.61 (d, J = 8 Hz, 1H), 6.75-6.79 (m, 2H), 6.96-7.03 (m, 2H) |
|---|---|---|---|
| 39 | OH | 2,4-diF-C6H3-O- | ¹H NMR (CDCl₃) δ1.49-1.54 (m, 2H), 1.64-1.77 (m, 8H), 1.89-2.05 (m, 6H), 2.17-2.29 (m, 6H), 3.96 (s, 1H), 4.15 (s, 2H), 4.53-4.55 (m, 1H), 4.62 (d, J = 8 Hz, 1H), 6.76-6.90 (m, 3H) |
| 40 | OH | 3,4-diF-C6H3-O- | ¹H NMR (CDCl₃) δ1.48-1.54 (m, 3H), 1.64-1.70 (m, 4H), 1.77 (m, 4H), 1.89-2.04 (m, 5H), 2.14-2.29 (m, 6H), 3.96 (m, 1H), 4.15 (s, 2H), 4.53-4.55 (m, 1H), 4.62 (d, J = 8 Hz, 1H), 6.76-6.90 (m, 3H) |
| 41 | OH | 4-pyridyl-O- | ¹H NMR (CDCl₃) δ1.48-1.51 (m, 2H), 1.64-1.90 (m, 12H), 2.08-2.11(m, 7H), 2.54 (s, 1H), 3.95 (m, 1H), 4.25 (s, 2H), 4.91 (d, J = 8 Hz, 1H), 4.74-4.82 (m, 1H), 6.74-6.76 (m, 2H), 8.36-8.37 (m, 2H) |
| 42 | OH | 2-pyridyl-O- | ¹H NMR (CDCl₃) δ1.50-1.53 (m, 3H), 1.63-1.76 (m, 6H), 1.89-2.05 (m, 6H), 2.14 (s, 3H), 2.19-2.27 (m, 4H), 3.96-3.38 (m, 1H), 4.16 (s, 2H), 4.61 (d, J = 8 Hz, 1H), 5.35-5.37 (m, 1H), 6.69 (d, J = 8 Hz, 1H), 6.83-6.86 (m, 1H), 7.55-7.59 (m, 1H), 8.12-8.14 (m, 1H) |
| 43 | CONH₂ | 2-pyridyl-O- | ¹H NMR (CDCl₃) δ1.57-1.64 (m, 2H), 1.76-1.78 (m, 2H), 1.91-2.04 (m, 11H), 2.10 (m, 2H), 2.20-2.27 (m, 4H), 3.98-4.00 (m, 1H), 4.17 (s, 2H), 4.67 (d, J = 8 Hz, 1H), 5.23 (s, 1H), 5.35-5.38 (m, 1H), 5.60 (s, 1H), 6.70 (d, J = 8 Hz, 1H), 6.83-6.86 (m, 1H), 7.55-7.60 (m, 1H), 8.12-8.14 (m, 1H) |

TABLE 5

| 44 | CONH₂ | 3-pyridyl-O- | ¹H NMR (CDCl₃) δ1.61-1.64 (m, 2H), 1.75-1.90 (m, 9H), 2.00-2.14 (m, 10H), 3.98 (m, 1H), 4.27 (m, 2H), 4.70-4.75 (m, 2H), 5.37 (s, 1H), 5.64 (s, 1H), 7.19-7.23 (m, 2H), 8.21-8.22 (m, 1H), 8.29-8.30 (m, 1H) |
|---|---|---|---|
| 45 | OH | 3-pyridyl-O- | ¹H NMR (CDCl₃) δ1.47-1.55 (m, 3H), 1.67-1.70 (m, 2H), 1.73-1.78 (m, 6H), 1.82-1.92 (m, 4H), 2.08-2.15 (m, 7H), 3.98 (m, 1H), 4.26 (s, 2H), 4.65-4.76 (m, 2H), 7.18-7.23 (m, 2H), 8.21-8.22 (m, 1H), 8.30 (m, 1H) |
| 46 | OH | 2-F-C6H4-O- | ¹H NMR (CDCl₃) δ1.48-1.74 (m, 9H), 1.87-1.90 (m, 2H), 1.97-2.02 (m, 4H), 2.12-2.29 (m, 7H), 3.95 (m, 1H), 4.13 (m, 2H), 4.62 (t, J = 4.8 Hz, 2H), 6.82-6.89 (m, 2H), 7.00-7.09 (m, 2H) |
| 47 | OH | 3-F-C6H4-O- | ¹H NMR (CDCl₃) δ1.49-1.75 (m, 9H), 1.87-2.02 (m, 6H), 2.12-2.24 (m, 7H), 3.95 (m, 1H), 4.12 (m, 2H), 4.58 (t, J = 4.8 Hz, 2 H), 6.50-6.54 (m, 1H), 6.50-6.65 (m, 2H), 7.17-7.23 (m, 1H) |
| 48 | CONH₂ | 2-F-C6H4-O- | ¹H NMR (CDCl₃) δ1.59-1.77 (m, 7H), 1.89-2.07 (m, 10H), 2.19-2.28 (m, 4H), 3.96 (m, 1H), 4.14 (m, 2H), 4.62 (t, J = 4.8 Hz, 1H), 4.78 (s, 1H), 5.25 (s, 1H), 5.62 (s, 1H), 6.82-6.90 (m, 2H), 7.00-7.09 (m, 2H) |

TABLE 5-continued

| | | | |
|---|---|---|---|
| 49 | CONH₂ | 3-F, 3-OMe-phenyl | ¹H NMR (CDCl₃) δ1.59-1.78 (m, 7H), 1.89-2.08 (m, 10H), 2.15-2.25 (m, 4H), 3.95 (m, 1H), 4.13 (m, 2H), 4.58 (t, J = 6.0 Hz, 1H), 4.88 (s, 1H), 5.27 (s, 1H), 5.64 (s, 1H), 6.50-6.69 (m, 3H), 7.17-7.24 (m, 1H) |
| 50 | OH | 4-CN, 1-OMe-phenyl | ¹H NMR (CDCl₃) δ1.45-1.76 (m, 11H), 1.87-2.27 (m, 12H), 3.96 (m, 1H), 4.14 (m, 1H), 4.59-4.67 (m, 2H), 6.85 (d, J = 9 Hz, 2H), 7.57 (d, J = 9 Hz, 2H) |
| 51 | OH | ethyl-phenyl | ¹H NMR (CDCl₃) δ1.23-1.29 (m, 2H), 1.42-1.60 (m, 4H), 1.72-1.88 (m, 10H), 2.04-2.21 (m, 7H), 2.69 (d, J = 6.8 Hz, 2H), 3.92 (m, 1H), 4.10 (m, 2H), 4.56 (m, 1H), 7.09-7.28 (m, 5H) |
| 52 | OH | 3-methyl-pyridine | ¹H NMR (CDCl₃) δ1.47-1.56 (m, 4H), 1.64-1.88 (m, 9H), 2.02-2.28 (m, 9H), 3.13-3.18 (m, 1H), 4.40-4.48 (m, 2H), 4.69 (d, J = 9 Hz, 1H), 6.52 (d, J = 8 Hz, 1H), 7.23 (s, 1H), 7.58-7.62 (m, 1H), 8.46 (dd, J 3 Hz, 6 Hz, 1H), 8.59 (m, 1H) |
| 53 | OH | 3-OMe, 1-CF₃-phenyl | ¹H NMR (CDCl₃) δ1.48-1.75 (m, 9H), 1.87-2.03 (m, 6H), 2.13-2.25 (m, 7H), 3.95 (m, 1H), 4.13 (m, 2H), 4.62-4.66 (m, 2H), 6.95-7.03 (m, 2H), 7.17 (d, J = 10 Hz, 1H), 7.37 (t, J = 10.8 Hz, 1H) |

TABLE 6

| | | | |
|---|---|---|---|
| 54 | OH | 3-OMe, 1-OCH₃-phenyl | ¹H NMR (CDCl₃) δ1.48-1.75 (m, 8H), 1.86-2.02 (m, 6H), 2.12-2.21 (m, 7H), 3.77 (s, 3H), 3.94 (m, 1H), 4.11 (m, 2H), 4.58 (t, J = 6.4 Hz, 1H), 4.64 (s, 1H), 6.36 (t, J = 4.8 Hz, 1H), 6.39-6.42 (m, 1H), 6.46-6.50 (m, 1H), 7.16 (t, J = 11.2 Hz, 1H) |
| 55 | OH | 3-OMe, 1-OCF₃-phenyl | ¹H NMR (CDCl₃) δ1.49-2.31 (m, 22H), 3.93 (m, 1H), 4.13 (m, 2H), 4.61 (t, J = 4.4 Hz, 1H), 4.67 (s, 1H), 6.65 (s, 1H), 6.71-6.80 (m, 2H), 7.23-7.29 (m, 1H) |
| 56 | OH | 4-OMe, 1-Cl-phenyl | ¹H NMR (CDCl₃) δ1.48-1.75 (m, 9H), 1.86-2.02 (m, 6H), 2.12-2.22 (m, 7H), 3.95 (m, 1H), 4.12 (m, 2H), 4.56 (t, J = 6.4 Hz, 1H), 4.68 (s, 1H), 6.70-6.76 (m, 2H), 7.19-7.23 (m, 2H) |
| 57 | OH | 2-OMe, 1-CH₃-phenyl | ¹H NMR CDCl₃) δ1.48-1.75 (m, 9H), 1.87-2.04 (m, 6H), 2.13 (m, 4H), 2.19-2.26 (m, 6H), 3.94 (m, 1H), 4.14 (m, 2H), 4.61 (t, J = 6.4 Hz, 1H), 4.68 (s, 1H), 6.63 (d, J = 10.4 Hz, 1H), 6.79-6.84 (m, 1H), 7.09-7.16 (m, 2H) |
| 58 | OH | 4-OMe, 1-OCH₂CH₃-C(O)-phenyl | ¹H NMR (CDCl₃) δ1.36 (t, J = 6.0 Hz, 3H), 1.48-1.75 (m, 9H), 1.86-2.29 (m, 13H), 3.93 (m, 1H), 4.13 (m, 2H), 4.32 (q, J = 6.0 Hz, 2H), 4.69 (m, 1H), 4.83 (m, 1H), 6.81 (d, J = 12 Hz, 2H), 7.97 (d, J = 12 Hz, 2H) |
| 59 | OH | N(CH₃)-phenyl | ¹H NMR (CDCl₃) δ1.43-1.45 (m, 1H), 1.52-1.84 (m, 12H), 1.90-2.01 (m, 4H), 2.05-2.16 (m, 5H), 2.69 (s, 3H), 3.99 (m, 1H), 4.20-4.24 (m, 3H), 4.66 (d, J = 8 Hz, 1H), 6.72 (t, J = 8 Hz, 1H), 6.78 (d, J = 8 Hz, 2H), 7.21-7.25 (m, 2H) |

| | | |
|---|---|---|
| | TABLE 6-continued | |
| 60 OH | 5-methoxy-1,3-benzodioxole group | ¹H-NMR (CDCl₃) 1.50-1.76 (m, 8H), 1.89-2.04 (m, 6H), 1.89-2.04 (m, 6H), 2.13-2.22 (m, 8H), 3.96 (m, 1H), 4.13 (m, 2H), 4.48 (m, 1H), 4.60 (d, J = 8, 12 Hz, 1H), 5.91 (s, 2H), 6.25 (dd, J = 1, 12 Hz, 1H), 6.43 (d, J = 4 Hz, 1H), 6.70 (d, 8.1 Hz, 1H) |
| 61 OH | 3-methoxypyridine group | ¹H NMR (CDCl₃) δ1.51-1.55 (m, 2H), 1.61-1.77 (m, 8H), 1.90-2.05 (m, 5H), 2.14-2.27 (m, 7H), 3.97 (m, 1H), 4.16 (m, 2H), 4.62-4.68 (m, 2H), 7.10-7.13 (m, 1H), 7.21-7.24 (m, 1H), 8.20-8.25 (m, 2H) |
| 62 OH | 4-methoxypyridine group | ¹H NMR (CDCl₃) δ1.50-1.55 (m, 2H), 1.65-1.78 (m, 9H), 1.90-1.98 (m, 3H), 2.02-2.16 (m, 6H), 2.27 (dt, J = 12 Hz, 4 Hz, 2H), 3.96-3.98 (m, 1H), 4.16 (m, 2H), 4.63 (d, J = 8 Hz, 1H), 4.70 (t, J = 4 Hz, 1H), 6.72-6.74 (m, 2H), 8.42-8.44 (m, 2H) |
| 63 OH | 4-(trifluoromethoxy)benzyloxy group | ¹H NMR (CDCl₃) δ1.50-1.53 (m, 2H), 1.62-1.70 (m, 4H), 1.74-1.77 (m, 4H), 1.89-1.99 (m, 5H), 2.00-2.20 (m, 7H), 3.73 (m, 1H), 3.96 (m, 1H), 4.12 (m, 2H), 4.49 (s, 2H), 4.59 (d, J = 8 Hz, 1H), 7.20 (d, J = 8 Hz, 2H), 7.35 (d, J = 8 Hz, 2H) |

| | | |
|---|---|---|
| | TABLE 7 | |
| 64 OH | 4-methyl-(methylsulfonyl)phenyl group | ¹H NMR (CDCl₃) δ1.47-1.60 (m, 3H), 1.63-1.79 (m, 11H), 1.85-1.99 (m, 4H), 2.11-1.17 (m, 5H), 3.04 (s, 3H), 4.00 (m, 1H), 4.28 (m, 2H), 4.67 (dd, J = 4 Hz, 8 Hz, 1H), 7.40 (dd, J = 8 Hz, 8 Hz, 2H), 7.80 (d, J = 8 Hz, 2H) |
| 65 OH | 4-methoxybenzoic acid group | ¹H NMR (CD₃OD) δ1.47 (m, 2H), 1.74-2.23 (m, 20H), 3.82 (m, 1H), 4.29 (m, 2H), 4.78 (s, 1H), 5.74 (d, J = 8.0 Hz, 1H), 6.90-6.94 (m, 2H), 7.94-7.98 (m, 2H) |
| 66 OH | 2,6-difluoro-methoxyphenyl group | ¹H NMR (CDCl₃) δ1.47-1.74 (m, 9H), 1.86-2.41 (m, 13H), 3.93 (m, 1H), 4.15 (m, 2H), 4.43 (t, J = 4.8 Hz, 1H), 4.73 (s, 1H), 6.85-6.95 (m, 3H) |
| 67 OH | 2,4-difluoro-methoxyphenyl group | ¹H NMR (CDCl₃) δ1.49-1.75 (m, 9H), 1.87-2.04 (m, 6H), 2.12 (m, 3H), 2.20-2.26 (m, 4H), 3.94 (m, 1H), 4.14 (m, 2H), 4.57 (t, J = 4.8 Hz, 1H), 4.76 (s, 1H), 6.54-6.58 (m, 2H), 6.98-7.04 (m, 1H) |
| 68 OH | 2,3-difluoro-methoxyphenyl group | ¹H NMR (CDCl₃) δ1.49-1.75 (m, 9H), 1.87-2.04 (m, 6H), 2.12 (m, 3H), 2.21-2.25 (m, 4H), 3.95 (m, 1H), 4.14 (m, 2H), 4.63 (t, J = 4.8 Hz, 1H), 4.71 (s, 1H), 6.59-6.63 (m, 1H), 6.71-6.77 (m, 1H), 6.91-6.98 (m, 1H) |
| 69 OH | 4-methoxy-N-acetylaminophenyl group | ¹H NMR (CDCl₃) δ1.48-1.74 (m, 9H), 1.86-2.00 (m, 6H), 2.12-2.22 (m, 10H), 3.93 (m, 1H), 4.11(m, 2H), 4.57 (t, J = 4.8 Hz, 1H), 4.81 (s, 1H), 6.76 (d, J = 8.8 Hz, 2H), 7.12 (s, 1H), 7.36 (d, J = 8.8 Hz, 2H) |

TABLE 7-continued

| 70 | OH | (indane with OMe) | ¹H NMR (CDCl₃) δ1.48-1.74 (m, 9H), 1.86-2.26 (m, 15H), 2.80-2.87 (m, 4H), 3.93 (m, 1H), 4.11 (m, 2H), 4.58 (t, J = 4.8 Hz, 1H), 4.63 (s, 1H), 6.58-6.61 (m, 1H), 7.00 (m, 1H), 7.09 (d, J = 8.4 Hz, 1H) |
| --- | --- | --- | --- |
| 71 | OH | (4-morpholinophenyl OMe) | ¹H NMR (CDCl₃) δ1.48-1.74 (m, 9H), 1.87-1.99 (m, 6H), 2.12-2.21 (m, 7H), 3.05 (m, 4H), 3.84 (m, 4H), 3.95 (m, 1H), 4.11 (m, 2H), 4.52 (t, J = 4.8 Hz, 1H), 4.58 (d, J = 7.6 Hz, 1H), 6.75-6.88 (m, 4H) |
| 72 | OH | (4-phenylphenyl OMe) | ¹H NMR (CDCl₃) δ1.49-1.75 (m, 9H), 1.87-2.25 (m, 13H), 3.94 (m, 1H), 4.14 (m, 2H), 4.66 (t, J = 4.8 Hz, 1H), 4.78 (s, 1H), 6.88 (d, J = 8.0 Hz, 2H), 7.27 (t, J = 7.2 Hz, 1H), 7.40 (t, J = 7.2 Hz, 2H), 7.49-7.54 (m, 4H) |

TABLE 8

| 73 | OH | (tetrahydronaphthyl OMe) | ¹H NMR (CDCl₃) δ1.49-1.79 (m, 13H), 1.88-2.02 (m, 6H), 2.12 (m, 3H), 2.19-2.24 (m, 4H), 2.66 (t, J = 6.0 Hz, 2H), 2.73 (t, J = 6.0 Hz, 2H), 3.94-3.96 (m, 1H), 4.13 (m, 2H), 4.57 (t, J = 4.8 Hz, 1H), 4.67 (s, 1H), 6.44 (d, J = 8.0 Hz, 1H), 6.65 (d, J = 8.0 Hz, 1H), 7.01 (t, J = 8.0 Hz, 1H) |
| --- | --- | --- | --- |
| 74 | OH | (3,5-difluorophenyl OMe) | ¹H NMR (CDCl₃) δ1.49-1.75 (m, 9H), 1.87-2.26 (m, 13H), 3.94 (m, 1H), 4.13 (m, 2H), 4.54 (t, J = 4.8 Hz, 1H), 4.73 (s, 1H), 6.31-6.41 (m, 3H) |

Example 75

[(3-Endo)-3-hydroxy-8-azabicyclo[3.2.1]oct-8-yl][(3-endo)-3-phenoxy-8-azabicyclo[3.2.1]oct-8-yl]methanone

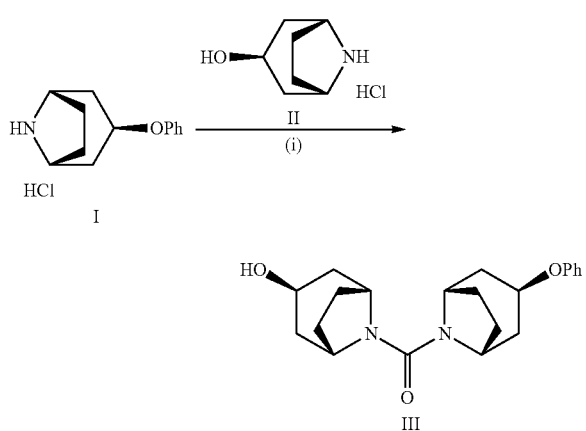

Step (i):

To an ice-cold mixture of Compound I (59 mg), triethylamine (0.10 mL) and dichloromethane (2.5 mL) was added triphosgene (25 mg), and the mixture was stirred for 3 hours. To this reaction solution was added a mixture of Compound II (40 mg), triethylamine (0.10 mL) and dichloromethane (2.5 mL), and then the mixture was stirred at room temperature overnight. The reaction mixture was poured into 1N aqueous sodium hydroxide solution, and the mixture was extracted with chloroform. The organic layer was washed with 1N hydrochloric acid, and dehydrated with sodium sulfate, and concentrated under reduced pressure. To the resultant were added diisopropylether and hexane, and the obtained solid was collected by filtration and dried under reduced pressure to give the title compound III (10 mg).

¹H NMR (CDCl₃) δ1.72-2.21 (m, 17H), 4.11 (m, 5H), 4.61 (m, 1H), 6.80-6.82 (m, 2H), 6.82-6.93 (m, 1H), 7.27 (m, 2H)

The compounds of Example 76 and Example 77 were synthesized by a similar method to that of Example 75.

TABLE 9

| Ex. No. | —X¹ | —Z¹—R² | NMR (solvent) δ |
|---|---|---|---|
| 76 | ◂OH | ⁝⁝⁝O-Ph | ¹H NMR (CDCl₃) δ1.35 (m, 1H), 1.67-1.99 (m, 9H), 2.11-2.19 (m, 6H), 4.13-4.21 (m, 6H), 4.58-4.64 (m, 1H), 6.87-6.95 (m, 3H), 7.23-7.28 (m, 2H) |
| 77 | ⁝⁝⁝OH | O-Ph | ¹H NMR (CDCl₃) δ1.60-1.63 (m, 4H), 1.92-2.20 (m, 13H), 4.11-4.16 (m, 5H), 4.61 (t, J = 4.8 Hz, 1H), 6.81 (d, J = 8.4 Hz, 2H), 6.91 (t, J = 7.6 Hz, 1H), 7.27 (m, 2H) |

Example 78

(3-Endo)-3-(4-carbamoylphenoxy)-N-[(E)-5-hydroxyadamantan-2-yl]-8-azabicyclo-[3.2.1]octane-8-carboxamide

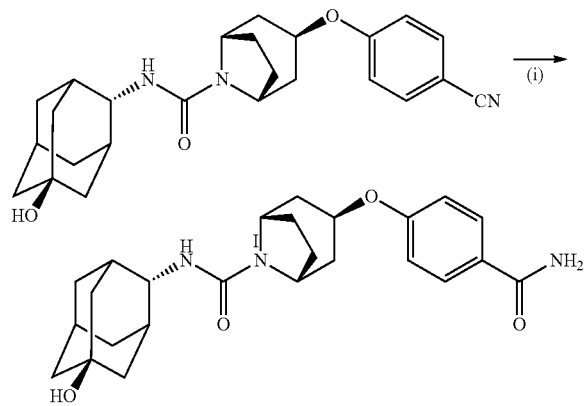

Step (i):

To a mixture of Compound I (50 mg) and methanol (5 mL) at room temperature were added 1N aqueous sodium hydroxide solution (0.2 mL), 35% aqueous hydrogen peroxide solution (0.03 mL). After the addition was complete, the mixture was stirred at room temperature overnight. To the mixture was added an aqueous sodium thiosulfate solution, and the solvent was concentrated under reduced pressure. The residue was extracted with chloroform and brine. The organic layer was dried over sodium sulfate, filtered, concentrated, and dried to give the title compound II (43.2 mg) as a result.

¹H-NMR (CDCl₃) δ1.52-1.55 (m, 2H), 1.67-1.77 (m, 8H), 1.89-2.03 (m, 6H), 2.14-2.27 (m, 6H), 3.97 (m, 1H), 4.15 (m, 1H), 4.63 (d, J=8 Hz, 1H), 4.70 (m, 1H), 5.68-5.97 (m, 2H), 6.86 (d, J=8 Hz, 2H), 7.78 (d, J=12 Hz, 2H)

The compounds of Examples 79 to 82 were synthesized in a similar manner to Example 3.

TABLE 10

| Ex. No. | —Z¹—R² | NMR (solvent) δ |
|---|---|---|
| 79 | O-(2,6-difluorophenyl) | ¹H NMR (CDCl₃) δ1.60-1.78 (m, 4H), 1.89-2.07 (m, 13H), 2.20-2.25 (m, 4H), 3.96 (brs, 1H), 4.14 (brs, 2H), 4.57 (t, J = 4.8 Hz, 1H), 4.72 (brs, 1H), 5.23 (brs, 1H), 5.57 (brs, 1H), 6.53-6.58 (m, 2H), 6.98-7.04 (m, 1H) |

TABLE 10-continued

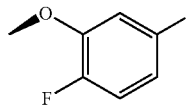

| Ex. No. | —Z¹—R² | NMR (solvent) δ |
|---|---|---|
| 80 | 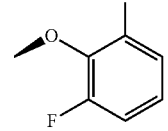 | $^1$H NMR (CDCl$_3$) δ1.57-1.62 (m, 2H), 1.74-1.77 (m, 2H), 1.89-2.07 (m, 13H), 2.20-2.25 (m, 4H), 3.96 (brs, 1H), 4.14 (brs, 2H), 4.63 (t, J = 4.4 Hz, 1H), 4.72 (brs, 1H), 5.19 (brs, 1H), 5.57 (brs, 1H), 6.59-6.62 (m, 1H), 6.71-6.77 (m, 1H), 6.91-6.98 (m, 1H) |
| 81 | 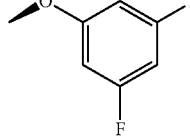 | $^1$H NMR (CDCl$_3$) δ1.56-1.76 (m, 4H), 1.88-2.06 (m, 13H), 2.16-2.20 (m, 2H), 2.37-2.39 (m, 2H), 3.95 (brs, 1H), 4.15 (brs, 2H), 4.43 (t, J = 4.4 Hz, 1H), 4.71 (brs, 1H), 5.17 (brs, 1H), 5.56 (brs, 1H), 6.86-6.98 (m, 3H) |
| 82 | 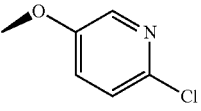 | $^1$H NMR (CDCl$_3$) δ1.58-1.62 (m, 2H), 1.74-1.77 (m, 2H), 1.89-2.25 (m, 17H), 3.96 (brs, 1H), 4.13 (brs, 2H), 4.54 (t, J = 4.8 Hz, 1H), 4.73 (brs, 1H), 5.19 (brs, 1H), 5.57 (brs, 1H), 6.31-6.41 (m, 3H) |

The compounds of Examples 83 to 137 were synthesized in a similar manner to Example 3, and purified by HPLC.

TABLE 11

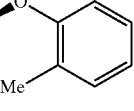

| Ex. No. | —Z¹—R² | tR (min) Obs [M + 1] Measurement method |
|---|---|---|
| 83 | 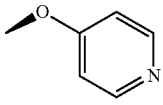 | 1.99 458 SA4 |
| 84 | 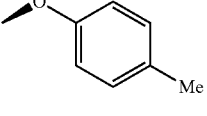 | 1.35 424 SA4 |
| 85 | 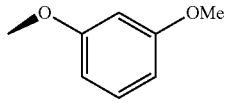 | 2.09 454 SA4 |

TABLE 11-continued

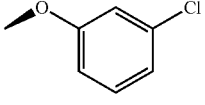

| Ex. No. | —Z¹—R² | tR (min) Obs [M + 1] Measurement method |
|---|---|---|
| 86 | | 1.93 438 SA4 |
| 87 | | 1.92 438 SA4 |
| 88 | | 1.58 458 SA4 |

TABLE 11-continued

| Ex. No. | —Z¹—R² | tR (min) Obs [M + 1] Measurement method |
|---|---|---|
| 89 | 4-OMe-phenoxy | 1.44 / 454 / SA4 |
| 90 | 5-indanyloxy | 2.05 / 464 / SA4 |
| 91 | 3-Cl-5-pyridyloxy | 1.69 / 458 / SA4 |
| 92 | 3-CF₃-phenoxy | 1.59 / 492 / SA4 |
| 93 | 2-OCF₃-phenoxy | 1.59 / 508 / SA4 |
| 94 | 3-OEt-phenoxy | 1.53 / 468 / SA4 |
| 95 | 3-OCF₃-phenoxy | 2.14 / 507 / SA4 |
| 96 | 3-Cl-4-F-phenoxy | 2.10 / 475 / SA4 |
| 97 | 3-F-4-Cl-phenoxy | 1.97 / 475 / SA4 |
| 98 | 3-Me-phenoxy | 1.92 / 438 / SA4 |
| 99 | 2-Cl-phenoxy | 1.55 / 457 / SA4 |
| 100 | 2-OMe-phenoxy | 1.42 / 454 / SA4 |
| 101 | 2-F-3-Cl-phenoxy | 1.95 / 476 / SA4 |
| 102 | 2-Cl-5-F-phenoxy | 1.95 / 475 / SA4 |
| 103 | 2-CF₃-phenoxy | 1.57 / 492 / SA4 |
| 104 | 4-CF₃-phenoxy | 1.60 / 492 / SA4 |
| 105 | 4-OCF₃-phenoxy | 1.63 / 508 / SA4 |
| 106 | 3-Oi-Pr-phenoxy | 1.57 / 482 / SA4 |

TABLE 12

| 107 | 3-i-Pr-phenoxy | 1.66 / 466 / SA4 |

TABLE 12-continued

| # | Structure | Data |
|---|---|---|
| 108 | 4-(i-Pr)-phenyl-OMe | 1.68, 466, SA4 |
| 109 | 2-Cl-4-F-phenyl-OMe | 1.96, 476, SA4 |
| 110 | benzo[d][1,3]dioxol-5-yl-OMe | 1.41, 468, SA4 |
| 111 | 5-CF3-pyridin-2-yl-OMe | 1.52, 493, SA4 |
| 112 | 4-OMe-pyridin-2-yl-OMe | 1.18, 455, SA4 |
| 113 | benzoxazol-5-yl-OMe | 1.32, 465, SA4 |
| 114 | 2-CN-phenyl-OMe | 1.35, 449, SA4 |
| 115 | 2-Me-benzoxazol-6-yl-OMe | 1.36, 478, SA4 |
| 116 | 2,3-dihydrobenzofuran-5-yl-OMe | 1.42, 466, SA4 |
| 117 | 5-Me-pyridin-2-yl-OMe | 1.60, 439, SA4 |
| 118 | 4-CO2Et-phenyl-OMe | 1.52, 496, SA4 |
| 119 | 4-NHAc-phenyl-OMe | 1.22, 481, SA4 |
| 120 | 4-Me-pyridin-2-yl-OMe | 1.08, 439, SA4 |
| 121 | pyridin-3-yl-OMe | 0.91, 425, SA4 |
| 122 | 4-Cl-phenyl-OMe | 1.57, 457, SA4 |
| 123 | 6-Me-pyridin-2-yl-OMe | 1.21, 439, SA4 |
| 124 | 4-CN-phenyl-OMe | 1.38, 449, SA4 |
| 125 | pyrazin-2-yl-OMe | 1.21, 426, SA4 |
| 126 | 2,3-dihydrobenzofuran-7-yl-OMe | 1.43, 466, SA4 |
| 127 | 2-Me-benzothiazol-5-yl-OMe | 1.45, 495, SA4 |
| 128 | 4-Ms-phenyl | 1.64, 486, SA4 |

TABLE 13

| # | Structure | Data |
|---|---|---|
| 129 | 3-F-benzyl-OMe | 1.97, 456, SA4 |
| 130 | benzyl-OMe | 1.85, 438, SA4 |
| 131 | 4-OCF3-benzyl-OMe | 1.64, 522, SA4 |
| 132 | 2-F-benzyl-OMe | 1.66, 456, SA4 |

TABLE 13-continued

| | | |
|---|---|---|
| 133 | | 2.08<br>472<br>SA4 |
| 134 | | 1.60<br>516<br>SA4 |
| 135 | | 1.87<br>456<br>SA4 |
| 136 | | 1.72<br>484<br>SA4 |
| 137 | benzyl | 1.57<br>438<br>SA4 |

Example 138

(3-Endo)-3-[(2-fluorobenzyl)oxy]-N-[(E)-5-hydroxyadamantan-2-yl]-8-azabicyclo-[3.2.1]octane-8-carboxamide

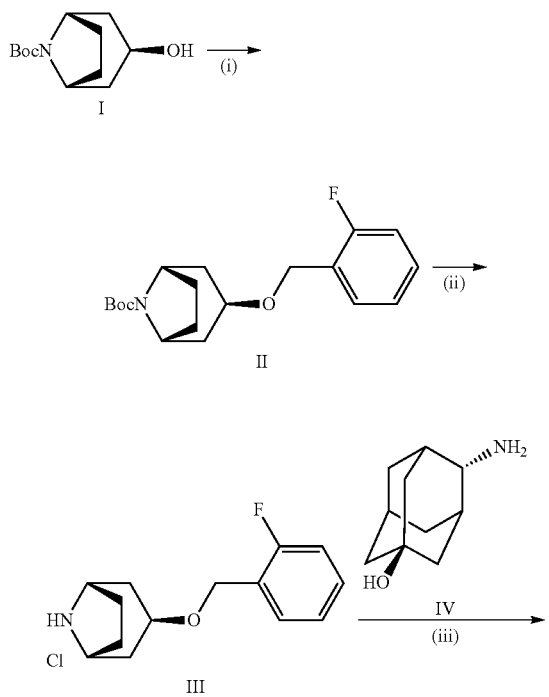

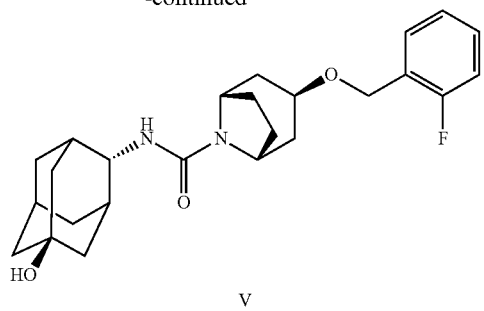

Step (i):

To a solution of Compound I (540 mg) in DMF (10 mL) were added sodium hydride (156 mg) and 2-fluorobenzyl bromide (0.44 mL), and then the mixture was stirred at 80° C. overnight. To the reaction mixture was added brine, and the resulting mixture was extracted with ethyl acetate. The organic layer was dried over sodium sulfate, and concentrated under reduced pressure. The residue was purified by silica gel column chromatography (eluent: hexane/ethyl acetate=10/1) to give Compound II (510 mg).

$^1$H-NMR (CDCl$_3$) δ1.47 (s, 9H), 1.92-2.13 (m, 8H), 3.74 (m, 1H), 4.13-4.22 (m, 2H), 4.54 (s, 2H), 7.03 (m, 1H), 7.04 (m, 1H), 7.27 (m, 1H), 7.42 (m, 1H)

Step (ii):

A mixture of Compound II (510 mg) and 4N hydrochloric acid-dioxane (3 mL) was stirred at room temperature for 3 hours. The reaction mixture was concentrated under reduced pressure, and the obtained solid was washed with ethyl acetate to give Compound III (500 mg).

Step (iii):

To a mixture of Compound IV (45 mg) and THF (2 mL) were added triethylamine (142 μL) and p-nitrophenyl chloroformate (68 mg), and the mixture was stirred at room temperature for 30 minutes. To the mixture was added a mixture of Compound III (55.7 mg), triethylamine (71 μL) and THF (1.7 mL), and the resulting mixture was stirred at room temperature overnight. The reaction mixture was concentrated under reduced pressure, and to the residue was added 1N sodium hydroxide, and the mixture was extracted with chloroform. The organic layer was washed with a saturated aqueous sodium bicarbonate solution and 1N hydrochloric acid, dried over sodium sulfate, and concentrated under reduced pressure. The residue was purified by silica gel column chromatography (chloroform/methanol, 10:1) to give the title compound V (50 mg).

$^1$H-NMR (CDCl$_3$) δ1.50-1.53 (m, 2H), 1.67-1.77 (m, 6H), 1.89-1.96 (m, 6H), 2.05-2.21 (m, 8H), 3.74 (m, 1H), 3.96 (m, 1H), 4.12 (m, 2H), 4.55 (s, 2H), 4.59 (d, J=8 Hz, 1H), 7.01-7.06 (m, 1H), 7.13-7.16 (m, 1H), 7.25-7.30 (m, 1H), 7.40-7.44 (m, 1H)

The compounds of Examples 139 to 144 were synthesized in a similar manner to Example 138.

TABLE 14

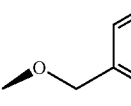

| Ex. No. | —Z¹—R² | NMR (solvent) δ |
|---|---|---|
| 139 | 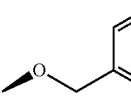 | ¹H-NMR (CDCl₃) δ1.41 (s, 1H), 1.50-1.77 (m, 9H), 1.89-1.99 (m, 5H), 2.05-2.21 (m, 7H), 3.72 (m, 1H), 3.96 (m, 1H), 4.12 (m, 2H), 4.49 (s, 2H), 4.60 (d, J = 4 Hz, 1H), 6.95-6.99 (m, 1H), 7.04-7.09 (m, 2H), 7.29-7.33 (m, 1H) |
| 140 | 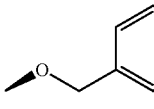 | ¹H-NMR (CDCl₃) δ1.40 (s, 1H), 1.50-1.76 (m, 8H), 1.90-1.98 (m, 6H), 2.04-2.20 (m, 7H), 3.72 (m, 1H), 3.96 (m, 1H), 4.12 (m, 2H), 4.45 (s, 2H), 4.59 (d, J = 8 Hz, 1H), 7.01-7.06 (m, 2H), 7.29-7.31 (m, 2H) |
| 141 | 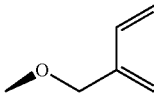 | ¹H-NMR (CDCl₃) δ1.47 (s, 1H), 1.50-1.77 (m, 9H), 1.89-2.01 (m, 5H), 2.07-2.19 (m, 7H), 3.06 (S, 3H), 3.75 (m, 1H), 3.96 (m, 1H), 4.12 (m, 2H), 4.59 (s, 2H), 4.60 (d, J = 8 Hz, 1H), 7.53 (d, J = 8 Hz, 2H), 7.93 (d, J = 8 Hz, 2H) |
| 142 | 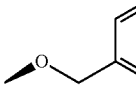 | ¹H-NMR (CDCl₃) δ1.43 (s, 1H), 1.49-1.76 (m, 11H), 1.89-1.97 (m, 5H), 2.03-2.06 (m, 1H), 2.12-2.20 (m, 4H), 2.48 (s, 3H), 3.70 (m, 1H), 3.95 (m, 1H), 4.11 (m, 2H), 4.44 (s, 2H), 4.58 (d, J = 8 Hz, 1H), 7.25 (m, 4H) |
| 143 | 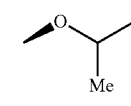 | ¹H-NMR (CDCl₃) δ1.45 (s, 1H), 1.49-1.53 (m, 2H), 1.62-1.76 (m, 6H), 1.89-1.97 (m, 6H), 2.04-2.19 (m, 7H), 3.71 (m, 1H), 3.95 (m, 1H), 4.11 (m, 2H), 4.45 (s, 2H), 4.58 (d, J = 8 Hz, 1H), 7.25 (d, J = 8 Hz, 2H), 7.31 (d, J = 8 Hz, 2H) |
| 144 | 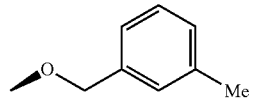 | ¹H-NMR (CDCl₃) δ1.38 (d, J = 4 Hz, 3H), 1.45-1.73 (m, 10H), 1.85-1.98 (m, 7H), 2.07-2.10 (m, 3H), 2.19-2.29 (m, 2H), 3.50 (m, 1H), 3.91 (m, 1H), 4.02 (m, 1H), 4.13 (m, 1H), 4.46 (q, J = 4 Hz, 1H), 4.53 (d, J = 8 Hz, 1H), 7.21-7.33 (m, 5H) |

The compounds of Examples 145 to 164 were synthesized in a similar manner to Example 138.

TABLE 15

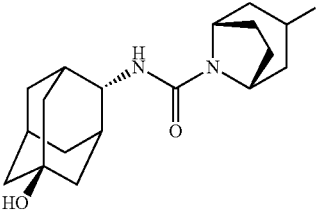

| Ex. No. | —Z¹—R² | tR (min) Obs [M + 1] Measurement method |
|---|---|---|
| 145 | 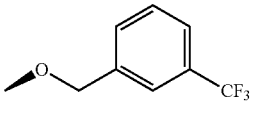 | 1.97 488 SA4 |
| 146 | 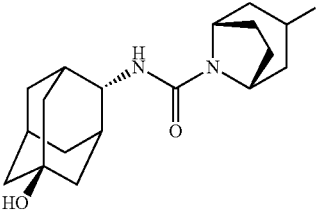 | 2.13 479 SA4 |

TABLE 15-continued

| Ex. No. | —Z¹—R² | tR (min) Obs [M + 1] Measurement method |
|---|---|---|
| 147 | benzodioxane-CH₂-O- | 1.42 / 469 / SA4 |
| 148 | 4-CF₃-C₆H₄-CH₂-O- | 2.04 / 479 / SA4 |
| 149 | 3-OCF₃-C₆H₄-CH₂-O- | 2.06 / 495 / SA4 |
| 150 | 3-OCHF₂-C₆H₄-CH₂-O- | 2.10 / 477 / SA4 |
| 151 | pyridin-3-yl-CH₂-O- | 1.44 / 412 / SA4 |
| 152 | pyridin-4-yl-CH₂-O- | 1.21 / 412 / SA4 |
| 153 | 4-OCHF₂-C₆H₄-CH₂-O- | 1.89 / 477 / SA4 |
| 154 | 3-OMe-pyridin-2-yl-CH₂-O- | 1.55 / 442 / SA4 |
| 155 | 4-Me-C₆H₄-CH₂-O- | 2.08 / 425 / SA4 |
| 156 | 3-Cl-4-OCF₃-C₆H₃-CH₂-O- | 2.28 / 529 / SA4 |

TABLE 15-continued

| Ex. No. | —Z¹—R² | tR (min) Obs [M + 1] Measurement method |
|---|---|---|
| 157 | 4-CN-pyridin-... -CH₂-O- | 1.79 / 436 / SA4 |
| 158 | 3-Cl-C₆H₄-CH₂-O- | 2.00 / 445 / SA4 |
| 159 | 4-Cl-3-OCF₃-C₆H₃-CH₂-O- | 2.17 / 529 / SA4 |
| 160 | pyridin-2-yl-CH₂-O- | 1.25 / 412 / SA4 |
| 161 | 5-Me-pyridin-3-yl-CH₂-O- | 1.25 / 426 / SA4 |
| 162 | 4-F-3-OCF₃-C₆H₃-CH₂-O- | 2.06 / 513 / SA4 |
| 163 | 2,4-diMe-pyridin-6-yl-CH₂-O- | 1.20 / 440 / SA4 |
| 164 | 1,3-diMe-pyrazol-5-yl-CH₂-O- | 1.38 / 429 / SA4 |

Example 165

(3-Endo)-N-[(E)-5-hydroxyadamantan-2-yl]-3-(3-methylphenoxy)-8-azabicyclo[3.2.1]octane-8-carboxamide

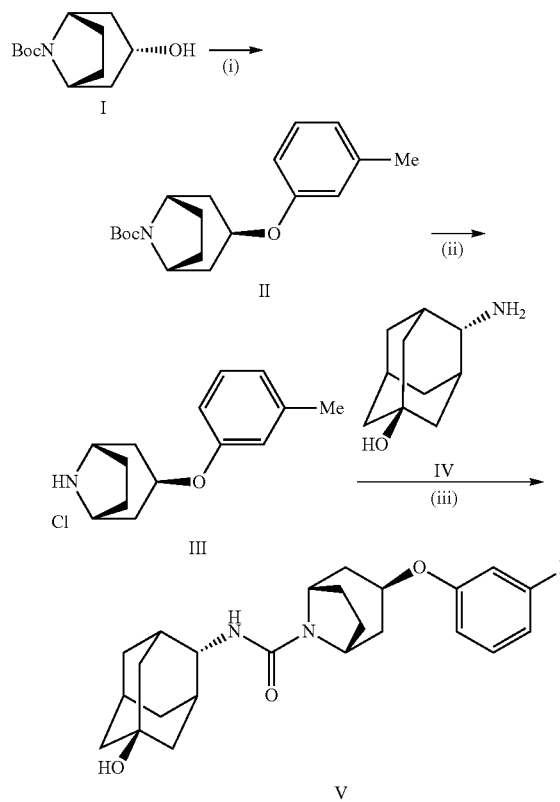

Step (i):
Compound I (400 mg) was dissolved in THF (6 mL), and thereto were added DIAD (523 μL), triphenylphosphine (692 mg), and 3-methylphenol (204 μL), and the resulting mixture was stirred at room temperature overnight. The reaction mixture was concentrated under reduced pressure, diluted with ethyl acetate, and washed with 1N aqueous sodium hydroxide solution and brine. The organic layer was dried over sodium sulfate, and concentrated under reduced pressure. The residue was purified by silica gel column chromatography (eluent: hexane/ethyl acetate=9/1) to give Compound II (150 mg).

Step (ii):
Compound II (150 mg) was added to 4N hydrochloric acid/dioxane (3 mL), and the mixture was stirred at room temperature for 3 hours. The reaction mixture was concentrated under reduced pressure, and the obtained solid was washed with ethyl acetate to give Compound III (134 mg).

Step (iii):
To a solution of Compound IV (31 mg) in THF (1.7 mL) were added triethylamine (71 μL) and p-nitrophenyl chloroformate (41 mg), and the mixture was stirred at room temperature. Thirty minutes later, to the mixture was added a solution of Compound III (43 mg) and triethylamine (71 μL) in THF (1.7 mL), and the resulting mixture was stirred at room temperature overnight. The reaction mixture was concentrated under reduced pressure, and the residue was diluted with 1N sodium hydroxide, and the mixture was extracted with chloroform. The organic layer was washed with a saturated sodium bicarbonate solution and 1N hydrochloric acid, dried over sodium sulfate, and concentrated under reduced pressure. The residue was purified by silica gel column chromatography (chloroform/methanol, 10:1), and the resulting solid was washed with ethyl acetate/diisopropylether to give the title compound V (25 mg).

$^1$H NMR (CDCl$_3$) δ1.48-1.74 (m, 9H), 1.87-2.02 (m, 6H), 2.12-2.23 (m, 7H), 2.30 (s, 3H), 3.93 (brs, 1H), 4.11 (brs, 2H), 4.60 (t, J=4.8 Hz, 1H), 4.73 (brs, 1H), 6.59-6.64 (m, 2H), 6.73-6.74 (d, J=7.6 Hz, 1H), 7.14 (t, J=7.6 Hz, 1H)

The compounds of Examples 166 to 203 were synthesized in a similar manner to Example 165.

TABLE 16

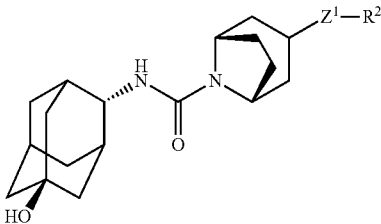

| Ex. No. | —Z$^1$—R$^2$ | NMR (solvent) δ |
|---|---|---|
| 166 | ![4-methylphenoxy] | $^1$H NMR (CDCl$_3$) δ1.48-1.74 (m, 9H), 1.87-2.02 (m, 6H), 2.12-2.22 (m, 7H), 2.26 (s, 3H), 3.95 (brs, 1H), 4.11 (brs, 2H), 4.57 (t, J = 4.4 Hz, 1H), 4.68 (brs, 1H), 6.71 (d, J = 8.0 Hz, 2H), 7.06 (d, J = 8.0 Hz, 2H) |
| 167 | ![2-methoxyphenoxy] | $^1$H NMR (CDCl$_3$) δ1.49-1.74 (m, 9H), 1.86-1.90 (m, 2H), 2.01-2.05 (m, 4H), 2.12 (brs, 3H), 2.21-2.25 (m, 2H), 2.33-2.36 (m, 2H), 3.82 (s, 3H), 3.92-3.94 (m, 1H), 4.12 (brs, 2H), 4.58 (t, J = 4.8 Hz, 1H), 4.76 (brs, 1H), 6.77-6.79 (m, 1H), 6.84-6.92 (m, 3H) |

TABLE 16-continued

[Structure: N-(2-hydroxyadamantyl)-carbamoyl-azabicyclic-Z¹-R²]

| Ex. No. | —Z¹—R² | NMR (solvent) δ |
|---|---|---|
| 168 | [4-methoxyphenoxymethyl] OMe | ¹H NMR (CDCl₃) δ1.48-1.74 (m, 9H), 1.86-2.00 (m, 6H), 2.12-2.23 (m, 7H), 3.75 (s, 3H), 3.93 (brs, 1H), 4.11 (brs, 2H), 4.51 (t, J = 5.2 Hz, 1H), 4.76 (brs, 1H), 6.75 (d, J = 9.2 Hz, 2H), 6.81 (d, J = 9.2 Hz, 2H) |
| 169 | [2-chlorophenoxymethyl] Cl | ¹H NMR (CDCl₃) δ1.49-1.75 (m, 9H), 1.87-2.13 (m, 9H), 2.23-2.35 (m, 4H), 3.95 (brs, 1H), 4.13 (brs, 2H), 4.66 (t, J = 4.8 Hz, 1H), 4.73 (brs, 1H), 6.75 (d, J = 7.2 Hz, 1H), 6.85 (dt, J = 1.2 Hz, 7.6 Hz, 1H), 7.15-7.19 (m, 1H), 7.36 (dd, J = 1.6 Hz, 7.6 Hz, 1H) |
| 170 | [3-chlorophenoxymethyl] Cl | ¹H NMR (CDCl₃) δ1.49-1.75 (m, 9H), 1.86-2.05 (m, 6H), 2.12-2.27 (m, 7H), 3.94 (brs, 1H), 4.13 (brs, 2H), 4.59 (t, J = 4.4 Hz, 1H), 4.90 (brs, 1H), 6.69 (dd, J = 2.4 Hz, 8.8 Hz, 1H), 6.81 (t, J = 2.0 Hz, 1H), 6.89-6.92 (m, 1H), 7.18 (t, J = 8.0 Hz, 1H) |
| 171 | [3-cyanophenoxymethyl] CN | ¹H NMR (CDCl₃) δ1.45-1.75 (m, 9H), 1.87-1.95 (m, 4H), 2.01-2.04 (m, 2H), 2.12-2.14 (m, 5H), 2.21-2.27 (m, 2H), 3.93-3.95 (m, 1H), 4.14 (brs, 2H), 4.62 (t, J = 4.8 Hz, 1H), 4.67 (brs, 1H), 7.03-7.05 (m, 2H), 7.21-7.23 (m, 1H), 7.36 (t, J = 8.0 Hz, 1H) |
| 172 | [4-isopropylphenoxymethyl] i-Pr | ¹H NMR (CDCl₃) δ1.20 (d, 7.2 Hz, 6H), 1.48-1.51 (m, 3H), 1.65-1.74 (m, 6H), 1.87-1.98 (m, 6H), 2.12-2.23 (m, 7H), 2.80-2.87 (m, 1H), 3.93-3.95 (m, 1H), 4.11 (brs, 2H), 4.57 (t, J = 4.8 Hz, 1H), 4.65 (brs, 1H), 6.73 (d, J = 8.4 Hz, 2H), 7.11 (d, J = 8.4 Hz, 2H) |

TABLE 17

| | | |
|---|---|---|
| 173 | [3-ethoxyphenoxymethyl] OEt | ¹H NMR (CDCl₃) δ1.37-1.40 (m, 4H), 1.48-1.52 (m, 2H), 1.65-1.74 (m, 6H), 1.87-1.98 (m, 6H), 2.12-2.21 (m, 7H), 3.95-4.02 (m, 3H), 4.11 (brs, 2H), 4.58 (t, J = 4.8 Hz, 1H), 4.65 (brs, 1H), 6.36 (t, J = 2.4 Hz, 1H), 6.39 (dd, J = 2.4 Hz, 8.0 Hz, 1H), 6.46 (dd, J = 2.4 Hz, 8.0 Hz, 1H), 7.14 (t, J = 8.0 Hz, 1H) |
| 174 | [2-trifluoromethylphenoxymethyl] F₃C | ¹H NMR (CDCl₃) δ1.37 (s, 1H), 1.49-1.52 (m, 2H), 1.65-1.75 (m, 6H), 1.87-1.99 (m, 6H), 2.13-2.30 (m, 7H), 3.96 (brs, 1H), 4.14 (brs, 2H), 4.60-4.66 (m, 2H), 6.79 (d, J = 8.8 Hz, 1H), 6.96 (t, J = 7.6 Hz, 1H), 7.44 (t, J = 7.6 Hz, 1H), 7.57 (d, J = 7.6 Hz, 1H) |
| 175 | [4-trifluoromethylphenoxymethyl] CF₃ | ¹H NMR (CDCl₃) δ1.37 (s, 1H), 1.49-1.52 (m, 2H), 1.65-1.75 (m, 6H), 1.87-2.02 (m, 6H), 2.13-2.24 (m, 7H), 3.93-3.95 (m, 1H), 4.13 (brs, 2H), 4.59 (d, J = 7.2 Hz, 1H), 4.66 (t, J = 4.8 Hz, 1H), 6.86 (d, J = 8.4 Hz, 2H), 7.52 (d, J = 8.4 Hz, 2H) |
| 176 | [2-trifluoromethoxyphenoxymethyl] CF₃O | ¹H NMR (CDCl₃) δ1.36 (s, 1H), 1.49-1.52 (m, 2H), 1.65-1.75 (m, 6H), 1.87-2.24 (m, 13H), 3.95 (brs, 1H), 4.13 (brs, 2H), 4.61 (brs, 2H), 6.82 (d, J = 8.0 Hz, 1H), 6.90 (t, J = 8.0 Hz, 1H), 7.18-7.24 (m, 2H) |
| 177 | [4-trifluoromethoxyphenoxymethyl] OCF₃ | ¹H NMR (CDCl₃) δ1.37 (s, 1H), 1.49-1.52 (m, 2H), 1.64-1.75 (m, 6H), 1.87-2.01 (m, 6H), 2.12-2.21 (m, 7H), 3.95 (brs, 1H), 4.13 (brs, 2H), 4.57 (brs, 2H), 6.77-6.80 (m, 2H), 7.12 (d, J = 8.4 Hz, 2H) |

TABLE 17-continued

| | | |
|---|---|---|
| 178 | 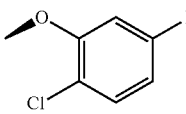 | $^1$H NMR (CDCl$_3$) δ1.37 (s, 1H), 1.49-1.53 (m, 2H), 1.65-1.75 (m, 6H), 1.87-2.30 (m, 13H), 3.94 (brs, 1H), 4.12 (brs, 2H), 4.59 (m, 2H), 6.49 (dd, J = 2.4 Hz, 10.4 Hz, 1H), 6.56-6.61 (m, 1H), 7.30 (dd, J = 6.0 Hz, 8.8 Hz, 1H) |
| 179 | 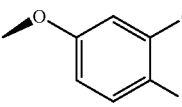 | $^1$H NMR (CDCl$_3$) δ1.36 (s, 1H), 1.49-1.52 (m, 2H), 1.64-1.75 (m, 6H), 1.87-2.03 (m, 6H), 2.12-2.20 (m, 7H), 3.93-3.95 (m, 1H), 4.12 (brs, 2H), 4.51 (t, J = 4.8 Hz, 1H), 4.58 (d, J = 7.2 Hz, 1H), 6.65 (dt, J = 3.2 Hz, 8.8 Hz, 1H), 6.83 (dd, J = 3.2 Hz, 6.4 Hz, 1H), 7.03 (t, J = 8.8 Hz, 1H) |
| 180 | 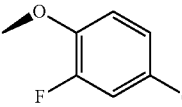 | $^1$H NMR (CDCl$_3$) δ1.36 (s, 1H), 1.48-1.52 (m, 2H), 1.64-1.74 (m, 6H), 1.86-2.00 (m, 6H), 2.12-2.20 (m, 7H), 3.93-3.94 (m, 1H), 4.12 (brs, 2H), 4.58 (brs, 2H), 6.76 (t, J = 8.8 Hz, 1H), 7.01 (dt, J = 2.0 Hz, 8.8 Hz, 1H), 7.10 (dd, J = 2.0 Hz, 10.4 Hz, 1H) |
| 181 | 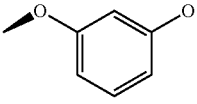 | $^1$H NMR (CDCl$_3$) δ1.31 (d, J = 8.0 Hz, 6H), 1.34 (s, 1H), 1.47-1.51 (m, 2H), 1.64-1.74 (m, 6H), 1.89-1.98 (m, 6H), 2.12-2.23 (m, 7H), 3.93-3.95 (m, 1H), 4.10 (brs, 2H), 4.46-4.59 (m, 3H), 6.34-6.39 (m, 2H), 6.46 (dd, J = 2.8 Hz, 10.8 Hz, 1H), 7.13 (t, J = 10.8 Hz, 1H) |
| 182 | 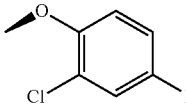 | $^1$H NMR (CDCl$_3$) δ1.34 (s, 1H), 1.48-1.52 (m, 2H), 1.64-1.75 (m, 6H), 1.86-2.03 (m, 6H), 2.12-2.33 (m, 7H), 3.93-3.95 (m, 1H), 4.13 (brs, 2H), 4.58-4.61 (m, 2H), 6.69 (dd, J = 6.4 Hz, 12.0 Hz, 1H), 6.89-6.92 (m, 1H), 7.13 (dd, J = 4.0 Hz, 10.8 Hz, 1H) |

TABLE 18

| | | |
|---|---|---|
| 183 | 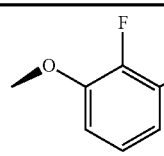 | $^1$H NMR (CDCl$_3$) δ1.36 (s, 1H), 1.48-1.52 (m, 2H), 1.64-1.75 (m, 6H), 1.86-2.03 (m, 6H), 2.12-2.26 (m, 7H), 3.95 (brs, 1H), 4.13 (brs, 2H), 4.58-4.61 (m, 2H), 6.71-6.76 (m, 1H), 6.94-6.96 (m, 2H) |
| 184 | 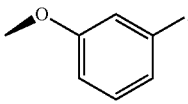 | $^1$H NMR (CDCl$_3$) δ1.22 (d, J = 6.0 Hz, 6H), 1.35 (s, 1H), 1.48-1.54 (m, 2H), 1.65-1.74 (m, 6H), 1.87-1.90 (m, 2H), 1.95-2.03 (m, 4H), 2.12-2.23 (m, 7H), 2.81-2.88 (m, 1H), 3.94 (brs, 1H), 4.11 (brs, 2H), 4.58-4.60 (m, 2H), 6.61 (dd, J = 2.4 Hz, 8.0 Hz, 1H), 6.68 (s, 1H), 6.79 (d, J = 8.0 Hz, 1H), 7.18 (t, J = 8.0 Hz, 1H) |
| 185 | 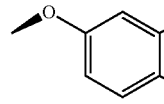 | $^1$H NMR (CDCl$_3$) δ1.35 (s, 1H), 1.49-1.57 (m, 2H), 1.64-1.75 (m, 6H), 1.87-2.21 (m, 13H), 3.95 (brs, 1H), 4.12 (brs, 2H), 4.53-4.59 (m, 2H), 6.55 (dd, J = 2.8 Hz, 9.2 Hz, 1H), 6.61 (dd, J = 2.8 Hz, 10.4 Hz, 1H), 7.23-7.27 (m, 1H) |
| 186 | 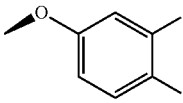 | $^1$H NMR (CDCl$_3$) δ1.34 (s, 1H), 1.47-1.55 (m, 2H), 1.63-1.74 (m, 6H), 1.86-1.99 (m, 6H), 2.12-2.22 (m, 7H), 3.93 (brs, 1H), 4.06-4.14 (m, 2H), 4.18-4.23 (m, 4H), 4.46 (brs, 1H), 4.57 (d, J = 9.6 Hz, 1H), 6.31-6.35 (m, 2H), 6.75 (d, J = 13.2 Hz, 1H) |
| 187 | 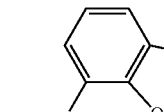 | $^1$H NMR (CDCl$_3$) δ1.34 (s, 1H), 1.47-1.52 (m, 2H), 1.64-1.74 (m, 6H), 1.86-2.03 (m, 6H), 2.12-2.18 (m, 5H), 2.26-2.33 (m, 2H), 3.20 (t, J = 12 Hz, 2H), 3.93 (brs, 1H), 4.11 (brs, 2H), 4.53-4.59 (m, 3H), 4.65 (t, J = 5.6 Hz, 1H), 6.64 (d, J = 10.0 Hz, 1H), 6.74 (t, J = 10.0 Hz, 1H), 6.82 (d, J = 10.0 Hz, 1H) |
| 188 | 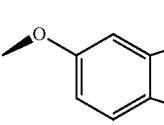 | $^1$H NMR (CDCl$_3$) δ1.36 (s, 1H), 1.48-1.55 (m, 2H), 1.64-1.74 (m, 6H), 1.87-1.99 (m, 6H), 2.11-2.23 (m, 7H), 3.16 (t, J = 8.4 Hz, 2H), 3.93-3.95 (m, 1H), 4.11 (brs, 2H), 4.45-4.59 (m, 4H), 6.56 (dd, J = 2.8 Hz, 8.8 Hz, 1H), 6.66 (d, J = 8.8 Hz, 1H), 6.71 (d, J = 2.8 Hz, 1H) |

TABLE 18-continued

| | | |
|---|---|---|
| 189 | 5-methoxy-2-methylbenzothiazole structure | ¹H NMR (CDCl₃) δ1.35 (s, 1H), 1.49-1.58 (m, 2H), 1.65-1.75 (m, 6H), 1.87-1.90 (m, 2H), 2.00-2.04 (m, 4H), 2.13-2.24 (m, 7H), 2.79 (s, 3H), 3.94 (brs, 1H), 4.13 (brs, 2H), 4.59-4.68 (m, 2H), 6.92 (dd, J = 2.4 Hz, 8.8 Hz, 1H), 7.32 (d, J = 2.4 Hz, 1H), 7.66 (d, J = 8.8 Hz, 1H) |
| 190 | methoxy-benzodioxine structure | ¹H NMR (CDCl₃) δ1.40 (s, 1H), 1.48-1.51 (m, 2H), 1.65-1.74 (m, 6H), 1.87-2.02 (m, 6H), 2.12-2.18 (m, 5H), 2.27-2.32 (m, 2H), 3.93-3.95 (m, 1H), 4.11 (brs, 2H), 4.22-4.26 (m, 4H), 4.56-4.59 (m, 2H), 6.36 (dd, J = 1.3 Hz, 8.0 Hz, 1H), 6.50 (dd, J = 1.2 Hz, 8.0 Hz, 1H), 6.71 (t, J = 8.0 Hz, 1H) |
| 191 | 2-methoxybenzonitrile structure | ¹H NMR (CDCl₃) δ1.45-1.75 (m, 9H), 1.87-1.90 (m, 2H), 1.97-2.13 (m, 7H), 2.25-2.34 (m, 4H), 3.93-3.95 (m, 1H), 4.15 (brs, 2H), 4.71-4.74 (m, 2H), 6.81 (d, J = 8.8 Hz, 1H), 6.98 (dt, J = 0.8 Hz, 8.0 Hz, 1H), 7.45-7.51 (m, 1H), 7.56 (dd, J = 1.2 Hz, 8.0 Hz, 1H) |

TABLE 19

| | | |
|---|---|---|
| 192 | 2-chloro-1,3-dimethoxybenzene structure | ¹H NMR (CDCl₃) δ1.34 (s, 1H), 1.49-1.56 (m, 2H), 1.65-1.75 (m, 6H), 1.87-2.00 (m, 6H), 2.13-2.23 (m, 5H), 2.33-2.35 (m, 2H), 3.89 (s, 3H), 3.94 (brs, 1H), 4.13 (brs, 2H), 4.59-4.66 (m, 2H), 6.42 (d, J = 8.4 Hz, 1H), 6.56 (d, J = 8.4 Hz, 1H), 7.12 (t, J = 8.4 Hz, 1H) |
| 193 | chloro-dimethoxybenzene structure | ¹H NMR (CDCl₃) δ1.33 (s, 1H), 1.49-1.58 (m, 2H), 1.65-1.75 (m, 6H), 1.87-2.00 (m, 6H), 2.13-2.34 (m, 7H), 3.75 (s, 3H), 3.95 (brs, 1H), 4.13 (brs, 2H), 4.59-4.60 (m, 2H), 6.32 (d, J = 2.4 Hz, 1H), 6.39 (dd, J = 2.8 Hz, 8.8 Hz, 1H), 7.20-7.30 (m, 1H) |
| 194 | OCHF₂-methoxybenzene structure | ¹H NMR (CDCl₃) δ1.35 (s, 1H), 1.49-1.53 (m, 2H), 1.64-1.75 (m, 6H), 1.87-2.03 (m, 6H), 2.12-2.21 (m, 7H), 3.94 (brs, 1H), 4.12 (brs, 2H), 4.59 (brs, 2H), 6.35 (d, J = 74 Hz, 1H), 6.57 (brs, 1H), 6.64-6.68 (m, 2H), 7.21-7.24 (m, 1H) |
| 195 | 1,2,3-trimethoxybenzene structure | ¹H NMR (CDCl₃) δ1.49-1.52 (m, 2H), 1.60 (m, 3H), 1.66-1.69 (m, 2H), 1.73-1.76 (m, 3H), 1.88-1.91 (m, 2H), 1.97-2.04 (m, 4H), 2.13-2.22 (m, 4H), 2.31-2.36 (m, 2H), 3.83 (s, 3H), 3.85 (s, 3H), 3.96 (m, 1H), 4.13 (m, 1H), 4.59 (m, 2H), 6.45 (m, 1H), 6.55 (m, 1H), 6.95 (m, 1H) |
| 196 | 1,2,4-trimethoxybenzene structure | ¹H NMR (CDCl₃) δ1.49-1.52 (m, 2H), 1.66-1.75 (m, 7H), 1.88-2.03 (m, 6H), 2.13-2.24 (m, 7H), 3.82 (s, 3H), 3.85 (s, 3H), 3.95 (m, 1H), 4.13 (m, 1H), 4.52 (m, 1H), 4.60 (d, J = 8, 1H), 6.30 (dd, J = 4 Hz, 8 Hz, 1H), 6.44 (d, J = 4 Hz, 1H), 6.66 (d, J = 8 Hz, 1H) |
| 197 | 3,5-dimethoxy-methyl benzene structure | ¹H NMR (CDCl₃) δ1.51 (m, 3H), 1.65-1.75 (m, 7H), 1.88-2.04 (m, 4H), 2.12-2.23 (m, 6H), 2.28 (m, 3H), 3.76 (s, 3H), 3.95 (m, 1H), 4.11 (m, 2H), 4.57-4.61 (m, 2H), 6.17 (m, 1H), 6.25 (m, 1H), 6.31 (m, 1H) |
| 198 | 2-methoxy-(methoxymethyl)benzene structure | ¹H NMR (CDCl₃) δ1.44 (s, 1H), 1.50-1.54 (m, 2H), 1.66-1.69 (m, 2H), 1.74 (m, 4H), 1.88-2.01 (m, 5H), 2.13-2.24 (m, 8H), 3.38 (s, 3H), 3.96 (m, 1H), 4.13 (m, 2H), 4.42 (s, 2H), 4.59-4.65 (m, 2H), 6.74 (m, 1H), 6.82 (m, 1H), 6.88 (m, 1H), 7.22-7.26 (m, 1H) |
| 199 | dimethoxy-fluorobenzene structure | ¹H NMR (CDCl₃) δ1.34 (s, 1H), 1.51-1.55 (m, 2H), 1.67-1.77 (m, 6H), 1.89-2.22 (m, 13H), 3.89 (s, 3H), 3.95 (brs, 1H), 4.14 (brs, 2H), 4.54 (brs, 1H), 4.59 (brs, 1H), 6.27-6.28 (m, 1H), 6.45-6.48 (m, 1H), 6.94-7.00 (m, 1H) |

TABLE 20

| | | |
|---|---|---|
| 200 | 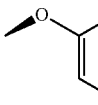 OMe / Me | ¹H NMR (CDCl₃) δ1.37 (s, 1H), 1.50-1.57 (m, 2H), 1.67-1.77 (m, 6H), 1.89-2.00 (m, 6H), 2.14-2.24 (m, 10H), 3.80 (s, 3H), 3.96 (brs, 1H), 4.13 (brs, 2H), 4.58-4.61 (m, 2H), 6.29 (dd, J = 2.4 Hz, 8.0 Hz, 1H), 6.36 (d, J = 2.4 Hz, 1H), 7.00 (d, J = 8.0 Hz, 1H) |
| 201 | 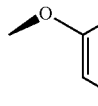 OEt / F | ¹H NMR (CDCl₃) δ1.37 (s, 1H), 1.45 (t, J = 7.2 Hz, 3H), 1.51-1.57 (m, 2H), 1.66-1.77 (m, 6H), 1.89-2.03 (m, 6H), 2.14-2.20 (m, 7H), 3.95 (brs, 1H), 4.07 (q, J = 7.2 Hz, 2H), 4.13 (brs, 2H), 4.52-4.54 (m, 1H), 4.60 (d, J = 6.8 Hz, 1H), 6.27 (dt, J = 2.8 Hz, 8.8 Hz, 1H), 6.45 (dd, J = 2.8 Hz, 7.2 Hz, 1H), 6.96 (dd, J = 8.8 Hz, 11.2 Hz, 1H) |
| 202 | 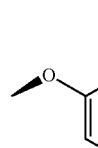 OMe / CN | ¹H NMR (CDCl₃) δ1.44-1.74 (m, 9H), 1.87-2.01 (m, 6H), 2.12 (brs, 3H), 2.19-2.24 (m, 4H), 3.84 (s, 3H), 3.93-3.95 (m, 1H), 4.12 (brs, 2H), 4.59 (d, J = 7.2 Hz, 1H), 4.67 (t, J = 4.8 Hz, 1H), 6.74 (d, J = 8.4 Hz, 1H), 7.07 (d, J = 2.0 Hz, 1H), 7.22 (dd, J = 2.0 Hz, 8.4 Hz, 1H) |
| 203 | 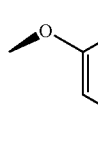 OEt / F | ¹H NMR (CDCl₃) δ1.35 (s, 1H), 1.40 (t, J = 7.2 Hz, 3H), 1.51-1.56 (m, 2H), 1.66-1.77 (m, 6H), 1.89-2.02 (m, 6H), 2.14-2.21 (m, 7H), 3.95-4.01 (m, 3H), 4.13 (brs, 2H), 4.53-4.56 (m, 1H), 4.59 (d, J = 7.6 Hz, 1H), 6.12-6.16 (m, 2H), 6.21 (dt, J = 2.0 Hz, 10.8 Hz, 1H) |

The compounds of Examples 204 to 253 were synthesized in a similar manner to Example 1.

TABLE 21

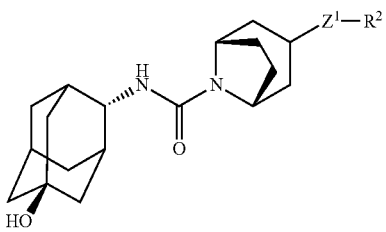

| Ex. No. | —Z¹—R² | NMR (solvent) δ |
|---|---|---|
| 204 | 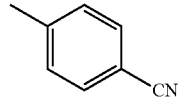 CN | ¹H NMR (CDCl₃) δ1.48 (s, 1H), 1.52-1.98 (m, 16H), 2.06-2.18 (m, 5H), 2.51-2.60 (m, 1H), 4.00 (m, 1H), 4.28 (m, 2H), 4.69 (m, 1H), 7.28-7.61 (m, 2H), 7.58-7.61 (m, 2H) |
| 205 | 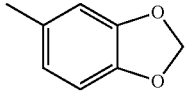 | ¹H NMR (CDCl₃) δ1.37 (s, 1H), 1.43-1.55 (m, 5H), 1.62-1.84 (m, 8H), 1.86-1.92 (m, 2H), 2.02-2.16 (m, 5H), 2.45-2.59 (m, 2H), 3.98 (m, 1H), 4.21 (m, 2H), 4.63 (m, 1H), 5.91 (s, 2H), 6.62-6.73 (m, 3H) |
| 206 | 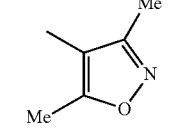 Me / Me | ¹H NMR (CDCl₃) δ1.39-1.54 (m, 5H), 1.61 (s, 6H), 1.66-1.69 (m, 1H), 1.76-1.82 (m, 4H), 1.97-2.21 (m, 8H), 2.25-2.32 (m, 4H), 2.95 (m, 1H), 3.99 (m, 1H), 4.22 (m, 2H), 4.67 (m, 1H) |
| 207 | 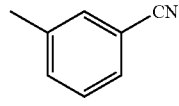 CN | ¹H NMR (CDCl₃) δ1.43 (s, 1H), 1.49-1.70 (m, 9H), 1.76-1.84 (m, 4H), 1.87-1.93 (m, 3H), 2.04-2.16 (m, 5H), 2.53 (m, 1H), 3.98 (m, 1H), 4.27 (m, 2H), 4.67 (m, 1H), 7.36-7.52 (m, 4H) |
| 208 | 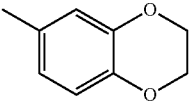 | ¹H NMR (CDCl₃) δ1.37 (s, 1H), 1.47-1.54 (m, 6H), 1.61-1.70 (m, 3H), 1.75-1.84 (m, 4H), 1.87-1.92 (m, 2H), 2.01-2.09 (m, 2H), 2.13-2.26 (m, 3H), 2.44-2.58 (m 2H), 3.97 (m, 1H), 4.22 (m, 6H), 4.64 (m, 1H), 6.63-6.71 (m, 2H), 6.75-6.78 (m, 1H) |

TABLE 21-continued

| Ex. No. | —Z¹—R² | NMR (solvent) δ |
|---|---|---|
| 209 | (3-methoxyphenyl)methyl | ¹H NMR (CDCl₃) δ1.45-1.78 (m, 12H), 1.81-1.97 (m, 4H), 2.04-2.17 (m, 5H), 2.48-2.55 (m, 1H), 2.61-2.66 (m, 1H), 3.79 (s, 3H), 3.98 (m, 1H), 4.24 (m, 2H), 4.65 (m, 1H), 6.71-6.81 (m, 3H), 7.18-7.22 (m, 1H) |
| 210 | (2-methoxyphenyl)methyl | ¹H NMR (CDCl₃) δ1.50 (s, 1H), 1.67-1.78 (m, 9H), 1.82-1.94 (m, 4H), 2.01-2.24 (m, 7H), 2.41-2.48 (m, 2H), 3.75 (s, 3H), 4.01 (m, 1H), 4.23 (m, 2H), 4.71 (m, 1H), 6.80-6.90 (m, 2H), 7.12-7.23 (m, 2H) |
| 211 | (3-trifluoromethoxyphenyl)methyl | ¹H NMR (CDCl₃) δ1.44 (s, 1H), 1.52-1.59 (m, 4H), 1.62-1.67 (m, 3H), 1.76-1.78 (m, 4H), 1.90-1.93 (m, 2H), 2.03-2.09 (m, 2H), 2.11-2.17 (m, 4H), 2.50-2.57 (m, 2H), 2.69 (m, 1H), 3.98 (m, 1H), 4.24 (m, 2H), 4.67 (d, J = 8 Hz, 1H), 7.03-7.05 (m, 2H), 7.14 (m, 1H), 7.29 (m, 1H) |
| 212 | (3-fluorophenyl)methyl | ¹H NMR (CDCl₃) δ1.46 (s, 1H), 1.51-1.59 (m, 4H), 1.62-1.77 (m, 5H), 1.76-1.78 (m, 3H), 1.90-1.92 (m, 2H), 2.04-2.16 (m, 5H), 2.48-2.55 (m, 2H), 2.63-2.69 (m, 1H), 3.98 (m, 1H), 4.23 (m, 2H), 4.67 (d, J = 8 Hz, 1H), 6.84-6.99 (m, 3H), 7.20-7.23 (m, 1H) |

TABLE 22

| Ex. No. | —Z¹—R² | NMR (solvent) δ |
|---|---|---|
| 213 | (2-fluorophenyl)methyl | ¹H-NMR (CDCl₃) δ1.51 (s, 1H), 1.63-1.78 (m, 11H), 1.90 (m, 2H), 2.03-2.17 (m, 6H), 2.46-2.54 (m, 2H), 2.87 (m, 1H), 3.99 (m, 1H), 4.25 (m, 2H), 4.70 (d, J = 8 Hz, 1H), 6.95-6.99 (m, 1H), 7.05 (m, 1H), 7.13-7.21 |
| 214 | (4-fluorophenyl)methyl | ¹H-NMR (CDCl₃) δ1.47 (s, 1H), 1.50-1.54 (m, 3H), 1.62-1.71 (m, 5H), 1.75-1.78 (m, 4H), 1.90-1.93 (m, 2H), 2.03-2.09 (m, 2H), 2.13-2.16 (m, 3H), 3.98 (m, 1H), 4.23 (m, 2H), 4.67 (d, J = 4 Hz, 1H), 6.93-6.98 (m, 2H), 7.12-7.16 (m, 2H) |
| 215 | (3-ethoxyphenyl)methyl | ¹H-NMR (CDCl₃) δ1.40 (t, J = 8 Hz, 3H), 1.51-1.58 (m, 4H), 1.63-1.78 (m, 9H), 1.90-1.93 (m, 2H), 2.03-2.07 (m, 2H), 2.13-2.16 (m, 3H), 2.47-2.54 (m, 2H), 2.62 (m, 1H), 3.98 (m, 1H), 4.00 (q, J = 8 Hz, 2H), 4.22 (m, 2H), 4.67 (d, J = 8 Hz, 2H), 6.69-6.79 (m, 3H), 7.18 (t, J = 8 Hz, 1H) |
| 216 | (3-isopropoxyphenyl)methyl | ¹H-NMR (CDCl₃) δ1.32 (d, J = 8 Hz, 6H), 1.51-1.58 (m, 5H), 1.63-1.78 (m, 8H), 1.90-1.92 (m, 2H), 2.03-2.07 (m, 2H), 2.13-2.16 (m, 3H), 2.47-2.54 (m, 2H), 2.61 (m, 1H), 3.98 (m, 1H), 4.22 (m, 2H), 4.52 (m, 1H), 4.67 (d, J = 8 Hz, 1H), 6.69-6.77 (m, 3H), 7.17 (t, J = 8 Hz, 1H) |
| 217 | (pyridin-2-yl)methyl | ¹H-NMR (CDCl₃) δ1.47-1.51(m, 3H), 1.57-1.78 (m, 10H), 1.89-1.92 (m, 3H), 2.13-2.18 (m, 5H), 2.39-2.46 (m, 2H), 2.97 (m, 1H), 3.98 (m, 1H), 4.20 (m, 2H), 4.66 (d, J = 8 Hz, 1H), 7.10 (m, 1H), 7.25 (m, 1H), 7.58 (m, 1H), 8.53 (m, 1H) |
| 218 | (3-methanesulfonylphenyl)methyl | ¹H-NMR (CDCl₃) δ1.52-1.58 (m, 4H), 1.63-1.70 (m, 5H), 1.76-1.78 (m, 4H), 1.90-1.92 (m, 2H), 2.07-2.17 (m, 5H), 2.51-2.58 (m, 2H), 2.75 (m, 1H), 3.04 (s, 3H), 3.98 (m, 1H), 4.26 (m, 2H), 4.69 (d, J = 8 Hz, 1H), 7.47-7.50 (m, 2H), 7.74-7.78 (m, 2H) |

TABLE 22-continued

| | | |
|---|---|---|
| 219 | 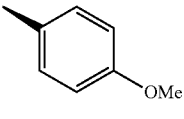 | ¹H-NMR (CDCl₃) δ1.48-1.54 (m, 4H), 1.63-1.78 (m, 9H), 1.90-1.93 (m, 2H), 2.03-2.07 (m, 2H), 2.13-2.16 (m, 3H), 2.45-2.52 (m, 2H), 2.56-2.63 (m, 1H), 3.77 (s, 3H), 3.98 (m, 1H), 4.22 (m, 2H), 4.68 (d, J = 8 Hz, 1H), 6.80-6.83 (m, 2H), 7.08-7.13 (m, 2H) |
| 220 | 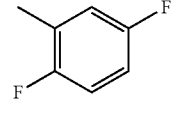 | ¹H-NMR (CDCl₃) δ1.43-1.56 (m, 3H), 1.67-1.79 (m, 9H), 1.83-1.94 (m, 3H), 2.09-2.16 (, m 5H), 2.46-2.56 (m, 2H), 2.87 (m, 1H), 3.99 (m, 1H), 4.26 (m, 1H), 4.71 (d, J = 8 Hz, 1H), 6.79-6.99 (m, 3H) |

TABLE 23

| | | |
|---|---|---|
| 221 | 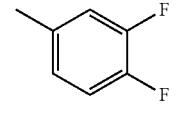 | ¹H-NMR (CDCl₃) δ1.42 (s, 1H), 1.45-1.80 (m, 11H), 1.90-1.94 (m, 2H), 2.04-2.17 (m, 6H), 2.47-2.58 (m, 2H), 2.63 (m, 1H), 3.97 (m, 1H), 4.24 (m, 2H), 4.67 (d, J = 8 Hz, 1H), 6.89-6.93 (m, 1H), 6.96-7.10 (m, 2H) |
| 222 | 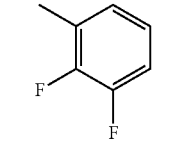 | ¹H-NMR (CDCl₃) δ1.48-1.79 (m, 12H), 1.88-2.00 (m, 3H), 2.10-2.18 (m, 5H), 2.48-2.56 (m, 2H), 2.90 (m, 1H), 4.01 (m, 1H), 4.27 (m, 2H), 4.71 (d, J = 8 Hz, 1H), 6.92-7.02 (m, 3H) |
| 223 | 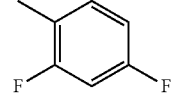 | ¹H-NMR (CDCl₃) δ1.46-1.55 (m, 4H), 1.69-1.79 (m, 8H), 1.90-1.94 (m, 3H), 2.09-2.17 (m, 5H), 2.44-2.54 (m, 2H), 2.84 (m, 1H), 3.99 (m, 1H), 4.25 (m, 2H), 4.70 (d, J = 8 Hz, 1H), 6.70-6.83 (m, 2H), 7.09-7.16 |
| 224 | 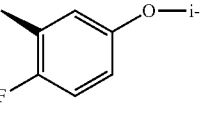 | ¹H-NMR (CDCl₃) δ1.30 (d, J = 4 Hz, 6H), 1.46-1.57 (m, 5H), 1.66-1.77 (m, 9H), 1.89-1.92 (m, 2H), 2.07-2.16 (m, 4H), 2.45-2.52 (m, 2H), 2.79-2.84 (m, 1H), 3.98 (m, 1H), 4.24 (m, 2H), 4.42 (m, 1H), 4.69 (d, J = 8 Hz, 1H), 6.62-6.69 (m, 2H), 6.86 (dd, J = 8, 12 Hz, 1H) |
| 225 | 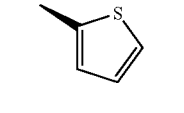 | ¹H-NMR (CDCl₃) δ1.50-1.54 (m, 3H), 1.64-1.77 (m, 7H), 1.88-1.95 (m, 6H), 2.14 (m, 4H), 2.49-2.56 (m, 2H), 3.17 (m, 1H), 3.96 (m, 1H), 4.19 (m, 2H), 4.63 (d, J = 4 Hz, 1H), 6.86-6.88 (m, 1H), 6.90-6.94 (m, 1H), 7.13-7.15 (m, 1H) |
| 226 | 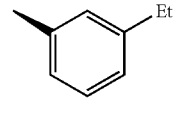 | ¹H-NMR (CDCl₃) δ1.21 (t, J = 8 Hz, 3H), 1.52-1.58 (m, 5), 1.65-1, 78 (m, 7H), 1.90-1.98 (m, 3H), 2.06-2.17 (m, 5H), 2.48-2.55 (m, 1H), 2.58-2.67 (m, 4H), 3.99 (m, 1H), 4.25 (m, 2H), 4.68 (d, J = 8.0 Hz, 1H), 6.98-7.04 (m, 3H), 7.18-7.22 (m, 1H) |
| 227 | 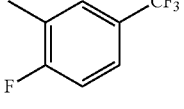 | ¹H-NMR (CDCl₃) δ1.47-1.56 (m, 4H),1.65-1.80 (m, 9H), 1.87-1.95 (m, 2H), 2.13-2.18 (m, 5H), 4.00 (, m 1H), 4.28 (m, 2H), 4.71 (d, J = 8 Hz, 1H), 7.06-7.14 (m, 1H), 7.44-7.46 (m, 2H) |
| 228 | 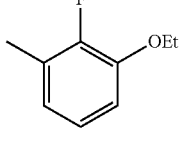 | ¹H-NMR (CDCl₃) δ1.45 (t, J = 8 Hz, 3H),1.53-1.61 (m, 5H), 1.68 -1.79 (m, 7H), 1.88-1.94 (m, 3H), 2.05-2.18 (m, 5H), 2.46-2.55 (m, 2H), 2.87 (m, 1H), 4.00 (m, 1H), 4.08 (t, J = 8 Hz, 2H), 4.25 (m, 1H), 4.70 (d, J = 8 Hz, 1H), 6.72-6.83 (m, 2H), 6.94-7.00 (m, 1H) |
| 229 | 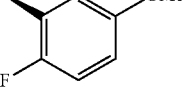 | ¹H-NMR (CDCl₃) δ1.49-1.55 (m, 6H), 1.57 (s, 1H), 1.70-1.80(m, 7H), 1.90-1.96 (m, 2H), 2.08-2.19 (m, 4H), 2.45-2.55 (m, 2H), 2.84 (m, 1H), 3.77 (s, 3H), 3.99 (m, 1H), 4.25 (m, 2H), 4.70 (d, J = 8 Hz, 1H), 6.63-6.72 (m, 2H), 6.89 (m, 1H) |
| 230 | 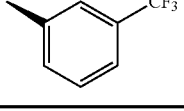 | ¹H-NMR (CDCl₃) δ1.47 (s, 1H),1.52-1.71 (m, 8H), 1.76-1.79 (m, 4H), 1.90-1.93 (m, 2H), 2.07-2.17 (m, 5H), 2.51-2.58 (m, 2H), 2.71 (m, 1H), 3.98 (m, 1H), 4.26 (m, 2H), 4.68 (d, J = 8 Hz, 1H), 7.38-7.39 (m, 2H), 7.44 (m, 2H) |

TABLE 24

| | | |
|---|---|---|
| 231 | 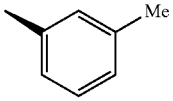 | ¹H-NMR (CDCl₃) δ1.47 (s, 1H), 1.52-1.71 (m, 8H), 1.76-1.79 (m, 4H), 1.90-1.93 (m, 2H), 2.07-2.17 (m, 5H), 2.51-2.58 (m, 2H), 2.71 (m, 1H), 3.98 (m, 1H), 4.26 (m, 2H), 4.68 (d, J = 8 Hz, 1H), 7.38-7.39 (m, 2H), 7.44 (m, 2H) |
| 232 | 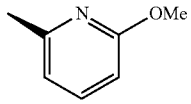 | ¹H-NMR (CDCl₃) δ1.44 (s, 3H), 1.51-1.54 (m, 2H), 1.61-1.66 (m, 4H), 1.70-1.77 (m, 4H), 1.85-1.92 (m, 4H), 2.16 (m, 3H), 2.24-2.29 (m, 2H), 2.35-2.42 (m, 2H), 2.97 (m, 1H), 3.92 (s, 3H), 3.99 (m, 1H), 4.17 (m, 2H), 4.65 (d, J = 8 Hz, 1H), 6.54 (d, J = 8 Hz, 1H), 6.85 (d, J = 8 Hz, 1H), 7.48 (d, J = 8 Hz, 1H) |
| 233 | 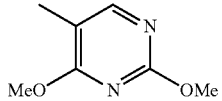 | ¹H-NMR (CDCl₃) δ1.47-1.53 (m, 3H), 1.64-1.75 (m, 10H), 1.81-1.98 (m, 2H), 2.06-2.14 (m, 5H), 2.39-2.46 (m, 2H), 2.70 (m, 1H), 3.94 (s, 6H), 3.95 (m, 1H), 4.22 (m, 2H), 4.67 (d, J = 8 Hz, 1H), 7.99 (s, 1H) |
| 234 | 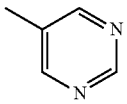 | ¹H-NMR (CDCl₃) δ1.46 (s, 1H), 1.52-1.66 (m, 6H), 1.76-2.00 (m, 8H), 2.09-2.15 (m, 5H), 2.53-2.61 (m, 2H), 2.73 (m, 1H), 3.98 (m, 1H), 4.28 (m, 2H), 4.68 (d, J = 8 Hz, 1H), 8.57-8.61 (m, 2H), 9.07 (m, 1H) |
| 235 | 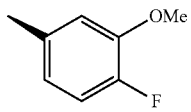 | ¹H-NMR (CDCl₃) δ1.46-1.54 (m, 3H), 1.63-1.77 (m, 10H), 1.80-1.92 (m, 5H), 2.06-2.15 (m, 5H), 2.51 (m, 1H), 3.86 (s, 3H), 3.98 (m, 1H), 4.25 (m, 1H), 4.64 (d, J = 8 Hz, 1H), 6.67-6.78 (m, 2H), 6.94-6.69 (m, 1H) |
| 236 | 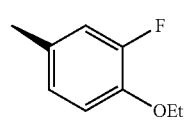 | ¹H-NMR (CDCl₃) δ1.41 (t, J 8 Hz, 3H), 1.49-1.53 (m, 3H), 1.61-1.92 (m, 12H), 2.02-2.15 (m, 5H), 2.44-2.52 (m, 2H), 2.59 (m, 1H), 3.99 (m, 1H), 4.06 (q, J = 8 Hz, 2H), 4.23 (m, 2H), 4.67 (d, J = 8 Hz, 1H), 6.82-6.94 (m, 3H) |
| 237 | 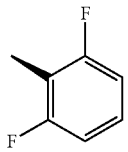 | ¹H-NMR (CDCl₃) δ1.48-1.55 (m, 5H), 1.61-1.70 (m, 5H), 1.76-1.78 (m, 3H), 1.89-1.92 (m, 2H), 2.03-2.09 (m, 2H), 2.15 (m, 3H), 2.48-2.55 (m, 2H), 2.61-2.70 (m, 1H), 3.97 (m, 1H), 4.23 (m, 2H), 4.67 (d, J = 4 Hz, 1H), 6.59-6.65 (m, 1H), 6.70-6.75 (m, 2H) |
| 238 | 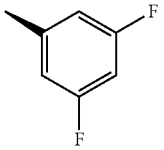 | ¹H-NMR (CDCl₃) δ1.48-1.55 (m, 5H), 1.61-1.70 (m, 5H), 1.76-1.78 (m, 3H), 1.89-1.92 (m, 2H), 2.03-2.09 (m, 2H), 2.15 (m, 3H), 2.48-2.55 (m, 2H), 2.61-2.70 (m, 1H), 3.97 (m, 1H), 4.23 (m, 2H), 4.67 (d, J = 4 Hz, 1H), 6.59-6.65 (m, 1H), 6.70-6.75 (m, 2H) |

TABLE 25

| | | |
|---|---|---|
| 239 | 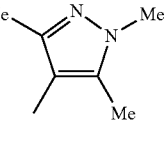 | ¹H-NMR (CDCl₃) δ1.45-1.56 (m, 5H), 1.67-1.82 (m, 8H), 1.89-1.92 (m, 2H), 2.01-2.17 (m, 13H), 2.31 (m, 1H), 3.65 (s, 3H), 3.98 (m, 1H), 4.19 (m, 2H), 4.67 (m, 1H) |
| 240 | 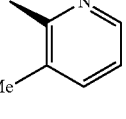 | ¹H-NMR (CDCl₃) δ1.50-1.59 (m, 3H), 1.69-1.93 (m, 14H), 2.03 (m, 1H), 2.13-2.16 (m, 2H), 2.25 (s, 3H), 2.27-2.44 (m, 2H), 3.00 (m, 1H), 4.00 (m, 1H), 4.23 (m, 2H), 4.70 (d, J = 4 Hz, 1H), 7.00 (dd, J 4 Hz, 8 Hz, 1H), 7.36 (d, J = 8 Hz, 1H), 8.38 (d, J = 8 Hz, 1H) |
| 241 | 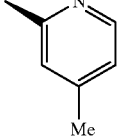 | ¹H-NMR (CDCl₃) δ1.50-1.53 (m, 2H), 1.58-1.71 (m, 8H), 1.90-1.91 (m, 5H), 2.08-2.15 (m, 5H), 2.30 (s, 3H), 2.33-2.44 (m, 2H), 2.90 (m, 1H), 3.97 (m,1H), 4.19 (m, 2H), 4.67 (d, J = 4 Hz, 1H), 6.90 (d, J = 4 Hz, 1H), 7.05 (m, 1H), 8.37 (d, J = 4 Hz, 1H) |

TABLE 25-continued

| # | Structure | NMR |
|---|---|---|
| 242 | 6-methyl-3-pyridyl (2-Me, 5-position attachment) | ¹H-NMR (CDCl₃) δ1.50-1.53 (m, 2H),1.58-1.63 (m, 2H), 1.68-1.75 (m, 6H), 1.89-1.92 (m, 5H), 2.10-2.15 (m, 5H), 2.28 (s, 3H), 2.36-2.43 (m, 2H), 2.91 (m,1H), 3.97 (m, 1H), 4.18 (m, 2H), 4.66 (d, J = 8 Hz, 1H), 7.14 (d, J = 8 Hz, 1H), 7.38 (d, J = 4 Hz, 1H), 8.34 (m, 1H) |
| 243 | 2,6-dimethyl-3-pyridyl | ¹H-NMR (CDCl₃) δ1.49-1.52 (m, 2H), 1.57-1.62 (m, 2H), 1.67-1.76 (m, 6H), 1.81-1.92 (m, 5H), 2.14 (m, 3H), 2.18-2.24 (m, 2H), 2.34-2.41 (m, 2H), 2.49 (s, 3H), 2.97 (m, 1H), 3.96 (m, 1H), 4.17 (m, 2H), 4.66 (d, J = 8 Hz, 1H), 6.92 (d, J = 8 Hz, 1H), 7.05 (d, J = 8 Hz, 1H), 7.45 (dd, J = 8 Hz, 1H) |
| 244 | 2-methyl-3-n-propoxy-5-fluorophenyl | ¹H-NMR (CDCl₃) δ0.96 (t, J = 7.2 Hz, 3H), 1.25-1.29 (m, 2H), 1.35 (t, J = 12.4 Hz, 2H), 1.58-1.70 (m, 10H), 1.86-2.00 (m, 7H), 2.21-2.29 (m, 2H), 2.87 (m, 1H), 3.67 (m, 1H), 3.84 (t, J = 6.4 Hz, 2H), 4.31 (m, 2H), 4.37 (s, 1H), 5.77 (d, J = 6.4 Hz, 1H), 6.85-6.93 (m, 2H), 7.01 (dd, J = 2.8, 10.4 Hz, 1H) |
| 245 | 2-methyl-3-trifluoromethylpyridyl | ¹H NMR (CDCl₃) δ1.47-1.55 (m, 3H), 1.65-1.86 (m,14H), 1.92-1.95 (m, 1H), 2.08-2.14 (m, 2H), 2.42-2.50 (m, 2H), 3.10-3.19 (m, 1H), 4.03 (m, 1H), 4.27 (m, 2H), 4.69 (d, J = 7.2 Hz, 1H), 7.22 (m, 1H), 7.87 (dd, J = 1.2, 8.0 Hz, 1H), 8.74 (dd, J = 0.8, 4.4 Hz, 1H) |
| 246 | 2-methyl-4-trifluoromethylpyridyl | ¹H NMR (CDCl₃) δ1.29 (d, J = 12.0 Hz, 2H), 1.39 (m, 1H), 1.59-1.68 (m, 8H), 1.87-1.98 (m, 6H), 2.07-2.13 (m, 2H), 2.25-2.32 (m, 2H), 3.05 (m, 1H), 3.66 (m, 1H), 4.29 (m, 2H), 4.38 (s, 1H), 5.86 (d, J = 6.4 Hz, 1H), 7.57 (d, J = 4.8 Hz, 1H), 7.75 (s, 1H), 8.77 (d, J = 5.2 Hz, 1H) |
| 247 | 2-methyl-4-fluoropyridyl | ¹H NMR (CDCl₃) δ1.52-1.56 (m, 2H), 1.58-1.63(m, 1H), 1.70-1.79 (m, 8H), 1.91-1.94 (m, 3H), 2.14-2.18 (m, 6H), 2.41-2.48 (m, 2H), 2.98 (m,1H), 3.99 (m,1H), 4.21 (m, 2H), 4.68 (d, J = 7.2 Hz, 1H), 6.87 (m, 1H), 7.01 (dd, J = 2.4, 10.4 Hz, 1H), 8.50 (dd, J = 5.6, 8.8 Hz, 1H) |

TABLE 26

| # | Structure | NMR |
|---|---|---|
| 248 | 2-methyl-4-ethylpyridyl | ¹H NMR (CDCl₃) δ1.16 (t, J = 7.6 Hz, 3H), 1.27-1.31 (m, 2H), 1.43-1.45 (m, 1H), 1.59-1.68 (m, 8H), 1.87-2.07 (m, 7H), 2.23 (m, 2H), 2.55-2.61 (m, 2H), 2.83 (m, 1H), 3.66 (m, 1H), 4.09 (m, 1H), 4.26 (m, 2H), 4.37 (s, 1H), 5.82 (d, J = 6.0 Hz, 1H), 7.03 (d, J = 4.8 Hz, 1H), 7.21 (s, 1H), 8.35 (d, J = 5.2 Hz, 1H) |
| 249 | (S)-2-methylphenyl | ¹H NMR (CDCl₃) δ1.50-1.59 (m, 3H), 1.69-1.96 (m, 14H), 2.01-2.04 (m, 1H), 2.13-2.16 (m, 2H), 2.25 (s, 3H), 2.37-2.44 (m, 2H), 3.00 (m, 1H), 4.00 (m, 1H), 4.23 (m, 2H), 4.70 (d, J = 4 Hz, 1H), 7.00 (dd, J = 4 Hz, 8 Hz, 1H), 7.34 (d, J = 8 Hz, 1H), 8.37 (d, J = 4H, 1H) |
| 250 | (S)-2,4-dimethylpyridyl | ¹H NMR (CDCl₃) δ1.46-1.50 (m, 2H), 1.65-1.99 (m, 14H), 2.03-2.12 (m, 6H), 2.28 (s, 3H), 3.24 (m, 1H), 3.95 (m, 1H), 4.25 (m, 2H), 4.65 (d, J = 8 Hz, 1H), 6.91 (d, J = 4 Hz, 1H), 6.94 (s, 1H), 8.30 (d, J = 4 Hz, 1H) |
| 251 | (S)-2,5-dimethylpyridyl | ¹H NMR (CDCl₃) δ1.43-1.51 (m, 3H), 1.66-1.99 (m, 15H), 2.04-2.13 (m, 4H), 2.27 (s, 3H), 3.27 (m, 1H), 3.96 (m, 1H), 4.26 (m, 1H), 4.63 (d, J = 4 Hz, 1H), 7.02 (d, J = 8 Hz, 1H), 7.40 (dd, J = 4 Hz, 8 Hz, 1H), 8.30 (m, 1H) |
| 252 | (S)-2,6-dimethylpyridyl | ¹H NMR (CDCl₃) δ1.48-1.52 (m, 2H), 1.65-2.15 (m, 20H), 2.49 (s, 3H), 3.26 (m, 1H), 3.98 (m, 1H), 4.25 (m, 1H), (d, J = 8 Hz, 1H), 6.92 (d, J = 8 Hz, 1H), 6.95 (d, J = 8 Hz, 1H), 7.48 (dd, J = 8 Hz, 8 Hz, 1H) |
| 253 | 2-methyl-4-methoxy-5-trifluoromethoxyphenyl | ¹H NMR (CDCl₃) δ1.29-1.35 (m, 4H), 1.60-1.70 (m, 8H), 1.89 (m, 4H), 1.97-2.02 (m, 3H), 2.23-2.30 (m, 2H), 2.90 (m, 1H), 3.68 (m, 1H), 3.74 (s, 3H), 4.32 (m, 2H), 4.39 (m, 1H), 5.86 (d, J = 6.0 Hz, 1H), 6.99 (d, J = 8.8 Hz, 1H), 7.16 (m, 2H) |

Using the intermediate synthesized in a similar manner to Reference Example 10, the compound was synthesized in a similar manner to Example 1.

Example 254

(3-Endo)-N-[(E)-5-carbamoyladamantan-2-yl]-3-(3-fluorophenyl)-8-azabicyclo[3.2.1]octane-8-carboxyamide

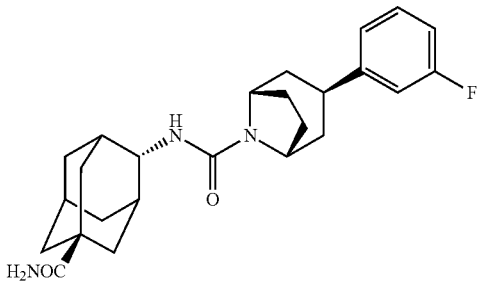 [SMILES: NC(=O)[C@]12CC3CC(C1)[C@@H](NC(=O)N1[C@@H]4CC[C@H]1C[C@@H](c1cccc(F)c1)C4)C(C3)C2]

$^1$H-NMR (CDCl$_3$) δ1.52-1.66 (m, 5H), 1.77-1.84 (m, 2H), 1.90 (m, 2H), 2.00-2.13 (m, 10H), 2.49-2.56 (m, 2H), 2.68 (m, 1H), 3.99 (m, 1H), 4.24 (m, 2H), 4.74 (d, J=8 Hz, 1H), 5.26 (s, 1H), 5.60 (s, 1H), 6.85-6.93 (m, 2H), 6.97-6.99 (m, 1H), 7.20-7.24 (m, 1H)

The compounds of Examples 255 to 287 were synthesized in a similar manner to Example 1, and further purified by HPLC.

| Ex. No. | —Z$^1$—R$^2$ | tR (min) Obs [M + 1] Measurement method |
|---|---|---|
| 255 | | 4.77 429.4 SA1 |
| 256 | | 1.459 461.5 SA3 |
| 257 | | 4.82 429.4 SA1 |
| 258 | | 4.61 443.4 SA1 |
| 259 | | 4.87 447.4 SA1 |
| 260 | | 5.03 461 SA2 |
| 261 | | 4.68 447.4 SA1 |
| 262 | | 0.550 412.4 SA3 |
| 263 | | 4.86 429 SA2 |
| 264 | | 4.28 387 SA2 |
| 265 | | 4.72 413 SA2 |
| 266 | | 4.88 447 SA2 |

TABLE 28

| 267 | | 1.92 395 SA4 |
| 268 | | 1.94 425 SA4 |
| 269 | | 1.95 467 SA4 |
| 270 | | 1.85 429 SA4 |

TABLE 28-continued

| | | | |
|---|---|---|---|
| 271 | 4-methyl-2-fluoro-1-ethoxybenzene | 1.66 443 SA4 | |
| 272 | 3-methyl-1-(isobutoxy)benzene | 1.82 453 SA4 | |
| 273 | 4-methyl-1-(isobutoxy)benzene | 1.82 453 SA4 | |
| 274 | 2-(trifluoromethyl)toluene | 1.54 449 SA4 | |
| 275 | 4-methyl-1-(trifluoromethoxy)benzene | 1.10 465 SA4 | |
| 276 | 4-fluoro-2-methyl-1-methyl benzene | 1.54 413 SA4 | |
| 277 | 4-methyl-3-methyl-1-methoxybenzene | 1.49 425 SA4 | |
| 278 | 1,4-dimethylbenzene | 1.96 395 SA4 | |
| 279 | 2,4-dimethyl-1-fluorobenzene | 1.92 413 SA4 | |
| 280 | 4-fluoro-3-methyl-1-methylbenzene | 1.90 413 SA4 | |
| 281 | 2-fluoro-4-methyl-1-methylbenzene | 1.68 413 SA4 | |
| 282 | 4-methyl-1-(isopropoxy)benzene | 1.71 439 SA4 | |
| 283 | 2-methyl-1-(isobutoxy)benzene | 1.80 453 SA4 | |
| 284 | 2-ethylpyridine | 0.48 396 SA3 | |
| 285 | 4-methyl-1-(trifluoromethyl)benzene | 1.97 449 SA4 | |
| 286 | 2-methylbenzonitrile | 1.38 406 SA4 | |
| 287 | 2-methyl-4-methyl-1-methoxybenzene | 1.57 425 SA4 | |

The compounds of Examples 288 to 313 were synthesized in a similar manner to Example 1.

TABLE 29

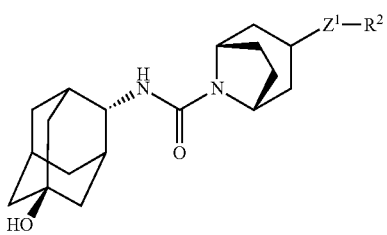

| Ex. No. | —Z¹—R² | NMR (solvent) δ |
|---|---|---|
| 288 | 2-methyl-6-methoxypyridine | $^1$H-NMR (CDCl$_3$) δ1.45 (s, 1H),1.49-1.53 (m, 2H), 1.62-1.76 (m, 7H), 1.89-2.06 (m, 6H), 2.13-2.24 (m, 6H), 2.39 (s, 3H), 3.96 (m, 1H), 4.12 (m, 2H), 4.59 (d, J = 8 Hz, 1H), 5.37 (m, 1H), 6.46 (d, J = 8 Hz, 1H), 6.67 (d, J = 8 Hz, 1H), 7.43 (dd, J = 8 Hz, 8 Hz, 1H) |

TABLE 29-continued

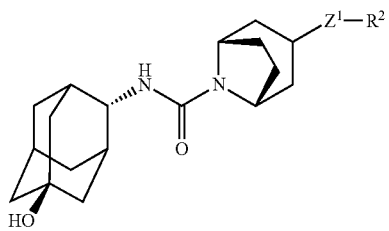

| Ex. No. | —Z¹—R² | NMR (solvent) δ |
|---|---|---|
| 289 | 2-methoxy-4-methylpyridin-5-yl via O | ¹H-NMR (CDCl₃) δ1.47 (s, 1H), 1.48-1.52 (m, 2H), 1.64-1.75 (m, 6H), 1.88-2.04 (m, 6H), 2.12-2.25 (m, 7H), 2.28 (s, 3H), 3.96 (m, 1H), 4.12 (m, 2H), 4.60 (d, J = 4 Hz, 1H), 5.32 (m, 1H), 6.51 (s, 1H), 6.67 (d, J = 4 Hz, 1H), 7.98 (d, J = 4 Hz, 1H) |
| 290 | 2-methoxy-5-methylpyridin-yl via O | ¹H-NMR (CDCl₃) δ1.48 (s, 1H),1.52-1.54 (m, 2H), 1.66-1.75 (m, 7H), 1.88-2.02 (m, 5H), 2.12-2.20 (m, 7H), 2.22 (s, 3H), 3.96 (m, 1H), 4.13 (m, 2H), 4.60 (d, J = 4 Hz, 1H), 5.28 (m, 1H), 6.59 (d, J = 8 Hz, 1H), 7.38 (dd, J = 4 Hz, 8 Hz, 1H), 7.92 (m, 1H) |
| 291 | 2-methoxy-5-trifluoromethylpyridinyl via O | ¹H-NMR (CDCl₃) δ1.46 (s, 1H), 1.50-1.53 (m, 2H), 1.58-1.76 (m, 9H), 1.89-2.29 (m, 10H), 3.96 (m, 1H), 4.16 (m, 2H), 4.60 (d, J = 4 Hz, 1H), 5.42 (m, 1H), 6.77 (d, J = 8 Hz, 1H), 7.76 (dd, J = 4 Hz, 8 Hz, 1H), 8.40 (m, 1H) |
| 292 | 2-methoxy-5-chloropyridinyl via O | ¹H-NMR (CDCl₃) δ1.50-1.53 (m, 2H), 1.66-1.76 (m, 7H), 1.88-1.97 (m, 4H), 2.03-2.16 (m, 7H), 2.25-2.29 (m, 2H), 3.94 (m, 1H), 4.15 (m, 2H), 4.62 (m, 1H), 4.80 (m, 1H), 7.10 (dd, J = 4 Hz, 8 Hz, 1H), 7.22-7.27 (m, 1H), 7.97 (d, J = 4 Hz, 1H) |
| 293 | 3-chloro-5-pyridinyl via O | ¹H-NMR (CDCl₃) δ1.50-1.53 (m, 2H), 1.65-1.76 (m, 6H), 1.88-1.96 (m, 4H), 2.03-2.13 (m, 8H), 2.24-2.30 (m, 2H), 3.95 (m, 1H), 4.16 (m, 2H), 4.65 (m, 2H), 7.18 (m, 1H), 8.16 (m, 1H) |
| 294 | 6-chloropyridin-3-yl via O | ¹H-NMR (CDCl₃) δ1.39 (s, 1H), 1.49-1.53 (m, 2H), 1.66-1.69 (m, 2H), 1.74 (m, 4H),1.89-1.93 (m, 4H), 1.99-2.04 (m, 2H), 2.13-2.25 (m, 7H), 3.16 (m, 1H), 4.14 (m, 1H), 4.51 (d, J = 4 HZ, 1H), 5.29 (m, 1H), 6.65 (d, J = 8 Hz, 1H), 7.52 (dd, J = 8 Hz, 1 Hz, 1H), 8.06 (dd J = 4, 1H) |
| 295 | pyrazinyl via O | ¹H-NMR (CDCl₃) δ1.51-1.77 (m, 10H), 1.89-1.96 (m, 4H), 2.05 -2.31 (m, 8H), 3.97 (m, 1H), 4.17 (m, 2H), 4.62 (m, 2H), 5.36 (m, 1H), 8.06 (m, 1H), 8.;10 (m, 1H), 8.18 (m, 1H) |

TABLE 30

| 296 | pyrimidin-2-yloxy | ¹H-NMR (CDCl₃) δ1.51-1.77 (m, 9H), 1.89-2.06 (m, 6H), 2.14 (m, 3H), 2.25-2.32 (m, 4H), 3.97 (m, 1H), 4.17 (m, 2H), 4.62 (d, J = 8 Hz, 1H), 5.33 (m, 1H), 6.92 (t, J = 8 Hz, 1H), 8.51 (d, J = 4H, 2H) |
| 297 | 6-methylpyridazin-3-yloxy | ¹H-NMR (CDCl₃) δ1.50-1.54 (m, 2H), 1.66-1.93 (m, 8H), 2.00-2.18 (m, 10H), 2.24-2.32 (m, 2H), 2.60 (s, 3H), 3.96 (m, 1H), 4.17 (m, 2H), 4.62 (d, J = 8 Hz, 1H), 5.58 (m, 1H), 6.84 (d, J = 12 Hz, 1H), 7.23 (d, J = 12 Hz, 1H) |
| 298 | benzothiazol-2-yloxy | ¹H-NMR (CDCl₃) δ1.50-1.59 (m, 4H), 1.66-1.76 (m, 6H), 1.89-1.91 (m, 2H), 2.02-2.18 (m, 8H), 2.29-2.35 (m, 2H), 3.96 (m, 1H), 4.17 (m, 2H), 4.61 (d, J = 8 Hz, 1H), 5.45 (m, 1H), 7.20-7.25 (m, 1H), 7.33-7.38 (m, 1H), 7.63-7.66 (m, 2H) |

TABLE 30-continued

| | | |
|---|---|---|
| 299 | [structure] | ¹H-NMR (CDCl₃) δ1.50-1.76 (m, 11H), 1.88-2.06 (m, 5H), 2.13-2.18 (m, 4H), 2.23-2.29 (m, 2H), 3.96 (m, 1H), 4.15 (m, 2H), 4.60 (d, J = 8 Hz, 1H), 5.41 (m, 1H), 6.86 (d, J = 8 Hz, 1H), 7.23 (d, J = 8 Hz, 1H), 7.70 (dd, J = 8 Hz, 8 Hz, 1H) |
| 300 | [structure] | ¹H NMR (CDCl₃) δ1.34 (s, 1H), 1.47-1.52 (m, 2H), 1.64-1.75 (m, 6H), 1.88-1.92 (m, 4H), 2.01-2.12 (m, 7H), 2.23-2.29 (m, 2H), 3.95 (brs, 1H), 4.14 (brs, 2H), 4.59 (d, J = 8.8 Hz, 1H), 5.42 (t, J = 4.8 Hz, 1H), 6.76 (d, J = 8.8 Hz, 1H), 7.77 (dd, J = 2.4 Hz, 8.8 Hz, 1H), 8.43 (d, J = 2.4 Hz, 1H) |
| 301 | [structure] | ¹H NMR (CDCl₃) δ1.37 (s, 1H), 1.48-1.55 (m, 2H), 1.64-1.74 (m, 6H), 1.87-2.02 (m, 6H), 2.12-2.21 (m, 7H), 2.47 (s, 3H), 3.95 (brs, 1H), 4.13 (brs, 2H), 4.58-4.59 (m, 2H), 6.99-7.06 (m, 2H), 8.09 (d, J = 2.8 Hz, 1H) |
| 302 | [structure] | ¹H-NMR (CDCl₃) δ1.50-1.53 (m, 2H), 1.66-1.80 (m, 8H), 1.89-1.97 (m, 4H), 2.03-2.08 (m, 2H), 2.13-2.28 (m, 6H), 2.51 (s, 3H), 3.96 (m, 1H), 4.16 (m, 2H), 4.58-4.63 (m, 2H), 6.90 (d, J = 4 Hz, 1H), 7.05 (dd, J = 4 Hz, 8 Hz, 1H), 8.05 (d, J = 4 Hz, 1H) |
| 303 | [structure] | ¹H NMR (CDCl₃) δ1.36 (s, 1H), 1.48-1.58 (m, 2H), 1.66-1.74 (m, 6H), 1.87-2.02 (m, 6H), 2.13-2.24 (m, 7H), 3.82 (s, 3H), 3.94-3.96 (m, 1H), 4.12 (brs, 2H), 4.59 (d, J = 7.6 Hz, 1H), 5.31 (t, J = 8.8 Hz, 1H), 6.24 (dd, J = 4.4 Hz, 8.0 Hz, 2H), 7.46 (t, J = 8.0 Hz, 1H) |
| 304 | [structure] | ¹H NMR (CDCl₃) δ1.36 (s, 1H), 1.48-1.54 (m, 2H), 1.65-1.74 (m, 6H), 1.87-2.02 (m, 6H), 2.12-2.24 (m, 7H), 3.80 (s, 3H), 3.94-3.96 (m, 1H), 4.13 (brs, 2H), 4.58 (d, J = 7.2 Hz, 1H), 5.32 (t, J = 5.2 Hz, 1H), 6.12 (d, J = 2.0 Hz, 1H), 6.43 (dd, J = 2.0 Hz, 5.6 Hz, 1H), 7.91 (d, J = 5.6 Hz, 1H) |

TABLE 31

| | | |
|---|---|---|
| 305 | [structure] | ¹H NMR (CDCl₃) δ1.35 (s, 1H), 1.49-1.53 (m, 2H), 1.64-1.67 (m, 2H), 1.75 (brs, 4H), 1.87-1.93 (m, 4H), 2.01-2.12 (m, 7H), 2.23-2.28 (m, 2H), 3.93 (brs, 1H), 4.14 (brs, 2H), 4.59 (d, J = 7.6 Hz, 1H), 4.66 (t, J = 4.8 Hz, 1H), 6.65 (dd, J = 2.4 Hz, 6.0 Hz, 1H), 6.74 (d, J = 2.4 Hz, 1H), 8.18 (d, J = 6.0 Hz, 1H) |
| 306 | [structure] | ¹H-NMR (CDCl₃) δ1.51 (s, 1H), 1.55 (m, 2H), 1.66-1.77 (m, 7H), 1.90-1.94 (m, 4H), 2.02-2.31 (m, 8H), 2.36 (s, 3H), 2.44 (s, 3H), 3.98 (m, 1H), 4.18 (m, 2H), 4.62 (d, J = 8 Hz), 5.42 (m, 1H), 7.83 (s, 1H) |
| 307 | [structure] | ¹H-NMR (CDCl₃) δ1.41 (s, 1H), 1.50-1.76 (m, 9H), 1.88-2.05 (m, 5H), 2.13-2.29 (m, 7H), 3.96 (m, 1H), 4.16 (m, 2H), 4.60 (d, J = 4 Hz, 1H), 5.40 (m, 1H), 6.90 (s, 1H), 7.05 (m, 1H), 8.27 (d, J = 8 Hz, 1H) |
| 308 | [structure] | ¹H-NMR (CDCl₃) δ1.24 (t, J = 12 Hz, 3H), 1.41 (m, 1H), 1.49-1.77 (m, 7H), 1.89-2.04 (m, 6H), 2.14-2.26 (m, 8H), 2.60 (q, J = 12 Hz, 2H), 3.97 (m, 1H), 4.16 (m, 2H), 4.61 (d, J = 8 Hz, 1H), 5.34 (m, 1H), 6.53 (m, 1H), 6.70 (m, 1H), 8.01 (d, J = 8 Hz, 1H) |
| 309 | [structure] | ¹H-NMR (CDCl₃) δ1.24 (d, J = 12, 6H), 1.49-1.77 (m, 10H), 1.89-2.04 (m, 5H), 2.14-2.26 (m, 7H), 2.84 (m, 1H), 3.97 (m, 1H), 4.16 (m, 2H), 4.61 (d, J = 8 Hz, 1H), 5.34 (m, 1H), 6.53 (s, 1H), 6.73 (d, J = 8 Hz, 1H), 8.02 (d, J = 8 Hz, 1H) |
| 310 | [structure] | ¹H NMR (CDCl₃) δ1.32-1.35 (m, 4H), 1.49-1.52 (m, 2H), 1.66-1.75 (m, 6H), 1.87-2.03 (m, 6H), 2.13-2.23 (m, 7H), 3.94-3.96 (m, 1H), 4.12 (brs, 2H), 4.23 (q, J = 7.2 Hz, 2H), 4.59 (d, J = 7.6 Hz, 1H), 5.29 (t, J = 4.8 Hz, 1H), 6.22 (dd, J = 2.4 Hz, 8.0 Hz, 2H), 7.45 (t, J = 8.0 Hz, 1H) |

TABLE 31-continued

| | | |
|---|---|---|
| 311 | (2-methoxy-6-chloropyridine structure) | ¹H NMR (CDCl₃) δ1.33 (s, 1H), 1.50-1.52 (m, 2H), 1.65-1.75 (m, 6H), 1.87-2.01 (m, 6H), 2.12-2.26 (m, 7H), 3.94-3.95 (m, 1H), 4.13 (brs, 2H), 4.57 (d, J = 7.6 Hz, 1H), 5.33 (t, J = 4.8 Hz, 1H), 6.59 (d, J = 8.0 Hz, 1H), 6.86 (d, J = 8.0 Hz, 1H), 7.50 (t, J = 8.0 Hz, 1H) |
| 312 | (2-methoxy-4-chloropyridine structure) | ¹H NMR (CDCl₃) δ1.33 (s, 1H), 1.47-1.51 (m, 2H), 1.61-1.74 (m, 6H), 1.88-1.92 (m, 4H), 2.00-2.03 (m, 2H), 2.12-2.25 (m, 7H), 3.94-3.96 (m, 1H), 4.13 (brs, 2H), 4.58 (d, J = 8.0 Hz, 1H), 5.33 (t, J = 4.8 Hz, 1H), 6.71 (d, J = 1.6 Hz, 1H), 6.84 (dd, J = 1.6 Hz, 5.2 Hz, 1H), 8.01 (t, J = 5.2 Hz, 1H) |
| 313 | (2-methoxy-4-ethoxypyridine structure) | ¹H NMR (CDCl₃) δ1.36 (s, 1H), 1.40 (t, J = 7.2 Hz, 3H), 1.48-1.53 (m, 2H), 1.64-1.74 (m, 6H), 1.87-2.01 (m, 6H), 2.12-2.22 (m, 7H), 3.95 (brs, 1H), 4, 03 (q, J = 7.2 Hz, 2H), 4.13 (brs, 2H), 4.58 (d, J = 7.6 Hz, 1H), 5.30 (t, J = 4.8 Hz, 1H), 6.11 (d, J = 2.4 Hz, 1H), 6.42 (dd, J = 2.4 Hz, 6.0 Hz, 1H), 7.90 (d, J = 6.0 Hz, 1H) |

Example 314

(1R,5S)-N-[(E)-5-Hydroxyadamantan-2-yl]-3-(phenoxymethyl)-8-azabicyclo[3.2.1]octane-8-carboxyamide

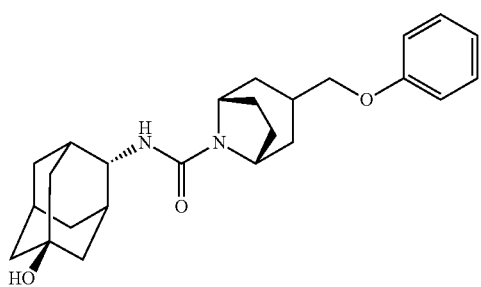 [SMILES: O=C(N[C@H]1C2CC3CC1C[C@](O)(C3)C2)N1[C@@H]2CC[C@H]1CC(COc1ccccc1)C2]

Using the compound of Reference Example 18, the compound was synthesized in a similar manner to Example 1.

¹H-NMR (CDCl₃) δ1.50-1.79 (m, 15H), 1.90-1.94 (m, 2H), 2.04-2.15 (m, 5H), 2.37-2.45 (m, 1H), 3.75 (d, J=8 Hz, 2H), 3.98 (m, 1H), 4.22 (m, 2H), 4.63 (d, J=12 Hz, 1H), 6.85-6.88 (m, 2H), 6.92-6.97 (m, 1H), 7.26-7.31 (m, 2H)

Example 315

(3-Endo)-N-[(E)-5-hydroxyadamantan-2-yl]-3-(phenylthio)-8-azabicyclo[3.2.1]octane-8-carboxyamide

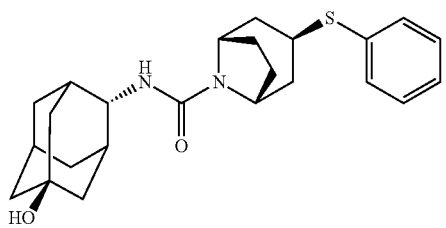 [SMILES: O=C(N[C@H]1C2CC3CC1C[C@](O)(C3)C2)N1[C@@H]2CC[C@H]1C[C@@H](Sc1ccccc1)C2]

Using the compound of Reference Example 21, the compound was synthesized in a similar manner to Example 1.

¹H-NMR (CDCl₃) δ1.45-1.50 (m, 2H), 1.61-1.67 (m, 3H), 1.72-1.74 (m, 4H), 1.79-1.89 (m, 4H), 2.03-2.15 (m, 5H), 2.25-2.30 (m, 2H), 2.34-2.40 (m, 2H), 3.62 (t, J=8 Hz, 1H), 3.93 (m, 1H), 4.14 (m, 2H), 4.56 (d, J=8 Hz, 1H), 7.19-7.24 (m, 1H), 7.27-7.36 (m, 4H)

Example 316

(3-Endo)-N-[(E)-5-hydroxyadamantan-2-yl]-3-[methyl(phenyl)amino]-8-azabicyclo-[3.2.1]octane-8-carboxamide

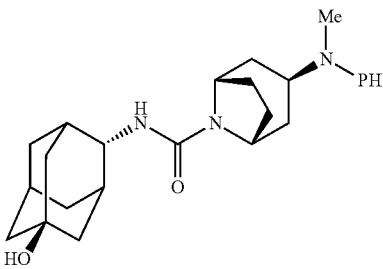

Using the compound of Reference Example 22, the compound was synthesized in a similar manner to Example 1.

¹H-NMR (CDCl₃) δ1.31 (m, 1H), 1.44-1.51 (m, 3H), 1.59-1.94 (m, 15H), 2.04-2.18 (m, 6H), 3.92 (m, 1H), 4.11 (m, 3H), 4.55 (m, 1H), 7.10 (m, 3H), 7.56 (m, 1H), 7.50 (m, 1H), 6.70-6.94 (m, 4H), 7.10-7.24 (m, 4H)

Example 317

(3-Endo)-N-[(E)-5-hydroxyadamantan-2-yl]-3-[(1-phenyl-4-piperidinyl)oxy]-8-azabicyclo-[3.2.1]octane-8-carboxyamide

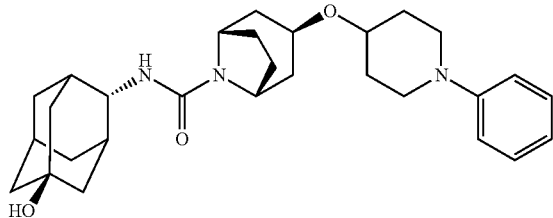 [SMILES: O=C(N[C@H]1C2CC3CC1C[C@](O)(C3)C2)N1[C@@H]2CC[C@H]1C[C@@H](OC1CCN(c3ccccc3)CC1)C2]

Using the compound of Reference Example 24, the compound was synthesized in a similar manner to Example 1.

$^1$H NMR (CDCl$_3$) δ 1.44-1.52 (m, 3H), 1.62-1.78 (m, 10H), 1.87-1.93 (m, 6H), 2.00-2.22 (m, 7H), 2.99-3.05 (m, 2H), 3.40-3.45 (m, 2H), 3.50 (m, 1H), 3.72 (m, 1H), 3.94 (m, 1H), 4.10 (m, 2H), 4.57 (d, J=4 Hz, 1H), 6.82 (t, J=8 Hz, 1H), 6.94 (d, J=8 Hz, 1H), 6.94 (d, J=8 Hz, 2H), 7.22-7.24 (m, 2H)

Example 318

(3-Endo)-N-[(E)-5-hydroxyadamantan-2-yl]-3-{[1-(2-pyridinyl)-4-piperidinyl]oxy}-8-azabicyclo[3.2.1]octane-8-carboxyamide

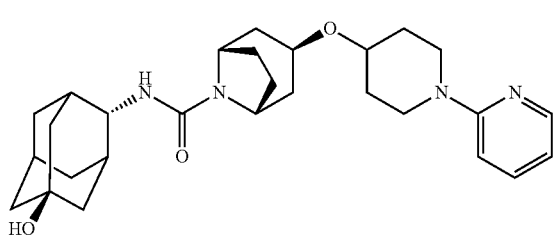 [SMILES: O=C(N[C@H]1C2CC3CC1C[C@](O)(C3)C2)N1[C@@H]2CC[C@H]1C[C@@H](OC1CCN(c3ccccn3)CC1)C2]

Using the compound of Reference Example 25, the compound was synthesized in a similar manner to Example 1.

$^1$H NMR (CDCl$_3$) δ 1.46 (s, 1H), 1.49-1.52 (m, 2H), 1.58-1.69 (m, 5H), 1.73-1.75 (m, 6H), 1.82-1.94 (m, 5H), 2.02-2.22 (m, 7H), 3.32-3.38 (m, 2H), 3.58 (m, 1H), 3.75 (m, 1H), 3.80-3.86 (m, 2H), 3.95 (m, 1H), 4.09 (m, 2H), 4.57 (d, J=8 Hz, 1H), 6.58 (m, 1H), 6.67 (d, J=8 Hz, 1H), 7.45 (m, 1H), 8.17 (m, 1H)

Examples 319 and 320

(3-Endo)-3-(2,3-dihydro-1H-indol-1-yl)-N-[(E)-5-hydroxyadamantan-2-yl]-8-azabicyclo-[3.2.1]octane-8-carboxamide (Compound V)

(3-Exo)-3-(2,3-dihydro-1H-indol-1-yl)-N-[(E)-5-hydroxyadamantan-2-yl]-8-azabicyclo-[3.2.1]octane-8-carboxamide (Compound VI)

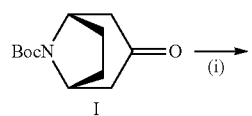

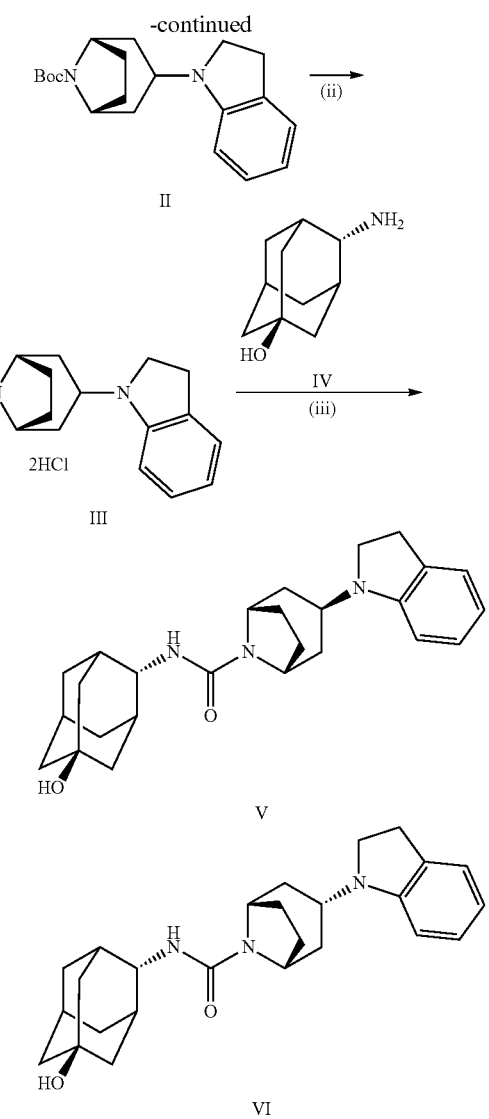

Step (i):
To a solution of Compound I (500 mg) and indoline (299 mg) in methylene chloride (11 mL) were added acetic acid (64 μL) and sodium triacetoxyborohydride (1.41 g), and the mixture was stirred at room temperature for 3 days, and then further stirred at 50° C. for 2 hours. To the reaction solution was added aqueous sodium bicarbonate solution, and the mixture was extracted with ethyl acetat. The organic layer was washed with brine, and concentrated under reduced pressure. The residue was purified by silica gel column chromatography (eluent: hexane/ethyl acetate=6/1) to give Compound II (210 mg).

Step (ii):
To a solution of Compound II (210 mg) in chloroform (1 mL) was added 4N hydrochloric acid/dioxane (1.5 mL), and the mixture was stirred for one hour. The reaction mixture was concentrated under reduced pressure to give Compound III as a crude product.

Step (iii):
To a solution of Compound IV in THF (6 mL) were added triethylamine (267 μL) and p-nitrochloroformate (155 mg), and the mixture was stirred at room temperature for one hour. The mixture was added to a solution of crude Compound III obtained in Step (ii) and triethylamine (267 μL) in THF (6 mL), and the resulting mixture was stirred at room temperature overnight. To the reaction mixture was added 1N aqueous sodium hydroxide solution, and the mixture was extracted with chloroform, and the organic layer was washed with 1N hydrochloric acid. The resultant was dried over sodium sulfate, and concentrated under reduced pressure. The residue was purified by reverse-phase column chromatography (acetonitrile:water=10:90→5:95) to give the titled low polar Compound V (major, 123 mg) and high polar Compound VI (minor, 23 mg).

Compound V: $^1$H-NMR (CDCl$_3$) δ 1.54 (d, 2H, J=12.8 Hz), 1.66 (d, 2H, J=12.7 Hz), 1.73-1.95 (m, 12H), 2.05-2.21 (m, 5H), 3.15 (t, 2H, J=8.0 Hz), 3.65 (t, 2H, J=8.2 Hz), 3.90-3.98 (m, 1H), 4.17-4.39 (m, 3H), 4.74 (br s, 1H), 7.14-7.34 (m, 4H)

Compound VI: $^1$H-NMR (CDCl$_3$) δ 1.33-1.62 (m, 6H), 1.67-1.82 (m, 8H), 1.88-1.96 (m, 2H), 2.01-2.21 (m, 4H), 2.36-2.48 (m, 1H), 2.93 (t, 2H, J=8.1 Hz), 3.33 (t, 2H, J=8.2 Hz), 3.45-3.59 (m, 1H), 3.96-4.03 (m, 1H), 4.19-4.30 (m, 2H), 4.65-4.72 (m, 1H), 6.38 (d, 1H, J=7.7 Hz), 6.62 (t, 1H, J=7.6 Hz), 6.99-7.06 (m, 2H)

Example 321 and Example 322

(3-Endo)-3-(5-fluoro-2,3-dihydro-1H-indol-1-yl)-N-[(E)-5-hydroxyadamantan-2-yl]-8-azabicyclo[3.2.1]octane-8-carboxamide (3-Exo)-3-(5-fluoro-2,3-dihydro-1H-indol-1-yl)-N-[(E)-5-hydroxyadamantan-2-yl]-8-azabicyclo[3.2.1]octane-8-carboxamide

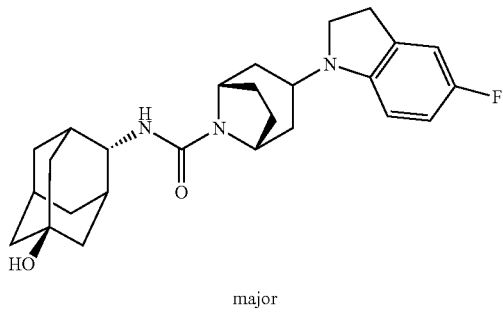

major

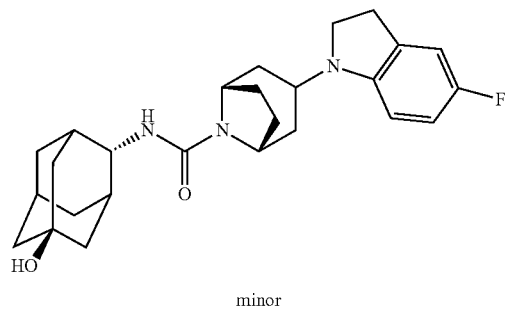

minor

The title compounds were synthesized in a similar manner to Examples 319 and 320.

Low polar compound (major, yield: 93 mg)

$^1$H-NMR (CDCl$_3$) δ 1.48-1.58 (m, 2H), 1.62-1.95 (m, 12H), 2.02-2.25 (m, 7H), 2.94 (t, 2H, J=8.3 Hz), 3.34 (t, 2H, J=8.3 Hz), 3.92-4.03 (m, 2H), 4.25 (br s, 2H), 4.66 (d, 1H, J=6.6 Hz), 6.48 (dd, 1H, J=8.5, 4.1 Hz), 6.76 (dd, 1H, J=9.2, 2.6 Hz), 6.79-6.85 (m, 1H)

High polar compound (minor, yield: 7 mg)

$^1$H-NMR (CDCl$_3$) δ 1.40-1.65 (m, 4H), 1.67-1.99 (m, 10H), 2.04-2.24 (m, 4H), 2.35-2.47 (m, 3H), 2.90 (t, 2H, J=8.2 Hz), 3.31 (t, 2H, J=8.2 Hz), 3.37-3.53 (m, 1H), 3.96-4.04 (m, 1H), 4.21-4.31 (m, 2H), 4.68 (d, 1H, J=7.2 Hz), 6.26 (dd, 1H, J=8.5, 4.1 Hz), 6.71 (td, 1H, J=8.9, 2.6 Hz), 6.78 (dd, 1H, J=8.2, 2.5 Hz)

Example 323 to Example 335

Using the compounds obtained in Reference Examples 41 to 43, or these compounds and compounds obtained in a similar manner to Reference Example 16, the compounds were synthesized in a similar manner to Example 1.

TABLE 32

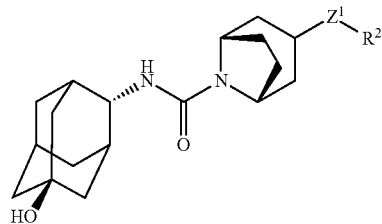

| Ex. No. | —Z$^1$—R$^2$ | NMR (solvent) δ |
|---|---|---|
| 323 | (2-methoxy-6-methyl-4-ethyl-pyridine via O linker) | $^1$H-NMR (CDCl$_3$) δ 1.22 (t, 3H, J = 7.6 Hz), 1.50-1.55 (m, 3H), 1.66-1.77 (m, 6H), 1.94-2.02 (m, 6H), 2.17-2.23 (m, 7H), 2.39 (s, 3H), 2.55 (q, 2H, J = 7.6 Hz), 3.97-3.99 (m, 1H), 4.13-4.16 (m, 2H), 4.61 (d, 1H, J = 7.2 Hz), 5.37-5.38 (m, 1H), 6.32 (s, 1H), 6.56 (s, 1H) |

TABLE 32-continued

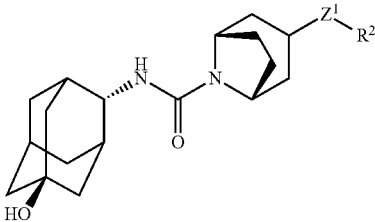

| Ex. No. | —Z¹—R² | NMR (solvent) δ |
|---|---|---|
| 324 | 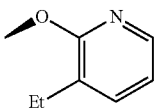 | ¹H-NMR (CDCl₃) δ 1.50-1.54 (m, 3H), 1.67-1.77 (m, 8H), 1.89-2.30 (m, 16H), 3.97-3.99 (m, 1H), 4.16-4.19 (m, 2H), 4.62 (d, 1H, J = 7.0 Hz), 5.40-5.43 (m, 1H), 6.76 (dd, 1H, J = 6.7, 4.0 Hz), 7.40 (d, 1H, J = 7.0 Hz), 7.96 (d, 1H, J = 3.9 Hz) |
| 325 | 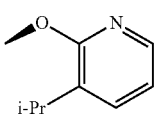 | ¹H-NMR (CDCl₃) δ 0.97 (t, 2H, J = 7.2 Hz), 1.24 (d, 1H, J = 7.0 Hz), 1.57-1.71 (m, 12H), 1.98-2.21 (m, 13H), 2.55 (t, 1H, J = 7.5 Hz), 3.97-4.01 (m, 1H), 4.18-4.23 (m, 2H), 4.62 (d, 1H, J = 7.2 Hz), 5.39-5.42 (m, 1H), 6.76-6.85 (m, 1H), 7.37-7.40 (m, 1H), 7.96-7.97 (m, 1H) |
| 326 | 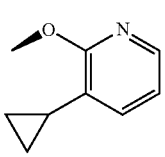 | ¹H-NMR (CDCl₃) δ 0.62-0.64 (m, 2H), 0.91-0.97 (m, 2H), 1.13 (d,1H, J = 6.1 Hz), 1.37-1.77 (m, 10H), 1.89-2.31 (m, 12H), 3.98-3.99 (m, 1H), 4.16-4.20 (m, 2H), 4.62 (d, 1H, J = 7.2 Hz), 5.45 (t, 1H, J = 4.6 Hz), 6.76 (dd, 1H, J = 7.2, 5.0 Hz), 7.15 (dd, 1H, J = 7.3, 1.7 Hz), 7.93 (dd, 1H, J = 5.0, 1.7 Hz) |
| 327 | 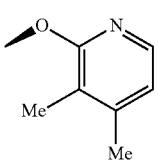 | ¹H-NMR (CDCl₃) δ 1.48-1.51 (m, 3H), 1.66-1.73 (m, 7H), 1.90-1.93 (m, 3H), 2.02-2.04 (m, 2H), 2.17-2.24 (m, 12H), 3.96-3.97 (m, 1H), 4.14-4.16 (m, 3H), 4.60 (d, 1H, J = 7.3 Hz), 5.37 (t, 1H, J = 4.9 Hz), 6.65 (d, 1H, J = 5.1 Hz), 7.81 (d, 1H, J = 5.1 Hz) |
| 328 | 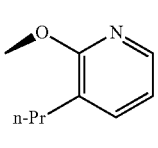 | ¹H-NMR (CDCl₃) δ 0.96 (t, 3H, J = 7.4 Hz), 1.41 (s, 1H), 1.49-1.76 (m, 12H), 1.90-1.95 (m, 3H), 2.02-2.07 (m, 2H), 2.12-2.15 (m, 3H), 2.18-2.30 (m, 3H), 2.54 (t, 2H, J = 7.7 Hz), 3.96-3.97 (m, 1H), 4.16-4.18 (m, 2H), 4.61 (d, 1H, J = 7.3 Hz), 5.39 (t, 1H, J = 4.9 Hz), 6.78 (dd, 1H, J = 7.2, 5.0 Hz), 7.38 (dd, 1H, J = 7.2, 1.8 Hz), 7.95 (dd, 1H, J = 5.0, 1.8 Hz) |
| 329 | 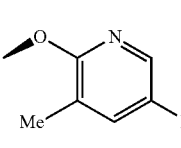 | ¹H-NMR (CDCl₃) δ 1.46-1.50 (m, 3H), 1.65-1.73 (m, 7H), 1.90-1.93 (m, 3H), 2.01-2.03 (m, 2H), 2.13-2.26 (m, 12H), 3.96-3.97 (m, 1H), 4.12-4.15 (m, 2H), 4.60 (d, 1H, J = 7.1 Hz), 5.35-5.36 (m, 1H), 7.22-7.24 (m, 2H), 7.73-7.75 (m, 1H) |
| 330 | 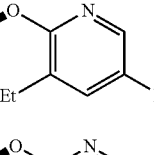 | ¹H-NMR (CDCl₃) δ 1.20 (t, 3H, J = 7.6 Hz), 1.51-1.54 (m, 3H), 1.68-1.73 (m, 7H), 1.91-2.01 (m, 5H), 2.13-2.27 (m, 10H), 2.56 (q, 2H, J = 7.4 Hz), 3.96-3.97 (m, 1H), 4.14-4.16 (m, 2H), 4.61 (d, 1H, J = 7.3 Hz), 5.34 (t, 1H, J = 4.6 Hz), 7.22 (s, 1H), 7.74 (s, 1H) |
| 331 | 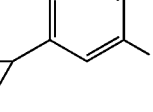 | ¹H-NMR (CDCl₃) δ 0.61 (dd, 2H, J = 10.1, 6.0 Hz), 0.89-0.94 (m, 2H), 1.48-1.51 (m, 3H), 1.66-1.73 (m, 7H), 1.92-2.00 (m, 6H), 2.17-2.25 (m, 10H), 3.96-3.98 (m, 1H), 4.15-4.17 (m, 2H), 4.61 (d, 1H, J = 6.8 Hz), 5.38-5.39 (m, 1H), 6.94 (d, 1H, J = 2.0 Hz), 7.70-7.72 (m, 1H) |
| 332 | 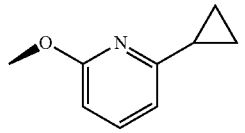 | ¹H-NMR (CDCl₃) δ 0.87-0.92 (m, 4H), 1.38-1.41 (m, 1H), 1.51-1.54 (m, 2H), 1.70-1.74 (m, 6H), 1.89-1.98 (m, 7H), 2.16-2.19 (m, 7H), 3.96-3.98 (m, 1H), 4.11-4.13 (m, 2H), 4.60 (d, 1H, J = 7.1 Hz), 5.29 (t, 1H, J = 4.5 Hz), 6.41 (d, 1H, J = 8.0 Hz), 6.73 (d, 1H, J = 7.1 Hz), 7.40 (t, 1H, J =+0 7.7 Hz) |

TABLE 32-continued

| Ex. No. | —Z¹—R² | NMR (solvent) δ |
|---|---|---|
| 333 | [pyridine with OMe and Et substituents] | ¹H-NMR (CDCl₃) δ 1.24 (t, 3H, J = 7.6 Hz), 1.37 (d, 1H, J = 4.9 Hz), 1.50-1.64 (m, 1H), 1.68-1.82 (m, 6H), 1.87-2.03 (m, 6H), 2.14-2.26 (m, 8H), 2.66 (q, 2H, J = 8.6 Hz), 3.97-3.98 (m, 1H), 4.14-4.14 (m, 2H), 4.60 (d, 1H, J = 7.3 Hz), 5.40 (t, 1H, J = 7.2 Hz), 6.48 (d, 1H, J = 8.0 Hz), 6.68 (d, 1H, J = 7.1 Hz), 7.46 (t, 1H, J = 7.7 Hz) |
| 334 | [pyridine with OMe and two Me substituents] | ¹H-NMR (CDCl₃) δ 1.41 (s, 1H), 1.49-1.75 (m, 7H), 1.89-2.04 (m, 6H), 2.15-2.20 (m, 8H), 2.23 (s, 3H), 2.35 (s, 3H), 3.96-3.96 (m, 1H), 4.11-4.14 (m, 2H), 4.59 (d, 1H, J = 7.1 Hz), 5.34 (t, 1H, J = 4.5 Hz), 6.30 (s, 1H), 6.53 (s, 1H) |
| 335 | [pyridine with OMe and cyclopropyl substituents] | ¹H-NMR (CDCl₃) δ 0.76-0.78 (m, 2H), 1.03-1.05 (m, 2H), 1.47-1.51 (m, 3H), 1.63-1.84 (m, 7H), 1.92-2.01 (m, 6H), 2.16-2.22 (m, 7H), 3.96-3.97 (m, 1H), 4.12-4.13 (m, 2H), 4.60 (d, 1H, J = 7.3 Hz), 5.31 (t, 1H, J = 4.8 Hz), 6.37-6.37 (m, 1H), 6.51 (dd, 1H, J = 5.4, 1.5 Hz), 7.95 (d, 1H, J = 5.4 Hz) |

Examples 336 to 345

Using the compounds obtained in Reference Examples 44 to 49 or compounds synthesized in a similar manner to the synthesis of these compounds, the compounds were synthesized in a similar manner to Example 1.

TABLE 33

| Ex. No. | —Z¹—R² | NMR (solvent) δ |
|---|---|---|
| 336 | [pyridine with OMe and CHF₂ substituents] | ¹H-NMR (CDCl₃) δ 1.42 (s, 1H), 1.56-1.72 (m, 6H), 1.92-2.00 (m, 4H), 2.05-2.11 (m, 7H), 2.28-2.33 (m, 2H), 3.98 (dd, 1H, J = 3.7, 3.1 Hz), 4.15 (t, 3H, J = 9.7 Hz), 4.63 (d, 1H, J = 7.2 Hz), 5.51 (t, 1H, J = 5.0 Hz), 6.79 (t, 1H, J = 47.3 Hz), 6.98 (dd, 1H, J = 8.1, 2.9 Hz), 7.86 (d, 1H, J = 6.4 Hz), 8.23 (d, 1H, J = 4.4 Hz) |
| 337 | [pyridine with OMe and CF₂H substituents] | ¹H-NMR (CDCl₃) δ 1.37 (s, 1H), 1.57-1.71 (m, 9H), 1.88-2.27 (m, 12H), 3.96-3.97 (m, 1H), 4.16-4.16 (m, 2H), 4.60 (d, 1H, J = 4.5 Hz), 5.40 (t, 1H, J = 4.3 Hz), 6.62 (t, 1H, J = 56.1 Hz), 6.76 (d, 1H, J = 2.0 Hz), 7.72-7.74 (m, 1H), 8.24 (s, 1H) |

TABLE 33-continued

| Ex. No. | —Z¹—R² | NMR (solvent) δ |
|---|---|---|
| 338 | 4-(1-fluoroethyl)-2-methoxypyridin-yl-oxy group (F, Me on CH attached to 2-methoxypyridine via O) | ¹H-NMR (CDCl₃) δ 1.42 (s, 1H), 1.50-1.77 (m, 12H), 1.89-2.05 (m, 5H), 2.16-2.23 (m, 7H), 3.97-3.98 (m, 1H), 4.17-4.19 (m, 2H), 4.61 (d, 1H, J = 7.3 Hz), 5.37 (t, 1H, J = 4.6 Hz), 5.57 (dq, 1H, J = 47.8, 6.6 Hz), 6.67 (d, 1H, J = 0.7 Hz), 6.78-6.80 (m, 1H), 8.12 (d, 1H, J = 5.1 Hz) |
| 339 | 4-(difluoromethoxy)-2-methoxypyridine linked via OCH₂ (OCF₂H shown) | ¹H-NMR (CDCl₃) δ 1.38 (s, 1H), 1.50-1.53 (m, 2H), 1.67-1.76 (m, 6H), 1.89-1.95 (m, 4H), 2.01-2.05 (m, 2H), 2.14-2.28 (m, 7H), 3.96-3.98 (m, 1H), 4.16 (br s, 2H), 4.61 (d, 1H, J = 7.1 Hz), 5.37 (t, 1H, J = 4.4 Hz), 6.37 (br s, 1H), 6.62 (t, 1H, J = 72.4 Hz), 6.63 (br s, 1H), 8.08 (d, 1H, J = 5.9 Hz) |
| 340 | 6-(difluoromethoxy)pyridin-2-yl linked via OCH₂ (OCF₂H) | ¹H-NMR (CDCl₃) δ 1.39 (s, 1H), 1.51-1.55 (m, 2H), 1.68-1.77 (m, 6H), 1.89-1.96 (m, 4H), 2.01-2.05 (m, 2H), 2.14-2.27 (m, 7H), 3.96-3.98 (m, 1H), 4.15 (s, 2H), 4.61 (d, 1H, J = 7.6 Hz), 5.21 (t, 1H, J = 4.8 Hz), 6.44 (d, 1H, J = 7.9 Hz), 6.49 (d, 1H, J = 7.9 Hz), 7.28 (t, 1H, J = 73.6 Hz), 7.61 (t, 1H, J = 7.9 Hz) |
| 341 | 4-(difluoromethyl)-2-methoxypyridin-yl linked via OCH₂ (CF₂H) | ¹H-NMR (CDCl₃) δ 1.39-1.42 (m, 1H), 1.46-1.57 (m, 2H), 1.65-1.82 (m, 5H), 1.87-1.98 (m, 4H), 2.00-2.08 (m, 2H), 2.12-2.33 (m, 7H), 3.94-4.02 (m, 1H), 4.17 (br s, 2H), 4.61 (d, 1H, J = 7.2 Hz), 5.40 (t, 1H, J = 5.0 Hz), 6.57 (t, 1H, J = 55.8 Hz), 6.82 (s, 1H), 6.97 (d, 1H, J = 5.0 Hz), 8.24 (d, 1H, J = 5.3 Hz) |
| 342 | 3-chloro-2-methoxy-5-(difluoromethyl)pyridin-yl linked via OCH₂ (Cl, CF₂H) | ¹H-NMR (CDCl₃) δ 1.51-1.55 (m, 3H), 1.65-1.84 (m, 7H), 1.92-1.95 (m, 4H), 2.05-2.16 (m, 4H), 2.26-2.32 (m, 4H), 3.97-3.99 (m, 1H), 4.16-4.20 (m, 2H), 4.62 (d, 1H, J = 7.2 Hz), 5.50 (t, 1H, J = 4.5 Hz), 6.62 (t, 1H, J = 55.8 Hz), 7.81 (d, 1H, J = 1.7 Hz), 8.14 (d, 1H, J = 1.8 Hz) |

TABLE 34

| Ex. No. | —Z¹—R² | NMR (solvent) δ |
|---|---|---|
| 343 | 3-(difluoromethoxy)benzyl-oxy group (OCF₂H) | ¹H-NMR (CDCl₃) δ 1.42 (s, 1H), 1.51-1.59 (m, 2H), 1.67-1.77 (m, 6H), 1.89-2.03 (m, 6H), 2.15-2.24 (m, 7H), 3.97 (br s, 1H), 4.14 (br s, 2H), 4.62-4.66 (m, 2H), 4.86 (s, 2H), 6.31 (t, 1H, J = 74.3 Hz), 6.78-6.84 (m, 2H), 6.93 (d, 1H, J = 7.6 Hz), 7.27-7.31 (m, 1H). |
| 344 | 2-(difluoromethoxy)-4-fluorobenzyl-oxy group (OCF₂H, F) | ¹H-NMR (CDCl₃) δ 1.35 (s, 1H), 1.49-1.60 (m, 2H), 1.66-1.77 (m, 6H), 1.89-2.05 (m, 6H), 2.15-2.24 (m, 7H), 3.96 (br s, 1H), 4.14 (br s, 2H), 4.53-4.55 (m, 2H), 6.55 (t, 1H, J = 73.2 Hz), 6.61-6.65 (m, 1H), 6.69-6.71 (m, 1H), 7.08 (t, 1H, J = 9.5 Hz). |
| 345 | 3-(difluoromethoxy)-5-fluorobenzyl-oxy group (OCF₂H, F) | ¹H-NMR (CDCl₃) δ 1.36 (s, 1H), 1.48-1.61 (m, 2H), 1.51-1.60 (m, 6H), 1.89-2.25 (m, 13H), 3.97 (br s, 1H), 4.15 (br s, 2H), 4.56-4.62 (m, 2H), 6.38-6.42 (m, 3H), 6.49 (t, 1H, J = 73.2 Hz). |

Examples 346 to 353

Using the compounds obtained in Reference Examples 50 to 56 or compounds synthesized in a similar manner to the synthesis of these compounds, the compounds were synthesized in a similar manner to Example 1.

TABLE 35

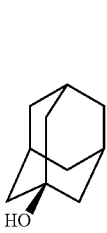

| Ex. No. | —Z¹—R² | NMR (solvent) δ |
|---|---|---|
| 346 | 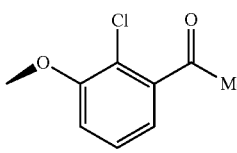 | ¹H-NMR (CDCl₃) δ 1.42-1.57 (m, 3H), 1.60-1.81 (m, 5H), 1.87-2.28 (m, 13H), 2.65 (s, 3H), 3.92-4.00 (m, 1H), 4.15 (br s, 2H), 4.58-4.65 (m, 2H), 6.86 (dd, 1H, J = 8.8, 3.1 Hz), 6.98 (d, 1H, J = 3.1 Hz), 7.31 (d, 1H, J = 8.6 Hz) |
| 347 | 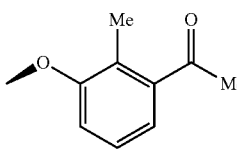 | ¹H-NMR (CDCl₃) δ 1.43-1.58 (m, 3H), 1.60-1.81 (m, 5H), 1.87-2.08 (m, 6H), 2.11-2.38 (m, 7H), 2.63 (s, 3H), 3.94-4.01 (m, 1H), 4.16 (br s, 2H), 4.63 (d, 1H, J = 7.2 Hz), 4.69 (t, 1H, J = 4.7 Hz), 6.85 (dd, 1H, J = 8.4, 1.1 Hz), 7.02 (dd, 1H, J = 7.7, 1.5 Hz), 7.25 (t, 1H, J = 8.0 Hz) |
| 348 | 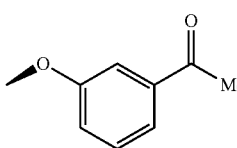 | ¹H-NMR (CDCl₃) δ 1.42-1.58 (m, 0H), 1.60-1.81 (m, 5H), 1.87-2.08 (m, 6H), 2.12-2.31 (m, 7H), 2.34 (s, 3H), 2.56 (s, 3H), 3.93-4.01 (m, 1H), 4.17 (br s, 2H), 4.59-4.66 (m, 2H), 6.78 (d, 1H, J = 7.5 Hz), 7.10-7.23 (m, 2H) |
| 349 | 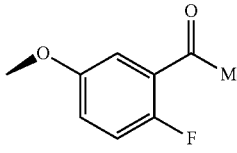 | ¹H-NMR (CDCl₃) δ 1.41 (s, 1H), 1.51-1.58 (m, 2H), 1.67-1.77 (m, 6H), 1.89-2.05 (m, 6H), 2.14-2.28 (m, 7H), 2.58 (s, 3H), 3.96-3.97 (m, 1H), 4.16 (br s, 2H), 4.61 (d, 1H, J = 7.6 Hz), 4.66 (t, 1H, J = 4.8 Hz), 6.74 (dt, 1H, J = 10.2, 2.3 Hz), 7.20-7.22 (m, 2H) |
| 350 | 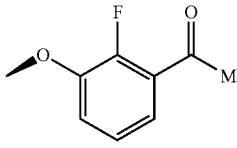 | ¹H-NMR (CDCl₃) δ 1.38 (s, 1H), 1.51-1.56 (m, 2H), 1.66-1.77 (m, 6H), 1.89-2.05 (m, 6H), 2.14-2.24 (m, 7H), 2.64 (d, 3H, J = 5.1 Hz), 3.95-3.97 (m, 1H), 4.14 (br s, 2H), 4.61 (br s, 2H), 6.97-7.01 (m, 1H), 7.07 (t, 1H, J = 9.6 Hz), 7.24-7.28 (m, 1H) |
| 351 | 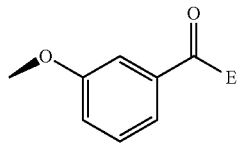 | ¹H-NMR (CDCl₃) δ 1.40 (s, 1H), 1.51-1.54 (m, 2H), 1.67-1.77 (m, 6H), 1.89-1.92 (m, 2H), 1.98-2.07 (m, 4H), 2.14 (br s, 3H), 2.22-2.30 (m, 4H), 2.65 (d, 3H, J = 4.9 Hz), 3.96-3.98 (m, 1H), 4.17 (br s, 2H), 4.62-4.66 (m, 2H), 7.02 (td, 1H, J = 7.9, 1.6 Hz), 7.11 (td, 1H, J = 8.0, 1.1 Hz), 7.37-7.41 (m, 1H) |
| 352 | | ¹H-NMR (CDCl₃) δ 1.22 (t, 3H, J = 7.2 Hz), 1.45-1.77 (m, 10H), 1.92-2.01 (m, 5H), 2.15-2.30 (m, 7H), 2.99 (q, 2H, J = 6.0 Hz), 3.96-3.98 (m, 1H), 4.14-4.17 (m, 2H), 4.62 (d, 1H, J = 7.3 Hz), 4.70-4.71 (m, 1H), 7.01-7.06 (m, 1H), 7.34-7.46 (m, 2H), 7.52-7.54 (m, 1H) |

TABLE 35-continued

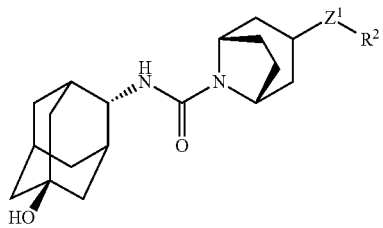

| Ex. No. | —Z¹—R² | NMR (solvent) δ |
|---|---|---|
| 353 | (2-methoxy-3-acetylpyridine group) | $^1$H-NMR (CDCl$_3$) δ 1.62-1.77 (m, 9H), 1.97-2.07 (m, 11H), 2.35 (dt, 2H, J = 15.0, 4.4 Hz), 2.68 (s, 3H), 3.97-3.98 (m, 1H), 4.16-4.19 (m, 2H), 4.63 (d, 1H, J = 7.2 Hz), 5.53 (t, 1H, J = 5.2 Hz), 6.96 (dd, 1H, J = 7.5, 5.0 Hz), 8.01 (dd, 1H, J = 7.5, 2.0 Hz), 8.26 (dd, 1H, J = 4.8, 2.0 Hz) |

Examples 354 to 376

Using the compounds obtained in Reference Examples 26 to 40 or compounds synthesized in a similar manner to the synthesis of these compounds and Reference Example 23, the compounds were synthesized in a similar manner to Example 1.

TABLE 36

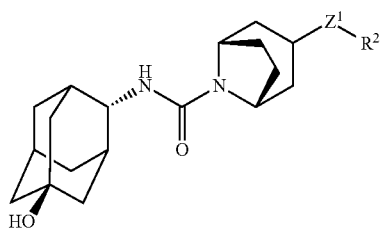

| Ex. No. | —Z¹—R² | NMR (solvent) δ |
|---|---|---|
| 354 | (3-methoxy-5-methylphenoxy-ethoxy-OMe) | $^1$H-NMR (CDCl$_3$) δ 1.46-1.52 (m, 2H), 1.62-1.77 (m, 9H), 1.91-1.99 (m, 5H), 2.14-2.24 (m, 6H), 2.28 (s, 3H), 3.45 (s, 3H), 3.73 (dd, 2H, J = 5.4, 3.9 Hz), 3.96-3.97 (m, 1H), 4.07-4.12 (m, 4H), 4.58-4.60 (m, 2H), 6.25-6.26 (m, 2H), 6.34 (s, 1H) |
| 355 | (3-methoxyphenoxy-ethyl-F) | $^1$H-NMR (CDCl$_3$) δ 1.51-1.55 (m, 3H), 1.65-1.84 (m, 7H), 1.92-1.95 (m, 4H), 2.05-2.16 (m, 4H), 2.26-2.32 (m, 4H), 3.97-3.99 (m, 1H), 4.16-4.20 (m, 2H), 4.62 (d, 1H, J = 7.2 Hz), 5.50 (t, 1H, J = 4.5 Hz), 6.62 (t, 1H, J = 55.8 Hz), 7.81 (d, 1H, J = 1.7 Hz), 8.14 (d, 1H, J = 1.8 Hz) |
| 356 | (3-methoxy-5-fluorobenzyl-Me) | $^1$H-NMR (CDCl$_3$) δ 1.55-1.71 (m, 10H), 1.89-2.03 (m, 5H), 2.16-2.21 (m, 7H), 3.39 (s, 3H), 3.96-3.99 (m, 1H), 4.12-4.16 (m, 2H), 4.39 (s, 2H), 4.58-4.61 (m, 2H), 6.45 (d, 1H, J = 10.8 Hz), 6.61-6.64 (m, 2H) |
| 357 | (2-methoxybenzyl-OMe) | $^1$H-NMR (CDCl$_3$) δ 1.44 (s, 1H), 1.51-1.56 (m, 2H), 1.61 (s, 2H), 1.68-1.78 (m, 5H), 1.90-1.94 (m, 2H), 1.97-2.00 (m, 1H), 2.04-2.06 (m, 2H), 2.21-2.25 (m, 7H), 3.45 (s, 3H), 3.98-3.99 (m, 1H), 4.15-4.18 (m, 2H), 4.51 (s, 2H), 4.64-4.65 (m, 2H), 6.71 (d, 1H, J = 8.1 Hz), 6.95 (t, 1H, J = 7.1 Hz), 7.23 (dd, 1H, J = 7.9, 1.7 Hz), 7.39 (dd, 1H, J = 7.4, 1.7 Hz) |

TABLE 36-continued

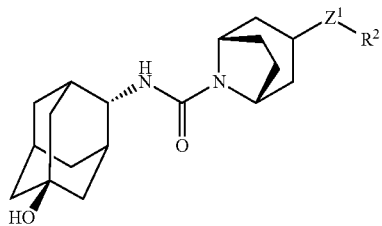

| Ex. No. | —Z¹—R² | NMR (solvent) δ |
|---|---|---|
| 358 | 3-methoxyphenyl-CH₂CH₂-OMe | ¹H-NMR (CDCl₃) δ 1.50-1.55 (m, 2H), 1.69-1.74 (m, 6H), 1.88-1.98 (m, 7H), 2.17-2.22 (m, 7H), 2.85 (t, 2H, J = 7.1 Hz), 3.36 (s, 3H), 3.60 (t, 2H, J = 7.0 Hz), 3.96-3.99 (m, 1H), 4.12-4.15 (m, 2H), 4.62-4.64 (m, 2H), 6.67-6.69 (m, 2H), 6.80 (d, 1H, J = 7.5 Hz), 7.20 (t, 1H, J = 7.8 Hz) |
| 359 | 3-methoxyphenyl-O-CH₂CH₂-OMe | ¹H-NMR (CDCl₃) δ 1.49-1.54 (m, 2H), 1.68-1.73 (m, 7H), 1.91-1.96 (m, 5H), 2.15-2.19 (m, 7H), 3.45 (s, 3H), 3.73-3.75 (m, 2H), 3.95-3.97 (m, 1H), 4.09-4.10 (m, 4H), 4.60-4.61 (m, 2H), 6.42-6.52 (m, 4H), 7.16 (t, 1H, J = 8.5 Hz) |
| 360 | 3-methoxy-4-fluorophenyl-CH₂-OMe | ¹H-NMR (CDCl₃) δ 1.49-1.53 (m, 3H), 1.67-1.73 (m, 8H), 1.90-1.99 (m, 5H), 2.16-2.24 (m, 6H), 3.36 (s, 3H), 3.94-3.96 (m, 1H), 4.12-4.15 (m, 2H), 4.36 (s, 2H), 4.61-4.63 (m, 2H), 6.84-6.86 (m, 2H), 7.04 (dd, 1H, J = 11.0, 8.3 Hz) |
| 361 | 3-methoxy-5-methylphenyl-CH₂-OMe | ¹H-NMR (CDCl₃) δ 1.49-1.54 (m, 2H), 1.68-1.74 (m, 6H), 1.91-1.96 (m, 7H), 2.16-2.20 (m, 7H), 2.31 (s, 3H), 3.38 (s, 3H), 3.96-3.99 (m, 1H), 4.11-4.14 (m, 2H), 4.38 (s, 2H), 4.60-4.63 (m, 2H), 6.61-6.68 (m, 3H) |
| 362 | 3-methoxyphenyl-CH₂-OEt | ¹H-NMR (CDCl₃) δ 1.25 (t, 3H, J = 7.0 Hz), 1.37 (s, 1H), 1.50-1.54 (m, 2H), 1.67-1.77 (m, 6H), 1.89-2.02 (m, 6H), 2.14-2.25 (m, 7H), 3.54 (q, 2H, J = 7.0 Hz), 3.96 (br s, 1H), 4.14 (br s, 2H), 4.47 (s, 2H), 4.60-4.65 (m, 2H), 6.74 (dd, 1H, J = 8.2, 2.3 Hz), 6.84 (br s, 1H), 6.90 (d, 1H, J = 7.3 Hz), 7.23-7.25 (m, 1H) |
| 363 | 3-methoxyphenyl-CH₂-O-CH₂-CF₂H | ¹H-NMR (CDCl₃) δ 1.39 (s, 1H), 1.51-1.54 (m, 2H), 1.67-1.77 (m, 6H), 1.89-2.03 (m, 6H), 2.15-2.23 (m, 7H), 3.68 (td, 2H, J = 14.0, 4.1 Hz), 3.98 (br s, 1H), 4.15 (br s, 2H), 4.58-4.65 (m, 4H), 5.90 (tt, 1H, J = 55.5, 4.0 Hz), 6.77 (dd, 1H, J = 8.3, 2.4 Hz), 6.82 (br s, 1H), 6.90 (d, 1H, J = 7.6 Hz), 7.25-7.31 (m, 1H) |
| 364 | 2-fluoro-3-methoxyphenyl-CH₂-OMe | ¹H-NMR (CDCl₃) δ 1.37 (s, 1H), 1.50-1.55 (m, 2H), 1.65-1.77 (m, 6H), 1.89-1.92 (m, 2H), 1.98-2.05 (m, 4H), 2.14-2.31 (m, 7H), 3.42 (s, 3H), 3.96 (br s, 1H), 4.15 (br s, 2H), 4.52 (d, 2H, J = 1.5 Hz), 4.60-4.64 (m, 2H), 6.81 (td, 1H, J = 7.9, 1.7 Hz), 6.96-7.06 (m, 2H) |
| 365 | 5-methoxy-2-fluorophenyl-CH₂-OMe | ¹H-NMR (CDCl₃) δ 1.48-1.57 (m, 2H), 1.64-2.06 (m, 12H), 2.09-2.24 (m, 7H), 3.42 (s, 3H), 3.93-4.00 (m, 1H), 4.11-4.16 (m, 2H), 4.48 (s, 2H), 4.57 (t, 1H, J = 4.5 Hz), 4.63 (d, 1H, J = 7.3 Hz), 6.70 (ddd, 1H, J = 8.9, 3.9, 3.3 Hz), 6.87 (dd, 1H, J = 5.9, 3.1 Hz), 6.96 (t, 1H, J = 9.1 Hz) |
| 366 | 5-methoxy-2-fluorophenyl-CH₂-OEt | ¹H-NMR (CDCl₃) δ 1.26 (t, 3H, J = 7.1 Hz), 1.48-1.57 (m, 2H), 1.63-2.07 (m, 12H), 2.09-2.26 (m, 7H), 3.58 (q, 2H, J = 7.0 Hz), 3.93-4.00 (m, 1H), 4.10-4.18 (m, 2H), 4.53 (s, 2H), 4.57 (t, 1H, J = 4.3 Hz), 4.63 (d, 1H, J = 7.3 Hz), 6.69 (dt, 1H, J = 8.7, 3.6 Hz), 6.88 (dd, 1H, J = 5.9, 3.1 Hz), 6.95 (t, 1H, J = 9.1 Hz) |
| 367 | 3-methoxyphenyl-CH₂-O-CH₂-CF₃ | ¹H-NMR (CDCl₃) δ 1.36 (s, 1H), 1.46-1.63 (m, 2H), 1.67-1.77 (m, 6H), 1.89-2.03 (m, 6H), 2.14-2.25 (m, 7H), 3.83 (q, 2H, J = 8.7 Hz), 3.95-3.98 (m, 1H), 4.14 (br s, 2H), 4.60-4.64 (m, 4H), 6.77-6.83 (m, 2H), 6.90 (d, 1H, J = 7.3 Hz), 7.24-7.30 (m, 1H) |

TABLE 37

| | | |
|---|---|---|
| 368 | *pyridine with OMe and CH2OMe substituents* | ¹H-NMR (CDCl₃) δ 1.40-1.41 (m, 1H), 1.50-1.53 (m, 2H), 1.60 (s, 1H), 1.55-1.76 (m, 6H), 1.89-2.04 (m, 5H), 2.12-2.15 (m, 3H), 2.20-2.25 (m, 4H), 3.43 (s, 3H), 3.96-3.97 (m, 1H), 4.14-4.16 (m, 2H), 4.42 (s, 2H), 4.60 (d, 1H, J = 7.3 Hz), 5.35 (t, 1H, J = 4.8 Hz), 6.68 (s, 1H), 6.78-6.80 (m, 1H), 8.08 (d, 1H, J = 5.1 Hz) |
| 369 | *pyridine with OMe and O-CH2-cyclopropyl substituents* | ¹H-NMR (CDCl₃) δ 0.29-0.33 (m, 2H), 0.58-0.61 (m, 2H), 1.25-1.26 (m, 1H), 1.40 (s, 1H), 1.51-1.54 (m, 2H), 1.68-1.81 (m, 5H), 1.94-1.99 (m, 5H), 2.15-2.24 (m, 7H), 3.97-4.01 (m, 3H), 4.12-4.14 (m, 2H), 4.13 (s, 2H), 4.61 (d, 1H, J = 7.3 Hz), 5.29 (t, 1H, J = 4.6 Hz), 6.24 (d, 1H, J = 7.8 Hz), 6.29 (d, 1H, J = 7.8 Hz), 7.47 (t, 1H, J = 7.9 Hz) |
| 370 | *pyridine with OMe and O-CH2-cyclopropyl substituents* | ¹H-NMR (CDCl₃) δ 0.34-0.36 (m, 2H), 0.64-0.68 (m, 2H), 1.25-1.28 (m, 1H), 1.67-1.74 (m, 8H), 1.92-2.03 (m, 6H), 2.15-2.21 (m, 8H), 3.81 (d, 2H, J = 7.1 Hz), 3.96-3.96 (m, 1H), 4.13-4.15 (m, 2H), 4.60 (d, 1H, J = 7.3 Hz), 5.31 (t, 1H, J = 4.6 Hz), 6.11-6.11 (m, 1H), 6.45 (dd, 1H, J = 6.1, 2.2 Hz), 7.92 (d, 1H, J = 5.9 Hz) |
| 371 | *pyridine with OMe and O-CH(Me)-CF3 substituents* | ¹H-NMR (CDCl₃) δ 1.45-1.54 (m, 6H), 1.66-1.74 (m, 7H), 1.92-2.00 (m, 5H), 2.19-2.23 (m, 7H), 3.96-3.98 (m, 1H), 4.11-4.18 (m, 2H), 4.62 (d, 1H, J = 7.6 Hz), 5.23-5.24 (m, 1H), 5.51-5.57 (m, 1H), 6.34 (t, 2H, J = 7.7 Hz), 7.52 (t, 1H, J = 7.8 Hz) |
| 372 | *pyridine with OMe and O-CH(Me)-CF3 substituents* | ¹H-NMR (CDCl₃) δ 1.44-1.53 (m, 5H), 1.61-1.76 (m, 8H), 1.89-2.03 (m, 5H), 2.16-2.22 (m, 7H), 3.96-3.97 (m, 1H), 4.14-4.16 (m, 2H), 4.60 (d, 1H, J = 7.1 Hz), 4.71-4.77 (m, 1H), 5.34 (t, 1H, J = 4.8 Hz), 6.18 (d, 1H, J = 2.0 Hz), 6.48 (dd, 1H, J = 6.1, 2.2 Hz), 7.99 (d, 1H, J = 5.9 Hz) |
| 373 | *pyridine with OMe and OCH2CF3 substituents* | ¹H-NMR (CDCl₃) δ 1.50-1.54 (m, 3H), 1.69-1.74 (m, 8H), 1.92-2.02 (m, 5H), 2.17-2.25 (m, 6H), 3.96-3.98 (m, 1H), 4.14-4.17 (m, 2H), 4.37 (q, 2H, J = 7.9 Hz), 4.61 (d, 1H, J = 7.2 Hz), 5.35 (t, 1H, J = 4.4 Hz), 6.18 (d, 1H, J = 2.2 Hz), 6.51 (dd, 1H, J = 5.9, 2.2 Hz), 8.00 (d, 1H, J = 5.9 Hz) |
| 374 | *pyridine with OMe and OCH2CF2H substituents* | ¹H-NMR (CDCl₃) δ 1.48-1.53 (m, 2H), 1.65-1.80 (m, 7H), 1.89-2.03 (m, 5H), 2.13-2.25 (m, 7H), 3.96-3.97 (m, 1H), 4.18-4.22 (m, 4H), 4.62 (d, 1H, J = 7.2 Hz), 5.34 (t, 1H, J = 4.6 Hz), 6.09 (td, 1H, J = 117.9, 59.0 Hz), 6.15 (d, 2H, J = 2.2 Hz), 6.48 (dd, 1H, J = 5.9, 2.2 Hz), 7.97 (d, 1H, J = 6.1 Hz) |
| 375 | *pyridine with OMe and O-CH(Me)-CF3 substituents* | ¹H-NMR (CDCl₃) δ 1.50-1.51 (m, 5H), 1.66-1.77 (m, 5H), 1.90-1.99 (m, 6H), 2.14-2.20 (m, 7H), 3.94-3.96 (m, 1H), 4.12-4.14 (m, 2H), 4.13 (s, 2H), 4.61 (d, 1H, J = 7.3 Hz), 4.70-4.76 (m, 1H), 5.31-5.33 (m, 1H), 6.16-6.17 (m, 1H), 6.47 (dd, 1H, J = 5.9, 2.0 Hz), 7.97 (d, 1H, J = 5.9 Hz) |
| 376 | *pyridine with OMe, CH2OMe and Me substituents* | ¹H-NMR (CDCl₃) δ 1.36-1.41 (m, 1H), 1.48-1.56 (m, 2H), 1.66-1.81 (m, 5H), 1.86-2.03 (m, 6H), 2.11-2.28 (m, 7H), 2.39 (s, 3H), 3.42 (s, 3H), 3.93-4.01 (m, 1H), 4.11-4.18 (m, 2H), 4.37 (s, 3H), 4.60 (d, 1H, J = 7.3 Hz), 5.38 (t, 1H, J = 5.0 Hz), 6.46 (s, 1H), 6.65 (s, 1H) |

Examples 377 to 379

Using the compounds obtained in Reference Examples 57 to 59, the compounds were synthesized in a similar manner to Example 1.

TABLE 38

| Ex. No. | —Z¹—R² | NMR (solvent) δ |
|---|---|---|
| 377 | (3-OMe, 5-F phenyl-O-CH2-) | ¹H-NMR (CDCl₃) δ 1.36 (s, 1H), 1.51-1.55 (m, 2H), 1.66-1.77 (m, 6H), 1.89-2.05 (m, 6H), 2.14-2.23 (m, 7H), 3.77 (s, 3H), 3.96 (br s, 1H), 4.13 (br s, 2H), 4.55 (t, 1H, J = 4.6 Hz), 4.60 (d, 1H, J = 7.3 Hz), 6.13-6.17 (m, 2H), 6.23 (dt, 1H, J = 10.5, 2.2 Hz) |
| 378 | (difluoro-benzodioxole-O-CH2-) | ¹H-NMR (CDCl₃) δ 1.38 (s, 1H), 1.51-1.55 (m, 2H), 1.66-1.77 (m, 6H), 1.89-2.04 (m, 6H), 2.14-2.23 (m, 7H), 3.97 (br s, 1H), 4.14 (br s, 2H), 4.53 (t, 1H, J = 4.5 Hz), 4.61 (d, 1H, J = 7.3 Hz), 6.49 (dd, 1H, J = 8.8, 2.4 Hz), 6.61 (d, 1H, J = 2.4 Hz), 6.94 (d, 1H, J = 8.8 Hz) |
| 379 | (5-F, 6-position indanone-O-CH2-) | ¹H-NMR (CDCl₃) δ 1.43-1.58 (m, 3H), 1.60-1.81 (m, 5H), 1.87-2.08 (m, 6H), 2.11-2.30 (m, 7H), 2.67-2.74 (m, 2H), 3.03-3.14 (m, 2H), 3.94-4.01 (m, 1H), 4.16 (br s, 2H), 4.62 (d, 1H, J = 7.5 Hz), 4.68 (t, 1H, J = 4.4 Hz), 7.15-7.22 (m, 2H) |

Examples 380 to 395

Using the compounds obtained in a similar manner to Reference Example 3 from the commercially available substituted pyridine derivative, the compounds were synthesized in a similar manner to Example 1.

TABLE 39

| Ex. No. | —Z¹—R² | NMR (solvent) δ |
|---|---|---|
| 380 | (2,3,4-trifluorophenyl-O-CH2-) | ¹H-NMR (CDCl₃) δ 1.39 (s, 1H), 1.50-1.53 (m, 2H), 1.66-1.76 (m, 6H), 1.88-1.91 (m, 2H), 2.03-2.04 (m, 9H), 2.33-2.38 (m, 2H), 3.94-3.96 (m, 1H), 4.17 (br s, 2H), 4.52 (t, 1H, J = 4.8 Hz), 4.61 (d, 1H, J = 7.3 Hz), 6.80-6.88 (m, 2H) |
| 381 | (2,3,6-trifluorophenyl-O-CH2-) | ¹H-NMR (CDCl₃) δ 1.38 (s, 1H), 1.50-1.56 (m, 2H), 1.66-1.76 (m, 6H), 1.88-1.91 (m, 2H), 2.03-2.24 (m, 9H), 2.33-2.38 (m, 2H), 3.95 (d, 1H, J = 7.3 Hz), 4.17 (br s, 2H), 4.52 (t, 1H, J = 4.8 Hz), 4.61 (d, 1H, J = 7.6 Hz), 6.80-6.86 (m, 2H) |

TABLE 39-continued

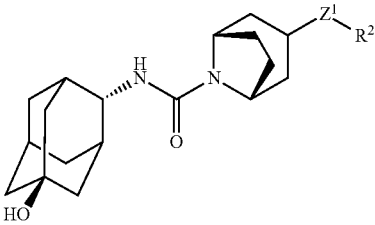

| Ex. No. | —Z¹—R² | NMR (solvent) δ |
|---|---|---|
| 382 | 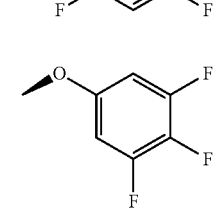 | ¹H-NMR (CDCl₃) δ 1.38 (s, 1H), 1.51-1.58 (m, 2H), 1.66-1.77 (m, 6H), 1.89-2.05 (m, 6H), 2.14-2.25 (m, 7H), 3.97 (br s, 1H), 4.15 (br s, 2H), 4.52 (t, 1H, J = 4.4 Hz), 4.61 (d, 1H, J = 7.3 Hz), 6.68-6.75 (m, 1H), 6.95-7.02 (m, 1H) |
| 383 | 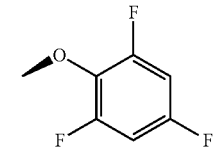 | ¹H-NMR (CDCl₃) δ 1.38 (s, 1H), 1.51-.156 (m, 2H), 1.66-1.77 (m, 6H), 1.90-2.24 (m, 13H), 3.95-3.97 (m, 1H), 4.15 (br s, 2H), 4.49 (t, 1H, J = 4.4 Hz), 4.61 (d, 1H, J = 7.6 Hz), 6.44 (dd, 2H, J = 9.4, 4.7 Hz) |
| 384 | 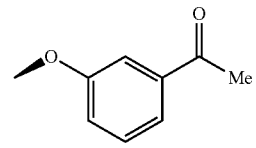 | ¹H-NMR (CDCl₃) δ 1.35-1.39 (m, 1H), 1.50-1.57 (m, 2H), 1.66-1.76 (m, 6H), 1.88-1.91 (m, 2H), 2.02-2.05 (m, 4H), 2.13-2.21 (m, 5H), 2.34-2.40 (m, 2H), 3.94-3.96 (m, 1H), 4.16 (br s, 2H), 4.32 (t, 1H, J = 4.8 Hz), 4.60 (d, 1H, J = 7.1 Hz), 6.69 (t, 2H, J = 8.5 Hz) |
| 385 | 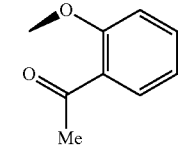 | ¹H-NMR (CDCl₃) δ 1.40 (s, 1H), 1.51-1.56 (m, 2H), 1.67-1.77 (m, 6H), 1.89-2.04 (m, 6H), 2.15-2.26 (m, 7H), 2.60 (s, 3H), 3.97 (br s, 1H), 4.15 (br s, 2H), 4.61 (d, 1H, J = 7.3 Hz), 4.70 (t, 1H, J = 4.6 Hz), 7.04 (dd, 1H, J = 8.2, 2.8 Hz), 7.36-7.41 (m, 2H), 7.51-7.53 (m, 1H) |
| 386 | 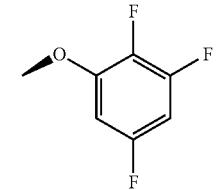 | ¹H-NMR (CDCl₃) δ 1.40 (s, 1H), 1.51-1.55 (m, 2H), 1.67-1.70 (m, 2H), 1.77 (br s, 4H), 1.89-1.92 (m, 2H), 2.00-2.14 (m, 9H), 2.31 (dt, 2H, J = 14.8, 4.5 Hz), 2.64 (s, 3H), 3.97 (br s, 1H), 4.16 (br s, 2H), 4.62 (d, 1H, J = 7.8 Hz), 4.70 (t, 1H, J = 5.1 Hz), 6.79 (d, 1H, J = 8.5 Hz), 6.98 (t, 1H, J = 7.6 Hz), 7.39-7.43 (m, 1H), 7.58 (dd, 1H, J = 7.7, 1.8 Hz) |
| 387 | 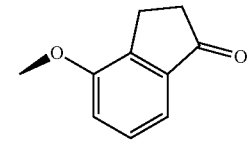 | ¹H-NMR (CDCl₃) δ 1.39 (s, 1H), 1.51-1.54 (m, 2H), 1.67-1.77 (m, 6H), 1.89-2.06 (m, 6H), 2.14-2.28 (m, 7H), 3.95-3.97 (m, 1H), 4.16 (br s, 2H), 4.59-4.63 (m, 2H), 6.36-6.41 (m, 1H), 6.49-6.56 (m, 1H) |
| 388 |  | ¹H-NMR (CDCl₃) δ 1.44-1.81 (m, 7H), 1.88-2.34 (m, 14H), 2.67-2.74 (m, 2H), 3.04-3.11 (m, 2H), 3.94-4.01 (m, 1H), 4.16-4.23 (m, 2H), 4.64 (d, 1H, J = 7.5 Hz), 4.73 (t, 1H, J = 4.6 Hz), 6.88 (dd, 1H, J = 6.6, 2.0 Hz), 7.28-7.37 (m, 2H) |

TABLE 39-continued

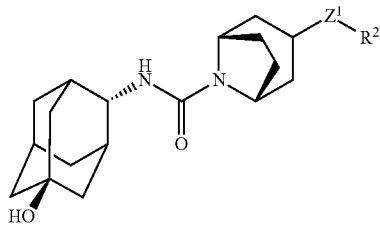

| Ex. No. | —Z¹—R² | NMR (solvent) δ |
|---|---|---|
| 389 | 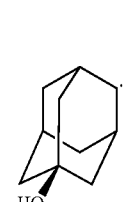 | ¹H-NMR (CDCl₃) δ 1.47-1.57 (m, 3H), 1.62-1.81 (m, 4H), 1.87-2.32 (m, 14H), 2.64-2.71 (m, 2H), 3.05-3.12 (m, 2H), 3.94-4.00 (m, 1H), 4.12-4.21 (m, 2H), 4.63 (d, 1H, J = 7.5 Hz), 4.73 (t, 1H, J = 4.7 Hz), 6.78-6.88 (m, 2H), 7.70 (d, 1H, J = 8.4 Hz) |
| 390 | 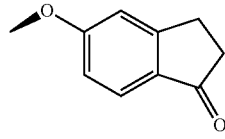 | ¹H-NMR (CDCl3) δ 1.43-1.81 (m, 8H), 1.87-2.07 (m, 6H), 2.09-2.27 (m, 7H), 2.68-2.75 (m, 2H), 3.04-3.11 (m, 2H), 3.93-4.00 (m, 1H), 4.11-4.18 (m, 2H), 4.61 (d, 1H, J = 7.3 Hz), 4.66 (t, 1H, J = 4.2 Hz), 7.10 (d, 1H, J = 2.4 Hz), 7.14 (dd, 1H, J = 8.3, 2.5 Hz), 7.39 (d, 1H, J = 8.3 Hz) |
| 391 | 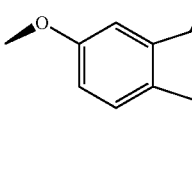 | ¹H-NMR (CDCl3 ) δ 1.47-1.81 (m, 8H), 1.87-1.95 (m, 2H), 1.99-2.07 (m, 4H), 2.11-2.18 (m, 3H), 2.22 (t, 1H, J = 4.0 Hz), 2.27 (t, 1H, J = 4.0 Hz), 2.48 (dd, 2H, J = 13.8, 6.3 Hz), 2.61-2.68 (m, 2H), 3.04-3.11 (m, 2H), 3.94-4.01 (m, 1H), 4.10-4.19 (m, 2H), 4.64 (d, 1H, J = 7.5 Hz), 4.74 (t, 1H, J = 4.3 Hz), 6.61 (d, 1H, J = 8.3 Hz), 6.98 (d, 1H, J = 7.5 Hz), 7.47 (t, 1H, J = 7.9 Hz) |
| 392 | 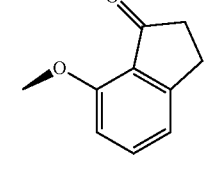 | ¹H-NMR (CDCl₃) δ 1.49-1.52 (m, 2H), 1.66-1.91 (m, 13H), 2.03-2.13 (m, 7H), 2.27 (s, 3H), 3.96 (m, 1H), 4.21-4.24 (m, 2H), 4.59-4.63 (m, 2H), 6.78 (d, 2H, J = 8.3 Hz), 7.05 (d, 2H, J = 8.3 Hz) |
| 393 | 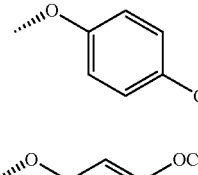 | ¹H-NMR (CDCl₃) δ 1.49-1.52 (m, 2H), 1.65-1.91 (m, 13H), 2.07-2.12 (m, 7H), 3.95-3.96 (m, 1H), 4.22-4.24 (m, 2H), 4.61-4.63 (m, 2H), 6.80 (d, 2H, J = 9.0 Hz), 7.02 (d, 2H, J = 8.8 Hz) |
| 394 | 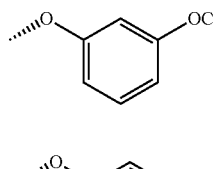 | ¹H-NMR (CDCl₃) δ 1.38 (s, 1H), 1.51-1.57 (m, 2H), 1.67-1.92 (m, 12H), 2.08-2.15 (m, 7H), 3.98 (br s, 1H), 4.25 (br s, 2H), 4.64-4.72 (m, 2H), 6.50 (t, 1H, J = 74.4 Hz), 6.64-6.75 (m, 3H), 7.21-7.26 (m, 1H) |
| 395 | 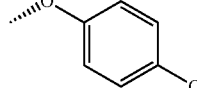 | ¹H-NMR (CDCl₃) δ 1.40 (s, 1H), 1.50-1.54 (m, 2H), 1.67-1.93 (m, 12H), 2.03-2.15 (m, 7H), 3.77 (s, 3H), 3.96-3.98 (m, 1H), 4.23 (br s, 2H), 4.47-4.58 (m, 1H), 4.64 (d, 1H, J = 7.3 Hz), 6.79-6.87 (m, 4H) |

Examples 396 to 418

Using the compounds obtained in a similar manner to Reference Examples 7 and 8 from the commercially available substituted pyridine derivative, the compounds were synthesized in a similar manner to Example 1.

TABLE 40

| Ex. No. | —Z¹—R² | NMR (solvent) δ |
|---|---|---|
| 396 | (2,6-disubstituted pyridine: 2-OMe, 6-Cl, 4-Cl) | ¹H-NMR (CDCl₃) δ 1.49-1.53 (m, 2H), 1.65-1.73 (m, 7H), 1.87-1.91 (m, 4H), 2.03-2.10 (m, 7H), 2.23-2.26 (m, 2H), 3.95-3.96 (m, 1H), 4.13-4.15 (m, 2H), 4.59 (d, 1H, J = 7.1 Hz), 5.34 (t, 1H, J = 4.5 Hz), 6.65 (s, 1H), 6.91 (s, 1H) |
| 397 | (pyridine: 2-OMe, 6-Me, 4-CF₃) | ¹H-NMR (CDCl₃) δ 1.40 (s, 1H), 1.52-1.56 (m, 3H), 1.68-1.75 (m, 6H), 1.90-1.92 (m, 4H), 2.02-2.03 (m, 2H), 2.18-2.23 (m, 6H), 2.46 (s, 3H), 3.96-3.97 (m, 1H), 4.14-4.16 (m, 2H), 4.60 (d, 1H, J = 7.6 Hz), 5.43 (t, 1H, J = 4.6 Hz), 6.70 (s, 1H), 6.88 (s, 1H) |
| 398 | (pyridine: 2-OMe, 6-Me, 4-Me) | ¹H-NMR (CDCl₃) δ 1.41 (s, 1H), 1.49-1.75 (m, 7H), 1.89-2.04 (m, 6H), 2.15-2.20 (m, 8H), 2.23 (s, 3H), 2.35 (s, 3H), 3.96 (m, 1H), 4.11-4.14 (m, 2H), 4.59 (d, 1H, J = 7.1 Hz), 5.34 (t, 1H, J = 4.5 Hz), 6.30 (s, 1H), 6.53 (s, 1H) |
| 399 | (pyridine: 2-OMe, 4-F) | ¹H-NMR (CDCl₃) δ 1.66-2.12 (m, 22H), 3.98 (s, 1H), 4.16 (s, 2H), 4.62 (d, 1H, J = 5.9 Hz), 5.37 (s, 1H), 6.40 (d, 1H, J = 10.3 Hz), 6.64 (s, 1H), 8.09 (t, 1H, J = 6.8 Hz) |
| 400 | (pyridine: 2-OMe, 3-F) | ¹H-NMR (CDCl₃) δ 1.50-1.54 (m, 2H), 1.66-2.28 (m, 20H), 3.99 (s, 1H), 4.17 (s, 2H), 4.63 (d, 1H, J = 7.2 Hz), 5.46 (s, 1H), 6.80-6.86 (m, 1H), 7.33 (t, 1H, J = 9.0 Hz), 7.89 (d, 1H, J = 4.8 Hz) |
| 401 | (pyridine: 2-OMe, 3-Cl) | ¹H-NMR (CDCl₃) δ 1.40-1.42 (m, 1H), 1.51-1.78 (m, 10H), 1.90-2.09 (m, 5H), 2.11-2.20 (m, 2H), 2.24-2.34 (m, 4H), 3.98-3.99 (m, 1H), 4.18-4.22 (m, 2H), 4.63 (d, 1H, J = 7.0 Hz), 5.47 (t, 1H, J = 4.3 Hz), 6.83 (dd, 1H, J = 7.5, 5.0 Hz), 7.65 (dd, 1H, J = 7.7, 1.7 Hz), 8.02 (dd, 1H, J = 5.0, 1.7 Hz) |
| 402 | (pyridine: 2-OMe, 3-F, 5-F) | ¹H-NMR (CDCl₃) δ 1.50-1.54 (m, 2H), 1.70-1.75 (m, 8H), 1.90-2.28 (m, 12H), 3.96-3.99 (m, 1H), 4.16 (s, 2H), 4.63 (d, 1H, J = 7.2 Hz), 5.39 (s, 1H), 7.18-7.24 (m, 1H), 7.79-7.80 (m, 1H) |
| 403 | (pyridine: 2-OMe, 3-CF₃) | ¹H-NMR (CDCl₃) δ 1.48-1.52 (m, 3H), 1.64-1.74 (m, 8H), 1.89-2.04 (m, 5H), 2.19-2.28 (m, 6H), 3.97-4.00 (m, 1H), 4.15-4.18 (m, 2H), 4.62 (d, 1H, J = 6.8 Hz), 5.51-5.54 (m, 1H), 6.95 (t, 1H, J = 6.1 Hz), 7.87 (d, 1H, J = 7.2 Hz), 8.28 (d, 1H, J = 3.9 Hz) |

TABLE 40-continued

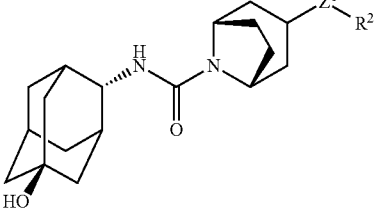

| Ex. No. | —Z¹—R² | NMR (solvent) δ |
|---|---|---|
| 404 | 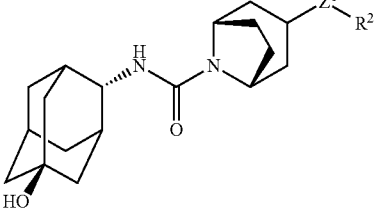 | ¹H-NMR (CDCl₃) δ 1.48-1.52 (m, 2H), 1.63-1.85 (m, 8H), 1.93-2.02 (m, 5H), 2.16-2.18 (m, 7H), 2.28 (s, 3H), 3.97-3.98 (m, 1H), 4.13-4.14 (m, 2H), 4.61 (d, 1H, J = 7.2 Hz), 5.25 (t, 1H, J = 4.3 Hz), 6.54 (d, 1H, J = 5.1 Hz), 7.86 (s, 1H) |
| 405 | 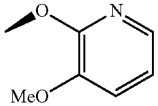 | ¹H-NMR (CDCl₃) δ 1.41 (s, 1H), 1.56-1.72 (m, 6H), 1.90-2.05 (m, 7H), 2.15-2.35 (m, 8H), 3.85 (s, 3H), 3.98-3.99 (m, 1H), 4.13-4.15 (m, 2H), 4.62 (d, 1H, J = 7.0 Hz), 5.43 (t, 1H, J = 4.5 Hz), 6.82 (dd, 1H, J = 7.8, 5.0 Hz), 7.06 (dd, 1H, J = 7.7, 1.5 Hz), 7.70 (dd, 1H, J = 5.1, 1.5 Hz) |
| 406 | 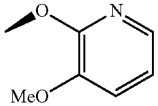 | ¹H-NMR (CDCl₃) δ 1.51-1.55 (m, 3H), 1.68-1.73 (m, 7H), 1.93-2.02 (m, 5H), 2.13-2.21 (m, 7H), 2.35 (d, 3H, J = 2.9 Hz), 3.95-3.97 (m, 1H), 4.12-4.14 (m, 2H), 4.60 (d, 1H, J - 7.1 Hz), 5.28-5.29 (m, 1H), 6.45 (dd, 1H, J = 8.7, 2.6 Hz), 7.23 (t, 1H, J = 8.7 Hz) |
| 407 | 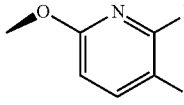 | ¹H-NMR (CDCl₃) δ 1.56-1.70 (m, 9H), 2.09 (s, 3H), 2.20-2.23 (m, 13H), 3.97-4.01 (m, 1H), 4.16-4.19 (m, 2H), 4.62 (d, 1H, J = 7.2 Hz), 5.40-5.43 (m, 1H), 6.76 (t, 1H, J = 6.1 Hz), 7.39 (d, 1H, J = 7.2 Hz), 7.96 (d, 1H, J = 4.0 Hz) |
| 408 | 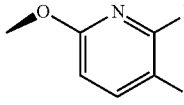 | ¹H-NMR (CDCl₃) δ 1.51-1.55 (m, 2H), 1.70-1.75 (m, 8H), 1.92-2.02 (m, 5H), 2.17-2.23 (m, 7H), 2.38 (s, 3H), 3.97 (d, 1H, J = 7.0 Hz), 4.13-4.17 (m, 2H), 4.61 (d, 1H, J = 7.3 Hz), 5.38-5.39 (m, 1H), 6.53 (s, 1H), 6.72 (s, 1H) |
| 409 | 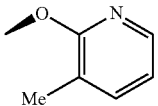 | ¹H-NMR (CDCl₃) δ 1.40 (s, 1H), 1.51-1.56 (m, 2H), 1.67-1.77 (m, 6H), 1.89-1.94 (m, 4H), 2.00-2.05 (m, 2H), 2.14-2.26 (m, 7H), 3.96-3.98 (m, 1H), 4.15 (br s, 2H), 4.61 (d, 1H, J = 10.0 Hz), 5.28 (t, 1H, J = 5.0 Hz), 6.67 (dd, 1H, J = 9.0, 3.7 Hz), 7.32-7.37 (m, 1H), 7.96 (d, 1H, J = 2.9 Hz) |
| 410 | 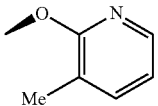 | ¹H-NMR (CDCl₃) δ 1.49-1.54 (m, 3H), 1.67-1.93 (m, 13H), 2.03-2.16 (m, 6H), 2.26 (s, 3H), 3.97-3.99 (m, 1H), 4.21-4.24 (m, 2H), 4.65 (d, 1H, J = 7.5 Hz), 5.46-5.57 (m, 1H), 6.47 (s, 1H), 6.66 (d, 1H, J = 5.1 Hz), 7.96 (d, 1H, J = 5.1 Hz) |
| 411 | 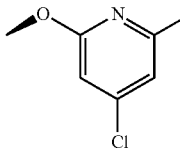 | ¹H-NMR (CDCl₃) δ 1.36 (s, 1H), 1.51-1.57 (m, 2H), 1.67-1.92 (m, 12H), 2.05-2.15 (m, 7H), 3.97 (br s, 1H), 4.23 (br s, 2H), 4.65 (d, 1H, J = 7.6 Hz), 5.47-5.55 (m, 1H), 6.67-6.68 (m, 1H), 6.84-6.85 (m, 1H), 8.00 (d, 1H, J = 5.6 Hz) |
| 412 | 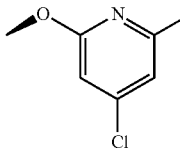 | ¹H-NMR (CDCl₃) δ 1.39-1.56 (m, 3H), 1.60-1.96 (m, 11H), 2.02-2.23 (m, 7H), 2.41 (s, 3H), 3.94-4.02 (m, 1H), 4.20-4.28 (m, 2H), 4.64 (d, 1H, J = 7.5 Hz), 5.46-5.57 (m, 1H), 6.44 (d, 1H, J = 8.3 Hz), 6.68 (d, 1H, J = 7.2 Hz), 7.42 (dd, 1H, J = 8.3, 7.2 Hz) |
| 413 | 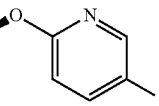 | ¹H-NMR (CDCl₃) δ 1.36-1.43 (m, 1H), 1.48-1.56 (m, 2H), 1.57-1.95 (m, 11H), 2.02-2.20 (m, 7H), 3.94-4.02 (m, 1H), 4.19-4.27 (m, 2H), 4.65 (d, 1H, J = 7.5 Hz), 5.38-5.49 (m, 1H), 6.62 (dd, 1H, J = 9.0, 3.7 Hz), 7.27-7.34 (m, 1H), 7.94 (d, 1H, J = 3.1 Hz) |
| 414 | 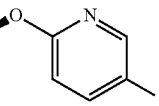 | ¹H-NMR (CDCl₃) δ 1.45-1.58 (m, 3H), 1.61-1.95 (m, 11H), 2.04-2.20 (m, 7H), 3.93-4.01 (m, 1H), 4.22-4.30 (m, 2H), 4.61-4.74 (m, 2H), 7.17 (dd, 1H, J = 8.8, 2.9 Hz), 7.22 (d, 1H, J = 8.6 Hz), 8.04 (d, 1H, J = 2.8 Hz) |

TABLE 40-continued

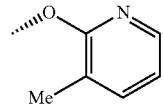

| Ex. No. | —Z¹—R² | NMR (solvent) δ |
|---|---|---|
| 415 | 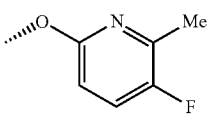 | $^1$H-NMR (CDCl$_3$) δ 1.39-1.57 (m, 3H), 1.60-1.99 (m, 11H), 2.02-2.22 (m, 7H), 2.11 (s, 3H), 3.96-4.03 (m, 1H), 4.19-4.28 (m, 2H), 4.66 (d, 1H, J = 7.3 Hz), 5.49-5.62 (m, 1H), 6.74 (dd, 1H, J = 7.1, 5.0 Hz), 7.35 (dq, 1H, J = 7.2, 0.9 Hz), 7.94 (dq, 1H, J = 5.0, 0.8 Hz) |
| 416 | 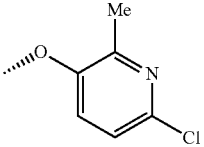 | $^1$H-NMR (CDCl$_3$) δ 1.41 (br s, 1H), 1.52 (br d, 2H, J = 12.8 Hz), 1.59-1.96 (m, 11H), 2.02-2.22 (m, 7H), 2.38 (d, 3H, J = 3.1 Hz), 3.97 (d, 1H, J = 7.5 Hz), 4.23 (s, 2H), 4.64 (d, 1H, J = 7.3 Hz), 5.36-5.50 (m, 1H), 6.43 (dd, 1H, J = 8.9, 2.8 Hz), 7.21 (t, 1H, J = 8.6 Hz) |
| 417 | 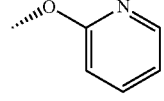 | $^1$H-NMR (CDCl$_3$) δ 1.41 (br s, 1H), 1.54 (br, d, 2H, J = 13.4 Hz), 1.59-1.96 (m, 11H), 2.04-2.20 (m, 7H), 2.38 (s, 3H), 3.95-4.02 (m, 1H), 4.23-4.29 (m, 2H), 4.53-4.69 (m, 2H), 7.05-7.12 (m, 2H) |
| 418 | 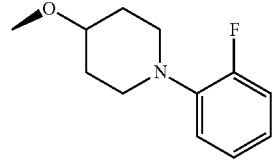 | $^1$H-NMR (CDCl$_3$) δ 1.44-1.57 (m, 3H), 1.62-1.98 (m, 11H), 2.02-2.22 (m, 7H), 3.95-4.02 (m, 1H), 4.20-4.27 (m, 2H), 4.65 (d, 1H, J = 7.3 Hz), 5.48-5.59 (m, 1H), 6.64 (dt, 1H, J = 8.3, 0.9 Hz), 6.83 (ddd, 1H, J = 7.1, 5.0, 1.0 Hz), 7.53 (ddd, 1H, J = 8.7, 6.7, 1.6 Hz), 8.11 (dq, 1H, J = 5.0, 0.9 Hz) |

Examples 419 to 424

Using the compounds obtained in a similar manner to Reference Example 24, the title compounds were synthesized in a similar manner to Example 1.

TABLE 41

| Ex. No. | —Z¹—R² | NMR (solvent) δ |
|---|---|---|
| 419 |  | $^1$H-NMR (CDCl$_3$) δ 1.37-1.81 (m, 12H), 1.85-1.98 (m, 6H), 2.00-2.16 (m, 5H), 2.17-2.25 (m, 2H), 2.90-3.02 (m, 2H), 3.27-3.38 (m, 2H), 3.45-3.56 (m, 1H), 3.71-3.77 (m, 1H), 3.91-3.99 (m, 1H), 4.10 (br s, 2H), 4.58 (d, 1H, J = 7.2 Hz), 6.84-7.01 (m, 4H). |

TABLE 41-continued
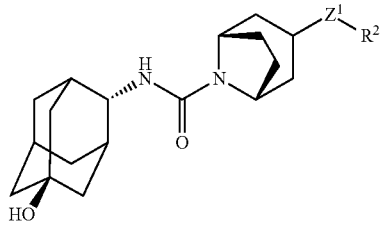
| Ex. No. | —Z¹—R² | NMR (solvent) δ |
|---|---|---|
| 420 | 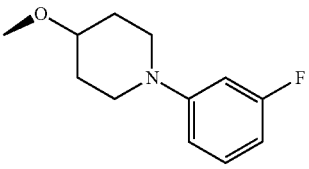 | ¹H-NMR (CDCl₃) δ 1.46-1.56 (m, 3H), 1.61-1.82 (m, 9H), 1.84-1.99 (m, 6H), 2.01-2.25 (m, 7H), 3.01-3.12 (m, 2H), 3.38-3.59 (m, 3H), 3.71-3.78 (m, 1H), 3.91-3.99 (m, 1H), 4.06-4.17 (m, 2H), 4.58 (d, 1H, J = 7.5 Hz), 6.49 (td, 1H, J = 8.2, 2.4 Hz), 6.60 (dt, 1H, J = 12.7, 2.4 Hz), 6.68 (dd, 1H, J = 8.3, 2.4 Hz), 7.17 (dd, 1H, J = 15.4, 8.3 Hz). |
| 421 | 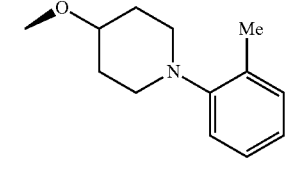 | ¹H-NMR (CDCl₃) δ 1.46-1.83 (m, 12H), 1.85-1.99 (m, 6H), 2.01-2.27 (m, 7H), 2.89-3.03 (m, 2H), 3.27-3.38 (m, 2H), 3.46-3.56 (m, 1H), 3.70-3.79 (m, 1H), 3.91-3.99 (m, 1H), 4.10 (br s, 2H), 4.57 (d, 1H, J = 7.3 Hz), 6.85-7.01 (m, 4H). |
| 422 | 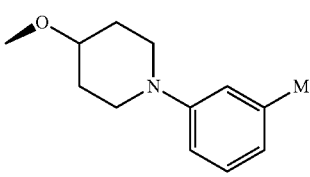 | ¹H-NMR (CDCl₃) δ 1.47-1.62 (m, 3H), 1.64.1.83 (m, 9H), 1.86-1.98 (m, 6H), 2.01-2.17 (m, 7H), 2.20-2.27 (m, 2H), 2.30 (s, 3H), 2.65-2.77 (m, 2H), 3.01-3.13 (m, 2H), 3.43-3.54 (m, 1H), 3.72-3.79 (m, 1H), 3.91-3.99 (m, 1H), 4.10 (br s, 2H), 4.58 (d, 1H, J = 7.3 Hz), 6.92-7.04 (m, 2H), 7.12-7.19 (m, 2H). |
| 423 | 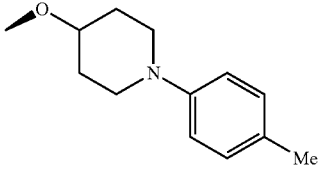 | ¹H-NMR (CDCl₃) δ 1.42-1.56 (m, 3H), 1.60-1.82 (m, 9H), 1.85-1.97 (m, 6H), 2.00-2.25 (m, 7H), 2.31 (s, 3H), 2.96-3.08 (m, 2H), 3.37-3.56 (m, 3H), 3.71-3.78 (m, 1H), 3.92-3.99 (m, 1H), 4.09 (br s, 2H), 4.58 (d, 1H, J = 7.3 Hz), 6.66 (d, 1H, J = 7.5 Hz), 6.73-6.80 (m, 2H), 7.10-7.18 (m, 1H). |
| 424 |  | ¹H-NMR (CDCl₃) δ 1.52-1.56 (m, 3H), 1.59-1.82 (m, 9H), 1.85-1.97 (m, 6H), 2.00-2.24 (m, 7H), 2.26 (s, 3H), 2.91-3.01 (m, 2H), 3.32-3.43 (m, 2H), 3.45-3.54 (m, 1H), 3.70-3.78 (m, 1H), 3.92-3.99 (m, 1H), 4.09 (br s, 2H), 4.57 (d, 1H, J = 7.3 Hz), 6.86 (d, 2H, J = 8.6 Hz), 7.06 (d, 2H, J = 8.3 Hz). |

Examples 425 to 428

Using the compounds obtained in a similar manner to Reference Example 25, the title compounds were synthesized in a similar manner to Example 1.

TABLE 42

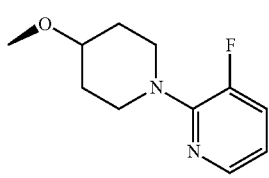

| Ex. No. | —Z¹—R² | NMR (solvent) δ |
|---|---|---|
| 425 | 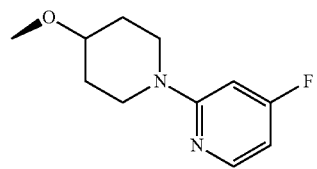 | ¹H-NMR (CDCl₃) δ 1.41-1.56 (m, 3H), 1.61-1.82 (m, 9H), 1.85-1.97 (m, 6H), 2.00-2.17 (m, 5H), 2.18-2.27 (m, 2H), 3.21-3.32 (m, 2H), 3.52-3.62 (m, 1H), 3.67-3.78 (m, 3H), 3.92-3.99 (m, 1H), 4.05-4.17 (m, 2H), 4.58 (d, 1H, J = 7.3 Hz), 6.72 (ddd, 1H, J = 7.9, 4.8, 3.0 Hz), 7.21 (ddd, 1H, J = 13.2, 7.9, 1.5 Hz), 7.99 (dt, 1H, J = 4.9, 1.4 Hz) |
| 426 | 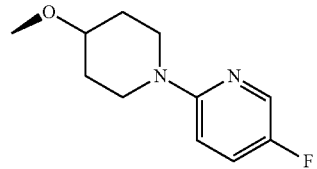 | ¹H-NMR (CDCl₃) δ 1.41-1.56 (m, 3H), 1.59-1.99 (m, 15H), 2.02-2.22 (m, 7H), 3.22-3.34 (m, 2H), 3.50-3.67 (m, 3H), 3.72-3.78 (m, 1H), 3.92-3.98 (m, 1H), 4.11 (br s, 2H), 4.58 (d, 1H, J = 7.0 Hz), 6.18 (s, 1H), 6.54 (d, 1H, J = 5.3 Hz), 7.86 (d, 1H, J = 6.2 Hz) |
| 427 | 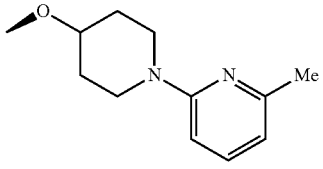 | ¹H-NMR (CDCl₃) δ 1.39-1.55 (m, 3H), 1.58-1.98 (m, 15H), 2.02-2.25 (m, 7H), 3.24-3.38 (m, 2H), 3.52-3.62 (m, 1H), 3.69-3.79 (m, 3H), 3.92-3.99 (m, 1H), 4.06-4.14 (m, 2H), 4.57 (d, 1H, J = 7.5 Hz), 6.63 (dd, 1H, J = 9.4, 3.3 Hz), 7.19-7.27 (m, 1H), 8.00-8.07 (m, 1H) |
| 428 | | ¹H-NMR (CDCl₃) δ 1.45-1.56 (m, 3H), 1.58-1.99 (m, 15H), 2.01-2.25 (m, 7H), 3.33-3.45 (m, 2H), 3.54-3.64 (m, 1H), 3.72-3.84 (m, 3H), 3.92-3.99 (m, 1H), 4.07-4.15 (m, 2H), 4.58 (d, 1H, J = 7.2 Hz), 6.13 (dd, 1H, J = 7.7, 2.9 Hz), 6.43 (dd, 1H, J = 8.3, 2.7 Hz), 7.50 (q, 1H, J = 8.3 Hz) |

Example 429 and Example 430

Using the compound obtained in Reference Example 60 or compounds synthesized in a similar manner to Reference Example 60, the title compounds were synthesized in a similar manner to Example 1.

TABLE 43

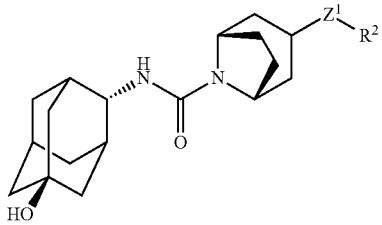

| Ex. No. | —Z¹—R² | NMR (solvent) δ |
|---|---|---|
| 429 | 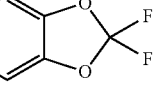 | $^1$H-NMR (CDCl$_3$) δ 1.41 (s, 1H), 1.50-1.82 (m, 9H), 1.84-2.23 (m, 12H), 3.71-3.73 (m, 1H), 3.95-3.97 (m, 1H), 4.12-4.17 (m, 2H), 4.46 (s, 2H), 4.59 (d, 1H, J = 7.3 Hz), 7.03 (d, 2H, J = 7.5 Hz), 7.08 (s, 1H) |
| 430 | 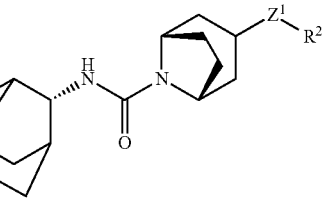 | $^1$H-NMR (CDCl$_3$) δ 1.54-1.69 (m, 12H), 1.96 (dq, 5H, J = 24.8, 8.1 Hz), 2.13 (s, 3H), 3.81-3.88 (m, 1H), 3.94-3.95 (m, 1H), 4.22-4.27 (m, 6H), 4.39 (s, 2H), 4.60 (d, 1H, J = 7.2 Hz), 6.76-6.84 (m, 3H) |

Example 431 and Example 432

Using the compounds obtained in Reference Examples 60 and 61, the title compounds were synthesized in a similar manner to Example 1.

TABLE 44

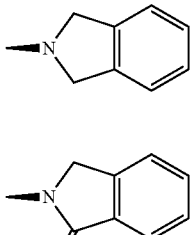

| Ex. No. | —Z¹—R² | NMR (solvent) δ |
|---|---|---|
| 431 | | $^1$H-NMR (CDCl$_3$) δ 1.50-1.55 (m, 2H), 1.70-1.75 (m, 6H), 1.91-1.95 (m, 6H), 2.05-2.14 (m, 8H), 2.83 (s, 1H), 3.98 (s, 5H), 4.11-4.13 (m, 2H), 4.62 (d, 1H, J = 7.2 Hz), 7.21 (s, 4H) |
| 432 | | $^1$H-NMR (CDCl$_3$) δ 1.33-1.47 (m, 1H), 1.48-1.85 (m, 12H), 1.86-1.99 (m, 1H), 2.01-2.25 (m, 6H), 2.51-2.63 (m, 2H), 3.95-4.01 (m, 1H), 4.18-4.40 (m, 5H), 4.68-4.75 (m, 1H), 7.43-7.57 (m, 3H), 7.83-7.84 (m, 1H) |

Examples 433 to 438

Using the compound synthesized in a similar manner to Reference Examples 6 and 10, the title compounds were synthesized in a similar manner to Example 1.

TABLE 45

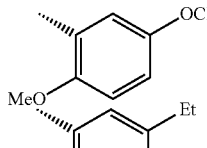

| Ex. No. | —Z¹—R² | NMR (solvent) δ |
|---|---|---|
| 433 | 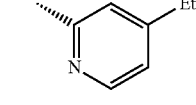 | ¹H-NMR (DMSO-d₆) δ 1.28 (d, J = 12.4 Hz, 2H), 1.48-1.51 (m, 2H), 1.59-1.99 (m, 16H), 3.48 (m, 1H), 3.68 (m, 1H), 3.78 (s, 3H), 4.09 (m, 1H), 4.30 (m, 2H), 4.37 (s, 1H), 5.85 (d, J = 5.6 Hz, 1H), 6.95 (m, 1H), 7.02 (d, J = 8.8 Hz, 1H), 7.15 (dd, J = 2.8, 8.8 Hz, 1H) |
| 434 | 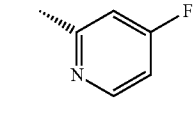 | ¹H-NMR (DMSO-d₆) δ 1.09 (t, J = 7.2 Hz, 3H), 1.21 (d, J = 12.4 Hz, 2H), 1.52-1.91 (m, 20H), 2.43 (m, 1H), 3.61 (m, 1H), 4.04-4.07 (m, 1H), 4.26 (m, 2H), 4.33 (s, 1H), 5.72 (d, J = 6.0 Hz, 1H), 6.96 (d, J = 5.2 Hz, 1H), 6.99 (s, 1H), 8.26 (d, J = 4.8 Hz, 1H) |
| 435 | 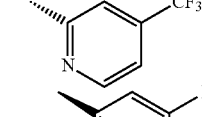 | ¹H-NMR (DMSO-d₆) δ 0.96 (t, J = 7.2 Hz, 3H), 1.25-1.29 (m, 2H), 1.35 (t, J = 12.4 Hz, 2H), 1.58-1.70 (m, 10H), 1.86-2.00 (m, 7H), 2.21-2.29 (m, 2H), 2.87 (m, 1H), 3.67 (m, 1H), 3.84 (t, J = 6.4 Hz, 2H), 4.31 (m, 2H), 4.37 (s, 1H), 5.77 (d, J = 6.4 Hz, 1H), 6.85-6.93 (m, 2H), 7.01 (dd, J = 2.8, 10.4 Hz, 1H) |
| 436 | 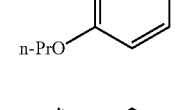 | ¹H-NMR (DMSO-d₆) δ 1.51-2.16 (m, 22H), 3.33 (m, 1H), 3.99 (m, 1H), 4.30 (m, 2H), 4.65 (d, J = 7.2 Hz, 1H), 6.85-6.89 (m, 2H), 8.45-8.49 (m, 1H) |
| 437 | 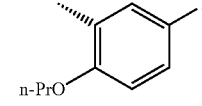 | ¹H-NMR (DMSO-d₆) δ 0.96 (t, J = 7.2 Hz, 3H), 1.25-1.29 (m, 2H), 1.35 (t, J = 12.4 Hz, 2H), 1.58-1.70 (m, 10H), 1.86-2.00 (m, 7H), 2.21-2.29 (m, 2H), 2.87 (m, 1H), 3.67 (m, 1H), 3.84 (t, J = 6.4 Hz, 2H), 4.31 (m, 2H), 4.37 (s, 1H), 5.77 (d, J = 6.4 Hz, 1H), 6.85-6.93 (m, 2H), 7.01 (dd, J = 2.8, 10.4 Hz, 1H) |
| 438 | 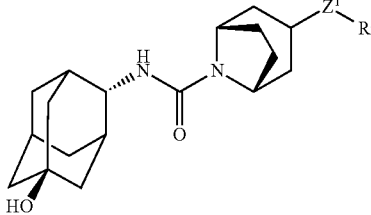 | ¹H-NMR (DMSO-d₆) δ 1.01 (t, J = 7.2 Hz, 3H), 1.28 (d, J = 12.4 Hz, 2H), 1.50-1.78 (m, 14H), 1.89 (m, 4H), 1.97 (m, 3H), 3.48 (m, 1H), 3.67 (m, 1H), 3.88 (t, J = 6.4 Hz, 2H), 4.32 (m, 2H), 4.37 (s, 1H), 5.81 (d, J = 6.4 Hz, 1H), 6.78-6.82 (m, 1H), 6.91-6.94 (m, 2H) |

In addition to the compounds of Examples as mentioned above, the following compounds are also included within the scope of the compounds of the formula (1).

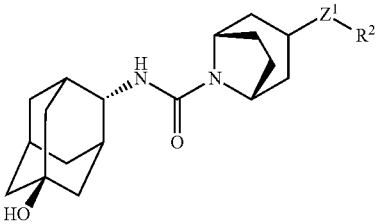

| | —Z¹—R² |
|---|---|
| 1 | 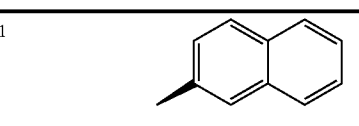 |
| 2 | 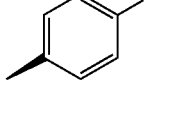 |

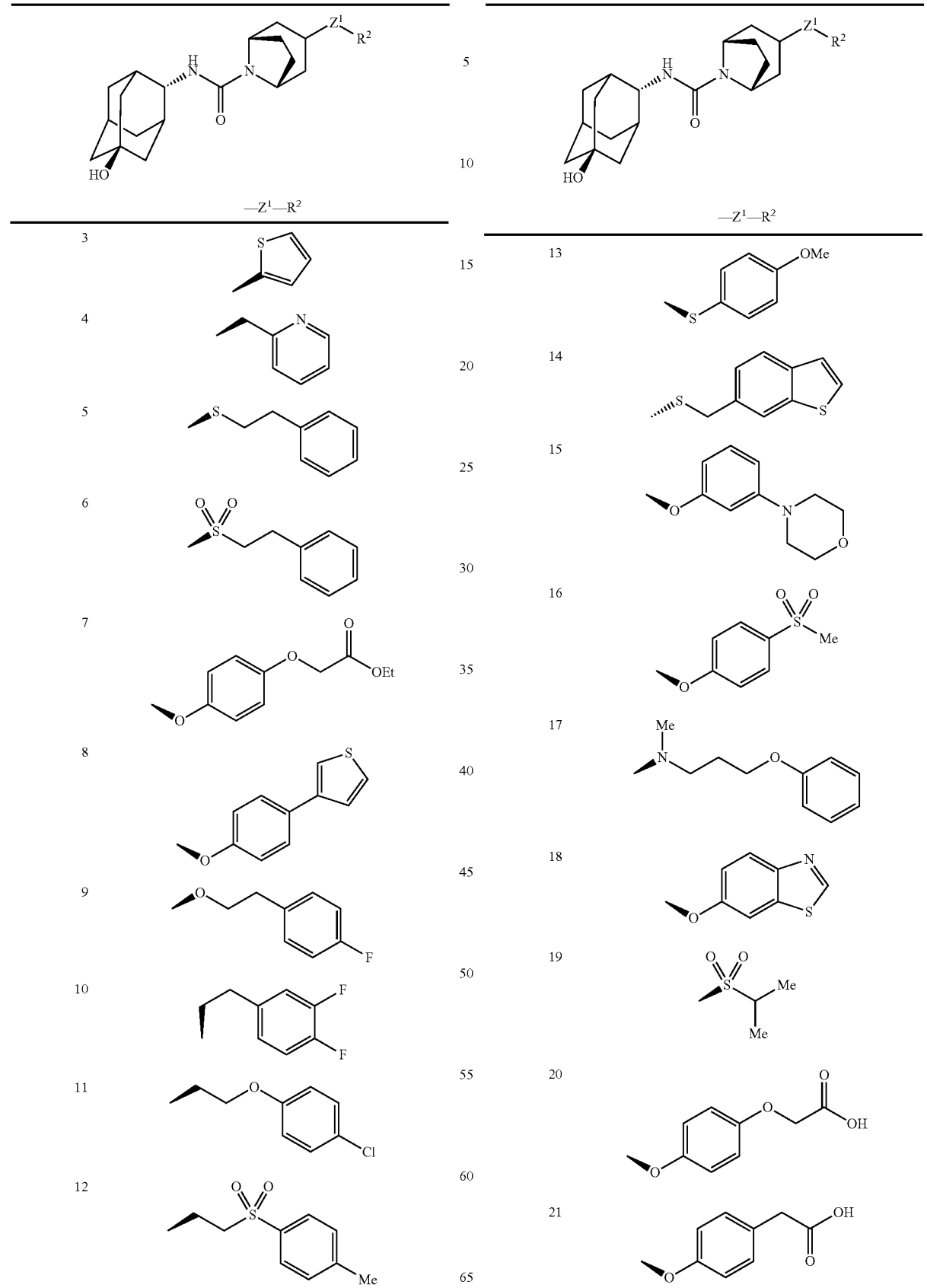

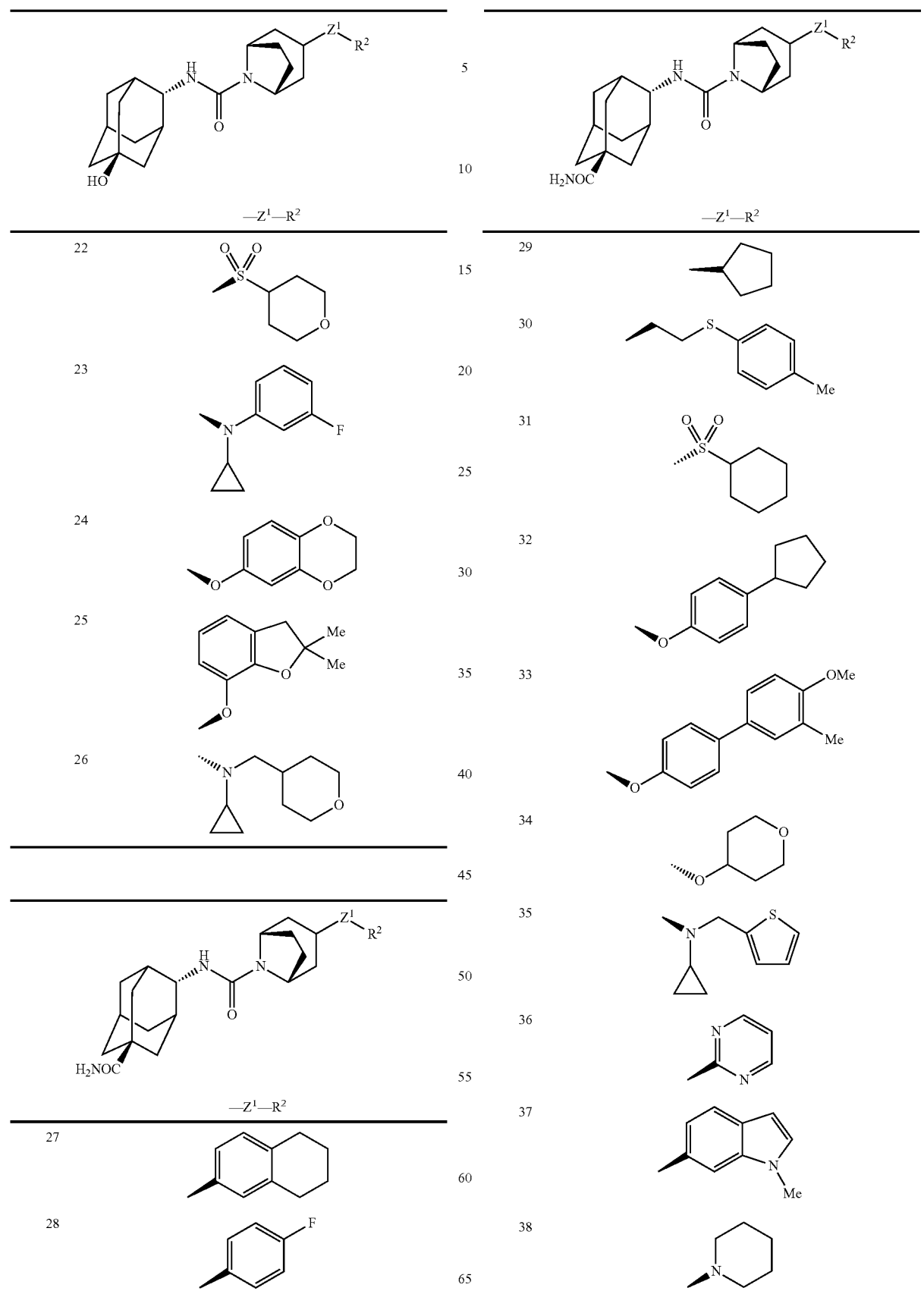

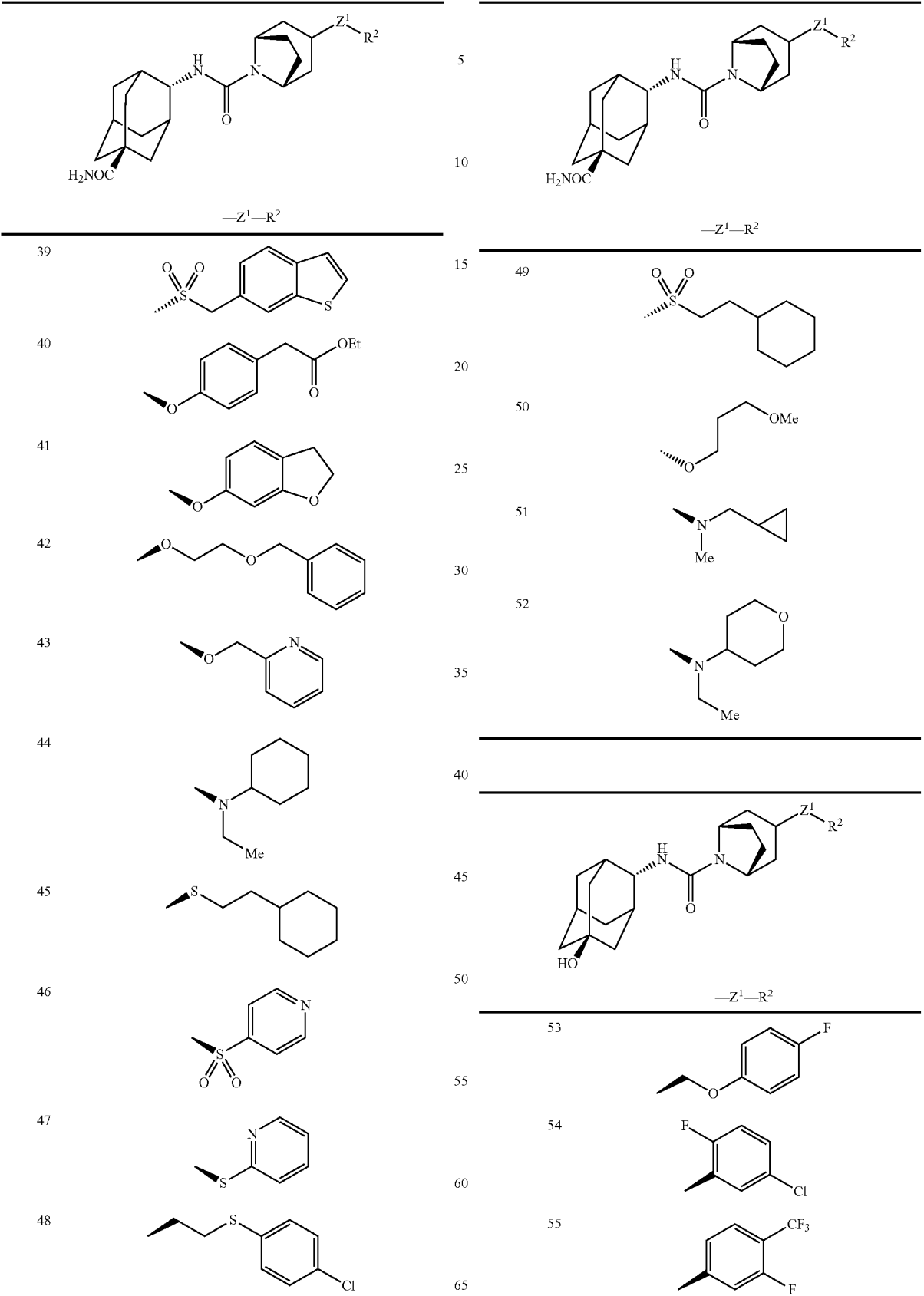

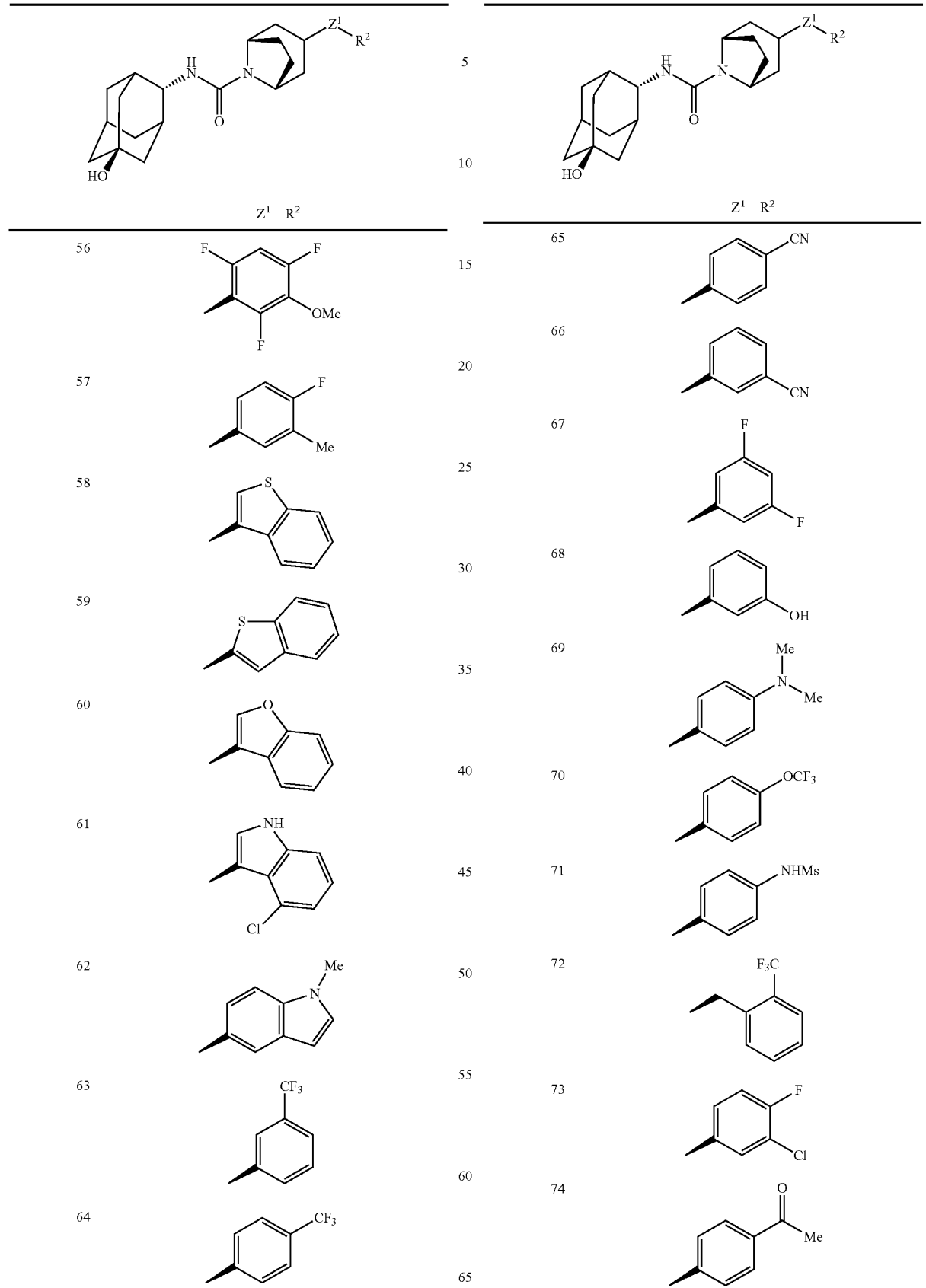

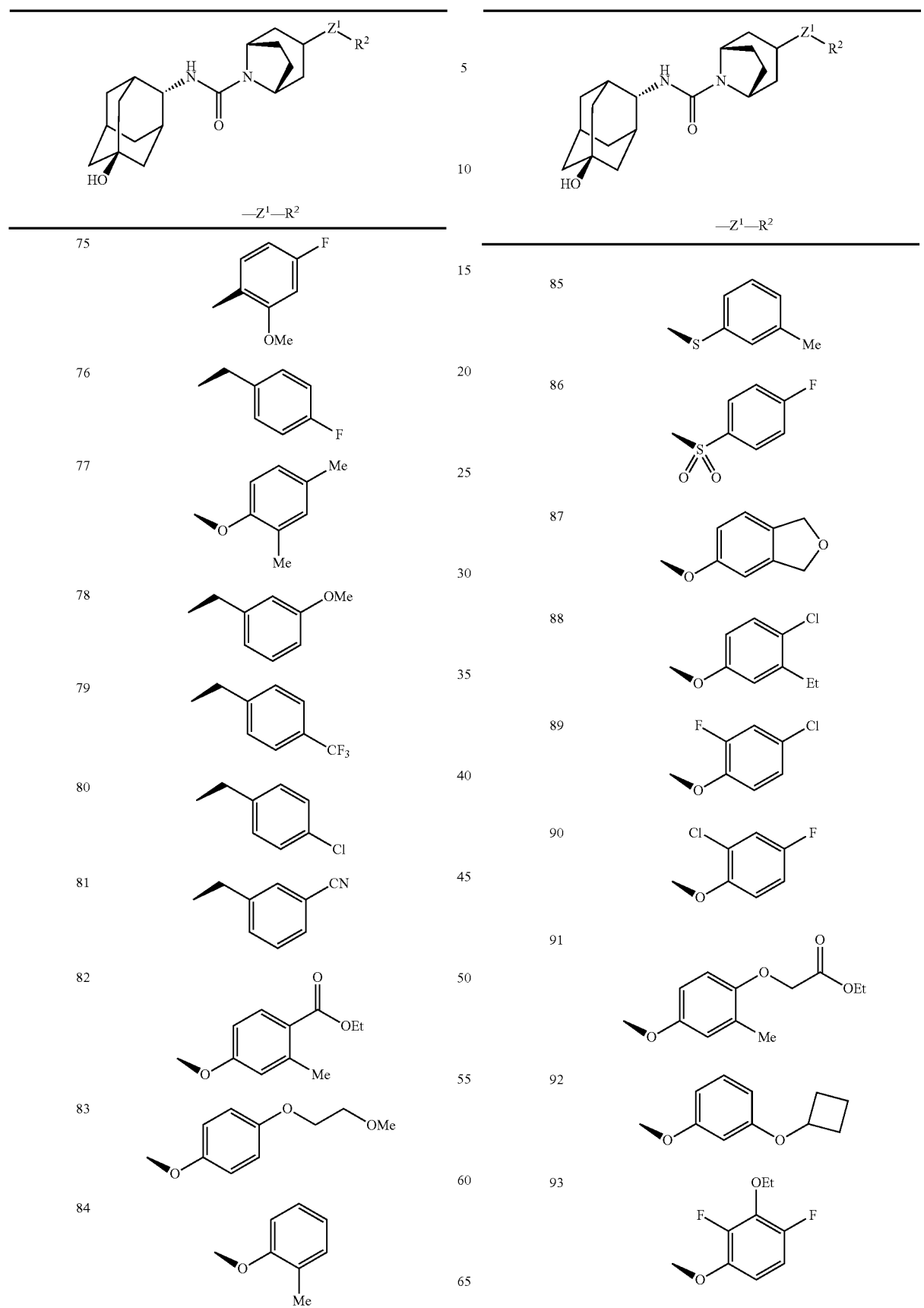

| 221 -continued | | 222 -continued | |
|---|---|---|---|
| 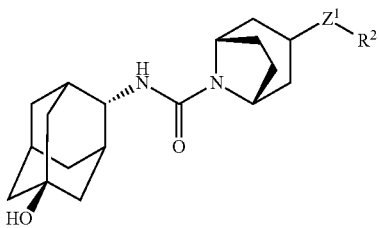 | | 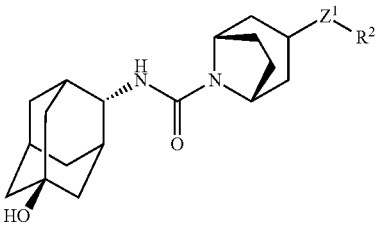 | |
| —Z¹—R² | | —Z¹—R² | |
| 94 | 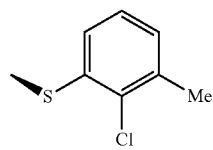 | 103 | 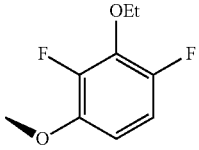 |
| 95 | 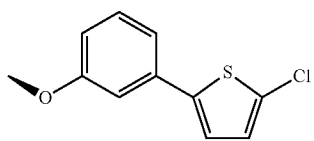 | 104 | 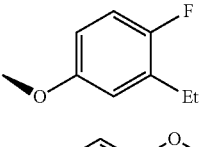 |
| 96 | 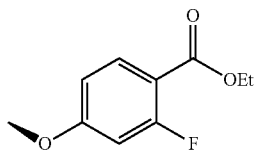 | 105 | 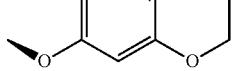 |
| 97 | 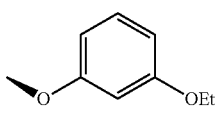 | 106 | 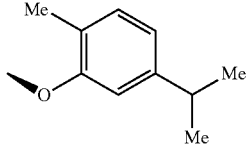 |
| 98 | 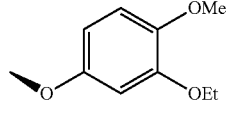 | 107 | 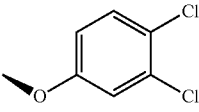 |
| 99 | 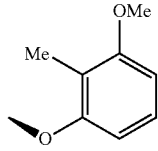 | 108 | 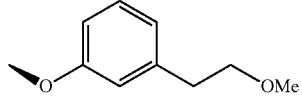 |
| 100 | 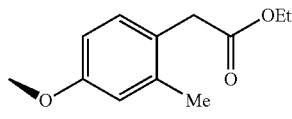 | 109 | 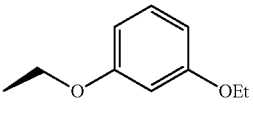 |
| 101 | 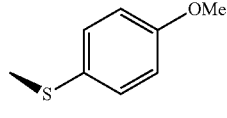 | 110 | 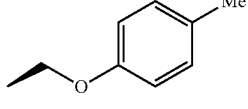 |
| 102 | 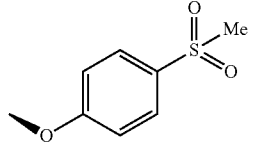 | 111 | 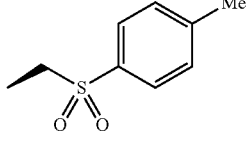 |
| | | 112 | 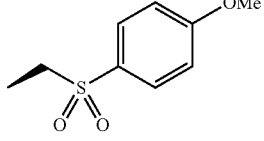 |

| 223 -continued | | 224 -continued | |
|---|---|---|---|
| 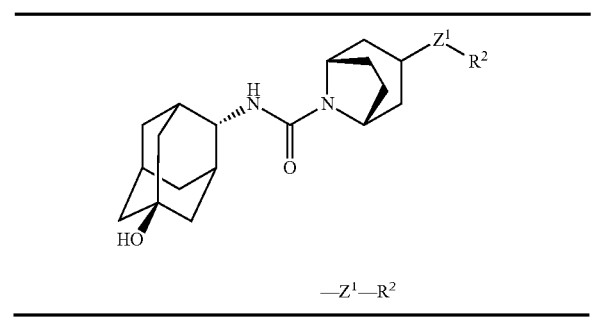 | | 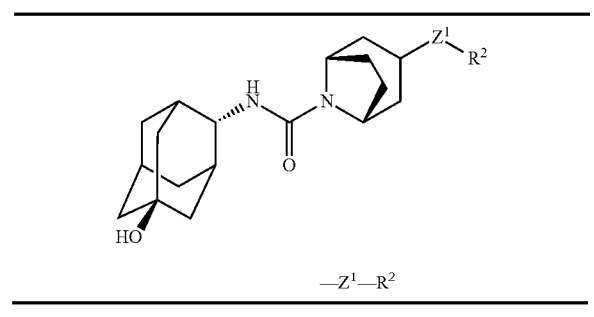 | |
| —Z¹—R² | | —Z¹—R² | |
| 113 | 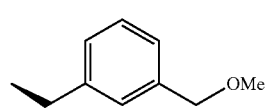 | 122 | 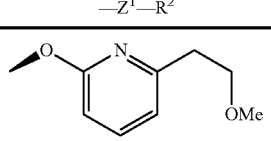 |
| 114 | 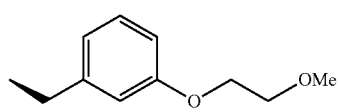 | 123 | 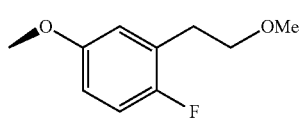 |
| 115 | 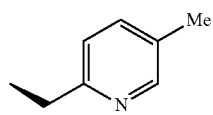 | 124 | 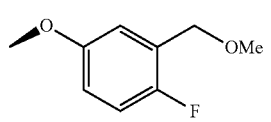 |
| 116 | 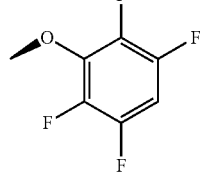 | 125 | 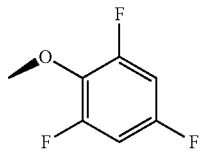 |
| 117 | 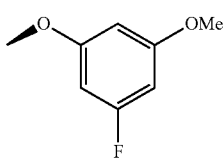 | 126 | 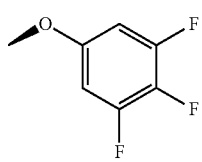 |
| 118 | 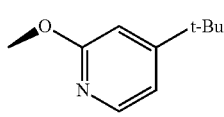 | 127 | 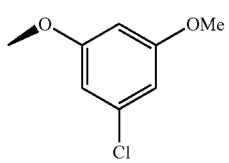 |
| 119 | 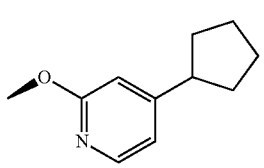 | 128 | 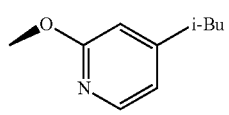 |
| 120 | 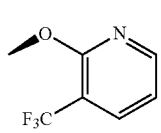 | 129 | 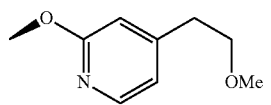 |
| 121 | 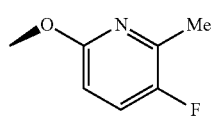 | 130 | 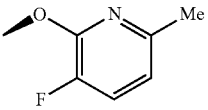 |
| | | 131 | 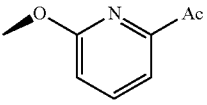 |

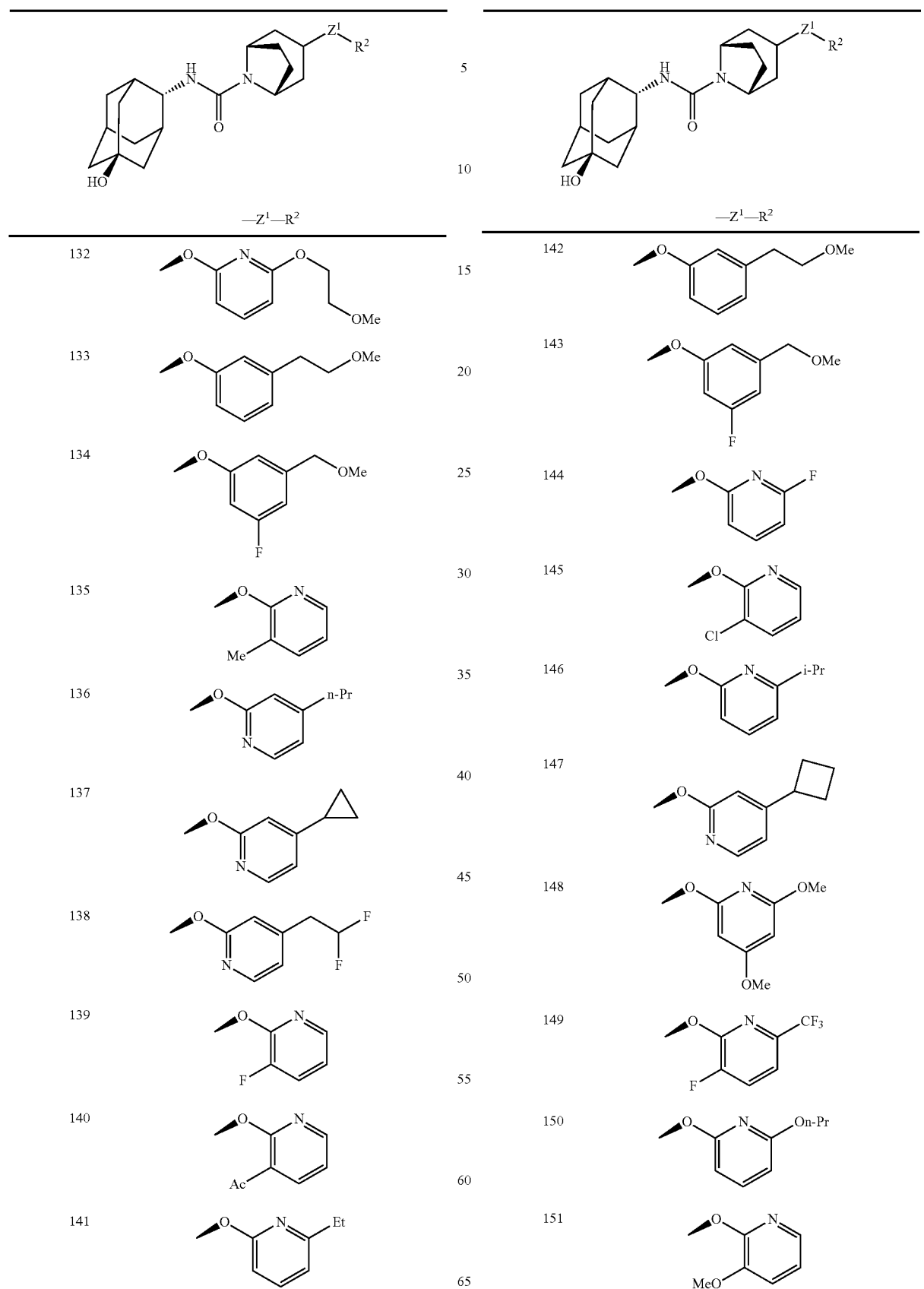

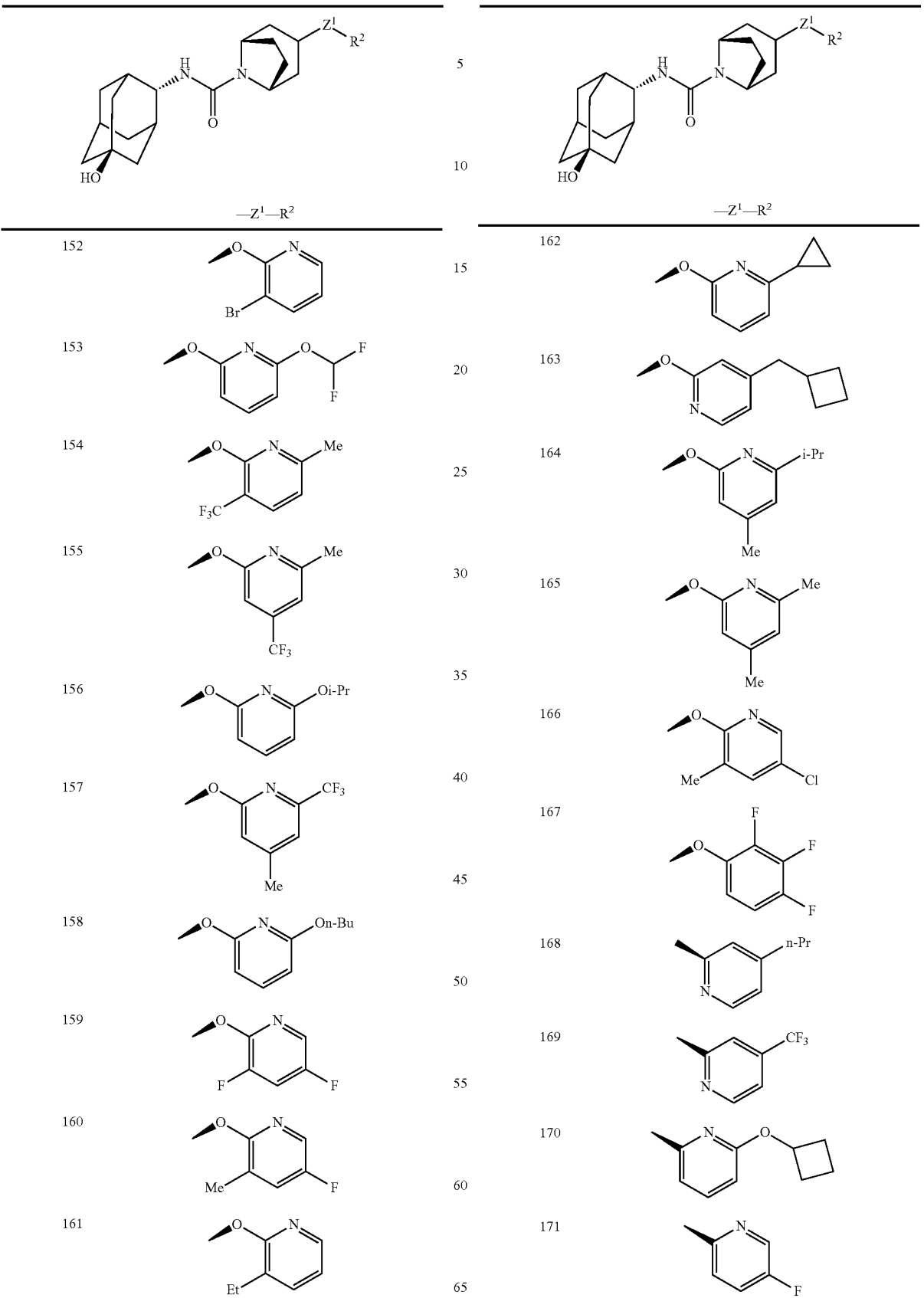

| | 229 -continued | | 230 -continued |
|---|---|---|---|
| 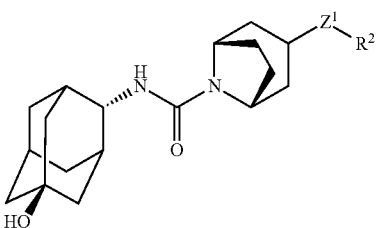 | | 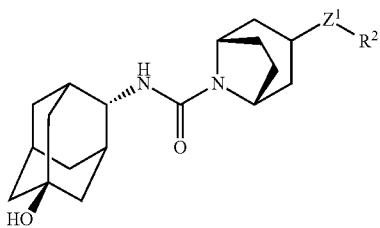 | |
| | —Z¹—R² | | —Z¹—R² |
| 172 | 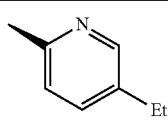 | 182 | 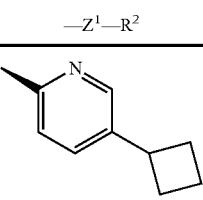 |
| 173 | 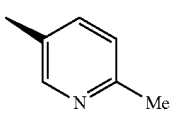 | 183 | 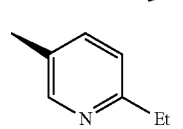 |
| 174 | 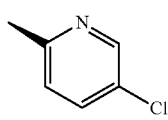 | 184 | 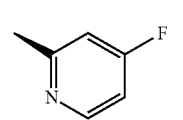 |
| 175 | 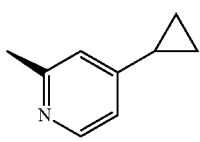 | 185 | 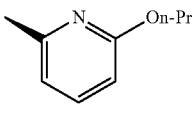 |
| 176 | 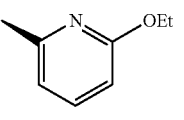 | 186 | 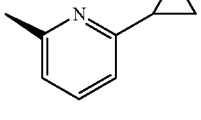 |
| 177 | 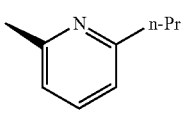 | 187 | 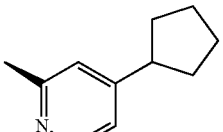 |
| 178 | 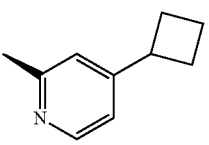 | 188 | 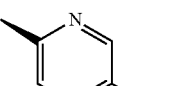 |
| 179 | 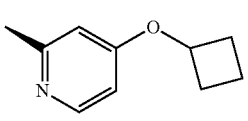 | 189 | 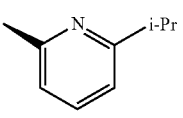 |
| 180 | 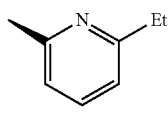 | 190 | 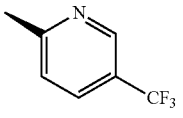 |
| 181 | 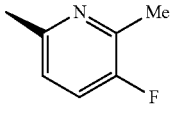 | 191 | 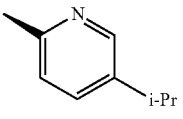 |

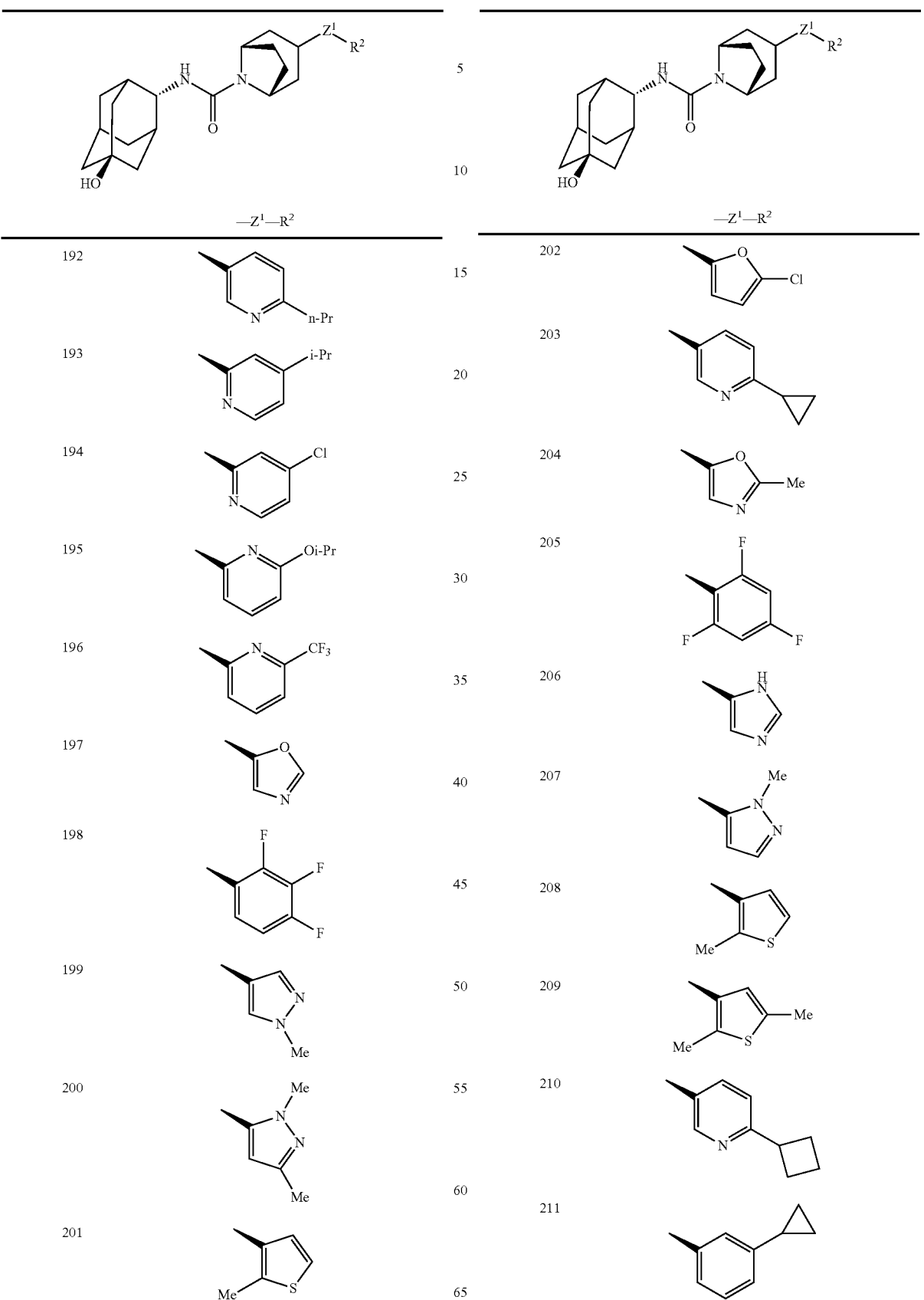

| 233 -continued | | 234 -continued | |
|---|---|---|---|
| 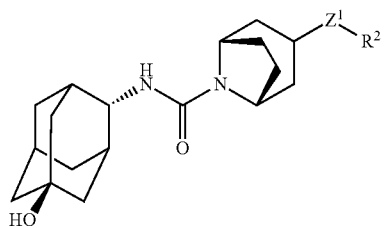 | | 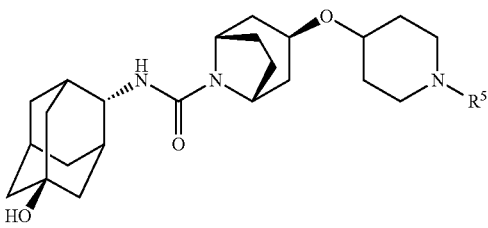 | |
| —Z¹—R² | | R⁵ | |
| 212 | 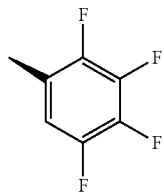 | 219 | 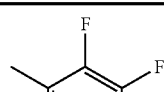 |
| 213 | 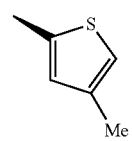 | 220 | 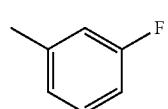 |
| 214 | 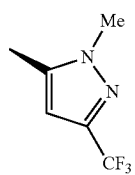 | 221 | 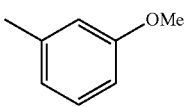 |
| 215 | 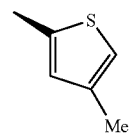 | 222 | 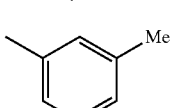 |
| 216 | 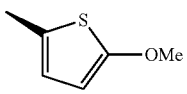 | 223 | 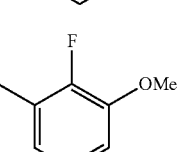 |
| 217 | 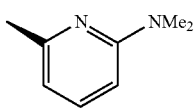 | 224 | 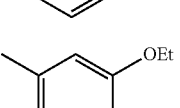 |
| 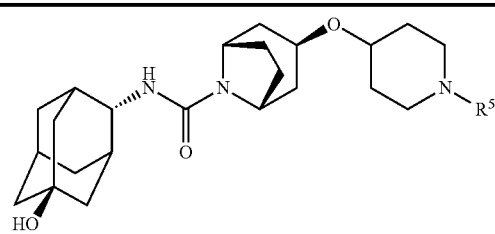 | | 225 | 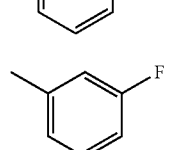 |
| R⁵ | | 226 | 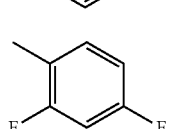 |
| 218 | 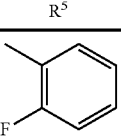 | 227 | 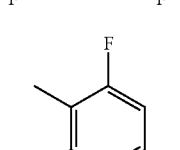 |
|  |  | 228 | 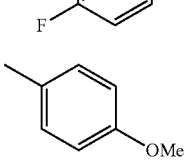 |

235
-continued
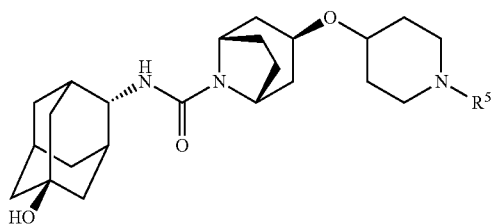
| | R⁵ |
|---|---|
| 229 | 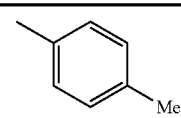 |
| 230 | 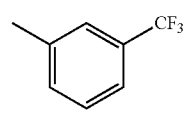 |
| 231 | 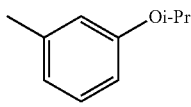 |
| 232 | 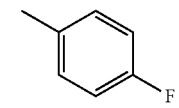 |
| 233 | 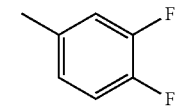 |
| 234 | 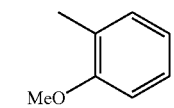 |
| 235 | 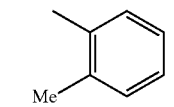 |
| 236 | 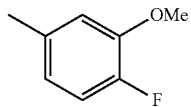 |
| 237 | 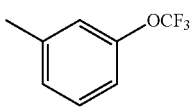 |
| 238 | 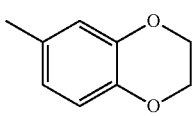 |
| 239 | 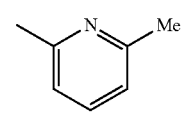 |
236
-continued
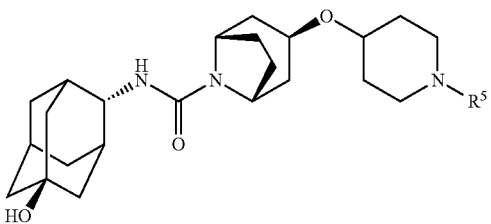
| | R⁵ |
|---|---|
| 240 | 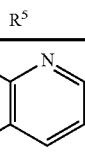 |
| 241 | 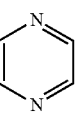 |
| 242 | 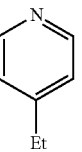 |
| 243 | 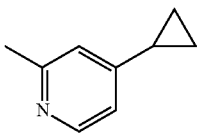 |
| 244 | 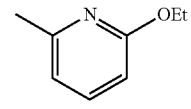 |
| 245 | 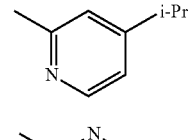 |
| 246 | 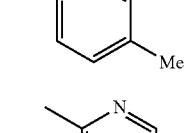 |
| 247 | 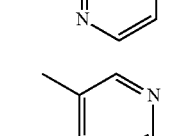 |
| 248 | 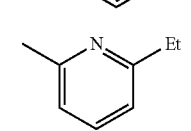 |
| 249 | 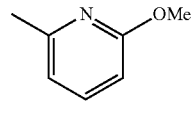 |
| 250 |  |

-continued

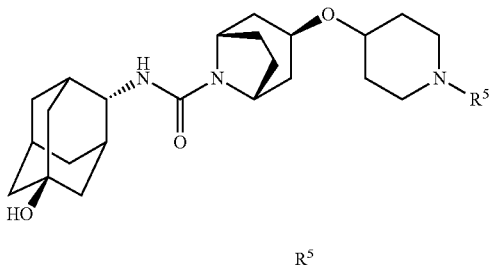

| | R[5] |
|---|---|
| 251 | 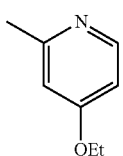 |
| 252 | 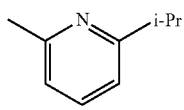 |
| 253 | 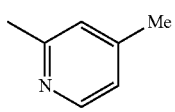 |
| 254 | 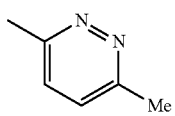 |
| 255 | 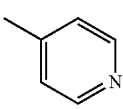 |
| 256 | 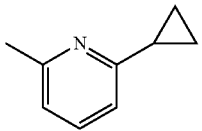 |
| 257 | 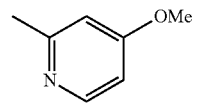 |
| 258 | 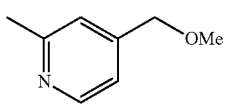 |
| 259 | 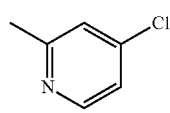 |

Experiment 1

Inhibitory Activity Assay Against Cortisone Reductase Activity of Cultured Human Adipocytes Normal human preadipocytes (HPrAD-vis, manufactured by Cambrex corporation) were inoculated onto a 48-well cell culture plate, and the differentiation induction was carried out according to Protocol attached to the kit. The medium for the cells on the 9-11 days of the differentiation was changed to D-MEM medium (0.2 ml; manufactured by GIBCO) containing 100 nM [1,2-$^3$H] cortisone (1 µCi/well, manufactured by Muromachi Yakuhin), 0.5% DMSO, a test compound (for test compound treated group, or DMSO only for the no-test compound treated group). The plate was incubated at 37° C. for 3 hours, and then the whole medium was collected. As a background group, the medium without cell was used. The medium was mixed with ethyl acetate (0.1 ml) in an Eppendorf tube. This mixture was voltexed, and then further centrifuged at 5,000 rpm for one minute at room temperature to separate the ethyl acetate layer (the upper layer). The ethyl acetate layer (10 µl) was spotted on an aluminium plate for thin layer chromatography (silica gel 60 angstrom, Merck & Co., Inc., hereinafter referred to as TLC plate). The developing solvent (chloroform/methanol (90:10, v/v)) was put into a sealed vessel, and the TLC plate was developed, and then dried at room temperature. An imaging plate (TR-2040, Fujifilm) was exposed onto the dried TLC plate for 16 hours or more. After the exposure was completed, the imaging plate was analyzed by Bioimage Analyzer (BAS2500, Fujifilm) and the [$^3$H] radioactivity on the part corresponding to the position of cortisol developed on the TLC plate. The inhibitory activity of a test compound against cortisone reductase was calculated according to the following equation.

(inhibitory activity (%))=100×((group without test compound)−(group with test compound))/((group without test compound)−(background group))

The IC$_{50}$ value was calculated by linear regression of logarithmic value of the concentration of test compound and the inhibitory activity value, using the data at 2 points showing around 50% of the inhibitory activity. The IC$_{50}$ value of the compounds of the present invention against cortisone reductase of human adipose cell is usually within the range of 0.01-1000 nM. The IC$_{50}$ value of the following compounds of the present invention against cortisone reductase of human adipose cell was determined.

The results thereof are shown in Table 46.

TABLE 46

| Ex. No. | IC$_{50}$ (nM) | Ex. No. | IC$_{50}$ (nM) |
|---|---|---|---|
| 2 | <1 | 326 | <3 |
| 23 | <3 | 336 | 8.4 |
| 34 | <1 | 339 | <3 |
| 37 | 1.1 | 355 | 12 |
| 51 | 7.8 | 373 | 17 |
| 67 | 6.8 | 378 | 14 |
| 76 | 5.5 | 383 | <3 |
| 146 | 16 | 390 | 11 |
| 192 | <3 | 404 | <3 |
| 236 | <3 | 409 | <3 |
| 241 | <3 | 413 | <3 |
| 306 | 6.3 | 427 | 15 |
| 314 | 19 | | |

From the data in Table 46, the compounds of the present invention are expected to inhibit the production of cortisol by inhibiting 11βHSD1 activity in human adipocyte as a target organ.

Experiment 2

Inhibitory Activity Assay Against Cortisone Reductase of Mouse Primary Adipocytes The adipose tissues adhered to the mesenterium and around the testicle of ten ICR male mice (9 to 11 weeks old, Japn SLC Inc.) (hereinafter, referred to as visceral fat tissue) were soaked in about 100 mL of a phospate buffer (0.20 g/L KCl, 0.20 g/L $KH_2PO_4$, 8.00 g/L NaCl, 2.16 g/L $Na_2HPO_4.7H_2O$, 100 unit/ml penicillin (GIBCO), 100 µg/ml streptomycin (GIBCO), 250 ng/ml amphotericin (GIBCO)) and washed at room temperature.

The excised visceral fat tissues was cut finely in about 5×5 mm with scissors in Dulbecco's modified Eagle medium (about 50 ml, containing 4.5 g/L D-glucose and 584 mg/L L-glutamine, GIBCO) to which collagenase (Type II, Sigma), penicillin (GIBCO), streptomycin (GIBCO) and amphotericin (GIBCO) were added in an amount so that the final concentrations thereof are adjusted to 1 mg/ml, 100 unit/ml, 100 µg/ml and 250 ng/ml, respectively. Then, the mixture was shaken at 37° C. for 30 minutes (about 170 rpm), filtered through nylon mesh (80S [the pore size: 250 µm], SANSHIN INDUSTRIAL CO., LTD.), and the filtrate (cell suspension) was collected. This filtrate was centrifuged at 1800 rpm at room temperature for 5 minutes, and then, the liquid layer was removed stilly by decantation to give a precipitate. This precipiate was suspended in Dulbecco's modified Eagle medium (30 ml, containing 4.5 g/L D-glucose and 584 mg/L L-glutamine, GIBCO; hereinafter, occasionally referred to as FBS-containing medium), to which fetal bovine serum (hereinafter referred to as FBS, GIBCO), ascorbic acid (Wako Pure Chemical Industries, Ltd.), penicillin (GIBCO), streptomycin (GIBCO) and amphotericin (GIBCO) are added thereto in an amount so that the final concentrations thereof were adjusted to 10%, 200 µM, 100 units/ml, 100 µg/ml and 250 ng/ml, respectively, and then the suspension was filtered through a nylon mesh (420S [pore size: 25 µm], SANSHIN INDUSTRIAL CO., LTD.). The filtrate was collected, and centrifuged at 1800 rpm at room temperature for 5 minutes. The liquid layer was removed stilly by decantation, and the precipitate was suspended again in the FBS-containing medium (30 ml). This suspension was treated by the same procedure (centrifugation, removal of liquid layer, suspension in FBS-containing medium) two times more, and the suspension (90 ml) was prepared. This suspension was put into cell culture flasks (T150, for adhered cell culture, Iwaki Glass) in a each volume of 30 ml, and incubated at 37° C. in the presence of 5% $CO_2$. At 5 to 6 hours after starting incubation, the medium was removed, and the wall of the flask was washed with the above-mentioned phosphate buffer (15 ml). The washing liquid was removed, and the washing procedure was repeated again, and the phosphate buffer was removed. To the flask was added FBS-containing medium (30 ml), and the mixture was incubated at 37° C. under the presence of 5% $CO_2$. On Day 1 or Day 2 after the culture started, the medium was removed, and the wall of the flask was washed with the phosphate buffer (15 ml) once. To the flask was added a trypsin-ethylenediamine tetraacetate (hereinafter, referred to as trypsin-EDTA) solution (0.05% trypsin, 0.53 mM EDTA 4Na, GIBCO) in such a volume that the cells are duly soaked, and the mixture was allowed to stand at 37° C. for 5 minutes. To this mixture was added the FBS-containing medium in about 10-times volume of that of the trypsin-EDTA solution, and then the cell suspension was obtained.

The cells in the cell suspension were counted with a counting chamber, and the cell suspension was diluted with the FBS-containing medium so that the concentration of the cell was adjusted to $1.4 \times 10^5$ cells/ml. Thus obtained cell dilution was put into a 48-well plate (for adherent cell culture, Iwaki Glass) in an amount of 300 µl per well, and the plate was incubated at 37° C. in the presence of 5% $CO_2$ for 1 to 2 days. The medium was removed from each well of the 48-well plate, and a FBS-containing medium (300 µl, containing 10 µg/ml insulin (Sigma), 0.25 µM dexamethasone (Wako Pure Chemical Industries, Ltd.), 0.5 mM 3-isobutyl-1-methyl-xanthine (Sigma) and 5 µM 15-deoxy-$\Delta^{12,14}$-prostaglandin $J_2$ (Cayman)) was added to each well, and then the plate was incubated at 37° C. in the presence of 5% $CO_2$ for 3 days. Then, the medium in each well was removed, and further thereto was added the FBS-containing medium (300 µl, containing 10 µg/ml insulin and 5 µM 15-deoxy-$\Delta^{12,14}$-prostaglandin J2), and the mixture was cultured for 2 days. Further, the medium in each well was removed, and to each well was added the FBS-containing medium (300 µl, containing 10 µg/ml insulin and 5 µM 15-deoxy-$\Delta^{12,14}$-prostaglandin J2), and cultured for 2 days.

The medium of adipocytes which were differentiated and induced as mentioned above were replaced with 0.2 ml of D-MEM media (Gibco) containing 100 nM [1, 2-3H] cortizone (1 µCi/well, Muromachi Yakuhin), 0.5% DMSO, test compounds (test compounds-additive group, DMSO only for test compounds additive-free group). After incubation at 37° C. for 3 hours, the whole media were collected. In a background group, the medium with no cells was used. The medium was mixed with ethyl acetate (0.1 ml) in an Eppendorf tube. This mixture was vortexed, and centrifuged at 5,000 rpm for 1 minute at room temperature to removed ethyl acetate (the upper layer). The ethyl acetate (10 µl) was spotted on the aluminum plate for thin layer chromatography (silica gel 60 angstrom, Merck & Co., Inc., hereinafter referred to as TLC plate). The developing solvent (chloroform/methanol=90:10, v/v) was added to a sealed vessel and the TLC plate was developed and dried at room temperature. To the dried TLC plate was exposured an imaging plate (TR-2040, FUJIFILM Corporation) for 16 hours or more. After the exposure was completed, the imaging plate was analyzed by bio-image analyzer (BAS2500, FUJIFILM Corporation), and the [$^3$H] radioactivity on the part of the TLC plate, which was a developing position of cortisol, was measured Inhibitory activities of cortisone reducing activity of test articles were calculated as follows.

(inhibitory activity (%))=100×((group without test compound)−(group with test compound))/((group without test compound)−(background group))

The $IC_{50}$ value was calculated by linear regression of logarithmic value of the concentration of test compound and the inhibitory activity, using the data at 2 points showing around 50% of the inhibitory activity. The $IC_{50}$ value of the compounds of the present invention against cortisone reductase of mouse adipose cell is usually within the range of 0.01-1000 nM. The $IC_{50}$ value of the following compounds of the present invention against cortisone reductase of mouse adipose cell was measured. The results thereof are shown in Table 47.

TABLE 47

| Example | $IC_{50}$ (nM) | Example | $IC_{50}$ (nM) |
|---|---|---|---|
| 5 | 7.0 | 324 | <3 |
| 19 | 20.5 | 342 | <3 |
| 42 | 15.9 | 353 | 7.9 |
| 49 | 1.0 | 364 | 7.7 |
| 60 | 15.8 | 367 | <3 |
| 145 | 6.2 | 400 | <3 |
| 240 | 17 | 407 | 4.1 |
| 307 | <1 | 423 | <3 |
| 309 | 4.1 | 428 | <3 |
| 311 | 8.8 | 431 | 27 |
| 316 | 18 | | |

Experiment 3

Administration of 11βHSD1 Inhibitor to Diabetes/Obesity Model Mice

The pharmacological evaluation of 11βHSD1 inhibitors obtained by a method disclosed in Examples agaist diabetes/obesity model mice can be carried out by the following procedure.

When C57BL/6J mice (CLEA Japan Inc.) was fed with a high-fat diet (D-12492, Research Diets Inc.) for a period of 2 weeks to 8 months, hyperglycemia, hyperinsulinemia, abnormal glucose tolerance, and obesity are induced. To the diabetes/obesity model mice was administered 11βHSD1 inhibitor (0.1-100 mg per 1 kg of body weight, solvent: 0.5% methylcellulose #400 solution (Nacalai Tesque Ltd.)) one or two times per day via oral tube. On 1 to 8 weeks after the administration, the venous blood of subjuct mice was collected, and the concentrations of glucose and insulin contained in the serum or plasma were measured. When the oral glucose tolerance test was carried out, a 20-30% glucose solution was administered in an amount of 10 ml per 1 kg of body weight to mice, which had been fasted for 18 hours or more, then the blood was taken from the tail vein serially for a period of 15 minutes to 3 hours after the administration. From the time-dependent change in the glucose and insulin contained in the blood, the area under the blood concentration-time curve (AUC) was calculated. As a control group, the same procedures were carried out in a group to which a solution containing methyl cellulose only was administered instead of the above-mentioned methyl cellulose containing 11βHSD1 inhibitor. By confirming that the blood glucose level, insulin level and AUC value in the test compound-treated group are statistical-significally lower than those of the control group, the test compound can be evaluated to show diabetic improving activity and insulin resistance improving activity.

In addition, by measuring the body weight of the mice during the test, compound-treated group was confirmed to be statistical-significally lower than that of the control group, then the test compound can be evaluated to have anti-obesity activity.

Further, the weight of visceral fats, i.e., mesenteric fat, fat around epididymis, retroperitoneum fat, of the test mice after the administration was measured. By confirming that the weight of each fat in the test compound-treated group is statistical-significally lower than those of the control group, the test compound can be evaluated to have visceral fat accumulation inhibitory activity or visceral fat reducing activity.

Experiment 4

Rat Forced Swimming Test

In the forced swimming test using male SD:Crl rats (body weight: 180-300 g, Charles River Laboratories Japan Inc.), the helplessness state was observed in the escape behavior from the swimming in the second trial after the first trial (training), which state resembles with the state of depression. Then, when the compound of the present invention was administered to the mice one or several times prior to the second trial, the escape time (swimming time) during the second trial was measured, by which the anti-depression (depression, manic depression) effect was evaluated.

Experiment 5

Cognitive Function Enhancing Activity in Mouse Object Recognition Test

In the novel object recognition test using Slc:dd Y mice (13-15 g, male, Japn SLC Inc.), the memory decrease against the familiar object was observed dependently on the interval time between the first trial (training) and the second trila (test). When the second trial was carried out 24 hours later, the remarkable oblivion was observed.

The compound of the present invention obtained in Example 38 was orally and repeatedly administered to the mice for 4 days, and then, the first trial was done on this mice, and the memory retenion ability of the mice in the second trial was evaluated after 24 hours of the first trial. As a result, the compound at a dose of 10 mg/kg showed a significantly cognitive function enhancing activity (DI value: 0.177) as compared to the mice of the solvent group (DI value: 0.097).

*DI value=(novel searching times−familiar searching times)/(novel searching times+familiar searching times)

The compounds of the present invention have good physiological properties as a medicament. The physiological properties include, for example, metabolic stability, and the metabolic stability can be measured, for example, by the method disclosed in Experiment 6 or other well-known methods.

Experiment 6

Metabolic Stability Test

A 100 μM solution of a test compound in DMSO (10 μL) was mixed with acetonitrile (90 μL). The mixture was further diluted ten times with acetonitrile. To thus obtained solution (5 μL) was added a cofactor solution (250 μL, a solution prepared from NADPH (220 mg) and 25 mM phosphate buffer (pH 7.4, 40.5 mL)) (referred to as "intermediate dilution").

The 2 wells of the "reactive sample" were prepared by shaking the intermediate dilution (50 μL) and microsome solution (50 μL) and then incubating the mixture with shaking at 37° C. for 30 minutes. The 2 wells of the "non-reactive sample" were prepared by incubating the intermediate dilution (50 μL) without adding the microsome solution (prepared from 25 mM phosphate buffer (pH 7.4, 50 mL), liver microsome (0.5 mL, human or rat, about 20 mg protein/ml, manufactured by Xenotech Inc.) in a similar manner to the above).

After the incubation was completed, methanol (400 μL) was added to each well of the "reactive sample" and the "non-reactive sample". To the wells of the "non-reactive sample" after the addition of methanol, the microsome solution (50 μL) was added, and allowed to stand at room temperature for 15 minutes or more.

Each well was subjected to deproteination, and allowed to stand at 4° C. for one hour. Then, the centrifuted supernatant was analyzed by LC-MS/MS (HPLC manufactered by Agilent Technology, Inc., and API3000 manufactured by MDS Sciex Inc.). Total 4 wells of the 2 wells of "reactive sample" and the 2 wells of the "non-reactive sample" were measured, and the arithmetic average of each chromatograph peak area was calculated. The clearance of the compound (mL/min/mg protein) was calculated by the following equation:

−Ln("reactive sample" a arithmetic average÷"non-reactive sample" arithmetic average)/30/0.1.

INDUSTRIAL APPLICABILITY

The compound of the present invention is useful as an 11βHSD1 inhibitor.

The invention claimed is:
1. A compound of formula (I):

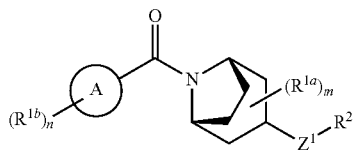
(1)

wherein A is a group of the following formula (A-1):

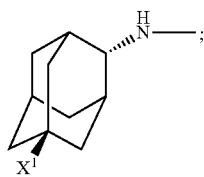
(A-1)

$R^{1a}$ and $R^{1b}$ are the same or different and each independently $C_{1-6}$ alkyl which may be optionally substituted by 1 to 3 halogen atoms;
m and n are each independently an integer of 0 to 5;
$X^1$ is hydroxyl, or aminocarbonyl;
$Z^1$ is a single bond, oxygen atom, sulfur atom, —SO—, —SO$_2$—, or —N($R^3$)—;
$R^2$ is cyano, optionally substituted $C_{1-6}$ alkyl, optionally substituted $C_{3-7}$ cycloalkyl, optionally substituted $C_{6-10}$ aryl, optionally substituted $C_{7-16}$ aralkyl, optionally substituted heterocycle, optionally substituted heterocyclic $C_{1-6}$ alkyl, optionally substituted 5 to 12-membered mono- or poly-cyclic heteroaryl, optionally substituted 5 to 12-membered mono- or poly-cyclic heteroaryl-$C_{1-6}$ alkyl, or optionally substituted 5 to 7-membered cyclic amino;
provided that if $R^2$ is cyano and optionally substituted 5 to 7-membered cyclic amino, then $Z^1$ is a single bond;
$R^3$ is hydrogen atom, optionally substituted $C_{1-6}$ alkyl, optionally substituted $C_{3-7}$ cycloalkyl, optionally substituted $C_{6-10}$ aryl, optionally substituted $C_{7-16}$ aralkyl, optionally substituted heterocycle, optionally substituted heterocyclic $C_{1-6}$ alkyl, optionally substituted 5 to 12-membered mono- or poly-cyclic heteroaryl, or optionally substituted 5 to 12-membered mono- or poly-cyclic heteroaryl-$C_{1-6}$ alkyl;
wherein the substituent group in the optionally substituted $C_{6-10}$ aryl, optionally substituted 5 to 12-membered mono- or poly-cyclic heteroaryl, optionally substituted $C_{7-16}$ aralkyl, and optionally substituted 5 to 12-membered mono- or poly-cyclic heteroaryl-$C_{1-6}$ alkyl in $R^2$ is selected from the group consisting of:

(1) halogen atom,
(2) cyano,
(3) hydroxy,
(4) $C_{1-4}$ alkoxy (in which the alkoxy may be optionally substituted by
 (a) 1 to 3 halogen atoms,
 (b) $C_{1-4}$ alkoxy,
 (c) carboxy,
 (d) $C_{1-4}$ alkoxycarbonyl,
 (e) $C_{7-16}$ aralkyloxycarbonyl,
 (f) mono- or di-$C_{1-6}$alkylaminocarbonyl,
 (g) 5 to 7-membered cyclic aminocarbonyl, or
 (h) $C_{3-6}$ cycloalkyl),
(5) $C_{1-4}$ alkylsulfonyl,
(6) $C_{3-6}$ cycloalkyl,
(7) $C_{3-6}$ cycloalkoxy,
(8) mono- or di-$C_{1-6}$ alkylamino,
(9) mono- or di-$C_{1-6}$alkylcarbonylamino,
(10) mono- or di-$C_{1-6}$alkylsulfonylamino,
(11) $C_{1-4}$ alkyl (in which the alkyl may be optionally substituted by
 (a) 1 to 3 halogen atoms,
 (b) $C_{1-4}$ alkoxy (in which the alkoxy may be optionally substituted by 1 to 3 halogen atoms),
 (c) carboxy,
 (d) $C_{1-4}$ alkoxycarbonyl,
 (e) $C_{7-16}$ aralkyloxycarbonyl,
 (f) mono- or di-$C_{1-6}$alkylaminocarbonyl,
 (g) 5 to 7-membered cyclic aminocarbonyl, or
 (h) $C_{3-6}$ cycloalkyl),
(12) $C_{1-6}$ alkylcarbonyl,
(13) carboxy,
(14) $C_{1-4}$ alkoxycarbonyl, and
(15) aminocarbonyl; or a pharmaceutically acceptable salt thereof.

2. The compound of claim 1, wherein m and n are 0, or a pharmaceutically acceptable salt thereof.
3. The compound of claim 1, wherein $X^1$ is hydroxyl, or a pharmaceutically acceptable salt thereof.
4. The compound of claim 1, wherein $X^1$ is aminocarbonyl, or a pharmaceutically acceptable salt thereof.
5. The compound of claim 1, wherein $Z^1$ has the following configuration in formula (I):

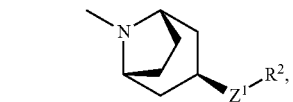

or a pharmaceutically acceptable salt thereof.
6. The compound of claim 1, wherein $Z^1$ has the following configuration in formula (I):

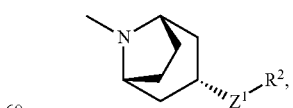

or a pharmaceutically acceptable salt thereof.
7. The compound of claim 1, wherein $Z^1$ is a single bond, oxygen atom, sulfur atom, or —SO$_2$—, or a pharmaceutically acceptable salt thereof.
8. The compound of claim 7, wherein $Z^1$ is a single bond, or oxygen atom, or a pharmaceutically acceptable salt thereof.

9. The compound of claim 8, wherein $Z^1$ is a single bond, or a pharmaceutically acceptable salt thereof.

10. The compound of claim 8, wherein $Z^1$ is oxygen atom, or a pharmaceutically acceptable salt thereof.

11. The compound of claim 1, wherein $R^2$ is optionally substituted $C_{1-6}$ alkyl, optionally substituted $C_{3-7}$ cycloalkyl, optionally substituted $C_{6-10}$ aryl, optionally substituted $C_{7-16}$ aralkyl, optionally substituted heterocycle, optionally substituted heterocyclic $C_{1-6}$ alkyl, optionally substituted 5 to 12-membered mono- or poly-cyclic heteroaryl, or optionally substituted 5 to 12-membered mono- or poly-cyclic heteroaryl-$C_{1-6}$ alkyl, or a pharmaceutically acceptable salt thereof.

12. The compound of claim 11, wherein $R^2$ is optionally substituted $C_{6-10}$ aryl, optionally substituted $C_{7-16}$ aralkyl, optionally substituted 5 to 12-membered mono- or poly-cyclic heteroaryl, or optionally substituted 5 to 12-membered mono- or poly-cyclic heteroaryl-$C_{1-6}$ alkyl, or a pharmaceutically acceptable salt thereof.

13. The compound of claim 1, wherein the substituent group in the optionally substituted $C_{6-10}$ aryl, optionally substituted 5 to 12-membered mono- or poly-cyclic heteroaryl, optionally substituted $C_{7-16}$ aralkyl, and optionally substituted 5 to 12-membered mono- or poly-cyclic heteroaryl-$C_{1-6}$ alkyl in $R^2$ is selected from the group consisting of:
   (1) halogen atom,
   (2) cyano,
   (3) hydroxy,
   (4) $C_{1-4}$ alkoxy (in which the alkoxy may be optionally substituted by
      (a) 1 to 3 halogen atoms,
      (b) $C_{1-4}$ alkoxy,
      (c) carboxy,
      (d) $C_{1-4}$ alkoxycarbonyl, or
      (e) $C_{3-6}$ cycloalkyl),
   (5) $C_{1-4}$ alkylsulfonyl,
   (6) $C_{3-6}$ cycloalkyl,
   (7) $C_{3-6}$ cycloalkoxy,
   (8) mono- or di-$C_{1-6}$ alkylamino,
   (9) mono- or di-$C_{1-6}$alkylcarbonylamino,
   (10) mono- or di-$C_{1-6}$alkylsulfonylamino,
   (11) $C_{1-4}$ alkyl (in which the alkyl may be optionally substituted by
      (a) 1 to 3 halogen atoms,
      (b) $C_{1-4}$ alkoxy (in which the alkoxy may be optionally substituted by 1 to 3 halogen atoms),
      (c) carboxy,
      (d) $C_{1-4}$ alkoxycarbonyl, or
      (e) $C_{3-6}$ cycloalkyl),
   (12) $C_{1-6}$ alkylcarbonyl,
   (13) carboxy,
   (14) $C_{1-4}$ alkoxycarbonyl, and
   (15) aminocarbonyl, or a pharmaceutically acceptable salt thereof.

14. The compound of claim 13, wherein the substituent group in the optionally substituted $C_{6-10}$ aryl, optionally substituted 5 to 12-membered mono- or poly-cyclic heteroaryl, optionally substituted $C_{7-16}$ aralkyl, and optionally substituted 5 to 12-membered mono- or poly-cyclic heteroaryl-$C_{1-6}$ alkyl in $R^2$ is the same or different 1 to 5 substituent groups selected from the group consisting of:
   (1) halogen atom,
   (2) cyano,
   (3) $C_{1-4}$ alkoxy (in which the alkoxy may be optionally substituted by
      (a) 1 to 3 halogen atoms,
      (b) $C_{3-6}$ cycloalkyl, or
      (c) $C_{1-4}$ alkoxy),
   (4) $C_{1-4}$ alkylsulfonyl,
   (5) $C_{3-6}$ cycloalkyl,
   (6) mono- or di-$C_{1-6}$alkylcarbonylamino,
   (7) $C_{1-4}$ alkyl (in which the alkyl may be optionally substituted by
      (a) 1 to 3 halogen atoms, or
      (b) $C_{1-4}$ alkoxy (in which the alkoxy may be optionally substituted by 1 to 3 halogen atoms)),
   (8) carboxy,
   (9) $C_{1-4}$ alkoxycarbonyl, and
   (10) aminocarbonyl, or a pharmaceutically acceptable salt thereof.

15. The compound of claim 14, wherein the substituent group in the optionally substituted $C_{6-10}$ aryl, optionally substituted 5 to 12-membered mono- or poly-cyclic heteroaryl, optionally substituted $C_{7-16}$ aralkyl, and optionally substituted 5 to 12-membered mono- or poly-cyclic heteroaryl-$C_{1-6}$ alkyl in $R^2$ is selected from the group consisting of:
   (1) halogen atom,
   (2) cyano,
   (3) $C_{1-4}$ alkoxy (in which the alkoxy may be optionally substituted by
      (a) 1 to 3 halogen atoms,
      (b) $C_{1-4}$ alkoxy, or
      (c) $C_{3-6}$ cycloalkyl),
   (4) $C_{3-6}$ cycloalkyl,
   (5) $C_{1-4}$ alkyl (in which the alkyl may be optionally substituted by
      (a) 1 to 3 halogen atoms,
      (b) $C_{1-4}$ alkoxy (in which the alkoxy may be optionally substituted by 1 to 3 halogen atoms), or
      (c) $C_{3-6}$ cycloalkyl), and
   (6) $C_{1-6}$ alkylcarbonyl, or a pharmaceutically acceptable salt thereof.

16. The compound of claim 15, wherein the substituent group in the optionally substituted $C_{6-10}$ aryl, optionally substituted 5 to 12-membered mono- or poly-cyclic heteroaryl, optionally substituted $C_{7-16}$ aralkyl, and optionally substituted 5 to 12-membered mono- or poly-cyclic heteroaryl-$C_{1-6}$ alkyl in $R^2$ is selected from the group consisting of:
   (1) halogen atom,
   (2) cyano,
   (3) $C_{1-4}$ alkyl (in which the group may be optionally substituted by
      (a) 1 to 3 halogen atoms, or
      (b) $C_{1-4}$ alkoxy (in which the alkoxy may be optionally substituted by 1 to 3 halogen atoms)), and
   (4) $C_{1-4}$ alkoxy (in which the group may be optionally substituted by
      (a) 1 to 3 halogen atoms,
      (b) $C_{3-6}$ cycloalkyl, or
      (c) $C_{1-4}$ alkoxy), or a pharmaceutically acceptable salt thereof.

17. The compound of claim 1, wherein $R^2$ is $C_{6-10}$ aryl (in which the aryl may be optionally substituted by the same or different 1 to 5 groups selected from the group consisting of:
   (1) halogen atom,
   (2) cyano,
   (3) hydroxy,
   (4) $C_{1-4}$ alkoxy (in which the alkoxy may be optionally substituted by
      (a) 1 to 3 halogen atoms,
      (b) $C_{1-4}$ alkoxy,
      (c) carboxy, (d) $C_{1-4}$ alkoxycarbonyl, or
(e) $C_{3-6}$ cycloalkyl),
(5) $C_{1-4}$ alkylsulfonyl,
(6) $C_{3-6}$ cycloalkyl,
(7) $C_{3-6}$ cycloalkoxy,
(8) mono- or di-$C_{1-6}$ alkylamino,
(9) mono- or di-$C_{1-6}$ alkylcarbonylamino,
(10) mono- or di-$C_{1-6}$ alkylsulfonylamino,
(11) $C_{1-4}$ alkyl (in which the alkyl may be optionally substituted by
  (a) 1 to 3 halogen atoms,
  (b) $C_{1-4}$ alkoxy (in which the alkoxy may be optionally substituted by 1 to 3 halogen atoms),
  (c) carboxyl,
  (d) $C_{1-4}$ alkoxycarbonyl, or
  (e) $C_{3-6}$ cycloalkyl),
(12) $C_{1-6}$ alkylcarbonyl,
(13) carboxy,
(14) $C_{1-4}$ alkoxycarbonyl, and
(15) aminocarbonyl), or a pharmaceutically acceptable salt thereof.

18. The compound of claim 17, wherein $R^2$ is $C_{6-10}$ aryl (in which the aryl may be optionally substituted by the group(s) is selected from the group consisting of:
(1) halogen atom,
(2) cyano,
(3) $C_{1-4}$ alkoxy (in which the alkoxy may be optionally substituted by
  (a) 1 to 3 halogen atoms,
  (b) $C_{1-4}$ alkoxy, or
  (c) $C_{3-6}$ cycloalkyl),
(4) $C_{3-6}$ cycloalkyl,
(5) $C_{1-4}$ alkyl (in which the alkyl may be optionally substituted by
  (a) 1 to 3 halogen atoms,
  (b) $C_{1-4}$ alkoxy (in which the alkoxy may be optionally substituted by 1 to 3 halogen atoms), or
  (c) $C_{3-6}$ cycloalkyl), and
(6) $C_{1-6}$ alkylcarbonyl), or a pharmaceutically acceptable salt thereof.

19. The compound of claim 18, wherein $R^2$ is $C_{6-10}$ aryl (in which the aryl may be optionally substituted by the group(s) is selected from the group consisting of:
(1) halogen atom,
(2) cyano,
(3) $C_{1-4}$ alkoxy (in which the group may be optionally substituted by
  (a) 1 to 3 halogen atoms,
  (b) $C_{1-4}$ alkoxy, or
  (c) $C_{3-6}$ cycloalkyl), and
(4) $C_{1-4}$ alkyl (in which the alkyl may be optionally substituted by
  (a) 1 to 3 halogen atoms,
  (b) $C_{1-4}$ alkoxy (in which the alkoxy may be optionally substituted by 1 to 3 halogen atoms), or
  (c) $C_{3-6}$ cycloalkyl)), or a pharmaceutically acceptable salt thereof.

20. The compound of claim 1, wherein $R^2$ is $C_{7-16}$ aralkyl (in which the aryl may be optionally substituted by the same or different 1 to 5 groups selected from the group consisting of:
(1) halogen atom,
(2) cyano,
(3) $C_{1-4}$ alkoxy (in which the alkoxy may be optionally substituted by
  (a) 1 to 3 halogen atoms, or
  (b) $C_{1-4}$ alkoxy),
(4) $C_{1-4}$ alkylsulfonyl, and
(5) $C_{1-4}$ alkyl (in which the alkyl may be optionally substituted by
  (a) 1 to 3 halogen atoms, or
  (b) $C_{1-4}$ alkoxy), or a pharmaceutically acceptable salt thereof.

21. The compound of claim 20, wherein $R^2$ is $C_{7-16}$ aralkyl (in which the aryl may be optionally substituted by the same or different 1 to 5 groups selected from the group consisting of:
(1) halogen atom,
(2) cyano,
(3) $C_{1-4}$ alkoxy (in which the alkoxy may be optionally substituted by 1 to 3 halogen atoms),
(4) $C_{1-4}$ alkylsulfonyl, and
(5) $C_{1-4}$ alkyl (in which the alkyl may be optionally substituted by 1 to 3 halogen atoms)), or a pharmaceutically acceptable salt thereof.

22. The compound of claim 1, wherein $R^2$ is 5 to 12-membered mono- or poly-cyclic heteroaryl (in which the heteroaryl may be optionally substituted by the same or different 1 to 3 groups selected from the group consisting of:
(1) halogen atom,
(2) cyano,
(3) $C_{1-4}$ alkoxy (in which the alkoxy may be optionally substituted by
  (a) 1 to 3 halogen atoms,
  (b) $C_{1-4}$ alkoxy, or
  (c) $C_{3-6}$ cycloalkyl),
(4) $C_{3-6}$ cycloalkyl,
(5) $C_{3-6}$ cycloalkylalkoxy,
(6) $C_{1-4}$ alkyl (in which the alkyl may be optionally substituted by
  (a) 1 to 3 halogen atoms,
  (b) $C_{1-4}$ alkoxy, or
  (c) $C_{3-6}$ cycloalkyl), and
(7) $C_{1-6}$ alkylcarbonyl), or a pharmaceutically acceptable salt thereof.

23. The compound of claim 22, wherein $R^2$ is 5 to 12-membered mono- or poly-cyclic heteroaryl (in which the heteroaryl may be optionally substituted by the same or different 1 to 3 groups selected from the group consisting of:
(1) halogen atom,
(2) cyano,
(3) $C_{1-4}$ alkoxy (in which the group may be optionally substituted by
  (a) 1 to 3 halogen atoms,
  (b) $C_{1-4}$ alkoxy, or
  (c) $C_{3-6}$ cycloalkyl), and
(4) $C_{1-4}$ alkyl (in which the alkyl may be optionally substituted by
  (a) 1 to 3 halogen atoms,
  (b) $C_{1-4}$ alkoxy, or
  (c) $C_{3-6}$ cycloalkyl)), or a pharmaceutically acceptable salt thereof.

24. The compound of claim 1, wherein $R^2$ is
(1) $C_{1-6}$ alkyl (in which the group may be optionally substituted by
  (a) $C_{6-10}$ aryloxy (in which the aryl may be optionally substituted by
    halogen atom,
    $C_{1-4}$ alkyl, or
    $C_{1-4}$ alkoxy),
  (b) $C_{6-10}$ arylthio (in which the aryl may be optionally substituted by
    halogen atom, or
    $C_{1-4}$ alkyl), (c) $C_{6-10}$ arylsulfonyl (in which the aryl may be optionally substituted by
  halogen atom,
  $C_{1-4}$ alkyl, or
  $C_{1-4}$ alkoxy),
(d) $C_{3-6}$ cycloalkyl,
(e) $C_{1-4}$ alkoxy, or
(f) $C_{7-14}$ aralkyloxy),
(2) $C_{3-7}$ cycloalkyl,
(3) $C_{6-10}$ aryl (in which the aryl may be optionally substituted by the same or different 1 to 5 groups selected from the group consisting of:
  (a) halogen atom,
  (b) cyano,
  (c) hydroxy,
  (d) $C_{1-4}$ alkoxy (in which the alkoxy may be optionally substituted by
    1 to 3 halogen atoms,
    $C_{1-4}$ alkoxy,
    carboxy,
    $C_{1-4}$ alkoxycarbonyl, or
    $C_{3-6}$ cycloalkyl),
  (e) $C_{1-4}$ alkylsulfonyl,
  (f) $C_{3-6}$ cycloalkyl,
  (g) $C_{3-6}$ cycloalkoxy,
  (h) mono- or di-$C_{1-6}$ alkylamino,
  (i) mono- or di-$C_{1-6}$ alkylcarbonylamino,
  (j) mono- or di-$C_{1-6}$ alkylsulfonylamino,
  (k) $C_{1-4}$ alkyl (in which the alkyl may be optionally substituted by
    1 to 3 halogen atoms,
    $C_{1-4}$ alkoxy (in which the alkoxy may be optionally substituted by 1 to 3 halogen atoms),
    carboxyl,
    $C_{1-4}$ alkoxycarbonyl, or
    $C_{3-6}$ cycloalkyl),
  (l) $C_{1-6}$ alkylcarbonyl,
  (m) carboxy,
  (n) $C_{1-4}$ alkoxycarbonyl, and
  (o) aminocarbonyl),
(4) $C_{7-16}$ aralkyl (in which the group may be optionally substituted by the same or different 1 to 5 groups selected from the group consisting of:
  (a) halogen atom,
  (b) cyano,
  (c) $C_{1-4}$ alkoxy (in which the alkoxy may be optionally substituted by
    1 to 3 halogen atoms,
    $C_{3-6}$ cycloalkyl, or
    $C_{1-4}$ alkoxy),
  (d) $C_{1-4}$ alkylsulfonyl, and
  (e) $C_{1-4}$ alkyl (in which the alkyl may be optionally substituted by
    1 to 3 halogen atoms, or
    $C_{1-4}$ alkoxy),
(5) heterocycle,
(6) heterocyclic $C_{1-6}$ alkyl,
(7) 5 to 12-membered mono- or poly-cyclic heteroaryl (in which the heteroaryl may be optionally substituted by the same or different 1 to 3 groups selected from the group consisting of:
  (a) halogen atom,
  (b) cyano,
  (c) $C_{1-4}$ alkoxy (in which the alkoxy may be optionally substituted by
    1 to 3 halogen atoms,
    $C_{1-4}$ alkoxy, or
    $C_{3-6}$ cycloalkyl),
  (d) $C_{3-6}$ cycloalkyl,
  (e) $C_{3-6}$ cycloalkylalkoxy,
  (f) mono- or di-$C_{1-6}$ alkylamino,
  (g) $C_{1-4}$ alkyl (in which the alkyl may be optionally substituted by
    1 to 3 halogen atoms,
    $C_{1-4}$ alkoxy, or
    $C_{3-6}$ cycloalkyl), and
  (h) $C_{1-6}$ alkylcarbonyl),
(8) 5 to 10-membered mono- or poly-cyclic heteroaryl-$C_{1-6}$ alkyl (in which the group may be optionally substituted by $C_{1-4}$ alkyl, or $C_{1-4}$ alkoxy), or
(9) 5 to 7-membered cyclic amino, or a pharmaceutically acceptable salt thereof.

25. The compound of claim 24, wherein $R^2$ is
(1) $C_{1-6}$ alkyl (in which the group may be optionally substituted by $C_{6-10}$ aryloxy),
(2) $C_{6-10}$ aryl (in which the aryl may be optionally substituted by the same or different 1 to 5 groups selected from the group consisting of:
  (a) halogen atom,
  (b) cyano,
  (c) $C_{1-4}$ alkoxy (in which the alkoxy may be optionally substituted by
    1 to 3 halogen atoms, or
    $C_{1-4}$ alkoxy),
  (d) $C_{1-4}$ alkylsulfonyl,
  (e) mono- or di-$C_{1-6}$ alkylcarbonylamino,
  (f) $C_{1-4}$ alkyl (in which the alkyl may be optionally substituted by
    1 to 3 halogen atoms, or
    $C_{1-4}$ alkoxy (in which the alkoxy may be optionally substituted by 1 to 3 halogen atoms)),
  (g) $C_{1-4}$ alkylcarbonyl,
  (h) carboxy,
  (i) $C_{1-4}$ alkoxycarbonyl, and
  (j) aminocarbonyl),
(3) $C_{7-16}$ aralkyl (in which the group may be optionally substituted by the same or different 1 to 5 groups selected from the group consisting of:
  (a) halogen atom,
  (b) cyano,
  (c) $C_{1-4}$ alkoxy (in which the alkoxy may be optionally substituted by 1 to 3 halogen atoms),
  (d) $C_{1-4}$ alkylsulfonyl, and
  (e) $C_{1-4}$ alkyl (in which the alkyl may be optionally substituted by 1 to 3 halogen atoms),
(4) heterocycle,
(5) 5 to 12-membered mono- or poly-cyclic heteroaryl (in which the heteroaryl may be optionally substituted by the same or different 1 to 3 groups selected from the group consisting of:
  (a) halogen atom,
  (b) cyano,
  (c) $C_{1-4}$ alkoxy (in which the alkoxy may be optionally substituted by
    1 to 3 halogen atoms, or
    $C_{3-6}$ cycloalkyl),
  (d) $C_{1-4}$ alkyl (in which the alkyl may be optionally substituted by
    1 to 3 halogen atoms, or
    $C_{1-4}$ alkoxy),
  (e) $C_{1-4}$ alkylcarbonyl, and
  (f) $C_{3-6}$ cycloalkyl), or (6) 5 to 10-membered mono- or poly-cyclic heteroaryl-$C_{1-6}$ alkyl (in which the group may be optionally substituted by
(a) $C_{1-4}$ alkyl, or
(b) $C_{1-4}$ alkoxy), or a pharmaceutically acceptable salt thereof.

26. The compound of claim 24, wherein $R^2$ is
(1) $C_{6-10}$ aryl (in which the aryl may be optionally substituted by the same or different 1 to 5 groups selected from the group consisting of:
(a) halogen atom,
(b) cyano,
(c) $C_{1-4}$ alkoxy (in which the alkoxy may be optionally substituted by
    1 to 3 halogen atoms, or
    $C_{3-6}$ cycloalkyl),
(d) $C_{1-4}$ alkylsulfonyl,
(e) mono- or di-$C_{1-6}$ alkylcarbonylamino,
(f) $C_{1-4}$ alkyl (in which the alkyl may be optionally substituted by
    1 to 3 halogen atoms, or
    $C_{1-4}$ alkoxy (in which the alkoxy may be optionally substituted by 1 to 3 halogen atoms)),
(g) $C_{1-4}$ alkylcarbonyl,
(h) carboxy,
(i) $C_{1-4}$ alkoxycarbonyl, and
(j) aminocarbonyl), or
(2) 5 to 12-membered mono- or poly-cyclic heteroaryl (in which the heteroaryl may be optionally substituted by the same or different 1 to 3 groups selected from the group consisting of:
(a) halogen atom,
(b) cyano,
(c) $C_{1-4}$ alkoxy (in which the alkoxy may be optionally substituted by
    1 to 3 halogen atoms, or
    $C_{3-6}$ cycloalkyl), and
(d) $C_{1-4}$ alkyl (in which the alkyl may be optionally substituted by
    1 to 3 halogen atoms, or
    $C_{1-4}$ alkoxy)), or a pharmaceutically acceptable salt thereof.

27. The compound of claim 1, wherein $R^2$ is optionally substituted heterocycle, or a pharmaceutically acceptable salt thereof.

28. The compound of claim 27, wherein $R^2$ is heterocycle, or a pharmaceutically acceptable salt thereof.

29. The compound of claim 27, wherein the heterocycle in $R^2$ is 4-piperidinyl, or a pharmaceutically acceptable salt thereof.

30. The compound of claim 1, wherein the aryl moiety of $C_{6-10}$ aryl and $C_{7-14}$ aralkyl in $R^2$ and the aryl moiety of the substituent group $C_{6-10}$ aryloxy of $C_{1-6}$ alkyl in $R^2$ are phenyl, or a pharmaceutically acceptable salt thereof.

31. The compound of claim 1, wherein the heteroaryl moiety of 5 to 12-membered mono- or poly-cyclic heteroaryl and 5 to 12-membered mono- or poly-cyclic heteroaryl-$C_{1-6}$ alkyl in $R^2$, the substituent group heteroaryl of heterocycle in $R^2$, and the heteroaryl moiety of the substituent group heteroaryloxy of $C_{1-6}$ alkyl in $R^2$ are heteroaryl selected from the group consisting of the following groups:

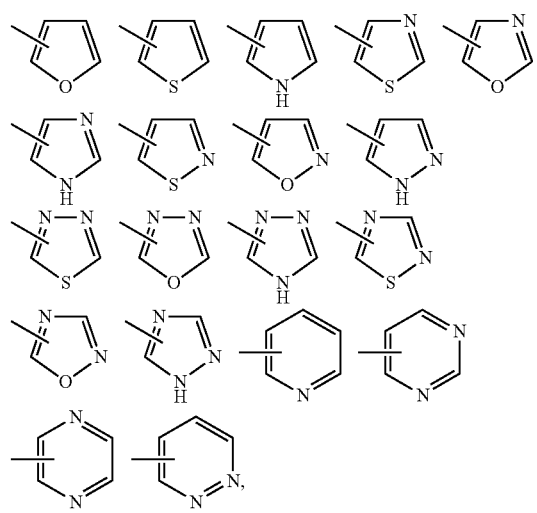

or a pharmaceutically acceptable salt thereof.

32. The compound of claim 31, wherein the heteroaryl moiety of 5 to 12-membered mono- or poly-cyclic heteroaryl and 5 to 12-membered mono- or poly-cyclic heteroaryl-$C_{1-6}$ alkyl in $R^2$, and the heteroaryl moiety of the substituent group heteroaryloxy of $C_{1-6}$ alkyl in $R^2$ are heteroaryl selected from the group consisting of the following groups:

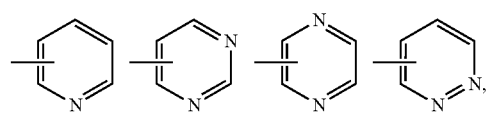

or a pharmaceutically acceptable salt thereof.

33. The compound of claim 32, wherein the heteroaryl moiety of 5 to 12-membered mono- or poly-cyclic heteroaryl and 5 to 12-membered mono- or poly-cyclic heteroaryl-$C_{1-6}$ alkyl in $R^2$, and the heteroaryl moiety of the substituent group heteroaryloxy of $C_{1-6}$ alkyl in $R^2$ are heteroaryl of the following formula:

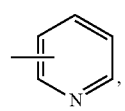

or a pharmaceutically acceptable salt thereof.

34. The compound of claim 11, wherein $R^3$ is hydrogen atom, optionally substituted $C_{1-6}$ alkyl, optionally substituted $C_{3-7}$ cycloalkyl, optionally substituted heterocycle, optionally substituted $C_{7-14}$ aralkyl, or optionally substituted 5 to 12-membered mono- or poly-cyclic heteroaryl-$C_{1-6}$ alkyl, or a pharmaceutically acceptable salt thereof.

35. The compound of claim 34, wherein $R^3$ is
(1) hydrogen atom,
(2) $C_{1-6}$ alkyl (in which the alkyl may be optionally substituted by
(a) $C_{6-10}$ aryloxy,
(b) saturated heterocycle, or
(c) $C_{3-6}$ cycloalkyl),
(3) $C_{3-7}$ cycloalkyl, (4) saturated heterocycle,
(5) $C_{7-16}$ aralkyl, or
(6) 5 to 6-membered monocyclic heteroaryl-$C_{1-6}$ alkyl,
or a pharmaceutically acceptable salt thereof.

36. A medicament, comprising as the active ingredient the compound of claim 1 or a pharmaceutically acceptable salt thereof.

37. A therapeutic agent for type II diabetes, abnormal glucose tolerance, hyperglycemia, insulin resistance, abnormality of lipid metabolism, hypertension, arteriosclerosis, angiostenosis, obesity, Cushing's syndrome, subclinical Cushing's syndrome, glaucoma, osteoporosis, metabolic syndrome, cardiovascular disease, atherosclerosis, cognitive disorder, dementia, Alzheimer's disease, depression, anxiety or manic depression, comprising as the active ingredient the compound of claim 1 or a pharmaceutically acceptable salt thereof.

38. (3-Exo)-3-(4-fluorophenoxy)-N-[(E)-5-hydroxyadamantan-2-yl]-8-azabicyclo¬[3.2.1]octane-8-carboxamide, or a pharmaceutically acceptable salt thereof.

39. (3-Exo)-N-[(E)-5-carbamoyladamantan-2-yl]-3-(4-fluorophenoxy)-8-azabicyclo¬[3.2.1]octane-8-carboxamide, or a pharmaceutically acceptable salt thereof.

40. (3-Endo)-N-[(E)-5-carbamoyladamantan-2-yl]-3-(4-fluorophenoxy)-8-azabicyclo¬[3.2.1]octane-8-carboxamide, or a pharmaceutically acceptable salt thereof.

41. (3-Endo)-3-(4-fluorophenoxy)-N-[(E)-5-hydroxyadamantan-2-yl]-8-azabicyclo¬[3.2.1]octane-8-carboxamide, or a pharmaceutically acceptable salt thereof.

42. (3-Endo)-3-[(5-fluoro-2-pyridinyl)oxy]-N-[(2S,5R)-5-hydroxyadamantan-2-yl]-8-azabicyclo¬[3.2.1]octane-8-carboxamide, or a pharmaceutically acceptable salt thereof.

* * * * *